(12) United States Patent
Heron et al.

(10) Patent No.: US 12,252,717 B2
(45) Date of Patent: *Mar. 18, 2025

(54) MODIFIED HELICASES

(71) Applicant: Oxford Nanopore Technologies PLC, Oxford (GB)

(72) Inventors: Andrew John Heron, Oxford (GB); James Anthony Clarke, Oxford (GB); Ruth Moysey, Oxford (GB); Elizabeth Jayne Wallace, Oxford (GB); Mark John Bruce, Oxford (GB); Lakmal Jayasinghe, Oxford (GB); Domenico Caprotti, Oxford (GB); Szabolcs Soeroes, Oxford (GB); Luke McNeill, Oxford (GB); David Antoni Alves, Oxford (GB); Rebecca Victoria Bowen, Oxford (GB); John Milton, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 155 days.

This patent is subject to a terminal disclaimer.

(21) Appl. No.: 18/047,589

(22) Filed: Oct. 18, 2022

(65) Prior Publication Data

US 2023/0227799 A1 Jul. 20, 2023

Related U.S. Application Data

(63) Continuation of application No. 17/064,329, filed on Oct. 6, 2020, now Pat. No. 11,525,126, which is a continuation of application No. 14/415,453, filed as application No. PCT/GB2013/051925 on Jul. 18, 2013, now Pat. No. 10,808,231.

(60) Provisional application No. 61/774,862, filed on Mar. 8, 2013, provisional application No. 61/673,452, filed on Jul. 19, 2012.

(51) Int. Cl.
*C12N 9/14* (2006.01)
*C12N 9/90* (2006.01)
*C12Q 1/6827* (2018.01)

(52) U.S. Cl.
CPC ............. *C12N 9/14* (2013.01); *C12N 9/90* (2013.01); *C12Q 1/6827* (2013.01); *C12Y 306/04012* (2013.01); *C12Y 599/01002* (2013.01); *C12Y 599/01003* (2013.01); *C07K 2319/80* (2013.01)

(58) Field of Classification Search
None
See application file for complete search history.

(56) References Cited

U.S. PATENT DOCUMENTS

| | | |
|---|---|---|
| 7,338,807 B2 | 3/2008 | Harris et al. |
| 7,625,706 B2 | 12/2009 | Akeson et al. |
| 7,745,116 B2 | 6/2010 | Williams |
| 7,851,203 B2 | 12/2010 | Letant et al. |
| 7,947,454 B2 | 5/2011 | Akeson et al. |
| 8,105,846 B2 | 1/2012 | Bayley et al. |
| 8,785,211 B2 | 7/2014 | Bayley et al. |
| 8,828,208 B2 | 9/2014 | Canas et al. |
| 9,617,591 B2 | 4/2017 | Moysey et al. |
| 9,758,823 B2 | 9/2017 | Moysey et al. |
| 9,797,009 B2 | 10/2017 | Heron et al. |
| 10,221,450 B2 | 3/2019 | Heron et al. |
| 10,322,150 B2 | 6/2019 | Honda et al. |
| 10,385,382 B2 | 8/2019 | Moysey et al. |
| 10,392,658 B2 | 8/2019 | Bowen et al. |
| 10,443,097 B2 | 10/2019 | Jayasinghe et al. |
| 10,480,026 B2 | 11/2019 | Garalde et al. |
| 10,724,018 B2 | 7/2020 | Bruce et al. |
| 10,724,087 B2 | 7/2020 | Moysey et al. |
| 10,808,231 B2 | 10/2020 | Heron et al. |
| 10,844,432 B2 | 11/2020 | Jayasinghe et al. |
| 11,180,741 B2 | 11/2021 | Heron et al. |
| 11,525,125 B2 | 12/2022 | Bruce et al. |
| 11,525,126 B2 | 12/2022 | Heron et al. |
| 11,634,763 B2 | 4/2023 | Moysey et al. |
| 11,965,183 B2 | 4/2024 | Heron et al. |
| 2003/0010638 A1 | 1/2003 | Hansford et al. |
| 2004/0058378 A1 | 3/2004 | Kong et al. |
| 2004/0248114 A1 | 12/2004 | Taira et al. |
| 2006/0063171 A1 | 3/2006 | Akeson et al. |
| 2008/0293045 A1 | 11/2008 | Piepenburg et al. |
| 2008/0311582 A1 | 12/2008 | Bayley et al. |
| 2009/0256116 A1 | 10/2009 | Shumaker-Parry et al. |
| 2009/0269744 A1 | 10/2009 | Krause et al. |
| 2010/0035260 A1 | 2/2010 | Olasagasti et al. |
| 2010/0092960 A1 | 4/2010 | Fehr |
| 2010/0120098 A1 | 5/2010 | Grunenwald et al. |

(Continued)

FOREIGN PATENT DOCUMENTS

| | | |
|---|---|---|
| CA | 2927728 A1 | 4/2015 |
| CA | 2937411 A1 | 7/2015 |

(Continued)

OTHER PUBLICATIONS

Extended European Search Report for Application No. EP 20171363.3, mailed Sep. 28, 2020.

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The invention relates to modified helicases with reduced unbinding from polynucleotides. The helicases can be used to control the movement of polynucleotides and are particularly useful for sequencing polynucleotides.

13 Claims, 23 Drawing Sheets

Specification includes a Sequence Listing.

(56) References Cited

U.S. PATENT DOCUMENTS

| | | |
|---|---|---|
| 2010/0221212 A1 | 9/2010 | Stagliano et al. |
| 2010/0331194 A1 | 12/2010 | Turner et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0107802 A1 | 5/2012 | Stoddart et al. |
| 2013/0048499 A1 | 2/2013 | Mayer et al. |
| 2013/0118902 A1 | 5/2013 | Akeson et al. |
| 2013/0149769 A1 | 6/2013 | Kizaki et al. |
| 2013/0225421 A1 | 8/2013 | Li et al. |
| 2013/0327644 A1 | 12/2013 | Turner et al. |
| 2014/0051069 A1 | 2/2014 | Jayasinghe et al. |
| 2014/0186823 A1 | 7/2014 | Clarke et al. |
| 2014/0255921 A1 | 9/2014 | Moysey et al. |
| 2014/0262784 A1 | 9/2014 | Clarke et al. |
| 2014/0335512 A1 | 11/2014 | Moysey et al. |
| 2015/0008126 A1 | 1/2015 | Maglia et al. |
| 2015/0031020 A1 | 1/2015 | Jayasinghe et al. |
| 2015/0065354 A1 | 3/2015 | Moysey et al. |
| 2015/0152492 A1 | 6/2015 | Brown et al. |
| 2015/0191709 A1 | 7/2015 | Heron et al. |
| 2015/0197796 A1 | 7/2015 | White et al. |
| 2015/0218629 A1 | 8/2015 | Heron et al. |
| 2016/0257942 A1 | 9/2016 | Bruce et al. |
| 2017/0002406 A1 | 1/2017 | Bowen et al. |
| 2018/0030530 A1 | 2/2018 | Moysey et al. |
| 2018/0037874 A9 | 2/2018 | Bruce et al. |
| 2018/0179500 A1 | 6/2018 | Heron et al. |
| 2018/0230526 A1 | 8/2018 | Heron et al. |
| 2019/0203288 A1 | 7/2019 | Gutierrez et al. |
| 2019/0345550 A1 | 11/2019 | Bowen et al. |
| 2021/0009971 A1 | 1/2021 | Bruce et al. |
| 2021/0123032 A1 | 4/2021 | Heron et al. |
| 2021/0139972 A1 | 5/2021 | Jayasinghe et al. |
| 2021/0172011 A1 | 6/2021 | Moysey et al. |
| 2022/0135956 A1 | 5/2022 | Heron et al. |
| 2022/0372568 A1 | 11/2022 | Moysey et al. |
| 2023/0212535 A1 | 7/2023 | Bruce et al. |
| 2024/0060126 A1 | 2/2024 | Jayasinghe et al. |

FOREIGN PATENT DOCUMENTS

| | | |
|---|---|---|
| CN | 104039979 A | 9/2014 |
| JP | 2006-500028 A | 1/2006 |
| WO | WO 2000/028312 A1 | 5/2000 |
| WO | WO 2002/092821 A1 | 11/2002 |
| WO | WO 2004/027025 A2 | 4/2004 |
| WO | WO 2005/124888 A1 | 12/2005 |
| WO | WO 2006/028508 A2 | 3/2006 |
| WO | WO 2006/100484 A2 | 9/2006 |
| WO | WO 2007/057668 A1 | 5/2007 |
| WO | WO 2008/102120 A1 | 8/2008 |
| WO | WO 2008/102121 A1 | 8/2008 |
| WO | WO 2008/124107 A1 | 10/2008 |
| WO | WO 2009/035647 A1 | 3/2009 |
| WO | WO 2009/044170 A1 | 4/2009 |
| WO | WO 2009/077734 A2 | 6/2009 |
| WO | WO 2010/004265 A1 | 1/2010 |
| WO | WO 2010/004273 A1 | 1/2010 |
| WO | WO 2010/034018 A2 | 3/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/109197 A2 | 9/2010 |
| WO | WO 2010/117470 A2 | 10/2010 |
| WO | WO 2010/122293 A1 | 10/2010 |
| WO | WO 2011/067559 A1 | 6/2011 |
| WO | WO 2012/033524 A2 | 3/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/153359 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | O 2014/064444 A1 | 5/2014 |
| WO | WO 2014/064443 A2 | 5/2014 |
| WO | WO 2014/135838 A1 | 9/2014 |
| WO | WO 2014/158665 A1 | 10/2014 |
| WO | WO 2015/022544 A1 | 2/2015 |
| WO | WO 2015/055981 A2 | 4/2015 |
| WO | WO 2015/110777 A1 | 7/2015 |
| WO | WO 2015/110813 A1 | 7/2015 |
| WO | WO 2015/124935 A1 | 8/2015 |
| WO | WO 2015/150786 A1 | 10/2015 |
| WO | WO 2016/034591 A2 | 3/2016 |
| WO | WO 2016/055777 A2 | 4/2016 |
| WO | WO 2016/059363 A1 | 4/2016 |
| WO | WO 2018/060740 A1 | 4/2018 |
| WO | WO 2018/100370 A1 | 6/2018 |

OTHER PUBLICATIONS

International Search Report and Written Opinion for Application No. PCT/GB2013/051925, mailed Oct. 18, 2013.

International Preliminary Report on Patentability for Application No. PCT/GB2013/051925, mailed Jan. 20, 2015.

[No Author Listed] Antibodies bind specific molecules through their hypervariable loops. 33.3 Antibody Binding. 6th edition. 2007;953-954.

[No Author Listed] Data sheet SEQ ID No. 10 search results from STIC, printed on Oct. 29, 2018, pp. 1-38 (Year: 2018).

[No Author Listed] Data sheet SEQ ID No. 2 search results from STIC, printed on Oct. 29, 18, pp. 1-24 (Year: 2018).

[No Author Listed] Enterobacteria phage T4 helicase Dda E94C/A360C mutant, SEQ ID 8., XP055978108, Oct. 23, 2014, Retrieved from EBI accession No. GSP: BBM82447, Database accession No. BBM82447, Geneseq [online].

[No Author Listed] Escherichia phage PBECO4 DNA helicase, XP055978026, Jan. 25, 2013, retrieved from EBI accession No. UPI0002AB07E2, Database accession No. AGC35141.

[No Author Listed] Press release: Oxford Nanopore introduces DNA 'strand sequencing' on the high-throughput GridION platform and presents MinION, a sequencer the size of a USB; memory stick, Feb. 2012.

[No Author Listed] UniProt Database accession No. 17J3V8 sequence. Oct. 3, 2012.

[No Author Listed] UniProt Database accession No. k7nri8 sequence. Feb. 6, 2013.

Ali et al., Kinetic measurement of the step size of DNA unwinding by *Escherichia coli* UvrD helicase. Science. Jan. 17, 1997;275(5298):377-80. doi: 10.1126/science.275.5298.377. Erratum in: Science Apr. 4, 1997;276(5309):21.

Allen et al., The genome sequence of the psychrophilic archaeon, Methanococcoides burtonii: the role of genome evolution in cold adaptation. ISME J. Sep. 2009;3(9):1012-35. doi: 10.1038/ismej. 2009.45.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Arslan et al., Protein structure. Engineering of a superhelicase through conformational control. Science. Apr. 17, 2015;348(6232):344-7. doi: 10.1126/science.aaa0445.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Balakrishnan et al., Dna2 exhibits a unique strand end-dependent helicase function. J Biol Chem Dec. 10, 2010;285(50):38861-8. doi: 10.1074/jbc.M110.165191. Epub Oct. 6, 2010.

(56) References Cited

OTHER PUBLICATIONS

Balci et al., Single-molecule nanopositioning: structural transitions of a helicase-DNA complex during ATP hydrolysis. Biophys J. Aug. 17, 2011;101(4):976-84. doi: 10.1016/j.bpj.2011.07.010.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Bennett et al., Association of yeast DNA topoisomerase III and Sgs1 DNA helicase: studies of fusion proteins. Proc Natl Acad Sci U S A. Sep. 25, 2001;98(20):11108-13. Epub Sep. 11, 2001.
Berger, SnapShot: nucleic acid helicases and translocases. Cell. Sep. 5, 2008;134(5):888- 888.e1. doi: 10.1016/j.cell.2008.08.027.
Bessler et al., The amino terminus of the *Saccharomyces cerevisiae* DNA helicase Rrm3p modulates protein function ltering replication and checkpoint activity. Genetics. Nov. 2004;168(3):1205-18.
Blast ® NCBI. Sequence ID No. 10; ZSYBNHWV114. Sep. 18, 2015.
Blast ® NCBI. Sequence ID No. 52; ZT1133A811N. Sep. 18, 2015.
Braha et al., Designed protein pores as components for biosensors. Chem Biol. Jul. 1997;4(7):497-505.
Breyer et al., A structural basis for processivity. Protein Sci. Sep. 2001;10(9):1699-711. doi: 10.1110/ps.10301.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Buttner et al., Structural basis for DNA duplex separation by a superfamily-2 helicase. Nat Struct Mol Biol. Jul. 2007;14(7):647-52.
Byrd et al., A parallel quadruplex DNA is bound tightly but unfolded slowly by pif1 helicase. J Biol Chem. Mar. 6, 2015;290(10):6482-94. doi:10.1074/jbc.M114.630749. Epub Jan. 14, 2015.
Byrd et al., Dda helicase tightly couples translocation on single-stranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.
Byrd et al., Superfamily 2 helicases. Front Biosci (Landmark Ed). Jun. 1, 2012;17:2070-88.
Chandler et al., A new microparticle size calibration standard for use in measuring smaller microparticles using a new flow cytometer. J Thromb Haemost. Jun. 2011;9(6):1216-24. doi: 10.1111/j.1538-7836.2011.04283.x.
Cheng et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Colas et al., Microscopical investigations of nisin-loaded nanoliposomes prepared by Mozafari method and their bacterial targeting. Micron. 2007;38(8):841-7.
Comer et al., Microscopic mechanics of hairpin DNA translocation through synthetic nanopores. Biophys J. Jan. 2009;96(2):593-608. doi: 10.1016/j.bpj.2008.09.023.
Deamer, Nanopore analysis of nucleic acids bound to exonucleases and polymerases. Annu Rev Biophys. 2010;39:79-90. doi: 10.1146/annurev.biophys.093008.131250.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95.
Dong et al., Wza the translocon for E. coli capsular polysaccharides defines a new class of membrane protein. Nature. Nov. 9, 2006;444(7116):226-9. doi: 10.1038/nature05267. Epub Nov. 1, 2006. Author Manuscript, 14 pages.
Dostál et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.

Dou et al., The DNA binding properties of the *Escherichia coli* RecQ helicase. J Biol Chem. Feb. 20, 2004;279(8):6354-63. Epub Dec. 9, 2003.
Durrieu et al., Interactions between neuronal fusion proteins explored by molecular dynamics. Biophys J. May 1, 2008;94(9):3436-46. doi: 10.1529/biophysj. 107.123117. Epub Jan. 22, 2008.
Eliseev et al., Molecular Recognition of Nucleotides, Nucleosides, and Sugars by Aminocyclodextrins. J. Am. Chem. Soc., vol. 116:6081-6088 (1994).
Eoff et al., The Kinetic Mechanism for DNA Unwinding by Multiple Molecules of Dda Helicase Aligned on DNA. Biochemistry. Jun. 1, 2010; 49(21): 4543-4553. doi: 10.1021/bi100061v. Author Manuscript.
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Farah et al., The RecBCD enzyme initiation complex for DNA unwinding:enzyme positioning and DNA opening. J Mol Biol. Oct. 10, 1997;272(5):699-715.
Garalde et al., Highly parallel direct RNA sequencing on an array of nanopores. bioRxiv. 2016. doi: http://dx.doi.org/10.1101/068809.
Garcillán-Barcia et al., The diversity of conjugative relaxases and its application in plasmid classification. FEMS Microbiol Rev. May 2009;33(3):657-87.
Genbank accession No. AEA72977 sequence. Apr. 6, 2011.
Genbank Submission. NCBI; Accession No. AM778123. Richards et al.; Sep. 18, 2008.
GenPept Accession No. XP 003728286. Jun. 7, 2012.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Graham et al., Sequence-specific assembly of FtsK hexamers establishes directional translocation on DNA. Proc Natl Acad Sci U S A. Nov. 23, 2010;107(47):20263-8. doi: 10.1073/pnas.1007518107. Epub Nov. 3, 2010.
Grant et al., A facile method for attaching nitroxide spin labels at the 5' terminus of nucleic acids. Nucleic Acids Res. 2007;35(10):e77. Epub May 21, 2007.
Green et al., Quantitative evaluation of the lengths of homobifunctional protein cross-linking reagents used as molecular rulers. Protein Sci. Jul. 2001;10(7):1293-304.
Guo et al., Protein tolerance to random amino acid change. Proc Natl Acad Sci U S A. Jun. 22, 2004;101(25):9205-10. doi: 10.1073/pnas.0403255101. Epub Jun. 14, 2004.
Guo et al., The linker region between the helicase and primase domains of the bacteriophage T7 gene 4 protein is critical for hexamer formation. J Biol Chem. Oct. 15, 1999;274(42):30303-9.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al, The T4 phage SF1B helicase Dda is structurally optimized to perform DNA strand separation. Structure. Jul. 3, 2012;20(7):1189-200. doi:10.1016/j.str.2012.04.013. Epub May 31, 2012.
Heron et al., Simultaneous measurement of ionic current and fluorescence from single protein pores. J Am Chem Soc. Feb. 11, 2009;131(5):1652-3. doi: 10.1021/ja808128s.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hopfner et al., Mechanisms of nucleic acid translocases: lessons from structural biology and single-molecule biophysics. Curr Opin Struct Biol. Feb. 2007;17(1):87-95. Epub Dec. 6, 2006.
Hornblower et al., Single-molecule analysis of DNA-protein complexes using nanopores. Nat Methods. Apr. 2007;4(4):315-7. Epub Mar. 4, 2007.
Howorka et al., Nanopore analytics: sensing of single molecules. Chem Soc Rev. Aug. 2009;38(8):2360-84. doi: 10.1039/b813796j. Epub Jun. 15, 2009.

(56) References Cited

OTHER PUBLICATIONS

Ivanov et al., DNA tunneling detector embedded in a nanopore. Nano Lett. Jan. 12, 2011;11(1):279-85. doi: 10.1021/nl103873a. Epub Dec. 6, 2010.

James, Aptamers. Encyclopedia of Analytical Chemistry. R.A. Meyers (Ed.). 4848-4871. John Wiley & Sons Ltd, Chichester, 2000.

Jankowsky, RNA helicases at work: binding and rearranging. Trends Biochem Sci. Jan. 2011;36(1):19-29. doi: 10.1016/j.tibs.2010.07.008.

Japrung et al., Urea facilitates the translocation of single-stranded DNA and RNA through the alpha-hemolysin nanopore. Biophys J. May 19, 2010;98(9):1856-63. doi: 10.1016/j.bpj.2009.12.4333.

Jezewska et al., Interactions of *Escherichia coli* replicative helicase PriA protein with single-stranded DNA. Biochemistry. Aug. 29, 2000;39(34):10454-67.

Jia et al., Rotations of the 2B Sub-domain of *E. coli* UvrD Helicase/Translocase Coupled to Nucleotide and DNA Binding. J Mol Biol. Aug. 19, 2011; 411(3): 633-648. EPub Jun. 17, 2011. doi: 10.1016/j.jmb.2011.06.019.

Jones et al., Protein secondary structure prediction based on position-specific scoring matrices. J Mol Biol. Sep. 17, 1999;292(2):195-202. doi: 10.1006/jmbi.1999.3091.

Kabsch et al., Dictionary of protein secondary structure: pattern recognition of hydrogen-bonded and geometrical features. Biopolymers. Dec. 1983;22(12):2577-637. doi: 10.1002/bip.360221211.

Kafri et al., Dynamics of molecular motors and polymer translocation with sequence heterogeneity. Biophys J. Jun. 2004;86(6):3373-91.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316. Epub Oct. 31, 2013.

Kankia et al., Folding of the thrombin aptamer into a G-quadruplex with Sr(2+): stability, heat, and hydration. J Am Chem Soc. Nov. 7, 2001;123(44):10799-804.

Kar et al., Defining the structure-function relationships of bluetongue virus helicase protein VP6. J Virol. Nov. 2003;77(21):11347-56.

Keyser, Controlling molecular transport through nanopores. J R Soc Interface. Oct. 7, 2011;8(63):1369-78. doi: 10.1098/rsif.2011.0222. Epub Jun. 29, 2011.

Khafizov, Single Molecule Force Spectroscopy Of Single Stranded Dna Binding Protein And Rep Helicase. University of Illinois at Urbana-Champaign Dissertation. 2012.

Korolev et al., Major domain swiveling revealed by the crystal structures of complexes of *E. coli* Rep helicase bound to single-stranded DNA and ADP. Cell. Aug. 22, 1997;90(4):635-47.

Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.

Kuper et al., Functional and structural studies of the nucleotide excision repair helicase XPD suggest a polarity for DNA translocation. EMBO J. Jan. 18, 2012;31(2):494-502. doi: 10.1038/emboj.2011.374.

Kutyavin et al., Oligonucleotides containing 2-aminoadenine and 2-thiothymine act as selectively binding complementary agents. Biochemistry. Aug. 27, 1996;35(34):11170-6.

Langecker et al., Synthetic lipid membrane channels formed by designed DNA nanostructures. Science. Nov. 16, 2012;338(6109):932-6. doi: 10.1126/science. 1225624.

Lee et al., Cooperative translocation enhances the unwinding of duplex DNA by SARS coronavirus helicase nsP13. Nucleic Acids Res. Nov. 2010;38(21):7626-36. doi: 10.1093/nar/gkq647. Epub Jul. 29, 2010.

Lee et al., Direct imaging of single UvrD helicase dynamics on long single-stranded DNA. Nat Commun. 2013;4:1878. doi:10.1038/ncomms2882.

Levin et al., Helicase from hepatitis C virus, energetics of DNA binding. J Biol Chem. Aug. 16, 2002;277(33): 29377-85. Epub May 28, 2002.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.

Liu et al., Adding new chemistries to the genetic code. Annu Rev Biochem. 2010;79:413-44. doi: 10.1146/annurev.biochem.052308.105824.

Liu et al., Structure of the DNA repair helicase XPD. Cell. May 30, 2008;133(5):801-12. doi: 10.1016/j.cell.2008.04.029.

Lohman et al., Mechanisms of helicase-catalyzed DNA unwinding. Annu Rev Biochem. 1996;65:169-214.

Lohman et al., Non-hexameric DNA helicases and translocases:mechanisms and regulation. Nat Rev Mol Cell Biol. May 2008;9(5):391-401. doi:10.1038/nrm2394.

Ma et al., Bright functional rotaxanes. Chem Soc Rev. Jan. 2010;39(1):70-80. doi: 10.1039/b901710k. Epub Jul. 21, 2009.

Maddox et al., Elevated serum levels in human pregnancy of a molecule immunochemically similar to eosinophil granule major basic protein. J Exp Med. Oct. 1, 1983;158(4):1211-26.

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Marathias et al., Structures of the potassium-saturated, 2:1, and intermediate, 1:1, forms of a quadruplex DNA. Nucleic Acids Res. May 1, 2000;28(9):1969-77.

Marini et al., A human DNA helicase homologous to the DNA cross-link sensitivity protein Mus308. J Biol Chem. Mar. 8, 2002;277(10):8716-23. Epub Dec. 18, 2001.

Marsault et al., Macrocycles are great cycles: applications, opportunities, and challenges of synthetic macrocycles in drug discovery. J Med Chem. Apr. 14, 2011;54(7):1961-2004. doi: 10.1021/jm1012374. Epub Mar. 7, 2011.

Marušič et al., Solution-state structure of an intramolecular G-quadruplex with propeller, diagonal and edgewise loops. Nucleic Acids Res. Aug. 2012;40(14):6946-56. doi: 10.1093/nar/gks329. Epub Apr. 24, 2012.

Mechanic et al., *Escherichia coli* DNA helicase II is active as a monomer. J Biol Chem. Apr. 30, 1999;274(18): 12488-98.

Miles et al., Properties of Bacillus cereus hemolysin II: a heptameric transmembrane pore. Protein Sci. Jul. 2002;11(7):1813-24.

Montal et al., Formation of bimolecular membranes from lipid monolayers and a study of their electrical properties. Proc Natl Acad Sci U S A. Dec. 1972;69(12):3561-6.

Morris et al., Evidence for a functional monomeric form of the bacteriophage T4 DdA helicase. Dda does not form stable oligomeric structures. J Biol Chem. Jun. 8, 2001;276(23):19691-8. Epub Feb. 27, 2001.

Ngo et al., Computational complexity, protein structure prediction, and the levinthal paradox. 14. The protein folding problem teritary structure prediction. Ed(s):Merz et al. Birkhauser, Boston, Ma. 1994. 433, 492-5.

Nikolov et al., Behavior of giant vesicles with anchored DNA molecules. Biophys J. Jun. 15, 2007;92(12):4356-68. Epub Mar. 23, 2007.

Nishikiori et al., Crystal structure of the superfamily 1 helicase from Tomato mosaic virus. J Virol. Jul. 2012;86(14):7565-76. doi: 10.1128/JVI.00118-12. Epub May 9, 2012.

O'Shea et al., X-ray structure of the GCN4 leucine zipper, a two-stranded, parallel coiled coil. Science. Oct. 25, 1991;254(5031):539-44.

Pfeiffer et al., Bivalent cholesterol-based coupling of oligonucletides to lipid membrane assemblies. J Am Chem Soc. Aug. 25, 2004;126(33):10224-5.

Pinero-Fernandez et al., Indole transport across *Escherichia coli* membranes. J Bacteriol. Apr. 2011;193(8):1793-8. doi:10.1128/JB.01477-10. Epub Feb. 4, 2011.

Portakal et al., Construction of recB-recD genetic fusion and functional analysis of RecBDC fusion enzyme in *Escherichia coli*. BMC Biochem. Oct. 10, 2008;9:27. doi: 10.1186/1471-2091-9-27.

Raney et al., Structure and Mechanisms of SF1 DNA Helicases. Adv Exp Med Biol. 2013;767:17-46. doi: 10.1007/978-1-4614-5037-5_2.

(56) References Cited

OTHER PUBLICATIONS

Remaut et al., Protein-protein interaction through beta-strand addition. Trends Biochem Sci. Aug. 2006;31(8):436-44. Epub Jul. 7, 2006.

Richards et al., Structure of the DNA repair helicase hel308 reveals DNA binding and autoinhibitory domains. J Biol Chem. Feb. 22, 2008;283(8):5118-26. Epub Dec. 4, 2007.

Rudolf et al., The DNA repair helicases XPD and FancJ have essential iron-sulfur domains. Mol Cell. Sep. 15, 2006;23(6):801-8.

Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.

Saariaho et al., Characteristics of MuA transposase-catalyzed processing of model transposon end DNA hairpin substrates. Nucleic Acids Res. Jun. 6, 2006;34(10):3139-49. Print 2006.

Satapathy et al., ATPase activity of RecD is essential for growth of the Antarctic Pseudomonas syringae Lz4W at low temperature. FEBS J. Apr. 2008;275(8):1835-51. doi: 10.1111/j.1742-4658.2008.06342.x. Epub Mar. 9, 2008.

Sathiyamoorthy et al., The crystal structure of *Escherichia coli* group 4 capsule protein GfcC reveals a domain organization resembling that of Wza. Biochemistry. Jun. 21, 2011;50(24):5465-76. doi: 10.1021/bi101869h.

Schneider et al., DNA sequencing with nanopores. Nat Biotechnol. Apr. 10, 2012;30(4):326- 8. doi: 10.1038/nbt.2181.

Sequence ID No. 2 Search Results. US-14-351-038-2. Sep. 16, 2015. 69 pages.

Singleton et al., Structure and mechanism of helicases and nucleic acid translocases. Annu Rev Biochem. 2007;76:23-50.

Soni et al., Synchronous optical and electrical detection of biomolecules traversing through solid-state nanopores. Rev Sci Instrum. Jan. 2010;81(1):014301. doi: 10.1063/1.3277116.

Stelter et al., Structural and mechanistic insight into DNA unwinding by Deinococcus radiodurans UvrD. PLOS One. Oct. 15, 2013;8(10):e77364. doi: 10.1371/journal.pone.0077364.

Stoddart et al., Single-nucleotide discrimination in immobilized DNA oligonucleotides with a biological nanopore. Proc Natl Acad Sci U S A. May 12, 2009;106(19):7702-7 and Supplementary Info. doi: 10.1073/pnas.0901054106. Epub Apr. 20, 2009.

Theissen et al., Cooperative binding of ATP and RNA induces a closed conformation in a DEAD box RNA helicase. Proc Natl Acad Sci U S A. Jan. 15, 2008;105(2):548-53. doi: 10.1073/pnas.0705488105. Epub Jan. 9, 2008.

Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.

Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.

UniProt Database accession No. a4sle1 sequence. May 15, 2007.

UniProt Database accession No. b4kac8 sequence. Sep. 23, 2008.

UniProt Database accession No. D0KN27. Dec. 15, 2009.

UniProt Database accession No. D7RM26 sequence. Aug. 10, 2010.

UniProt Database accession No. elqus6 sequence. Nov. 30, 2010.

UniProt Database accession No. i3d0e7 sequence. Jul. 11, 2012.

UniProt Database accession No. I6ZR75 sequence. Oct. 3, 2012.

UniProt Database accession No. k0im99 sequence. Nov. 28, 2012.

UniProt Database accession No. Q12WZ6 sequence. Apr. 12, 2017.

UniProt Database accession No. Q7Y5C3 sequence. Oct. 1, 2003.

Utama et al., Role of the DExH motif of the Japanese encephalitis virus and hepatitis C virus NS3 proteins in the ATPase and RNA helicase activities. Virology. Aug. 1, 2000;273(2):316-24. doi: 10.1006/viro.2000.0417.

Van Heel et al., Single-particle electron cryo-microscopy:towards atomic resolution. Q Rev Biophys. Nov. 2000;33(4):307-69.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.

Venkatesan et al., Nanopore sensors for nucleic acid analysis. Nat Nanotechnol. Sep. 18, 2011;6(10):615-24. doi: 10.1038/nnano.2011.129.

Vinson, Proteins in motion. Introduction. Science. Apr. 10, 2009;324(5924):197. doi: 10.1126/science.324.5924.197.

Von Ossowski et al., Engineering the exo-loop of Trichoderma reesei cellobiohydrolase, Cel7A. A comparison with Phanerochaete chrysosporium Cel7D. J Mol Biol. Oct. 31, 2003;333(4):817-29. doi: 10.1016/s0022-2836(03)00881-7.

Wang et al., DNA helicase activity of the RecD protein from Deinococcus radiodurans. J Biol Chem. Dec. 10, 2004;279(50):52024-32.

White, Structure, function and evolution of the XPD family of iron-sulfur-containing 5'→3' DNA helicases. Biochem Soc Trans. 2009;37:547-551.

Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.

Woodman et al., Molecular biology of Hel308 helicase in archaea. Biochem Soc Trans. Feb. 2009;37(Pt 1):74-8. doi: 10.1042/BST0370074.

Woodman et al., Winged helix domains with unknown function in Hel308 and related helicases. Biochem Soc Trans. Jan. 2011;39(1):140-4. doi:10.1042/BST0390140.

Yoshina-Ishii et al., Arrays of mobile tethered vesicles on supported lipid bilayers. J Am Chem Soc. Apr. 2, 2003;125(13):3696-7.

Yusko et al., Controlling the translocation of proteins through nanopores with bioinspired fluid walls. Nat Nanotechnol. Nat Nanotechnol. Apr. 2011; 6(4): 253-260. EPub Feb. 20, 2011. doi: 10.1038/nnano.2011.12 Author manuscript; available in PMC Oct. 1, 2011.

Zhang et al., DNA Binding and Unwinding Functional Analyses of Recombinant *E. coli* Helicase II (UvrD). Chinese J. of Biochem. Mol. Biol. 2007;23(9):764-9.

Zhang et al., Structural evidence for consecutive Hel308-like modules in the spliceosomal ATPase Brr2. Nat Struct Mol Biol. Jul. 2009;16(7):731-9. doi: 10.1038/nsmb.1625.

Fig. 21
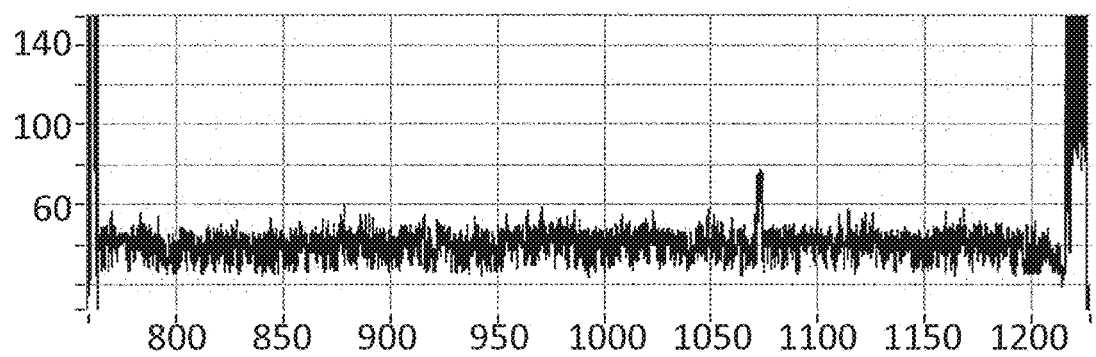
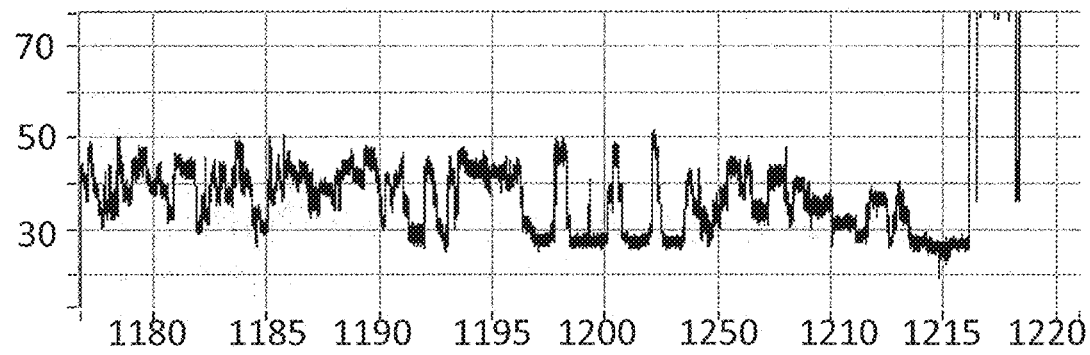

Fig. 22
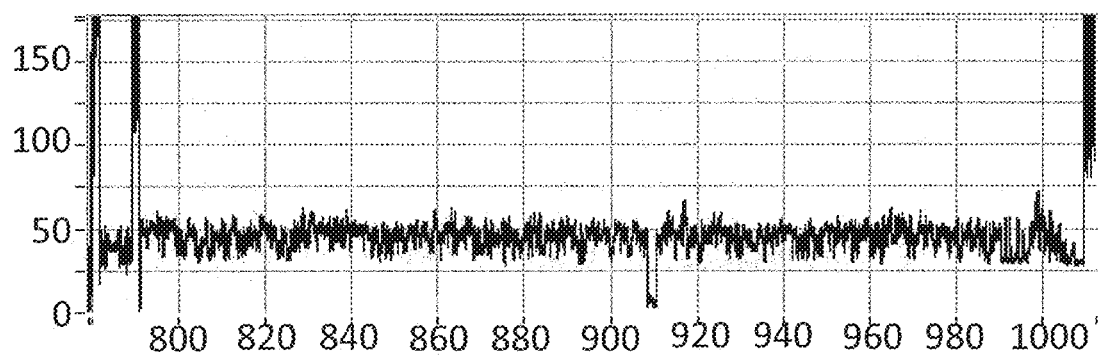
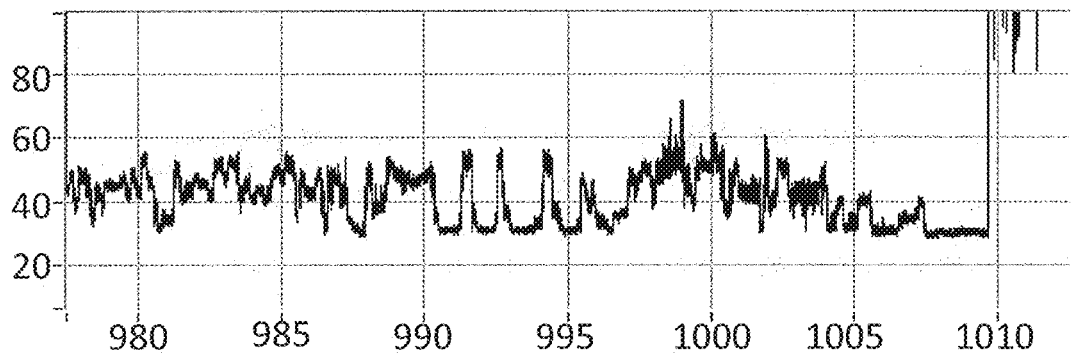

Fig. 23
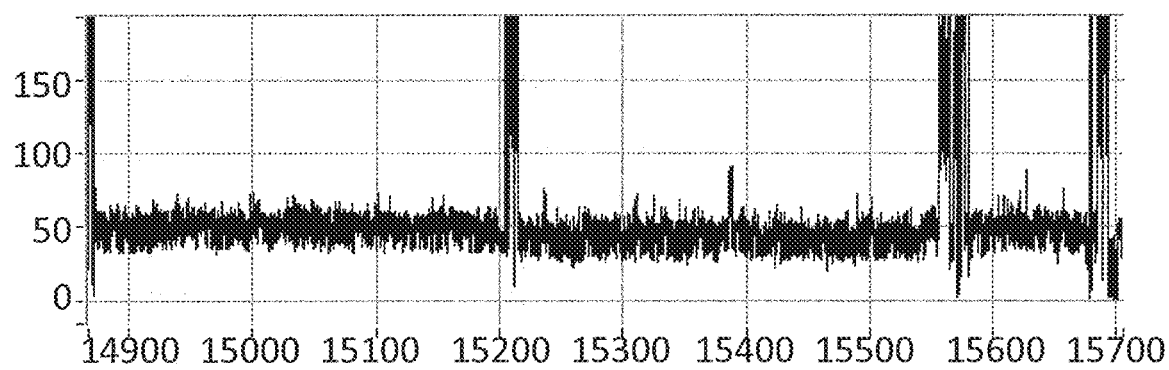
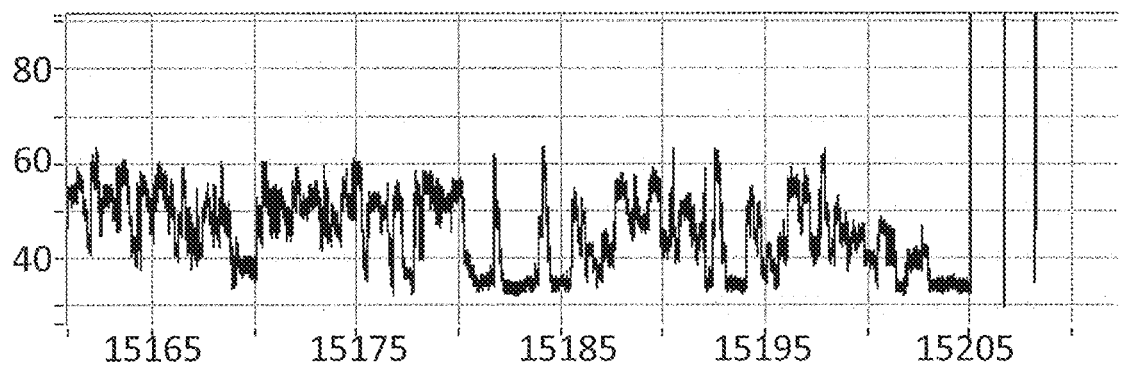

MODIFIED HELICASES

RELATED APPLICATIONS

This application is a continuation of U.S. application Ser. No. 17/064,329, filed Oct. 6, 2020, which is a continuation of U.S. application Ser. No. 14/415,453, filed Jan. 16, 2015, which is a national stage filing under 35 U.S.C. § 371 of International Patent Application No. PCT/GB2013/051925, filed Jul. 18, 2013, which claims the benefit of priority under 35 U.S.C. § 119(e) to U.S. Application No. 61/774,862, filed Mar. 8, 2013 and U.S. Application No. 61/673,452, filed Jul. 19, 2012, each of which is incorporated herein by reference in its entirety contents of these applications are incorporated herein by reference in their entirety.

REFERENCE TO AN ELECTRONIC SEQUENCE LISTING

The content of the electronic sequence listing (0036670025US04-SEQ-MSB.xml; Size: 239,543 bytes; and Date of Creation: Oct. 18, 2022) is herein incorporated by reference in its entirety.

FIELD OF THE INVENTION

The invention relates to modified helicases with reduced unbinding from polynucleotides. The helicases can be used to control the movement of polynucleotides and are particularly useful for sequencing polynucleotides.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing" method, a single polynucleotide strand is passed through the pore and the identity of the nucleotides are derived. Strand sequencing can involve the use of a nucleotide handling protein, such as a helicase, to control the movement of the polynucleotide through the pore.

SUMMARY OF THE INVENTION

Helicases are enzymes that are capable of binding to and controlling the movement of polynucleotides. Several helicases, including Hel308 helicases, have a polynucleotide binding domain which in at least one conformational state has an opening through which the polynucleotide can bind or unbind from the helicase. This allows the helicase to disengage from a polynucleotide, even if the helicase is not positioned at an end of the polynucleotide.

The inventors have surprisingly demonstrated that the ability of a helicase to control the movement of a polynucleotide can be improved by reducing the size of the opening through which the polynucleotide unbinds. In particular, the helicase's ability to control the movement of a polynucleotide can be improved by closing the opening. In accordance with the invention, the size of the opening is reduced or the opening is closed by connecting at least two parts of the helicase.

This result is surprising because a reduction in the size of the opening or a closing of the opening does not prevent the helicase from binding to a polynucleotide. Once a helicase modified in accordance with the invention has bound to a polynucleotide, it is capable of controlling the movement of most of, if not all of, the polynucleotide without unbinding or disengaging. In particular, the inventors have surprisingly demonstrated that helicases modified in accordance with the invention will strongly bind to a long polynucleotide, such as a polynucleotide comprising 400 nucleotides or more, and will control the movement of most of, if not all of, the polynucleotide. This allows the effective control of the movement of the polynucleotide, especially during Strand Sequencing.

The inventors have surprisingly demonstrated that the ability of a Hel308 helicase to control the movement of a polynucleotide can be improved by introducing one or more cysteine residues and/or one or more non-natural amino acids at specific positions. Irrespective of whether or not the introduced residues are connected, the modified Hel308 helicase is capable of controlling the movement of most of, if not all of, a polynucleotide without unbinding or disengaging.

Accordingly, the invention provides a helicase formed from one or more monomers and comprising a polynucleotide binding domain which comprises in at least one conformational state an opening through which a polynucleotide can unbind from the helicase, wherein the helicase is modified such that two or more parts on the same monomer of the helicase are connected to reduce the size of the opening and wherein the helicase retains its ability to control the movement of the polynucleotide.

The invention also provides:
- a Hel308 helicase in which one or more cysteine residues and/or one or more non-natural amino acids have been introduced at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10), wherein the helicase retains its ability to control the movement of a polynucleotide;
- a construct comprising a helicase of the invention and an additional polynucleotide binding moiety, wherein the helicase is attached to the polynucleotide binding moiety and the construct has the ability to control the movement of a polynucleotide;
- a method of controlling the movement of a polynucleotide, comprising contacting the polynucleotide with a helicase of the invention or a construct of the invention and thereby controlling the movement of the polynucleotide;
- method of characterising a target polynucleotide, comprising (a) contacting the target polynucleotide with a transmembrane pore and a helicase of the invention or a construct of the invention such that the helicase or the construct controls the movement of the target polynucleotide through the pore and (b) taking one or more measurements as the polynucleotide moves with respect to the pore wherein the measurements are indicative of one or more characteristics of the target polynucleotide and thereby characterising the target polynucleotide;

a method of forming a sensor for characterising a target polynucleotide, comprising forming a complex between (a) a pore and (b) a helicase of the invention or a construct of the invention and thereby forming a sensor for characterising the target polynucleotide;

a sensor for characterising a target polynucleotide, comprising a complex between (a) a pore and (b) a helicase of the invention or a construct of the invention;

use of a helicase of the invention or a construct of the invention to control the movement of a target polynucleotide through a pore;

a kit for characterising a target polynucleotide comprising (a) a pore and (b) a helicase of the invention or a construct of the invention;

an apparatus for characterising target polynucleotides in a sample, comprising (a) a plurality of pores and (b) a plurality of helicases of the invention or a plurality of constructs of the invention;

a method of producing a helicase of the invention, comprising (a) providing a helicase formed from one or more monomers and comprising a polynucleotide binding domain which comprises an opening through which a polynucleotide can unbind from the helicase and (b) modifying the helicase such that two or more parts on the same monomer of the helicase are connected to reduce the size of the opening and thereby producing a helicase of the invention;

a method of producing a modified Hel308 helicase of the invention, comprising (a) providing a Hel308 helicase and (b) introducing one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10) and thereby producing a modified Hel308 helicase of the invention; and a method of producing a construct of the invention, comprising attaching a helicase of the invention to an additional polynucleotide binding moiety and thereby producing a construct of the invention.

TraI-Cba-N691C/Q346C-bidmaleimidePEG11 (SEQ ID NO: 126 with the mutations N691C/Q346C connected by a bismaleimide PEG11 linker). It was clear from the gel that the reaction to attach the mal-PEG11-mal linker did not go to completion as a band for unmodified starting material (labelled C) TrwC Cba-N691C/Q346C (SEQ ID NO: 126 with the mutations N691C/Q346C) was observed.

Figure 15:
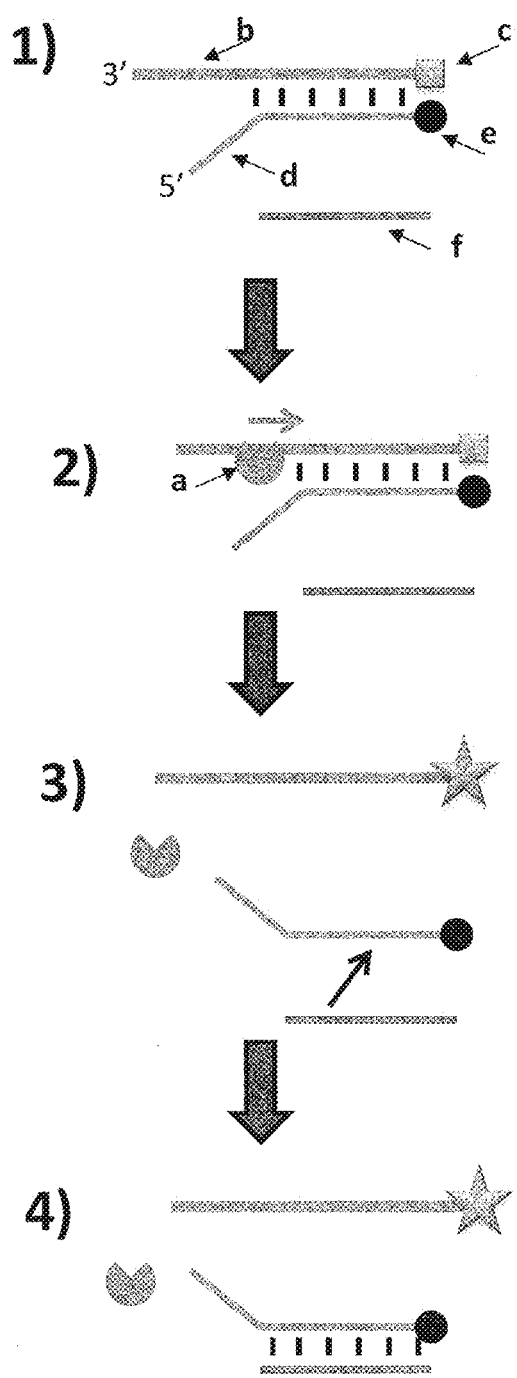

FIG. 15 shows a fluorescence assay for testing the rate of turnover of dsDNA molecules ($min^{-1}enzyme^{-1}$). A custom fluorescent substrate was used to assay the ability of the helicase (a) to displace hybridised dsDNA. 1) The fluorescent substrate strand (50 nM final, SEQ ID NO: 151 and 152) has both a 3' and 5' ssDNA overhang. The upper strand (b) has a carboxyfluorescein base (c) near the 5' end (the carboxyfluorescein is attached to a modified thymine at position 6 in SEQ ID NO: 151), and the hybridised complement (d) has a black-hole quencher (BHQ-1) base (e) near the 3' end (the black-hole quencher is attached to a modified thymine at position 81 in SEQ ID NO: 152). When hybridised, the fluorescence from the fluorescein is quenched by the local BHQ-1, and the substrate is essentially non-fluorescent. 1 µM of a capture strand (f, SEQ ID NO: 153) that is part-complementary to the lower strand of the fluorescent substrate is included in the assay. 2) In the presence of ATP (1 mM) and $MgCl_2$ (10 mM), helicase (10 nM) added to the substrate binds to the 3' tail of the fluorescent substrate, moves along the upper strand, and displaces the complementary strand (d) as shown. 3) Once the complementary strand with BHQ-1 is fully displaced the fluorescein on the major strand fluoresces. 4) Displaced lower strand (d) preferentially anneals to an excess of capture strand (f) to prevent re-annealing of initial substrate and loss of fluorescence.

Figure 16:
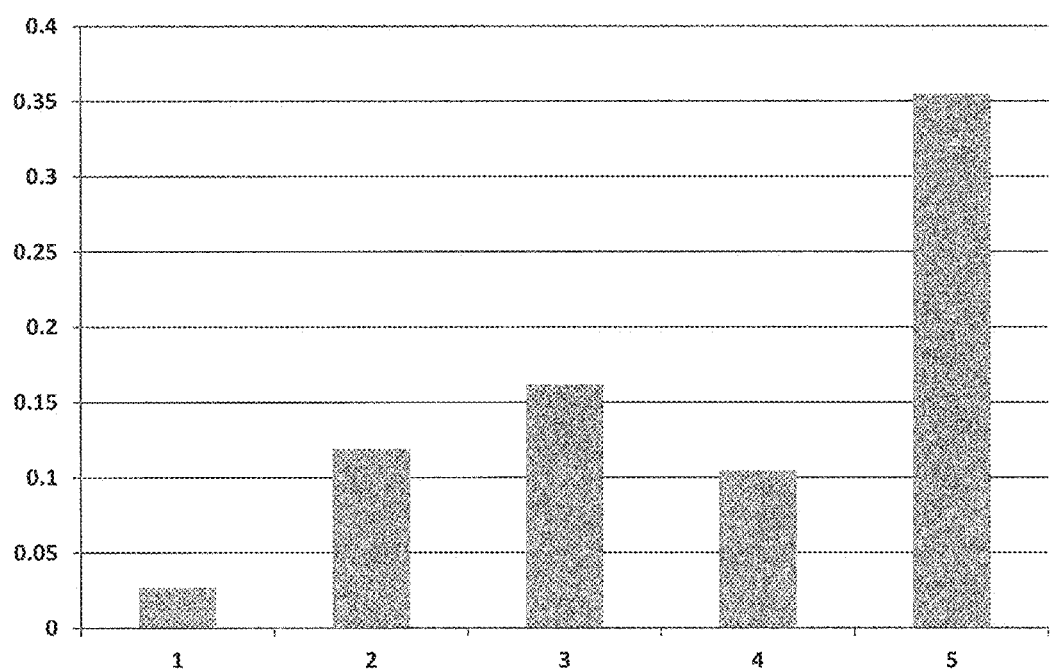

FIG. 16 shows dsDNA turnover ($enzyme^{-1}min^{-1}$) in buffer (400 mM KCl, 100 mM Hepes pH 8.0, 1 mM ATP, 10 mM $MgCl_2$, 50 nM fluorescent substrate DNA (SEQ ID NOs: 151 and 152), 1 µM capture DNA (SEQ ID NO: 153)) for a number of helicases (Hel308 Mbu (labelled 1, SEQ ID NO: 10), Hel308 Mbu-E284C (labelled 2, SEQ ID NO: 10 with the mutation E284C), Hel308 Mbu-E284C/C301A (labelled 3, SEQ ID NO: 10 with the mutations E284C/C301A), Hel308 Mbu-E285C (labelled 4, SEQ ID NO: 10 with the mutation E285C) and Hel308 Mbu-S288C (labelled 5, SEQ ID NO: 10 with the mutation S288C)). Hel308 Mbu-E284C (SEQ ID NO: 10 with the mutation E284C), Hel308 Mbu-E284C/C301A (SEQ ID NO: 10 with the mutations E284C/C301A), Hel308 Mbu-E285C (SEQ ID NO: 10 with the mutation E285C) and Hel308 Mbu-S288C (SEQ ID NO: 10 with the mutation S288C) showed increased rate of turnover of dsDNA molecules ($min^{-1}enzyme^{-1}$) when compared to Hel308 Mbu (SEQ ID NO: 10).

Figure 17:
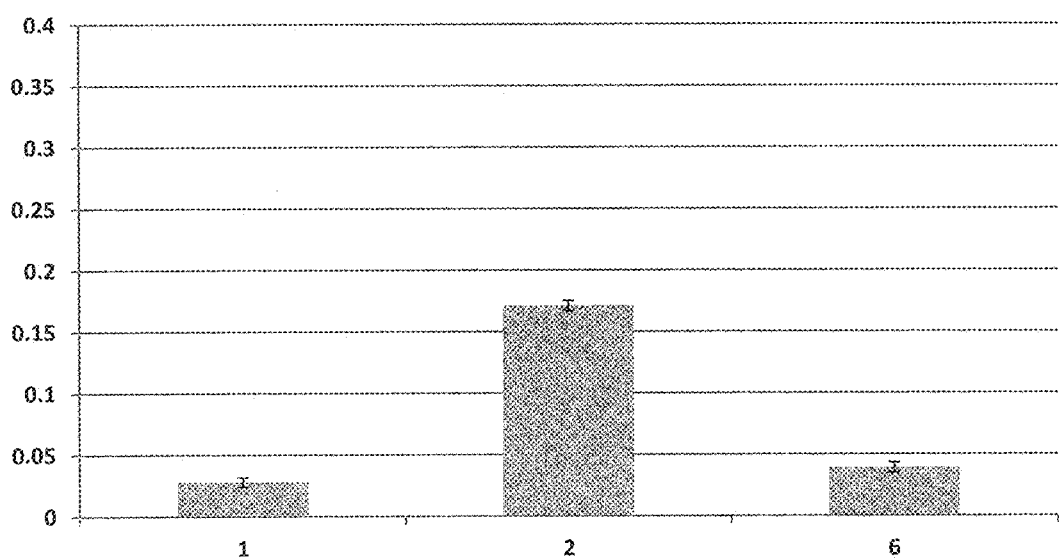

FIG. 17 shows dsDNA turnover ($enzyme^{-1}min^{-1}$) in buffer (400 mM KCl, 100 mM Hepes pH 8.0, 1 mM ATP, 10 mM $MgCl_2$, 50 nM fluorescent substrate DNA (SEQ ID NOs: 151 and 152), 1 µM capture DNA (SEQ ID NO: 153)) for a number of helicases (Hel308 Mbu (labelled 1, SEQ ID NO: 10), Hel308 Mbu-E284C (labelled 2, SEQ ID NO: 10 with the mutation E284C) and Hel308 Mbu-D274C (labelled 6, SEQ ID NO: 10 with the mutation D274C)). Hel308 Mbu-E284C (SEQ ID NO: 10 with the mutation E284C) and Hel308 Mbu-D274C (SEQ ID NO: 10 with the mutations D274C) showed increased rate of turnover of dsDNA molecules ($min^{-1}enzyme^{-1}$) when compared to Hel308 Mbu (SEQ ID NO: 10).

Figure 18:
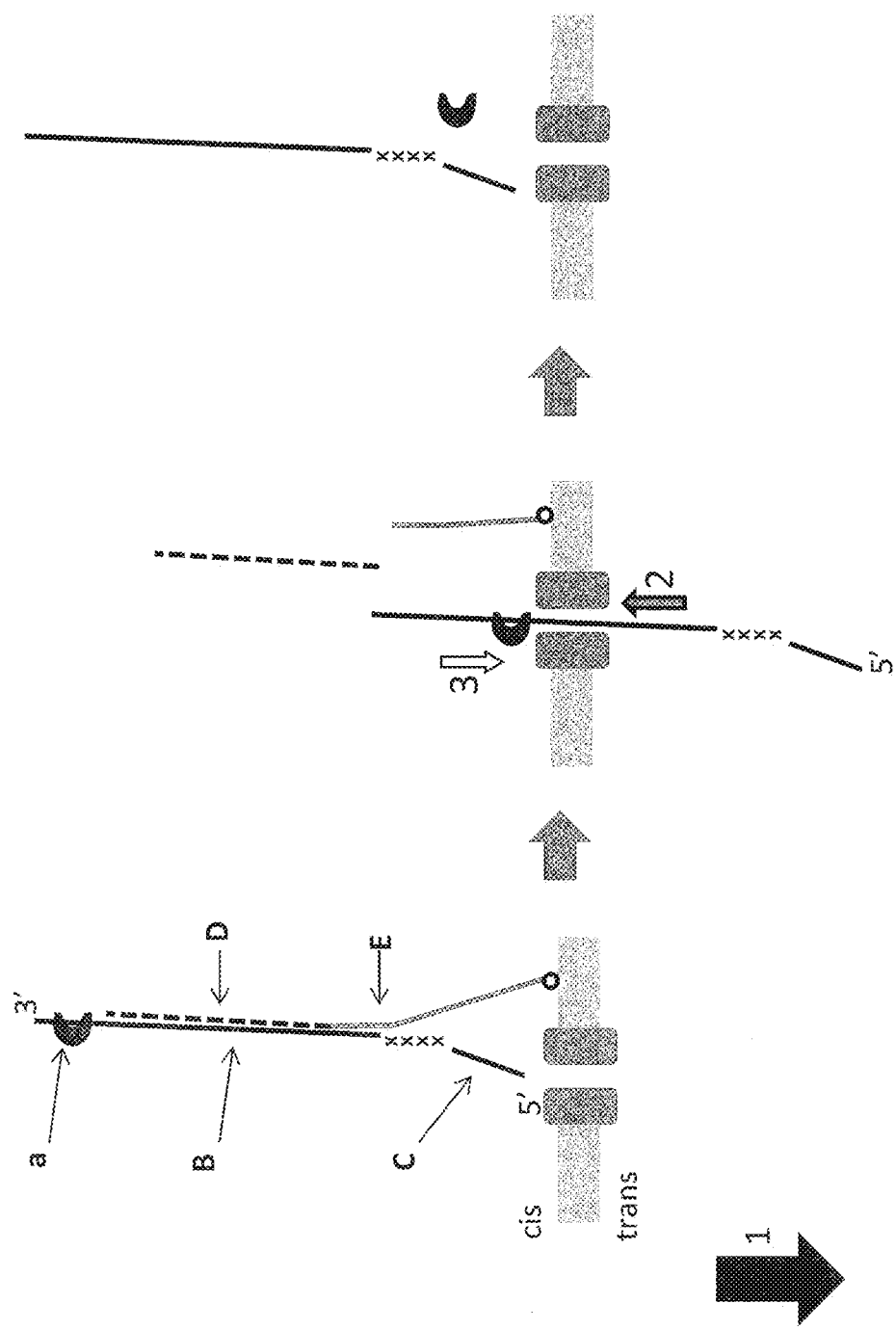

FIG. 18 shows a schematic of enzyme controlled translocation of a polynucleotide through a nanopore in a membrane, where the enzyme controls the movement of the polynucleotide against the force of the applied field. The schematic shows the example of a 3' to 5' enzyme (labelled A), where the capture of a polynucleotide (the polynucleotide sequences used in Example 9 are SEQ ID NO: 154 (labelled B in FIG. 18), SEQ ID NO: 155 (labelled C in FIG. 18) and SEQ ID NO: 156 (labelled D in FIG. 18) and SEQ ID NO: 117 (labelled E in FIG. 18)) in the pore by the 5' end leads to the enzyme controlling the movement of the polynucleotide against the force of the applied field (the direction of the applied field is indicated by arrow 1). During DNA capture the hybridised strands are unzipped. Arrow 2 denotes the direction of DNA movement through the nanopore and the arrow 3 denotes the direction of enzyme movement along the DNA. As long as the enzyme does not dissociate from the DNA the enzyme will pull the DNA out of the pore until it is finally ejected on the cis side of the membrane.

Figure 19:
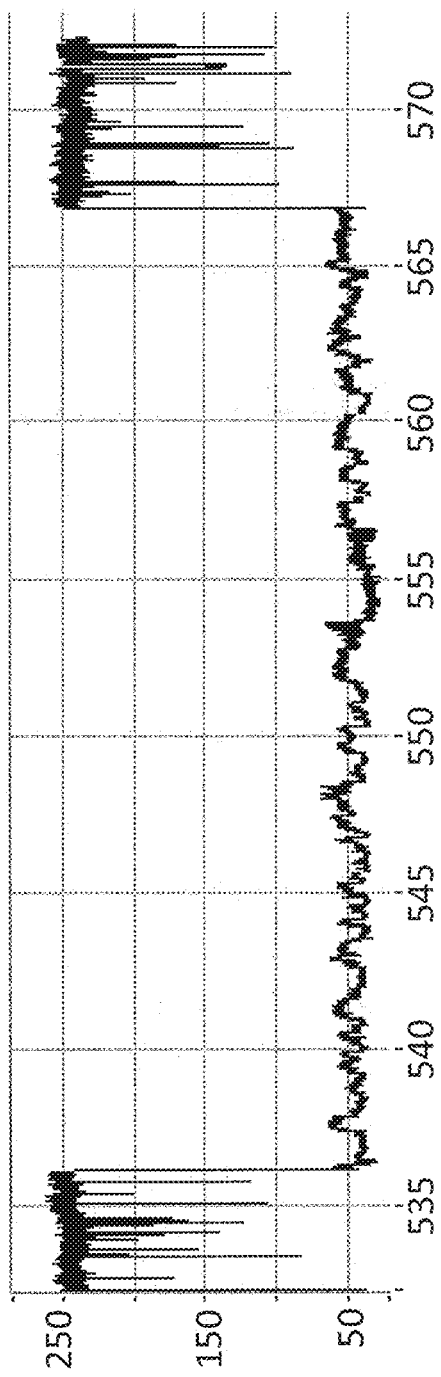

FIG. 19 shows an example current trace (y-axis=current (pA), x-axis=time (s)) observed when Hel308 Mbu (SEQ ID NO: 10) controls the translocation of DNA (+120 mV, (960 mM KCl, 25 mM potassium phosphate, 3 mM potassium ferrocyanide, 1 mM potassium ferricyanide pH 8.0, 10 mM $MgCl_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The electrical trace shows the open pore current (~250 pA) dropping to a DNA level (~50 pA) when DNA is captured under the force of the applied potential (+120 mV). DNA with enzyme attached results in a long block that shows stepwise changes in current as the enzyme moves the DNA through the pore.

Figure 20:
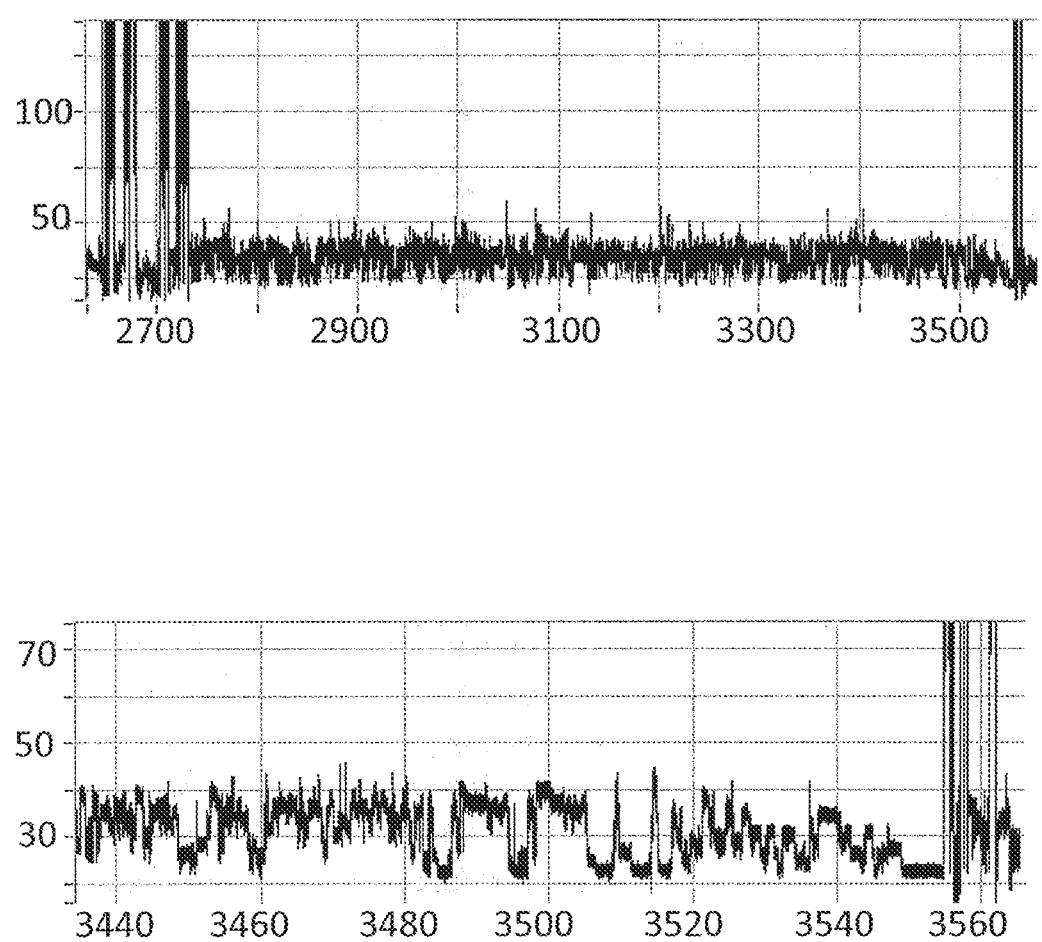

FIG. 20 shows example current traces (y-axis=current (pA), x-axis=time (s) for both traces) observed when Hel308 Mbu-E284C (SEQ ID NO: 10 with the mutation E284C) controls the translocation of DNA (+120 mV, (960 mM KCl, 25 mM potassium phosphate, 3 mM potassium ferrocyanide, 1 mM potassium ferricyanide pH 8.0, 10 mM $MgCl_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The upper electrical trace shows the DNA level (~35 pA) when DNA is captured under the force of the applied potential (+120 mV). DNA with enzyme attached results in a long block that shows stepwise changes in current as the enzyme moves the DNA through the pore. The lower trace shows a zoomed in view of the helicase controlled DNA movement shown in the upper trace.

FIG. 21 shows example current traces (y-axis=current (pA), x-axis=time (s) for both traces) observed when Hel308 Mbu-S288C (SEQ ID NO: 10 with the mutation S288C) controls the translocation of DNA (+120 mV, (960 mM KCl, 25 mM potassium phosphate, 3 mM potassium ferrocyanide, 1 mM potassium ferricyanide pH 8.0, 10 mM $MgCl_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The upper electrical trace shows the DNA level (~40 pA) when DNA is captured under the force of the applied potential (+120 mV). DNA with enzyme attached results in a long block that shows stepwise changes in current as the enzyme moves the DNA through the pore. The lower trace shows a zoomed in view of the helicase controlled DNA movement shown in the upper trace.

FIG. 22 shows example current traces (y-axis=current (pA), x-axis=time (s) for both traces) observed when Hel308 Mbu-E284Faz (SEQ ID NO: 10 with the mutation E284Faz) controls the translocation of DNA (+120 mV, (960 mM KCl, 25 mM potassium phosphate, 3 mM potassium ferrocyanide, 1 mM potassium ferricyanide pH 8.0, 10 mM MgCl$_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The upper electrical trace shows the DNA level (~50 pA) when DNA is captured under the force of the applied potential (+120 mV). DNA with enzyme attached results in a long block that shows stepwise changes in current as the enzyme moves the DNA through the pore. The lower trace shows a zoomed in view of the helicase controlled DNA movement shown in the upper trace.

FIG. 23 shows example current traces (y-axis=current (pA), x-axis=time (s) for both traces) observed when heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block) controls the translocation of DNA (+120 mV, (960 mM KCl, 25 mM potassium phosphate, 3 mM potassium ferrocyanide, 1 mM potassium ferricyanide pH 8.0, 10 mM MgCl$_2$ and 1 mM ATP) 0.2 nM DNA ((SEQ ID NO: 154 attached at its 5' end to four nitroindoles the last of which is attached to the 3' end of SEQ ID NO: 155), SEQ ID NO: 156 and SEQ ID NO: 117) through an MspA nanopore (MS(B1-G75S/G77S/L88N/Q126R)8 MspA (SEQ ID NO: 2 with mutations G75S/G77S/L88N/Q126R). The upper electrical trace shows the DNA level (~50 pA) for a number of helicase controlled DNA movements (each movement is numbered 1-3) when DNA is captured under the force of the applied potential (+120 mV). DNA with enzyme attached results in a long block that shows stepwise changes in current as the enzyme moves the DNA through the pore. The lower trace shows a zoomed in view of the helicase controlled DNA movement labelled 1 in the upper trace.

DESCRIPTION OF THE SEQUENCE LISTING

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N ((α-HL-NN; Stoddart et al., PNAS, 2009; 106(19): 7702-7707).

SEQ ID NO: 4 shows the amino acid sequence of one monomer of (α-HL-NN.

SEQ ID NOs: 5 to 7 show the amino acid sequences of MspB, C and D.

SEQ ID NO: 8 shows the amino acid sequence of the Hel308 motif.

SEQ ID NO: 9 shows the amino acid sequence of the extended Hel308 motif.

SEQ ID NOs: 10 to 58 show the amino acid sequences of Hel308 helicases in Table 1.

SEQ ID NO: 59 shows the RecD-like motif I.

SEQ ID NOs: 60 to 62 show the extended RecD-like motif 1.

SEQ ID NO: 63 shows the RecD motif I.

SEQ ID NO: 64 shows a preferred RecD motif I, namely G-G-P-G-T-G-K-T.

SEQ ID NOs: 65 to 67 show the extended RecD motif I.

SEQ ID NO: 68 shows the RecD-like motif V.

SEQ ID NO: 69 shows the RecD motif V.

SEQ ID NOs: 70 to 77 show the MobF motif III.

SEQ ID NOs: 78 to 84 show the MobQ motif III.

SEQ ID NO: 85 shows the amino acid sequence of TraI Eco.

SEQ ID NO: 86 shows the RecD-like motif I of TraI Eco.

SEQ ID NO: 87 shows the RecD-like motif V of TraI Eco.

SEQ ID NO: 88 shows the MobF motif III of TraI Eco.

SEQ ID NO: 89 shows the XPD motif V.

SEQ ID NO: 90 shows XPD motif VI.

SEQ ID NO: 91 shows the amino acid sequence of XPD Mbu.

SEQ ID NO: 92 shows the XPD motif V of XPD Mbu.

SEQ ID NO: 93 shows XPD motif VI of XPD Mbu.

SEQ ID NO: 94 shows the amino acid sequence of a preferred HhH domain.

SEQ ID NO: 95 shows the amino acid sequence of the ssb from the bacteriophage RB69, which is encoded by the gp32 gene.

SEQ ID NO: 96 shows the amino acid sequence of the ssb from the bacteriophage T7, which is encoded by the gp2.5 gene.

SEQ ID NO: 97 shows the amino acid sequence of the UL42 processivity factor from Herpes virus 1.

SEQ ID NO: 98 shows the amino acid sequence of subunit 1 of PCNA.

SEQ ID NO: 99 shows the amino acid sequence of subunit 2 of PCNA.

SEQ ID NO: 100 shows the amino acid sequence of subunit 3 of PCNA.

SEQ ID NO: 101 shows the amino acid sequence of Phi29 DNA polymerase.

SEQ ID NO: 102 shows the amino acid sequence (from 1 to 319) of the UL42 processivity factor from the Herpes virus 1.

SEQ ID NO: 103 shows the amino acid sequence of the ssb from the bacteriophage RB69, i.e. SEQ ID NO: 95, with its C terminus deleted (gp32RB69CD).

SEQ ID NO: 104 shows the amino acid sequence (from 1 to 210) of the ssb from the bacteriophage T7 (gp2.5T7-R211Del). The full length protein is shown in SEQ ID NO: 96.

SEQ ID NO: 105 shows the amino acid sequence of the 5$^{th}$ domain of Hel308 Hla.

SEQ ID NO: 106 shows the amino acid sequence of the 5$^{th}$ domain of Hel308 Hvo.

SEQ ID NO: 107 shows the amino acid sequence of the (HhH)2 domain.

SEQ ID NO: 108 shows the amino acid sequence of the (HhH)2-(HhH)2 domain.

SEQ ID NO: 109 shows the amino acid sequence of the peptide linker used to form a helicase in which the opening has been closed.

SEQ ID NOs: 110 to 117 show polynucleotide sequences used in the Examples.

SEQ ID NO: 118 shows the amino acid sequence of the human mitochondrial SSB (HsmtSSB).

SEQ ID NO: 119 shows the amino acid sequence of the p5 protein from Phi29 DNA polymerase.

SEQ ID NO: 120 shows the amino acid sequence of the wild-type SSB from *E. coli*.

SEQ ID NO: 121 shows the amino acid sequence of the ssb from the bacteriophage T4, which is encoded by the gp32 gene.

SEQ ID NO: 122 shows the amino acid sequence of EcoSSB-CterAla.

SEQ ID NO: 123 shows the amino acid sequence of EcoSSB-CterNGGN.

SEQ ID NO: 124 shows the amino acid sequence of EcoSSB-Q152del.

SEQ ID NO: 125 shows the amino acid sequence of EcoSSB-G117del.

SEQ ID NO: 126 shows the amino acid sequence of TrwC Cba.

SEQ ID NO: 127 shows part of the polynucleotide sequence used in Example 5. Attached to the 3' end of this sequence are four iSpC3 spacers units the last of which is attached to the 5' end of SEQ ID NO: 128.

SEQ ID NO: 128 shows part of the polynucleotide sequence used in Example 5. Attached to the 5' end of this sequence are four iSpC3 spacers units the last of which is attached to the 3' end of SEQ ID NO: 127.

SEQ ID NO: 129 shows the amino acid sequence of Topoisomerase V Mka (*Methanopyrus Kandleri*).

SEQ ID NO: 130 shows the amino acid sequence of domains H-L of Topoisomerase V Mka (*Methanopyrus Kandleri*).

SEQ ID NOs: 131 to 139 show some of the TraI sequences shown in Table 3.

SEQ ID NO: 140 shows the amino acid sequence of Mutant S (*Escherichia coli*).

SEQ ID NO: 141 shows the amino acid sequence of Sso7d (*Sufolobus solfataricus*).

SEQ ID NO: 142 shows the amino acid sequence of Sso10b1 (*Sulfolobus solfataricus* P2).

SEQ ID NO: 143 shows the amino acid sequence of Sso10b2 (*Sulfolobus solfataricus* P2).

SEQ ID NO: 144 shows the amino acid sequence of Tryptophan repressor (*Escherichia coli*).

SEQ ID NO: 145 shows the amino acid sequence of Lambda repressor (*Enterobacteria phage lambda*).

SEQ ID NO: 146 shows the amino acid sequence of Cren7 (*Histone crenarchaea* Cren7 Sso).

SEQ ID NO: 147 shows the amino acid sequence of human histone (*Homo sapiens*).

SEQ ID NO: 148 shows the amino acid sequence of dsbA (*Enterobacteria phage* T4).

SEQ ID NO: 149 shows the amino acid sequence of Rad51 (*Homo sapiens*).

SEQ ID NO: 150 shows the amino acid sequence of PCNA sliding clamp (*Citromicrobium bathyomarinum* JL354).

SEQ ID NO: 151 shows one of the sequences used in Example 7. This sequence has a carboxyfluorescein attached to a modified thymine located at position 6.

SEQ ID NO: 152 shows one of the sequences used in Example 7. This sequence has a black-hole quencher (BHQ-1) attached to a modified thymine at position 81.

SEQ ID NO: 153 shows one of the sequences used in Example 7.

SEQ ID NO: 154 shows one of the sequences used in Example 9. This sequence is attached at its 5' end by four nitroindoles to the 3' end of SEQ ID NO: 155.

SEQ ID NO: 155 shows one of the sequences used in Example 9. This sequence is attached at its 3' end by four nitroindoles to the 5' end of SEQ ID NO: 154.

SEQ ID NO: 156 shows one of the sequences used in Example 9.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a helicase" includes "helicases", reference to "an opening" includes two or more such openings, reference to "a transmembrane protein pore" includes two or more such pores, and the like.

All publications, patents and patent applications cited herein, whether supra or infra, are hereby incorporated by reference in their entirety.

Modified Helicases with Two or More Parts Connected

The present invention provides a modified helicase that is useful for controlling the movement of a polynucleotide. The modified helicase is based on an unmodified helicase having one or more monomers. In other words, the helicase may be monomeric or oligomeric/multimeric. This is discussed in more detail below. The modified helicase is based on an unmodified helicase comprising a polynucleotide binding domain which comprises in at least one conformational state an opening through which a polynucleotide can unbind from the helicase. In accordance with the invention, the helicase is modified such that two or more parts on the same monomer of the helicase are connected to reduce the size of the opening. The reduced size of the opening does not prevent the helicase from binding to a polynucleotide. For instance, the helicase may bind to a polynucleotide at one of its termini. The reduced size of the opening decreases the ability of the polynucleotide to unbind or disengage from the helicase, particularly from internal nucleotides of the polynucleotide. This is discussed in more detail below and allows the modified helicase to remain bound to the polynucleotide for longer. The modified helicase has the ability to control the movement of a polynucleotide. The modified helicase is artificial or non-natural.

The ability of a helicase to bind to and unbind from a polynucleotide can be determined using any method known in the art. Suitable binding/unbinding assays include, but are not limited to, native polyacrylamide gel electrophoresis (PAGE), fluorescence anisotropy, calorimetry and Surface plasmon resonance (SPR, such as Biacore™). The ability of a helicase to unbind from a polynucleotide can of course be determined by measuring the time for which the helicase can control the movement of a polynucleotide. This may also be determined using any method known in the art. The ability of a helicase to control the movement of a polynucleotide is typically assayed in a nanopore system, such as the ones described below. The ability of a helicase to control the movement of a polynucleotide can be determined as described in the Examples.

A modified helicase of the invention is a useful tool for controlling the movement of a polynucleotide during Strand Sequencing. A problem which occurs in sequencing polynucleotides, particularly those of 500 nucleotides or more, is that the molecular motor which is controlling the movement of the polynucleotide may disengage from the polynucleotide. This allows the polynucleotide to be pulled through the pore rapidly and in an uncontrolled manner in the direction of the applied field. A modified helicase of the invention is less likely to unbind or disengage from the polynucleotide being sequenced. The modified helicase can provide increased read lengths of the polynucleotide as they control the movement of the polynucleotide through a nanopore. The ability to move an entire polynucleotide through a nanopore under the control of a modified helicase of the invention allows characteristics of the polynucleotide, such as its sequence, to be estimated with improved accuracy and speed over known methods. This becomes more important as strand lengths increase and molecular motors are required with improved processivity. A modified helicase of the invention is particularly effective in controlling the movement of target polynucleotides of 500 nucleotides or more, for example 1000 nucleotides, 5000, 10000, 20000, 50000, 100000 or more.

A modified helicase of the invention is also a useful tool for isothermal polymerase chain reaction (PCR). In such methods, the strands of double stranded DNA are typically first separated by a helicase of the invention and coated by single stranded DNA (ssDNA)-binding proteins. In the second step, two sequence specific primers typically hybridise to each border of the DNA template. DNA polymerases may then be used to extend the primers annealed to the templates to produce a double stranded DNA and the two newly synthesized DNA products may then be used as substrates by the helicases of the invention, entering the next round of the reaction. Thus, a simultaneous chain reaction develops, resulting in exponential amplification of the selected target sequence.

The modified helicase has the ability to control the movement of a polynucleotide. The ability of a helicase to control the movement of a polynucleotide can be assayed using any method known in the art. For instance, the helicase may be contacted with a polynucleotide and the position of the polynucleotide may be determined using standard methods. The ability of a modified helicase to control the movement of a polynucleotide is typically assayed in a nanopore system, such as the ones described below and, in particular, as described in the Examples.

A modified helicase of the invention may be isolated, substantially isolated, purified or substantially purified. A helicase is isolated or purified if it is completely free of any other components, such as lipids, polynucleotides, pore monomers or other proteins. A helicase is substantially isolated if it is mixed with carriers or diluents which will not interfere with its intended use. For instance, a helicase is substantially isolated or substantially purified if it is present in a form that comprises less than 10%, less than 5%, less than 2% or less than 1% of other components, such as lipids, polynucleotides, pore monomers or other proteins.

A helicase for use in the invention comprises a polynucleotide binding domain. A polynucleotide binding domain is the part of the helicase that is capable of binding to a polynucleotide. Polynucleotides are defined below. The ability of a domain to bind a polynucleotide can be determined using any method known in the art. The polynucleotide binding domains of known helicases have typically been identified in the art. The domain (with or without bound polynucleotide) may be identified using protein modelling, x-ray diffraction measurement of the protein in a crystalline state (Rupp B (2009). Biomolecular Crystallography: Principles, Practice and Application to Structural Biology. New York: Garland Science), nuclear magnetic resonance (NMR) spectroscopy of the protein in solution (Mark Rance; Cavanagh, John; Wayne J. Fairbrother; Arthur W. Hunt III; Skelton, NNicholas J. (2007). Protein NMR spectroscopy: principles and practice (2nd ed.). Boston: Academic Press) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution.". Q Rev Biophys. 33: 307-69. Structural information of proteins determined by above mentioned methods are publicly available from the protein bank (PDB) database.

Protein modelling exploits the fact that protein structures are more conserved than protein sequences amongst homologues. Hence, producing atomic resolution models of proteins is dependent upon the identification of one or more protein structures that are likely to resemble the structure of the query sequence. In order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists, then the template sequence is "aligned" with the query sequence, i.e. residues in the query sequence are mapped onto the template residues. The sequence alignment and template structure are then used to produce a structural model of the query sequence. Hence, the quality of a protein model is dependent upon the quality of the sequence alignment and the template structure.

Proteins, such as helicases, are dynamic structures which are in constant motion. The conformational space that a protein can explore has been described by an energy landscape, in which different conformations are populated based on their energies, and rates of interconversion are dependent on the energy barriers between states (Vinson, *Science,* 2009: 324(5924): 197). Helicases can therefore exist in several conformation states whether in isolation or controlling the movement of a polynucleotide. In at least one conformational state, the polynucleotide binding domain of an unmodified helicase for use in the invention comprises an opening through which a polynucleotide can unbind from the helicase. The opening may be present in all conformational states of the helicase, but does not have to be. For instance, in all conformational states, the polynucleotide binding domain may comprise an opening through which a polynucleotide can unbind from the helicase. Alternatively, in one or more conformational states of the helicase, the polynucleotide binding domain may comprise an opening through which a polynucleotide cannot unbind from the helicase because the opening is too small. In one or more conformational states of the helicase, the polynucleotide binding domain may not comprise an opening through which a polynucleotide can unbind from the helicase.

The polynucleotide binding domain preferably comprises in at least one conformational state an opening through which one or more internal nucleotides of the polynucleotide can unbind from the helicase. An internal nucleotide is a nucleotide which is not a terminal nucleotide in the polynucleotide. For example, it is not a 3' terminal nucleotide or a 5' terminal nucleotide. All nucleotides in a circular polynucleotide are internal nucleotides. Reducing or preventing the unbinding from one or more internal nucleotides in accordance with the invention is advantageous because it results in modified helicases that are capable of binding to one terminus of a polynucleotide, controlling the movement of most, if not all of, the polynucleotide and then unbinding at the other terminus. Such helicases are particularly helpful for Strand Sequencing.

The ability of one or more internal nucleotide to unbind from the helicase may be determined by carrying out a comparative assay. For instance, the ability of a helicase to unbind from a control polynucleotide A is compared with its ability to unbind from the same polynucleotide but with a blocking group attached at the terminal nucleotides (polynucleotide B). The blocking group prevents any unbinding at the terminal nucleotide of strand B, and thus allows only internal unbinding of the helicase. Alternatively, the ability of a helicase to unbind from a circular polynucleotide may be assayed. Unbinding may be assayed as described above.

The opening may be a groove, pocket or recess in the polynucleotide binding domain.

The presence of an opening through which a polynucleotide can unbind from the helicase can be determined using any method known in the art. The presence of an opening can be determined by measuring the ability of a helicase to unbind from a polynucleotide, and in particular from internal nucleotides of the polynucleotide, as discussed in more detail above. Openings in the polynucleotide domain can be identified using protein modelling, x-ray diffraction, NMR spectroscopy or cryo-electron microscopy as discussed above.

In accordance with the invention, the helicase is modified by connecting two or more parts on the same monomer of the helicase. If the helicase is oligomeric or multimeric, the two or more parts cannot be on different monomers. Any number of parts, such as 3, 4, 5 or more parts, may be connected. Preferred methods of connecting the two or more parts are discussed in more detail below.

The two or more parts can be located anywhere on the monomer as long as they reduce the size of the opening when connected in accordance with the invention. The two or more parts may be in the polynucleotide domain or the opening, but do not have to be. For instance, one, both or all of the two or more parts may be outside the polynucleotide binding domain, such as on different domain of the helicase. The maximum distance between the two or more parts is the circumference of the helicase.

The two or more parts are preferably spatially proximate. The two or more parts are preferably less that 50 Angstroms (Å) apart, such as less than 40 Å apart, less than 30 Å apart, less than 25 Å apart, less than 20 Å apart, less than 10 Å apart or less than 10 Å apart.

At least one of the two or more parts preferably forms part of the opening, is adjacent to the opening or is near the opening. It is straightforward to identify parts of the opening, such as amino acids within the opening, as described above. Parts are adjacent to the opening if they are next to, but do not form part of the opening. For instance, an amino acid which is located next to an amino acid that forms part of the opening, but which itself does not form part of the opening is adjacent to the opening. In the context of the invention, "next to" may mean next to in the amino acid sequence of the helicase or next two in the three-dimensional structure of the helicase. A part is typically near to the opening if it is less than 20 Å from an amino acid that forms part of the opening, such as less than 15 Å, less than 10 Å, less than 5 Å or less than 2 Å apart from an amino acid that forms part of the opening. A part is typically near to the opening if it is within 1, 2, 3, 4 or 5 amino acids of an amino acid that forms part of the opening in the amino acid sequence of the helicase. Such amino acids may be identified as discussed above.

The two or more parts may be on opposite sides of the opening. The two or more parts may be on the same side of the opening. In this embodiment, the two or more parts of the helicase may be connected to form a loop, lid, constriction or flap that reduces the size of the opening.

The two or more parts are preferably on the surface of the monomer, i.e. on the surface of the helicase. It is straightforward to connect two or more parts on the surface as described in more detail below. Surface parts may be determined using protein modelling, x-ray diffraction, NMR spectroscopy or cryo-electron microscopy as discussed above.

The modified helicase retains its ability to control the movement of a polynucleotide. This ability of the helicase is typically provided by its three dimensional structure that is typically provided by its β-strands and α-helices. The α-helices and β-strands are typically connected by loop regions. In order to avoid affecting the ability of the helicase to control the movement of a polynucleotide, the two or more parts are preferably loop regions of the monomer. The loop regions of specific helicases can be identified using methods known in the art, such as protein modelling, x-ray diffraction, NMR spectroscopy or cryo-electron microscopy as discussed above.

For Hel308 helicases (SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58), β-strands can only be found in the two RecA-like engine domains (domains 1 and 2). These domains are responsible for coupling the hydrolysis of the fuel nucleotide (normally ATP) with movement. The important domains for ratcheting along a polynucleotide are domains 3 and 4, but above all domain 4. Interestingly, both of domains 3 and 4 comprise only α-helices. There is an important α-helix in domain 4 called the ratchet helix. As a result, in the Hel308 embodiments of the invention, the two or more parts are preferably not in any of the α-helixes.

The size of the opening may be reduced to any degree as long as it reduces the unbinding of the polynucleotides from the helicase. This may be determined as discussed above. Ways in which the size of the opening are reduced are discussed in more detail below.

The two or more parts are preferably connected to close the opening. If the opening is closed, the polynucleotide cannot unbind from the helicase through the opening. The helicase is more preferably modified such that it does not comprise the opening in any conformational state. If the opening is not present in any conformational state of the helicase, the polynucleotide cannot unbind from the helicase through the opening. The helicase is most preferably modified such that it is capable of forming a covalently-closed structure around the polynucleotide. Once the covalently-closed structure is bound to a polynucleotide, for instance at one end of the polynucleotide, it is capable of controlling the movement of the polynucleotide without unbinding until it reaches the other end.

Connection

The two or more parts may be connected in any way. The connection can be transient, for example non-covalent. Even transient connection will reduce the size of the opening and reduce unbinding of the polynucleotide from the helicase through the opening.

The two or more parts are preferably connected by affinity molecules. Suitable affinity molecules are known in the art. The affinity molecules are preferably (a) complementary polynucleotides (International Application No. PCT/GB10/000132 (published as WO 2010/086602), (b) an antibody or a fragment thereof and the complementary epitope (Biochemistry 6th Ed, W.H. Freeman and co (2007) pp 953-954), (c) peptide zippers (O'Shea et al., Science 254 (5031): 539-544), (d) capable of interacting by 3-sheet augmentation (Remaut and Waksman Trends Biochem. Sci. (2006) 31 436-444), (e) capable of hydrogen bonding, pi-stacking or forming a salt bridge, (f) rotaxanes (Xiang Ma and He Tian Chem. Soc. Rev., 2010, 39, 70-80), (g) an aptamer and the complementary protein (James, W. in Encyclopedia of Analytical Chemistry, R. A. Meyers (Ed.) pp. 4848-4871 John Wiley & Sons Ltd, Chichester, 2000) or (h) half-chelators (Hammerstein et al. J Biol Chem. 2011 Apr. 22; 286(16): 14324-14334). For (e), hydrogen bonding occurs between a proton bound to an electronegative atom and another electronegative atom. Pi-stacking requires two aromatic rings that can stack together where the planes of the rings are parallel. Salt bridges are between groups that can delocalize their electrons over several atoms, e. g. between aspartate and arginine.

The two or more parts may be transiently connected by a hexa-his tag or Ni-NTA. The two or more parts may also be modified such that they transiently connect to each other.

The two or more parts are preferably permanently connected. In the context of the invention, a connection is permanent if is not broken while the helicase is used or cannot be broken without intervention on the part of the user, such as using reduction to open —S—S— bonds.

The two or more parts are preferably covalently-attached. The two or more parts may be covalently attached using any method known in the art.

The two or more parts may be covalently attached via their naturally occurring amino acids, such as cysteines, threonines, serines, aspartates, asparagines, glutamates and glutamines. Naturally occurring amino acids may be modified to facilitate attachment. For instance, the naturally occurring amino acids may be modified by acylation, phosphorylation, glycosylation or farnesylation. Other suitable modifications are known in the art. Modifications to naturally occurring amino acids may be post-translation modifications. The two or more parts may be attached via amino acids that have been introduced into their sequences. Such amino acids are preferably introduced by substitution. The introduced amino acid may be cysteine or a non-natural amino acid that facilitates attachment. Suitable non-natural amino acids include, but are not limited to, 4-azido-L-phenylalanine (Faz), any one of the amino acids numbered 1-71 included in FIG. 1 of Liu C. C. and Schultz P. G., Annu. Rev. Biochem., 2010, 79, 413-444 or any one of the amino acids listed below. The introduced amino acids may be modified as discussed above.

In a preferred embodiment, the two or more parts are connected using linkers. Linker molecules are discussed in more detail below. One suitable method of connection is cysteine linkage. This is discussed in more detail below. The two or more parts are preferably connected using one or more, such as two or three, linkers. The one or more linkers may be designed to reduce the size of, or close, the opening as discussed above. If one or more linkers are being used to close the opening as discussed above, at least a part of the one or more linkers is preferably oriented such that it is not parallel to the polynucleotide when it is bound by the helicase. More preferably, all of the linkers are oriented in this manner. If one or more linkers are being used to close the opening as discussed above, at least a part of the one or more linkers preferably crosses the opening in an orientation that is not parallel to the polynucleotide when it bound by the helicase. More preferably, all of the linkers cross the opening in this manner. In these embodiments, at least a part of the one or more linkers may be perpendicular to the polynucleotide. Such orientations effectively close the opening such that the polynucleotide cannot unbind from the helicase through the opening.

Each linker may have two or more functional ends, such as two, three or four functional ends. Suitable configurations of ends in linkers are well known in the art.

One or more ends of the one or more linkers are preferably covalently attached to the helicase. If one end is covalently attached, the one or more linkers may transiently connect the two or more parts as discussed above. If both or all ends are covalently attached, the one or more linkers permanently connect the two or more parts.

At least one of the two or more parts is preferably modified to facilitate the attachment of the one or more linkers. Any modification may be made. The linkers may be attached to one or more reactive cysteine residues, reactive lysine residues or non-natural amino acids in the two or more parts. The non-natural amino acid may be any of those discussed above. The non-natural amino acid is preferably 4-azido-L-phenylalanine (Faz). At least one amino acid in the two or more parts is preferably substituted with cysteine or a non-natural amino acid, such as Faz.

The one or more linkers are preferably amino acid sequences and/or chemical crosslinkers.

Suitable amino acid linkers, such as peptide linkers, are known in the art. The length, flexibility and hydrophilicity of the amino acid or peptide linker are typically designed such that it reduces the size of the opening, but does not to disturb the functions of the helicase. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline. The amino acid sequence of a linker preferably comprises a polynucleotide binding moiety. Such moieties and the advantages associated with their use are discussed below.

Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulfonyl chloride reagents, isothiocyanates, acyl halides, hydrazines, disulphides, vinyl sulfones, aziridines and photoreactive reagents (such as aryl azides, diaziridines).

Reactions between amino acids and functional groups may be spontaneous, such as cysteine/maleimide, or may require external reagents, such as Cu(I) for linking azide and linear alkynes.

Linkers can comprise any molecule that stretches across the distance required. Linkers can vary in length from one carbon (phosgene-type linkers) to many Angstroms. Examples of linear molecules, include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT).

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate, di-maleimide PEG 1k, di-maleimide PEG 3.4k, di-maleimide PEG 5k, di-maleimide PEG 10k, bis(maleimido)ethane (BMOE), bis-maleimidohexane (BMH), 1,4-bis-maleimidobutane (BMB), 1,4 bis-maleimidyl-2,3-dihydroxybutane (BMDB), BM[PEO]2 (1,8-bis-maleimidodiethyleneglycol), BMI[PEO]3 (1,11-bis-maleinidotriethylene glycol), tris[2-maleimidoethyl]amine (TMEA). DTME dithiobismaleimidoethane, bis-maleimide PEG3. bis-maleimide PEG11, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S-S-PEG3-biotin, DBCO-S-S-PEG3-biotin, DBCO-S-S-PEG11-biotin, (succinimidyl 3-(2-pyridyldithio)propionate (SPDP) and maleimide-PEG(2 kDa)-maleimide (ALPHA,OMEGA-BIS-MALEIMIDO POLY(ETHYLENE GLYCOL)). The most preferred crosslinker is maleimide-propyl-SRDFWRS-(1,2-diaminoethane)-propyl-maleimide as used in the Examples.

The one or more linkers may be cleavable. This is discussed in more detail below.

The two or more parts may be connected using two different linkers that are specific for each other. One of the linkers is attached to one part and the other is attached to another part. The linkers should react to form a modified helicase of the invention. The two or more parts may be connected using the hybridization linkers described in International Application No. PCT/GB10/000132 (published as WO 2010/086602). In particular, the two or more parts may be connected using two or more linkers each comprising a hybridizable region and a group capable of forming a covalent bond. The hybridizable regions in the linkers hybridize and link the two or more parts. The linked parts are then coupled via the formation of covalent bonds between the groups. Any of the specific linkers disclosed in International Application No. PCT/GB10/000132 (published as WO 2010/086602) may be used in accordance with the invention.

The two or more parts may be modified and then attached using a chemical crosslinker that is specific for the two modifications. Any of the crosslinkers discussed above may be used.

The linkers may be labeled. Suitable labels include, but are not limited to, fluorescent molecules (such as Cy3 or AlexaFluor®555), radioisotopes, e.g. $^{125}3^5$s, enzymes, antibodies, antigens, polynucleotides and ligands such as biotin. Such labels allow the amount of linker to be quantified. The label could also be a cleavable purification tag, such as biotin, or a specific sequence to show up in an identification method, such as a peptide that is not present in the protein itself, but that is released by trypsin digestion.

A preferred method of connecting the two or more parts is via cysteine linkage. This can be mediated by a bi-functional chemical crosslinker or by an amino acid linker with a terminal presented cysteine residue. Linkage can occur via natural cysteines in the helicase. Alternatively, cysteines can be introduced into the two or more parts of the helicase. If the two or more parts are connected via cysteine linkage, the one or more cysteines have preferably been introduced to the two or more parts by substitution.

The length, reactivity, specificity, rigidity and solubility of any bi-functional linker may be designed to ensure that the size of the opening is reduced sufficiently and the function of the helicase is retained. Suitable linkers include bismaleimide crosslinkers, such as 1,4-bis(maleimido)butane (BMB) or bis(maleimido)hexane. One draw back of bi-functional linkers is the requirement of the helicase to contain no further surface accessible cysteine residues if attachment at specific sites is preferred, as binding of the bi-functional linker to surface accessible cysteine residues may be difficult to control and may affect substrate binding or activity. If the helicase does contain several accessible cysteine residues, modification of the helicase may be required to remove them while ensuring the modifications do not affect the folding or activity of the helicase. This is discussed in International Application No. PCT/GB10/000133 (published as WO 2010/086603). The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive S⁻ group. The reactivity of cysteine residues may be protected by thiol protective groups such as 5,5'-dithiobis-(2-nitrobenzoic acid) (dTNB). These may be reacted with one or more cysteine residues of the helicase before a linker is attached. Selective deprotection of surface accessible cysteines may be possible using reducing reagents immobilized on beads (for example immobilized tris(2-carboxyethyl) phosphine, TCEP). Cysteine linkage of the two or more parts is discussed in more detail below.

Another preferred method of attaching the two or more parts is via 4-azido-L-phenylalanine (Faz) linkage. This can be mediated by a bi-functional chemical linker or by a polypeptide linker with a terminal presented Faz residue. The one or more Faz residues have preferably been introduced to the helicase by substitution. Faz linkage of two or more helicases is discussed in more detail below.

Helicase

Any helicase formed of one or monomers and comprising a polynucleotide binding domain which comprises in at least one conformational state an opening through which a polynucleotide can unbind from the helicase may modified in accordance with the invention. Helicases are often known as translocases and the two terms may be used interchangeably.

Suitable helicases are well-known in the art (M. E. Fairman-Williams et al., Curr. Opin. Struct Biol., 2010, 20 (3), 313-324, T. M. Lohman et al., Nature Reviews Molecular Cell Biology, 2008, 9, 391-401).

The helicase is preferably a member of superfamily 1 or superfamily 2. The helicase is more preferably a member of one of the following families: Pif1-like, Upf1-like, UvrD/Rep, Ski-like, Rad3/XPD, NS3/NPH-II, DEAD, DEAH/RHA, RecG-like, REcQ-like, T1R-like, Swi/Snf-like and Rig-I-like. The first three of those families are in superfamily 1 and the second ten families are in superfamily 2. The helicase is more preferably a member of one of the following subfamilies: RecD, Upf1 (RNA), PcrA, Rep, UvrD, Hel308, Mtr4 (RNA), XPD, NS3 (RNA), Mss116 (RNA), Prp43 (RNA), RecG, RecQ, TlR, RapA and Hef (RNA). The first five of those subfamilies are in superfamily 1 and the second eleven subfamilies are in superfamily 2. Members of the Upf1, Mtr4, NS3, Mss116, Prp43 and Hef subfamilies are RNA helicases. Members of the remaining subfamilies are DNA helicases.

The helicase may be a multimeric or oligomeric helicase. In other words, the helicase may need to form a multimer or an oligomer, such as a dimer, to function. In such embodiments, the two or more parts cannot be on different monomers. The helicase is preferably monomeric. In other words, the helicase preferably does not need to form a multimer or an oligomer, such as a dimer, to function. Hel308, RecD, TraI and XPD helicases are all monomeric helicases. These are discussed in more detail below. Methods for determining whether or not a helicase is oligomeric/multimeric or monomeric are known in the art. For instance, the kinetics of radiolabelled or fluorescently-labelled polynucleotide unwinding using the helicase can be examined. Alternatively, the helicase can be analysed using size exclusion chromatography.

Monomeric helicases may comprise several domains attached together. For instance, TraI helicases and TraI subgroup helicases may contain two RecD helicase domains, a relaxase domain and a C-terminal domain. The domains typically form a monomeric helicase that is capable of functioning without forming oligomers. The two or more parts may be present on the same or different domains of a monomeric helicase. The unmodified helicase suitable for modification in accordance with the invention is preferably capable of binding to the target polynucleotide at an internal nucleotide. Internal nucleotides are defined above.

Generally, a helicase which is capable of binding at an internal nucleotide is also capable of binding at a terminal nucleotide, but the tendency for some helicases to bind at an internal nucleotide will be greater than others. For an unmodified helicase suitable for modification in accordance with the invention, typically at least 10% of its binding to a polynucleotide will be at an internal nucleotide. Typically, at least 20%, at least 30%, at least 40% or at least 50% of its binding will be at an internal nucleotide. Binding at a terminal nucleotide may involve binding to both a terminal nucleotide and adjacent nucleotides at the same time. For the purposes of the invention, this is not binding to the target polynucleotide at an internal nucleotide. In other words, the helicase for modification using the invention is not only capable of binding to a terminal nucleotide in combination with one or more adjacent internal nucleotides. The helicase may be capable of binding to an internal nucleotide without concurrent binding to a terminal nucleotide.

A helicase which is capable of binding at an internal nucleotide may bind to more than one internal nucleotide. Typically, the helicase binds to at least 2 internal nucleotides, for example at least 3, at least 4, at least 5, at least 10 or at least 15 internal nucleotides. Typically the helicase binds to at least 2 adjacent internal nucleotides, for example at least 3, at least 4, at least 5, at least 10 or at least 15 adjacent internal nucleotides. The at least 2 internal nucleotides may be adjacent or non-adjacent.

If modification in accordance with the invention closes the opening such that unbinding from internal nucleotides is prevented, it is preferred that the unmodified helicase is capable of at least some binding to a terminal nucleotide. This will allow the modified helicase to bind to a polynucleotide at one terminus and control the movement of the polynucleotide along its entire length without unbinding. The helicase will eventually unbind from the polynucleotide at the opposite terminus from which it became bound.

The ability of a helicase to bind to a polynucleotide at an internal nucleotide may be determined by carrying out a comparative assay. The ability of a helicase to bind to a control polynucleotide A is compared to the ability to bind to the same polynucleotide but with a blocking group attached at the terminal nucleotide (polynucleotide B). The blocking group prevents any binding at the terminal nucleotide of strand B, and thus allows only internal binding of a helicase. Alternatively, the ability of a helicase to bind to an internal nucleotide may also be assayed using circular polynucleotides.

Examples of helicases which are capable of binding at an internal nucleotide include, but are not limited to, Hel308 Tga, Hel308 Mhu and Hel308 Csy. Hence, the helicase preferably comprises (a) the sequence of Hel308 Tga (i.e. SEQ ID NO: 33) or a variant thereof or (b) the sequence of Hel308 Csy (i.e. SEQ ID NO: 22) or a variant thereof or (c) the sequence of Hel308 Mhu (i.e. SEQ ID NO: 52) or a variant thereof. Variants of these sequences are discussed in more detail below. Variants preferably comprise one or more substituted cysteine residues and/or one or more substituted Faz residues to facilitate attachment as discussed above.

The helicase is preferably a Hel308 helicase. Any Hel308 helicase may be used in accordance with the invention. Hel308 helicases are also known as ski2-ike helicases and the two terms can be used interchangeably. Suitable Hel308 helicases are disclosed in Table 4 of US Patent Application Nos. 61,549,998 and 61/599,244 and International Application No. PCT/GB2012/052579 (published as WO 2013/057495).

The Hel308 helicase typically comprises the amino acid motif Q-X1-X2-G-R-A-G-R (hereinafter called the Hel308 motif; SEQ ID NO: 8). The Hel308 motif is typically part of the helicase motif VI (Tuteja and Tuteja, Eur. J. Biochem. 271, 1849-1863 (2004)). X1 may be C, M or L. X1 is preferably C. X2 may be any amino acid residue. X2 is typically a hydrophobic or neutral residue. X2 may be A, F, M, C, V, L, I, S, T, P or R. X2 is preferably A, F, M, C, V, L, I, S, T or P. X2 is more preferably A, M or L. X2 is most preferably A or M.

The Hel308 helicase preferably comprises the motif Q-X1-X2-G-R-A-G-R-P (hereinafter called the extended Hel308 motif; SEQ ID NO: 9) wherein X1 and X2 are as described above.

The most preferred Hel308 helicases, Hel308 motifs and extended Hel308 motifs are shown in the Table 1 below.

TABLE 1

Preferred Hel308 helicases and their motifs

| SEQ ID NO: | Helicase | Names | % Identity Hel308 Pfu | % Identity Hel308 Mbu | Hel308 motif | Extended Hel308 motif |
|---|---|---|---|---|---|---|
| 10 | Hel308 Mbu | *Methanococcoides burtonii* | 37% | — | QMAGRAGR (SEQ ID NO: 11) | QMAGRAGRP (SEQ ID NO: 12) |
| 13 | Hel308 Pfu | *Pyrococcus furiosus* DSM 3638 | — | 37% | QMLGRAGR (SEQ ID NO: 14) | QMLGRAGRP (SEQ ID NO: 15) |
| 16 | Hel308 Hvo | *Haloferax volcanii* | 34% | 41% | QMMGRAGR (SEQ ID NO: 17) | QMMGRAGRP (SEQ ID NO: 18) |
| 19 | Hel308 Hla | *Halorubrum lacusprofundi* | 35% | 42% | QMCGRAGR (SEQ ID NO: 20) | QMCGRAGRP (SEQ ID NO: 21) |
| 22 | Hel308 Csy | *Cenarchaeum symbiosum* | 34% | 34% | QLCGRAGR (SEQ ID NO: 23) | QLCGRAGRP (SEQ ID NO: 24) |
| 25 | Hel308 Sso | *Sulfolobus solfataricus* | 35% | 33% | QMSGRAGR (SEQ ID NO: 26) | QMSGRAGRP (SEQ ID NO: 27) |
| 28 | Hel308 Mfr | *Methanogenium frigidum* | 37% | 44% | QMAGRAGR (SEQ ID NO: 11) | QMAGRAGRP (SEQ ID NO: 12) |
| 29 | Hel308 Mok | *Methanothermococcus okinawensis* | 37% | 34% | QCIGRAGR (SEQ ID NO: 30) | QCIGRAGRP (SEQ ID NO: 31) |
| 32 | Hel308 Mig | *Methanotorris igneus* Kol 5 | 40% | 35% | QCIGRAGR (SEQ ID NO: 30) | QCIGRAGRP (SEQ ID NO: 31) |
| 33 | Hel308 Tga | *Thermococcus gammatolerans* EJ3 | 60% | 38% | QMMGRAGR (SEQ ID NO: 17) | QMMGRAGRP (SEQ ID NO: 18) |
| 34 | Hel308 Tba | *Thermococcus barophilus* MP | 57% | 35% | QMIGRAGR (SEQ ID NO: 35) | QMIGRAGRP (SEQ ID NO: 36) |
| 37 | Hel308 Tsi | *Thermococcus sibiricus* MM 739 | 56% | 35% | QMMGRAGR (SEQ ID NO: 17) | QMMGRAGRP (SEQ ID NO: 18) |
| 38 | Hel308 Mba | *Methanosarcina barkeri* str. Fusaro | 39% | 60% | QMAGRAGR (SEQ ID NO: 11) | QMAGRAGRP (SEQ ID NO: 12) |
| 39 | Hel308 Mac | *Methanosarcina acetivorans* | 38% | 60% | QMAGRAGR (SEQ ID NO: 11) | QMAGRAGRP (SEQ ID NO: 12) |
| 40 | Hel308 Mmah | *Methanohalophilus mahii* DSM 5219 | 38% | 60% | QMAGRAGR (SEQ ID NO: 11) | QMAGRAGRP (SEQ ID NO: 12) |
| 41 | Hel308 Mmaz | *Methanosarcina mazei* | 38% | 60% | QMAGRAGR (SEQ ID NO: 11) | QMAGRAGRP (SEQ ID NO: 12) |
| 42 | Hel308 Mth | *Methanosaeta thermophila* PT | 39% | 46% | QMAGRAGR (SEQ ID NO: 11) | QMAGRAGRP (SEQ ID NO: 12) |
| 43 | Hel308 Mzh | *Methanosalsum zhilinae* DSM 4017 | 39% | 57% | QMAGRAGR (SEQ ID NO: 11) | QMAGRAGRP (SEQ ID NO: 12) |

TABLE 1-continued

Preferred Hel308 helicases and their motifs

| SEQ ID NO: | Helicase | Names | % Identity Hel308 Pfu | % Identity Hel308 Mbu | Hel308 motif | Extended Hel308 motif |
|---|---|---|---|---|---|---|
| 44 | Hel308 Mev | Methanohalobium evestigatum Z-7303 | 38% | 61% | QMAGRAGR (SEQ ID NO: 11) | QMAGRAGRP (SEQ ID NO: 12) |
| 45 | Hel308 Mma | Methanococcus maripaludis | 36% | 32% | QCIGRAGR (SEQ ID NO: 30) | QCIGRAGRP (SEQ ID NO: 31) |
| 46 | Hel308 Nma | Natrialba magadii | 37% | 43% | QMMGRAGR (SEQ ID NO: 17) | QMMGRAGRP (SEQ ID NO: 18) |
| 47 | Hel308 Mbo | Methanoregula boonei 6A8 | 38% | 45% | QMAGRAGR (SEQ ID NO: 11) | QMAGRAGRP (SEQ ID NO: 12) |
| 48 | Hel308 Fac | Ferroplasma acidarmanus | 34% | 32% | QMIGRAGR (SEQ ID NO: 35) | QMIGRAGRP (SEQ ID NO: 36) |
| 49 | Hel308 Mfe | Methanocaldococcus fervens AG86 | 40% | 35% | QCIGRAGR (SEQ ID NO: 30) | QCIGRAGRP (SEQ ID NO: 31) |
| 50 | Hel308 Mja | Methanocaldococcus jannaschii | 24% | 22% | QCIGRAGR (SEQ ID NO: 30) | QCIGRAGRP (SEQ ID NO: 31) |
| 51 | Hel308 Min | Methanocaldococcus infernus | 41% | 33% | QCIGRAGR (SEQ ID NO: 30) | QCIGRAGRP (SEQ ID NO: 31) |
| 52 | Hel308 Mhu | Methanospirillum hungatei JF-1 | 36% | 40% | QMAGRAGR (SEQ ID NO: 11) | QMAGRAGRP (SEQ ID NO: 12) |
| 53 | Hel308 Afu | Archaeoglobus fulgidus DSM 4304 | 40% | 40% | QMAGRAGR (SEQ ID NO: 11) | QMAGRAGRP (SEQ ID NO: 12) |
| 54 | Hel308 Htu | Haloterrigena turkmenica | 35% | 43% | QMAGRAGR (SEQ ID NO: 11) | QMMGRAGRP (SEQ ID NO: 12) |
| 55 | Hel308 Hpa | Haladaptatus paucihalophilus DX253 | 38% | 45% | QMFGRAGR (SEQ ID NO: 56) | QMFGRAGRP (SEQ ID NO: 57) |
| 58 | Hel308 Hsp ski2-like helicase | Halobacterium sp. NRC-1 | 36.8% | 42.0% | QMFGRAGR (SEQ ID NO: 56) | QMFGRAGRP (SEQ ID NO: 57) |

The most preferred Hel308 motif is shown in SEQ ID NO: 17. The most preferred extended Hel308 motif is shown in SEQ ID NO: 18.

The Hel308 helicase preferably comprises the sequence of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 or a variant thereof.

In Hel308 helicases, the polynucleotide domain and opening can be found between domain 2 (one of the ATPase domains) and domain 4 (the ratchet domain) and domain 2 and domain 5 (the molecular brake). The two or more parts connected in accordance with the invention are preferably (a) any amino acid in domain 2 and any amino acid in domain 4 or (b) any amino acid in domain 2 and any amino acid in domain 5. The amino acid residues which define domains 2, 4 and 5 in various Hel308 helicases are listed in Table 1 below.

TABLE 2

Amino acid residues which correspond to domains 2, 4 and 5 in various Hel 308 helicases

| SEQ ID NO: | Hel308 Homologue | Domain 2 | | Domain 4 | | Domain 5 | |
|---|---|---|---|---|---|---|---|
| | | Start | End | Start | End | Start | End |
| 10 | Mbu | W200 | E409 | Y506 | G669 | S670 | Q760 |
| 13 | Pfu | W198 | F398 | Y490 | G640 | I641 | S720 |
| 16 | Hvo | W201 | W418 | Y509 | G725 | V726 | E827 |
| 19 | Hla | W201 | W418 | Y513 | G725 | V726 | R824 |

TABLE 2-continued

Amino acid residues which correspond to domains 2, 4 and 5 in various Hel 308 helicases

| SEQ ID NO: | Hel308 Homologue | Domain 2 Start | Domain 2 End | Domain 4 Start | Domain 4 End | Domain 5 Start | Domain 5 End |
|---|---|---|---|---|---|---|---|
| 22 | Csy | W205 | G414 | Y504 | G644 | I645 | K705 |
| 25 | Sso | W204 | L420 | Y506 | G651 | I652 | S717 |
| 28 | Mfr | W193 | E397 | Y488 | G630 | I631 | I684 |
| 29 | Mok | W198 | G415 | Y551 | G706 | A707 | I775 |
| 32 | Mig | W200 | E408 | Y495 | G632 | A633 | I699 |
| 33 | Tga | W198 | R399 | Y491 | G639 | V640 | R720 |
| 34 | Tba | W219 | F420 | Y512 | G660 | V661 | K755 |
| 37 | Tsi | W221 | L422 | Y514 | G662 | V663 | K744 |
| 38 | Mba | W200 | E409 | Y498 | G643 | A644 | Y729 |
| 39 | Mac | W200 | E409 | Y499 | G644 | A645 | F730 |
| 40 | Mmah | W196 | G405 | Y531 | G678 | A679 | N747 |
| 41 | Mmaz | W200 | E409 | Y499 | G644 | A645 | Y730 |
| 42 | Mth | W203 | M404 | Y491 | G629 | A630 | A693 |
| 43 | Mzh | W200 | N409 | Y505 | G651 | I652 | T739 |
| 44 | Mev | W200 | D409 | Y499 | G643 | V644 | F733 |
| 45 | Mma | W196 | G405 | Y531 | G678 | A679 | N747 |
| 46 | Nma | W201 | W413 | Y541 | G688 | V689 | F799 |
| 47 | Mbo | W197 | E402 | Y493 | G637 | I638 | G723 |
| 48 | Fac | F197 | T390 | Y480 | G613 | V614 | R681 |
| 49 | Mfe | W199 | Q408 | Y494 | G629 | A630 | F696 |
| 50 | Mja | W197 | Q406 | Y492 | G627 | A628 | F694 |
| 51 | Min | W189 | Q390 | Y476 | G604 | A605 | I670 |
| 52 | Mhu | W198 | D402 | Y493 | G637 | V638 | C799 |
| 53 | Afu | W201 | F399 | Y487 | G626 | V627 | E696 |
| 54 | Htu | W201 | W413 | Y533 | G680 | V681 | F791 |
| 55 | Hpa | W201 | W412 | Y502 | G657 | V658 | E752 |
| 58 | Hsp (ski2-like helicase) | W210 | Y421 | Y512 | G687 | V688 | S783 |

The Hel308 helicase preferably comprises the sequence of Hel308 Mbu (i.e. SEQ ID NO: 10) or a variant thereof. In Hel308 Mbu, the polynucleotide domain and opening can be found between domain 2 (one of the ATPase domains) and domain 4 (the ratchet domain) and domain 2 and domain 5 (the molecular brake). The two or more parts of Hel308 Mbu connected are preferably (a) any amino acid in domain 2 and any amino acid in domain 4 or (b) any amino acid in domain 2 and any amino acid in domain 5. The amino acid residues which define domains 2, 4 and 5 for Hel308 Mbu are listed in Table 2 above. The two or more parts of Hel308 Mbu connected are preferably amino acids 284 and 615 in SEQ ID NO: 10. These amino acids are preferably substituted with cysteine (i.e. E284C and S615C) such that they can be connected by cysteine linkage.

The invention also provides a mutant Hel308 Mbu protein which comprises a variant of SEQ ID NO: 10 in which E284 and S615 are modified. E284 and S615 are preferably substituted. E284 and S615 are more preferably substituted with cysteine (i.e. E284C and S615C). The variant may differ from SEQ ID NO: 10 at positions other than E284 and S615 as long as E284 and S615 are modified. The variant will preferably be at least 30% homologous to SEQ ID NO: 10 based on amino acid identity as discussed in more detail below. E284 and S615 are not connected. The mutant Hel308 Mbu protein of the invention may be used to form a modified helicase of the invention in which E284 and S615 are connected.

The Hel308 helicase more preferably comprises (a) the sequence of Hel308 Tga (i.e. SEQ ID NO: 33) or a variant thereof, (b) the sequence of Hel308 Csy (i.e. SEQ ID NO: 22) or a variant thereof or (c) the sequence of Hel308 Mhu (i.e. SEQ ID NO: 52) or a variant thereof.

A variant of a Hel308 helicase is an enzyme that has an amino acid sequence which varies from that of the wild-type helicase and which retains polynucleotide binding activity. In particular, a variant of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 is an enzyme that has an amino acid sequence which varies from that of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 and which retains polynucleotide binding activity. Polynucleotide binding activity can be determined using methods known in the art. Suitable methods include, but are not limited to, fluorescence anisotropy, tryptophan fluorescence and electrophoretic mobility shift assay (EMSA). For instance, the ability of a variant to bind a single stranded polynucleotide can be determined as described in the Examples.

The variant retains helicase activity. This can be measured in various ways. For instance, the ability of the variant to translocate along a polynucleotide can be measured using electrophysiology, a fluorescence assay or ATP hydrolysis.

The variant may include modifications that facilitate handling of the polynucleotide encoding the helicase and/or facilitate its activity at high salt concentrations and/or room temperature. Variants typically differ from the wild-type helicase in regions outside of the Hel308 motif or extended Hel308 motif discussed above. However, variants may include modifications within these motif(s).

Over the entire length of the amino acid sequence of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58, a variant will preferably be at least 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed below with reference to SEQ ID NOs: 2 and 4.

A variant of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 preferably comprises the Hel308 motif or extended Hel308 motif of the wild-type sequence as shown in Table 1 above. However, a variant may comprise the Hel308 motif or extended Hel308 motif from a different wild-type sequence. For instance, a variant of SEQ ID NO: 10 may comprise the Hel308 motif or extended Hel308 motif from SEQ ID NO: 13 (i.e. SEQ ID NO: 14 or 15). Variants of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 may also include modifications within the Hel308 motif or extended Hel308 motif of the relevant wild-type sequence. Suitable modifications at X1 and X2 are discussed above when defining the two motifs. A variant of SEQ ID NO: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 or 58 preferably comprises one or more substituted cysteine residues and/or one or more substituted Faz residues to facilitate attachment as discussed above.

A variant of SEQ ID NO: 10 may lack the first 19 amino acids of SEQ ID NO: 10 and/or lack the last 33 amino acids of SEQ ID NO: 10. A variant of SEQ ID NO: 10 preferably comprises a sequence which is at least 70%, at least 75%, at least 80%, at least 85%, at least 90% or more preferably at least 95%, at least 97% or at least 99% homologous based on amino acid identity with amino acids 20 to 211 or 20 to 727 of SEQ ID NO: 10.

SEQ ID NO: 10 (Hel308 Mbu) contains five natural cysteine residues. However, all of these residues are located within or around the DNA binding grove of the enzyme. Once a DNA strand is bound within the enzyme, these natural cysteine residues become less accessible for external modifications. This allows specific cysteine mutants of SEQ ID NO: 10 to be designed and attached to the moiety using cysteine linkage as discussed above. Preferred variants of SEQ ID NO: 10 have one or more of the following substitutions: A29C, Q221C, Q442C, T569C, A577C, A700C and S708C. The introduction of a cysteine residue at one or more of these positions facilitates cysteine linkage as discussed above. Other preferred variants of SEQ ID NO: 10 have one or more of the following substitutions: M2Faz, R10Faz, F15Faz, A29Faz, R185Faz, A268Faz, E284Faz, Y387Faz, F400Faz, Y455Faz, E464Faz, E573Faz, A577Faz, E649Faz, A700Faz, Y720Faz, Q442Faz and S708Faz. The introduction of a Faz residue at one or more of these positions facilitates Faz linkage as discussed above.

The helicase is preferably a RecD helicase. Any RecD helicase may be used in accordance with the invention. The structures of RecD helicases are known in the art (FEBS J. 2008 Apr;275(8):1835-51. Epub 2008 Mar. 9. ATPase activity of RecD is essential for growth of the Antarctic *Pseudomonas syringae* Lz4W at low temperature. Satapathy A K. Pavankumar T L, Bhattacharjya S, Sankaranarayanan R, Ray MK; EMS Microbiol Rev. 2009 May; 33(3):657-87. The diversity of conjugative relaxases and its application in plasmid classification. Garcillán-Barcia M P, Francia M V, de la Cruz: J Biol Chem. 2011 Apr. 8; 286(14):12670-82. Epub 2011 Feb. 2. Functional characterization of the multidomain F plasmid TraI relaxase-helicase. Cheng Y, McNamara D E, Mily M, Nash R P, Redinbo M R).

The RecD helicase typically comprises the amino acid motif X1-X2-X3-G-X4-X5-X6-X7 (hereinafter called the RecD-like motif I; SEQ ID NO: 59), wherein X1 is G, S or A, X2 is any amino acid, X3 is P, A, S or G, X4 is T, A, V, S or C, X5 is G or A, X6 is K or R and X7 is T or S, X1 is preferably G. X2 is preferably G, I, Y or A. X2 is more preferably G. X3 is preferably P or A. X4 is preferably T. A, V or C. X4 is preferably T, V or C, X5 is preferably G. X6 is preferably K. X7 is preferably T or S. The RecD helicase preferably comprises Q-(X8)$_{16-18}$-X1-X2-X3-C-X4-X5-X6-X7 (hereinafter called the extended RecD-like motif I: SEQ ID NOs: 60, 61 and 62), wherein X1 to X7 are as defined above and X8 is any amino acid. There are preferably 16 X8 residues (i.e. (X8)ha) in the extended RecD-like motif I (SEQ ID NO: 60), Suitable sequences for (X8)$_{16}$ can be identified in SEQ ID NOs: 14, 17, 20, 23, 26, 29, 32, 35, 38, 41, 44, 47 and 50 of U.S. Patent Application No. 61/581,332 and SEQ ID NOs: 18, 21, 24, 25, 28, 30, 32, 35, 37, 39 41, 42 and 44 of International Application No. PCT/GB2012/053274 (published as WO 2012/098562).

The RecD helicase preferably comprises the amino acid motif G-G-P-G-Xa-G-K-Xb (hereinafter called the RecD motif I; SEQ ID NO: 63) wherein Xa is T, V or C and Xb is T or S. Xa is preferably T. Xb is preferably T. The Rec-D helicase preferably comprises the sequence G-G-P-G-T-G-K-T (SEQ ID NO: 64), The RecD helicase more preferably comprises the amino acid motif Q-(X8)$_{16-18}$-G-G-P-G-Xa-G-K-Xb (hereinafter called the extended RecD motif 1; SEQ ID NO: 65, 66 and 67), wherein Xa and Xb are as defined above and X8 is any amino acid. There are preferably 16 X8 residues (i.e. (X8)$_{16}$) in the extended RecD motif I (SEQ ID NO: 65). Suitable sequences for (X8) can be identified in SEQ ID NOs: 14, 17, 20, 23, 26, 29, 32, 35, 38, 41, 44, 47 and 50 of U.S. Patent Application No. 61/581,332 and SEQ ID NOs: 18, 21, 24, 25, 28, 30, 32, 35, 37, 39, 41, 42 and 44 of International Application No. PCT/GB2012/053274 (published as WO 2012/098562).

The RecD helicase typically comprises the amino acid motif X1-X2-X3-X4-X5-(X6)$_3$-Q-X7 (hereinafter called the RecD-like motif V: SEQ ID NO: 68), wherein N1 is Y, W or F, X2 is A, T, S, M, C or V. X3 is any amino acid. X4 is T. N or S, X5 is A. T. G, S, V or I, X6 is any amino acid and X7 is G or S. X1 is preferably Y. X2 is preferably A, M, C or V X2 is more preferably A. X3 is preferably L N or L. X3 is more preferably I or L. X4 is preferably T or S. X4 is more preferably T. X5 is preferably A, V or L, X5 is more preferably V or 1. X5 is most preferably V. (X6) is preferably H-K-S, H-M-A, H-G-A or H-R-S. (X6)$_3$ is more preferably H-K-S. X7 is preferably G. The RecD helicase preferably comprises the amino acid motif Xa-Xb-Xc-Xd-Xe-H-K-S-Q-G (hereinafter called the RecD motif V: SEQ I) NO: 69), wherein Xa is Y, W or F, Xb is A, M, C or V, Xc is L M or L, Xd is T or S and Xe is V or I. Xa is preferably Y. Xb is preferably A. Xd is preferably T. Xd is preferably V. Preferred RecD motifs 1 are shown in Table 5 of U.S. Patent Application No. 61/581,332. Preferred RecD-like motifs I are shown in Table 7 of U.S. Patent Application No. 61/581, 332 and International Application No. PCT/GB2012/053274 (published as WO 2012/098562). Preferred RecD-like motifs V are shown in Tables 5 and 7 of U.S. Patent Application No. 61/581,332 and International Application No. PCT/GB2012/053274 (published as WO 2012/098562).

The RecD helicase is preferably one of the helicases shown in Table 4 or 5 of U.S. Patent Application No. 61/581,332 and International Application No. PCT/GB2012/053274 (published as WO 2012/098562) or a variant thereof. Variants are described in U.S. Patent Application No. 61/581,332 and International Application No. PCT/GB2012/053274 (published as WO 2012/098562).

The RecD helicase is preferably a TraI helicase or a TraI subgroup helicase. TraI helicases and TraI subgroup helicases may contain two RecD helicase domains, a relaxase domain and a C-terminal domain. The TraI subgroup helicase is preferably a TrwC helicase. The TraI helicase or TraI subgroup helicase is preferably one of the helicases shown in Table 6 of U.S. Patent Application No. 61/581,332 and International Application No. PCT/GB2012/053274 (published as WO 2012/098562) or a variant thereof. Variants are described in U.S. Patent Application No. 61/581,332 and International Application No. PCT/GB2012/053274 (published as WO 2012/098562).

The TraI helicase or a TraI subgroup helicase typically comprises a RecD-like motif I as defined above (SEQ ID NO: 59) and/or a RecD-like motif V as defined above (SEQ ID NO: 68), The TraI helicase or a TraI subgroup helicase preferably comprises both a RecD-like motif 1 (SEQ ID NO: 59) and a RecD-like motif V (SEQ ID NO: 68). The TraI helicase or a TraI subgroup helicase typically further comprises one of the following two motifs:

The amino acid motif H-(X1)$_2$-X2-R-(X3)$_{5-12}$-H-X4-H (hereinafter called the MobF motif III; SEQ ID NOs: 70 to 77), wherein X1 and X2 are any amino acid and X2 and X4 are independently selected from any amino acid except D, E, K and R. (X1)$_2$ is of course X1a-X1b. X1a and X1b can be the same of different amino acid. X1 a is preferably D or E. X1b is preferably T or D. (X1)$_2$ is preferably DT or ED. (X1)$_2$ is most preferably DT. The 5 to 12 amino acids in (X3) can be the same or different. X2 and X4 arte independently selected from G, P. A, V, L, I, M, C, F, Y, W, H, N, S and T. X2 and X4 are preferably not charged. X2 and X4 are preferably not H. X2 is more preferably N, S or A. X2 is most preferably N. X4 is most preferably F or T. (X3)$_{5-12}$ is preferably 6 or 10 residues in length. Suitable embodiments of (X3)$_{5-12}$ can be derived from SEQ ID NOs: 58, 62, 66 and 70 shown in Table 7 of U.S. Patent Application No. 61/581,332 and SEQ ID NOs: 61, 65, 69, 73, 74, 82, 86, 90, 94, 98, 102, 110, 112, 113, 114, 117, 121, 124, 125. 129, 133, 136, 140, 144, 147, 151, 152, 156, 160, 164 and 168 of International Application No. PCT/GB2012/053274 (published as WO 2012/098562).

The amino acid motif G-X1-X2-X3-X4-X5-X6-X7-H-(X8)--H-X9 (hereinafter called the MobQ motif III; SEQ ID NOs: 78 to 84), wherein X1, X2, X3, X5, X6, X7 and X9 are independently selected from any amino acid except D, E, K and R. X4 is D or E and X8 is any amino acid. X1, X2, X3, X5, X6, X7 and X9 are independently selected from G, P, A, V, L, I, MK C, F, Y, W, H, Q, N, S and T. X1, X2, X3. X5, X6, X7 and X9 are preferably not charged. X1, X2, X3, X5, X6, X7 and X9 are preferably not H, The 6 to 12 amino acids in X8)$_{6-12}$ can be the same or different. Preferred MobF motifs II are shown in Table 7 of U.S. Patent Application No. 61/581,332 and International Application No. PCT/GB2012/053274 (published as WO 2012/098562), The TraI helicase or TraI subgroup helicase is more preferably one of the helicases shown in Table 6 or 7 of U.S. Patent Application No. 61/581,332 and International Application No. PCT/GB2012/053274 (published as WO 2012/098562) or a variant thereof. The TraI helicase most preferably comprises the sequence shown in SEQ ID NO: 85 or a variant thereof. SEQ ID NO: 85 is TraI Eco (NCBI Reference Sequence: NP_061483.1; Genbank AAQ98619.1; SEQ ID NO: 85). TraI Eco comprises the following motifs: RecD-like motif I (GYAGVGKT; SEQ ID NO: 86), RecD-like motif V (YAITAHGAQG; SEQ ID NO: 87) and Mob F motif III (HDTSRDQEPQLHTH; SEQ ID NO: 88).

The TraI helicase or TraI subgroup helicase more preferably comprises the sequence of one of the helicases shown in Table 3 below, i.e. one of SEQ ID NOs: 85, 126, 134 and 138, or a variant thereof.

TABLE 3

More preferred TraI helicase and TraI subgroup helicases

| SEQ ID NO | Name | Strain | NCBI ref | % Identity to TraI Eco | RecD-like motif 1 (SEQ ID NO:) | RecD-like motif V (SEQ ID NO:) | Mob F motif III (SEQ ID NO:) |
|---|---|---|---|---|---|---|---|
| 85 | TraI Eco | Escherichia coli | NCBI Reference Sequence: NP_061483.1 Genbank AAQ98619.1 | - | GYAGVGKT (86) | YAITAHGAQG (87) | HDTSRDQEPQLHTH (88) |
| 126 | TrwC Cba | Citromicrobium bathyomarinum JL354 | NCBI Reference Sequence: ZP_06861556.1 | 15% | GIAGAGKS (131) | YALNVHMAQG (132) | HDTNRNQEPNLHFH (133) |
| 134 | TrwC Hne | Halothiobacillus neapolitanus c2 | NCBI Reference Sequence: YP_003262832.1 | 11.5% | GAAGAGKT (135) | YCITIHRSQG (136) | HEDARTVDDIADPQLHTH (137) |
| 138 | TrwC Eli | Erythrobacter litoralis HTCC2594 | NCBI Reference Sequence: YP_457045.1 | 16% | GIAGAGKS (131) | YALNAHMAQG (139) | HDTNRNQEPNLHFH (133) |

The two or more parts of TrwC Cba connected are preferably (a) amino acids 691 and 346 in SEQ ID NO: 126; (b) amino acids 657 and 339 in SEQ ID NO: 126; (c) amino acids 691 and 350 in SEQ ID NO: 126; or (d) amino acids 690 and 350 in SEQ ID NO: 126. These amino acids are preferably substituted with cysteine such that they can be connected by cysteine linkage.

The invention also provides a mutant TrwC Cba protein which comprises a variant of SEQ ID NO: 126 in which amino acids 691 and 346; 657 and 339; 691 and 350; or 690 and 350 are modified. The amino acids are preferably substituted. The amino acids are more preferably substituted with cysteine. The variant may differ from SEQ ID NO: 126 at positions other than 691 and 346; 657 and 339; 691 and 350; or 690 and 350 as long as the relevant amino acids are modified. The variant will preferably be at least 10% homologous to SEQ ID NO: 126 based on amino acid identity as discussed in more detail below. Amino acid 691 and 346; 657 and 339; 691 and 350; or 690 and 350 are not connected. The mutant TrwC Cba protein of the invention may be used to form a modified helicase of the invention in which the modified amino acids are connected.

A variant of a RecD helicase, TraI helicase or TraI subgroup helicase is an enzyme that has an amino acid sequence which varies from that of the wild-type helicase and which retains polynucleotide binding activity. This can be measured as described above. In particular, a variant of SEQ ID NO: 85, 126, 134 or 138 is an enzyme that has an amino acid sequence which varies from that of SEQ ID NO: 85, 126, 134 or 138 and which retains polynucleotide binding activity. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of the motifs discussed above. However, variants may include modifications within these motif(s).

Over the entire length of the amino acid sequence of any one of SEQ ID NO: 85, 126, 134 and 138, a variant will preferably be at least 10% homologous to that sequence based on amino acid identity. More preferably, the variant polypeptide may be at least 20%, at least 25%, at least 30%, at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 85, 126, 134 and 138 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed above with reference to SEQ ID NOs: 2 and 4.

A variant of any one of SEQ ID NOs: 85, 126, 134 and 138 preferably comprises the RecD-like motif I and/or RecD-like motif V of the wild-type sequence. However, a variant of SEQ ID NO: 85, 126, 134 or 138 may comprise the RecD-like motif I and/or extended RecD-like motif V from a different wild-type sequence. For instance, a variant may comprise any one of the preferred motifs shown in Tables 5 and 7 of U.S. Patent Application No. 61/581,332 and International Application No. PCT/GB2012/053274 (published as WO 2012/098562). Variants of SEQ ID NOs: 85, 126, 134 and 138 may also include modifications within the RecD-like motifs I and V of the wild-type sequence. A variant of SEQ ID NO: 85, 126, 134 or 138 preferably comprises one or more substituted cysteine residues and/or one or more substituted Faz residues to facilitate attachment as discussed above.

The helicase is preferably an XPD helicase. Any XPD helicase may be used in accordance with the invention. XPD helicases are also known as Rad3 helicases and the two terms can be used interchangeably.

The structures of XPD helicases are known in the art (Cell 2008 May 30; 133(5):801-12. Structure of the DNA repair helicase XPD. Liu H, Rudolf J, Johnson K A, McMahon S A, Oke M, Carter L, McRobbie A M, Brown S E, Naismith J H, White M F). The XPD helicase typically comprises the amino acid motif X1-X2-X3-G-X4-X5-X6-E-G (hereinafter called XPD motif V; SEQ ID NO: 89). X1, X2, X5 and X6 are independently selected from any amino acid except D, F, K and R. X1, X2, X5 and X6 are independently selected from G, P, A, V, L 1, M, C, F, Y, W, H, Q, N. S and T. X 1, X2, X5 and X6 are preferably not charged. X 1, X2, X5 and X6 are preferably not H. X1 is more preferably V, L, 1, S or Y. X5 is more preferably V. L, I, N or F. X6 is more preferably S or A. X3 and X4 may be any amino acid residue. X4 is preferably K, R or T.

The XPD helicase typically comprises the amino acid motif Q-Xa-Xb-G-R-Xc-Xd-R-(Xe)$_3$-Xf-(Xg)$_7$-D-Xh-R (hereinafter called XPD motif VI; SEQ ID NO: 90). Xa, Xe and Xg may be any amino acid residue. Xb, Xc and Xd are independently selected from any amino acid except D, E, K and R Xb, Xc and Xd are typically independently selected from G, P, A, V, L, 1, M, C, F, Y, W, H, Q, N, S and T, Xb, Xc and Xd are preferably not charged. Xb, Xc and Xd are preferably not H. Xb is more preferably V, A, L, I or M. Xc is more preferably V, A, L, I, M or C. Xd is more preferably IL H, L, F. M or V. Xf may be D or E. (Xg) is $X_{g1}, X_{g2}, X_{g3}, X_{g4}, X_{g5}, X_{g6}$, and $X_{g7}$. $X_{g2}$ is preferably G, A, S or C. $X_{g5}$ is preferably F, V, L, I, M, A, W or Y. $X_{g6}$ is preferably L, F, Y, M, I or V. $X_{g7}$ is preferably A. C, V, L, Lo M or S.

The XPD helicase preferably comprises XPD motifs V and VL. The most preferred XPD motifs V and VI are shown in Table 5 of U.S. Patent Application No. 61/581,340 and International Application No. PCT/GB2012/053273 (published as WO 2012/098561).

The XPD helicase preferably further comprises an iron sulphide (FeS) core between two Walker A and B motifs (motifs I and II). An FeS core typically comprises an iron atom coordinated between the sulphide groups of cysteine residues. The FeS core is typically tetrahedral.

The XPD helicase is preferably one of the helicases shown in Table 4 or 5 of U.S. Patent Application No. 61/581,340 and International Application No. PCT/GB2012/ 053273 (published as WO 2012/098561) or a variant thereof. The XPD helicase most preferably comprises the sequence shown in SEQ ID NO: 91 or a variant thereof. SEQ ID NO: 91 is XPD Mbu (Methanococcoides burtonii; YP_566221.1; GI:91773529). XPD Mbu comprises YLWGTLSEG (Motif V; SEQ ID NO: 92) and QAMGRVVRSPTDYGARILLDGR (Motif VI; SEQ ID NO: 93).

A variant of a XPD helicase is an enzyme that has an amino acid sequence which varies from that of the wild-type helicase and which retains polynucleotide binding activity. This can be measured as described above. In particular, a variant of SEQ ID NO: 91 is an enzyme that has an amino acid sequence which varies from that of SEQ ID NO: 91 and which retains polynucleotide binding activity. The variant retains helicase activity. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of XPD motifs V and VI discussed above. However, variants may include modifications within one or both of these motifs.

Over the entire length of the amino acid sequence of SEQ ID NO: 91, such as SEQ ID NO: 10, a variant will preferably be at least 10%, preferably 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 91 over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described below. The variant may differ from the wild-type sequence in any of the ways discussed above with reference to SEQ ID NOs: 2 and 4.

A variant of SEQ ID NO: 91 preferably comprises the XPD motif V and/or the XPD motif VI of the wild-type sequence. A variant of SEQ ID NO: 91 more preferably comprises both XPD motifs V and VI of SEQ ID NO: 91. However, a variant of SEQ ID NO: 91 may comprise XPD motifs V and/or VI from a different wild-type sequence. For instance, a variant of SEQ ID NO: 91 may comprise any one of the preferred motifs shown in Table 5 of U.S. Patent Application No. 61/581,340 and International Application No. PCT/GB2012/053273 (published as WO 2012/098561). Variants of SEQ ID NO: 91 may also include modifications within XPD motif V and/or XPD motif VI of the wild-type sequence. Suitable modifications to these motifs are discussed above when defining the two motifs. A variant of SEQ ID NO: 91 preferably comprises one or more substituted cysteine residues and/or one or more substituted Faz residues to facilitate attachment as discussed above.

Modified Hel308 Helicases

The present invention also provides a modified Hel308 helicase that is useful for controlling the movement of a polynucleotide. In accordance with the invention, the helicase is modified by the introduction of one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10), wherein the helicase retains its ability to control the movement of a polynucleotide. The one or more cysteine residues and/or one or more non-natural amino acids are preferably introduced by substitution.

These modifications do not prevent the helicase from binding to a polynucleotide. For instance, the helicase may bind to a polynucleotide via internal nucleotides or at one of its termini. These modifications decrease the ability of the polynucleotide to unbind or disengage from the helicase, particularly from internal nucleotides of the polynucleotide. In other words, the one or more modifications increase the processivity of the Hel308 helicase by preventing dissociation from the polynucleotide strand. The thermal stability of the enzyme is also increased by the one or more modifications giving it an improved structural stability that is beneficial in Strand Sequencing. The modified Hel308 helicases of the invention have all of the advantages and uses discussed above.

The modified Hel308 helicase has the ability to control the movement of a polynucleotide. This can be measured as discussed above. The modified Hel308 helicase is artificial or non-natural.

A modified Hel308 helicase of the invention may be isolated, substantially isolated, purified or substantially purified as discussed above.

The Hel308 helicase preferably comprises a variant of one of the helicases shown in Table 1 above which comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10). The Hel308 helicase preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10).

The Hel308 helicase preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D274, E284, E285, E287, S288, T289, G290, E291, N316, K319, S615, K717 or Y720 in Hel308 Mbu (SEQ ID NO: 10).

Table 4a and 4b below show the positions in other Hel308 helicases which correspond to D274, E284, E285, S288, S615, K717, Y720, E287, T289, G290, E291, N316 and K319 in Hel308 Mbu (SEQ ID NO: 10). For instance, in Hel308 Hvo (SEQ ID NO:16), E283 corresponds to D274 in Hel308 Mbu, E293 corresponds to E284 in Hel308 Mbu, I294 corresponds to E285 in Hel308 Mbu, V297 corresponds to S288 in Hel308 Mbu, D671 corresponds to S615 in Hel308 Mbu, K775 corresponds to K717 in Hel308 Mbu and E778 corresponds to Y720 in Hel308 Mbu. The lack of a corresponding position in another Hel308 helicase is marked as a "-".

TABLE 4a

Positions which correspond to D274, E284, E285, S288, S615, K717 and Y720 in Hel308 Mbu (SEQ ID NO: 10).

| SEQ ID NO: | Hel308 homologue | A | B | C | D | E | F | G |
|---|---|---|---|---|---|---|---|---|
| 10 | Mbu | D274 | E284 | E285 | S288 | S615 | K717 | Y720 |
| 13 | Pfu | L265 | E275 | L276 | S279 | P585 | K690 | E693 |
| 16 | Hvo | E283 | E293 | I294 | V297 | D671 | K775 | E778 |
| 19 | Hla | E283 | E293 | I294 | G297 | D668 | R775 | E778 |
| 22 | Csy | D280 | K290 | I291 | S294 | P589 | T694 | N697 |
| 25 | Sso | L281 | K291 | Q292 | D295 | D596 | K702 | Q705 |
| 28 | Mfr | H264 | E272 | K273 | A276 | G576 | K678 | E681 |
| 29 | Mok | S279 | L289 | S290 | D293 | P649 | K753 | R756 |
| 32 | Mig | Y276 | L286 | S287 | D290 | P579 | K679 | K682 |
| 33 | Tga | L266 | S276 | L277 | Q280 | P583 | K689 | D692 |
| 34 | Tba | L287 | E297 | L298 | S301 | S604 | K710 | E713 |
| 37 | Tsi | L289 | Q299 | L300 | G303 | N606 | G712 | E715 |
| 38 | Mba | E274 | D284 | E285 | E288 | S589 | K691 | D694 |
| 39 | Mac | E274 | D284 | E285 | E288 | P590 | K692 | E695 |
| 40 | Mmah | H272 | L282 | S283 | D286 | P621 | K725 | K728 |
| 41 | Mmaz | E274 | D284 | E285 | E288 | P590 | K692 | E698 |
| 42 | Mth | A269 | L279 | A280 | L283 | H575 | K677 | E680 |
| 43 | Mzh | H274 | Q284 | E285 | E288 | P596 | K699 | Q702 |
| 44 | Mev | G274 | E284 | E285 | E288 | T590 | K691 | Y694 |
| 45 | Mma | H272 | L282 | S283 | D286 | P621 | K725 | K728 |
| 46 | Nma | G277 | T287 | E288 | E291 | D634 | K737 | E740 |
| 47 | Mbo | A270 | E277 | R278 | E281 | S583 | G685 | E688 |
| 48 | Fac | Q264 | F267 | E268 | E271 | P559 | K663 | K666 |
| 49 | Mfe | R275 | L285 | S286 | E289 | P576 | K676 | K679 |
| 50 | Mja | I273 | L283 | S284 | E287 | P574 | K674 | K677 |
| 51 | Min | R257 | L267 | S268 | D271 | P554 | K651 | K654 |
| 52 | Mhu | S269 | Q277 | E278 | R281 | S583 | G685 | R688 |
| 53 | Afu | K268 | K277 | A278 | E281 | D575 | R677 | E680 |
| 54 | Htu | D277 | D287 | D288 | D291 | D626 | K729 | E732 |
| 55 | Hpa | D276 | D286 | Q287 | D290 | D595 | K707 | E710 |
| 58 | Hsp (ski2-like helicase) | E286 | E296 | I297 | V300 | D633 | A737 | E740 |

TABLE 4b

Positions which correspond to E287, T289, G290, E291, N316 and K319 in Hel308 Mbu (SEQ ID NO: 10).

| SEQ ID NO: | Hel308 homologue | H | I | J | K | L | M |
|---|---|---|---|---|---|---|---|
| 10 | Mbu | E287 | T289 | G290 | E291 | N316 | K319 |
| 13 | Pfu | D278 | L280 | E281 | E282 | D307 | V310 |
| 16 | Hvo | D296 | S298 | D299 | T300 | E324 | T327 |
| 19 | Hla | S296 | S298 | D299 | T300 | E324 | A327 |
| 22 | Csy | S293 | G295 | G296 | E297 | D322 | S325 |
| 25 | Sso | D294 | I296 | E297 | E298 | A325 | D328 |
| 28 | Mfr | E275 | A277 | A278 | E279 | M304 | T307 |
| 29 | Mok | L292 | N294 | P295 | T296 | E320 | K323 |
| 32 | Mig | L289 | P291 | P292 | T293 | E317 | K320 |
| 33 | Tga | S279 | L281 | E282 | D283 | V308 | T311 |
| 34 | Tba | E300 | L302 | E303 | S304 | A329 | T332 |
| 37 | Tsi | D302 | L304 | D305 | T306 | T331 | S334 |
| 38 | Mba | L287 | N289 | S290 | E291 | P316 | E319 |
| 39 | Mac | L287 | N289 | S290 | E291 | P316 | E319 |
| 40 | Mmah | L285 | R287 | P288 | V289 | K313 | K316 |
| 41 | Mmaz | I287 | N289 | S290 | E291 | P316 | E319 |
| 42 | Mth | R282 | S284 | G285 | E286 | E311 | R314 |
| 43 | Mzh | G287 | A289 | G290 | E291 | E316 | R319 |
| 44 | Mev | L287 | T289 | S290 | D291 | A316 | K319 |
| 45 | Mma | L285 | R287 | P288 | V289 | K313 | K316 |
| 46 | Nma | R290 | D292 | S293 | D294 | T319 | S322 |
| 47 | Mbo | L280 | G282 | T283 | P284 | K309 | S312 |
| 48 | Fac | L270 | I272 | P273 | P274 | D299 | T302 |
| 49 | Mfe | L288 | P290 | P291 | T292 | Q316 | K319 |
| 50 | Mja | L286 | P288 | P289 | T290 | Q314 | K317 |
| 51 | Min | F270 | P272 | P273 | T274 | E298 | K301 |
| 52 | Mhu | R280 | L282 | R283 | D284 | Q309 | T312 |
| 53 | Afu | L280 | E282 | N283 | E284 | G309 | R312 |
| 54 | Htu | R290 | D292 | S293 | D294 | T319 | S322 |
| 55 | Hpa | R289 | V291 | S292 | D293 | D318 | S321 |
| 58 | Hsp (ski2-like helicase) | G299 | S301 | D302 | T303 | E327 | E330 |

The Hel308 helicase more preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D274, E284, E285, S288, S615, K717 and Y720 in Hel308 Mbu (SEQ ID NO: 10). The relevant positions are shown in columns A to G in Table 4a above.

The helicase may comprise a cysteine residue at one, two, three, four, five, six or seven of the positions which correspond to D274, E284, E285, S288, S615, K717 and Y720 in Hel308 Mbu (SEQ ID NO: 10). Any combination of these positions may be substituted with cysteine. For instance, for each row of Table 4a above, the helicase of the invention may comprise a cysteine at any of the following combinations of the positions labelled A to G in that row: {A}, {B}, {C}, {D}, {G}, {E}, {F}, {A and B}, {A and C}, {A and D}, {A and G}, {A and E}, {A and F}, {B and C}, {B and D}, {B and G}, {B and E}, {B and F}, {C and D}, {C and G}, {C and E}, {C and F}, {D and G}, {D and E}, {D and F}, {G and E}, {G and F}, {E and F}, {A, B and C}, {A, B and D}, {A, B and G}, {A, B and E}, {A, B and F}, {A, C and D}, {A, C and G}, {A, C and E}, {A, C and F}, {A, D and G}, {A, D and E}, {A, D and F}, {A, G and E}, {A, G and F}, {A, E and F}, {B, C and D}, {B, C and G}, {B, C and E}, {B, C and F}, {B, D and G}, {B, D and E}, {B, D and F}, {B, G and E}, {B, G and F}, {B, E and F}, {C, D and G}, {C, D and E}, {C, D and F}, {C, G and E}, {C, E and F}, {D, G and E}, {D, G and F}, {D, E and F}, {G, E and F}, {A, B, C and D}, {A, B, C and G}, {A, B, C and E}, {A, B, C and F}, {A, B, D and G}, {A, B, D and E}, {A, B, D and F}, {A, B, G and E}, {A, B, G and F}, {A, B, E and F}, {A, C, D and G}, {A, C, D and E}, {A, C, D and F}, {A, C, G and E}, {A, C, G and F}, {A, C, E and F}, {A, D, G and E}, {A, D, G and F}, {A, D, E and F}, {A, G, E and F}, {B, C, D and G}, {B, C, D and E}, {B, C, D and F}, {B, C, G and E}, {B, C, G and F}, {B, C, E and F}, {B, D, G and E}, {B, D, G and F}, {B, D, E and F}, {B, G, E and F}, {C, D, G and E}, {C, D, G and F}, {C, D, E and F}, {C, G, E and F}, {D, G, E and F}, {A, B, C, D and G}, {A, B, C, D and E}, {A, B, C, D and F}, {A, B, C, G and E}, {A, B, C, G and F}, {A, B, C, E and F}, {A, B, D, G and E}, {A, B, D, G and F}, {A, B, D, E and F}, {A, B, G, E and F}, {A, C, D, G and E}, {A, C, D, G and F}, {A, C, D, E and F}, {A, C, G, E and F}, {A, D, G, E and F}, {B, C, D, G and E}, {B, C, D, G and F}, {B, C, D, E and F}, {B, C, G, E and F}, {B, D, G, E and F}, {C, D, G, E and F}, {A, B, C, D, G and E}, {A, B, C, D, G and F}, {A, B, C, D, E and F}, {A, B, C, G, E and F}, {A, B, D, G, E and F}, {A, C, D, G, E and F}, {B, C, D, G, E and F}, or {A, B, C, D, G, E and F}.

The helicase may comprises a non-natural amino acid, such as Faz, at one, two, three, four, five, six or seven of the positions which correspond to D274, E284, E285, S288, S615, K717 and Y720 in Hel308 Mbu (SEQ ID NO: 10). Any combination of these positions may be substituted with a non-natural amino acid, such as Faz. For instance, for each row of Table 4a above, the helicase of the invention may comprise a non-natural amino acid, such as Faz, at any of the combinations of the positions labelled A to G above.

The helicase may comprise a combination of one or more cysteines and one or more non-natural amino acids, such as Faz, at two or more of the positions which correspond to D274, E284, E285, S288, S615, K717 and Y720 in Hel308 Mbu (SEQ ID NO: 10). Any combination of one or more cysteine residues and one or more non-natural amino acids, such as Faz, may be present at the relevant positions. For instance, for each row of Table 4a and 4b above, the helicase of the invention may comprise one or more cysteines and one or more non-natural amino acids, such as Faz, at any of the combinations of the positions labelled A to G above.

The Hel308 helicase more preferably comprises a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 which comprises one or more cysteine residues and/or one or more non-natural amino acids at one or more of the positions which correspond to D274, E284, E285, S288 and S615 in Hel308 Mbu (SEQ ID NO: 10). The relevant positions are shown in columns A to E in Table 4a above.

The helicase may comprise a cysteine residue at one, two, three, four or five, six or seven of the positions which correspond to D274, E284, E285, S288, S615, K717 and Y720 in Hel308 Mbu (SEQ ID NO: 10). Any combination of these positions may be substituted with cysteine. For instance, for each row of Table 4a above, the helicase of the invention may comprise a cysteine at any of the following combinations of the positions labelled A to E in that row: {A}, {B}, {C}, {D}, {E}, {A and B}, {A and C}, {A and D}, {A and E}, {B and C}, {B and D}, {B and E}, {C and D}, {C and E}, {D and E}, {A, B and C}, {A, B and D}, {A, B and E}, {A, C and D}, {A, C and E}, {A, D and E}, {B, C and D}, {B, C and E}, {B, D and E}, {C, D and E}, {A, B, C and D}, {A, B, C and E}, {A, B, D and E}, {A, C, D and E}, {B, C, D and E} or {A, B, C, D and E}.

The helicase may comprises a non-natural amino acid, such as Faz, at one, two, three, four or five of the positions which correspond to D274, E284, E285, S288, S615, K717 and Y720 in Hel308 Mbu (SEQ ID NO: 10). Any combination of these positions may be substituted with a non-natural amino acid, such as Faz. For instance, for each row of Table 4a above, the helicase of the invention may comprise a non-natural amino acid, such as Faz, at any of the combinations of the positions labelled A to E above.

The helicase may comprise a combination of one or more cysteines and one or more non-natural amino acids, such as Faz, at two or more of the positions which correspond to D274, E284, E285, S288 and S615 in Hel308 Mbu (SEQ ID NO: 10). Any combination of one or more cysteine residues and one or more non-natural amino acids, such as Faz, may be present at the relevant positions. For instance, for each row of Table 4a above, the helicase of the invention may comprise one or more cysteines and one or more non-natural amino acids, such as Faz, at any of the combinations of the positions labelled A to E above.

The Hel308 helicase preferably comprises a variant of the sequence of Hel308 Mbu (i.e. SEQ ID NO: 10) which comprises one or more cysteine residues and/or one or more non-natural amino acids at D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724. The variant preferably comprises D272C, N273C, D274C, G281C, E284C, E285C, E287C, S288C, T289C, G290C, E291C, D293C, T294C, N300C, R303C, K304C, N314C, S315C, N316C, H317C, R318C, K319C, L320C, E322C, R326C, N328C, S615C, K717C, Y720C, N721C or S724C. The variant preferably comprises D272Faz, N273Faz, D274Faz, G281Faz, E284Faz, E285Faz, E287Faz, S288Faz, T289Faz, G290Faz, E291Faz, D293Faz, T294Faz, N300Faz, R303Faz, K304Faz, N314Faz, S315Faz, N316Faz, H317 Faz, R318Faz, K319Faz, L320Faz, E322Faz, R326Faz, N328Faz, S615Faz, K717Faz, Y720Faz, N721Faz or S724Faz.

The Hel308 helicase preferably comprises a variant of the sequence of Hel308 Mbu (i.e. SEQ ID NO: 10) which comprises one or more cysteine residues and/or one or more non-natural amino acids at D274, E284, E285, S288, S615, K717 and Y720. The helicase of the invention may comprise one or more cysteines, one or more non-natural amino acids, such as Faz, or a combination thereof at any of the combinations of the positions labelled A to G above.

The Hel308 helicase preferably comprises a variant of the sequence of Hel308 Mbu (i.e. SEQ ID NO: 10) which comprises one or more cysteine residues and/or one or more non-natural amino acids at one or more of D274, E284, E285, S288 and S615. For instance, for Hel308 Mbu (SEQ ID NO: 10), the helicase of the invention may comprise a cysteine or a non-natural amino acid, such as Faz, at any of the following combinations of positions: {D274}, {E284}, {E285}, {S288}, {S615}, {D274 and E284}, {D274 and E285}, {D274 and S288}, {D274 and S615}, {E284 and E285}, {E284 and S288}, {E284 and S615}, {E285 and S288}, {E285 and S615}, {S288 and S615}, {D274, E284 and E285}, {D274, E284 and S288}, {D274, E284 and S615}, {D274, E285 and S288}, {D274, E285 and S615}, {D274, S288 and S615}, {E284, E285 and S288}, {E284, E285 and S615}, {E284, S288 and S615}, {E285, S288 and S615}, {D274, E284, E285 and S288}, {D274, E284, E285 and S615}, {D274, E284, S288 and S615}, {D274, E285, S288 and S615}, {E284, E285, S288 and S615} or {D274, E284, E285, S288 and S615}.

The helicase preferably comprises a variant of SEQ ID NO: 10 which comprises (a) E284C and S615C, (b), E284Faz and S615Faz, (c) E284C and S615Faz or (d) E284Faz and S615C.

The helicase more preferably comprises the sequence shown in SEQ ID NO: 10 with E284C and S615C.

Preferred non-natural amino acids for use in the invention include, but are not limited, to 4-Azido-L-phenylalanine (Faz), 4-Acetyl-L-phenylalanine, 3-Acetyl-L-phenylalanine, 4-Acetoacetyl-L-phenylalanine, O-Allyl-L-tyrosine, 3-(Phenylselanyl)-L-alanine, O-2-Propyn-1-yl-L-tyrosine, 4-(Dihydroxyboryl)-L-phenylalanine, 4-[(Ethylsulfanyl)carbonyl]-L-phenylalanine, (2S)-2-amino-3-{4-[(propan-2-ylsulfanyl)carbonyl]phenyl}propanoic acid, (2S)-2-amino-3-{4-[(2-amino-3-sulfanylpropanoyl)amino]phenyl}propanoic acid, O-Methyl-L-tyrosine, 4-Amino-L-phenylalanine, 4-Cyano-L-phenylalanine, 3-Cyano-L-phenylalanine, 4-Fluoro-L-phenylalanine, 4-Iodo-L-phenylalanine, 4-Bromo-L-phenylalanine, O-(Trifluoromethyl)tyrosine, 4-Nitro-L-phenylalanine, 3-Hydroxy-L-tyrosine, 3-Amino-L-tyrosine, 3-Iodo-L-tyrosine, 4-Isopropyl-L-phenylalanine, 3-(2-Naphthyl)-L-alanine, 4-Phenyl-L-phenylalanine, (2S)-2-amino-3-(naphthalen-2-ylamino)propanoic acid, 6-(Methylsulfanyl)norleucine, 6-Oxo-L-lysine, D-tyrosine, (2R)-2-Hydroxy-3-(4-hydroxyphenyl)propanoic acid, (2R)-2-Ammoniooctanoate3-(2,2'-Bipyridin-5-yl)-D-alanine, 2-amino-3-(8-hydroxy-3-quinolyl)propanoic acid, 4-Benzoyl-L-phenylalanine, S-(2-Nitrobenzyl)cysteine, (2R)-2-amino-3-[(2-nitrobenzyl)sulfanyl]propanoic acid, (2S)-2-amino-3-[(2-nitrobenzyl)oxy]propanoic acid, 0-(4,5-Dimethoxy-2-nitrobenzyl)-L-serine, (2S)-2-amino-6-({[(2-nitrobenzyl)oxy]carbonyl}amino)hexanoic acid, O-(2-Nitrobenzyl)-L-tyrosine, 2-Nitrophenylalanine, 4-[(E)-Phenyldiazenyl]-L-phenylalanine, 4-[3-(Trifluoromethyl)-3H-diaziren-3-yl]-D-phenylalanine, 2-amino-3-[[5-(dimethylamino)-1-naphthyl]sulfonylamino]propanoic acid, (2S)-2-amino-4-(7-hydroxy-2-oxo-2H-chromen-4-yl)butanoic acid, (2S)-3-[(6-acetylnaphthalen-2-yl)amino]-2-aminopropanoic acid, 4-(Carboxymethyl)phenylalanine, 3-Nitro-L-tyrosine, O-Sulfo-L-tyrosine, (2R)-6-Acetamido-2-ammoniohexanoate, 1-Methylhistidine, 2-Aminononanoic acid, 2-Aminodecanoic acid, L-Homocysteine, 5-Sulfanylnorvaline, 6-Sulfanyl-L-norleucine, 5-(Methylsulfanyl)-L-norvaline, $N^6$-{[(2R,3R)-3-Methyl-3,4-dihydro-2H-pyrrol-2-yl]carbonyl}-L-lysine, $N^6$-[(Benzyloxy)carbonyl]lysine, (2S)-2-amino-6-[(cyclopentylcarbonyl)amino]hexanoic acid, $N^6$-[(Cyclopentyloxy)carbonyl]-L-lysine, (2S)-2-amino-6-{[(2R)-tetrahydrofuran-2-ylcarbonyl]amino}hexanoic acid, (2S)-2-amino-8-[(2R,3S)-3-ethynyltetrahydrofuran-2-yl]-8-oxooctanoic acid, $N^6$-(tert-Butoxycarbonyl)-L-lysine, (2S)-2-Hydroxy-6-({[(2-methyl-2-propanyl)oxy]carbonyl}amino)hexanoic acid, $N^6$-[(Allyloxy)carbonyl]lysine, (2S)-2-amino-6-({[(2-azidobenzyl)oxy]carbonyl}amino)hexanoic acid, $N^6$-L-Prolyl-L-lysine, (2S)-2-amino-6-{[(prop-2-yn-1-yloxy)carbonyl]amino}hexanoic acid and $N^6$-[(2-Azidoethoxy)carbonyl]-L-lysine.

The most preferred non-natural amino acid is 4-azido-L-phenylalanine (Faz).

As discussed above, variant of a Hel308 helicase is an enzyme that has an amino acid sequence which varies from that of the wild-type helicase and which retains polynucleotide binding activity. In the Hel308 helicases of the invention, a variant of one of SEQ ID NOs: 10, 13, 16, 19, 22, 25, 28, 29, 32, 33, 34, 37, 38, 39, 40, 41, 42, 43, 44, 45, 46, 47, 48, 49, 50, 51, 52, 53, 54, 55 and 58 may comprise additional modifications as long as it comprises one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328, S615, K717, Y720, N721 and S724 in Hel308 Mbu (SEQ ID NO: 10). Suitable modifications and variants are discussed above with reference to the embodiments with two or more parts connected.

A variant may comprise the mutations in domain 5 disclosed in Woodman et al. (J. Mol. Biol. (2007)374, 1139-1144). These mutations correspond to R685A, R687A and R689A in SEQ ID NO: 10.

Connecting Two or More Parts of the Hel308 Helicases of the Invention

The Hel308 helicases modified in the invention comprise a polynucleotide binding domain. Polynucleotide binding domains are defined above. The polynucleotide binding domain of an unmodified Hel308 helicase for use in the invention comprises an opening through which a polynucleotide can unbind from the helicase.

In a preferred embodiment, the Hel308 helicase is further modified such that two or more parts of the helicase are connected to reduce the size of an opening in the polynucleotide binding domain through which a polynucleotide can unbind from the helicase. The two or more parts may be connected in any of the ways discussed above.

No Connection

In another embodiment, the Hel308 helicase is not modified such that two or more parts of the helicase are connected to reduce the size of an opening in the polynucleotide binding domain through which a polynucleotide can unbind from the helicase. Preferably, none of the one or more cysteines or one or more non-natural amino acids is connected to another amino acid in the helicase. Preferably, no two amino acids in the helicase are connected together via their natural or non-natural R groups.

Construct

The invention also provides a construct comprising a helicase of the invention and an additional polynucleotide binding moiety, wherein the helicase is attached to the polynucleotide binding moiety and the construct has the ability to control the movement of a polynucleotide. The helicase is attached to the additional polynucleotide binding moiety. The construct is artificial or non-natural.

A construct of the invention is a useful tool for controlling the movement of a polynucleotide during Strand Sequencing. A construct of the invention is even less likely than a modified helicase of the invention to disengage from the polynucleotide being sequenced. The construct can provide even greater read lengths of the polynucleotide as it controls the translocation of the polynucleotide through a nanopore.

A targeted construct that binds to a specific polynucleotide sequence can also be designed. As discussed in more detail below, the polynucleotide binding moiety may bind to a specific polynucleotide sequence and thereby target the helicase portion of the construct to the specific sequence.

The construct has the ability to control the movement of a polynucleotide. This can be determined as discussed above.

A construct of the invention may be isolated, substantially isolated, purified or substantially purified. A construct is isolated or purified if it is completely free of any other components, such as lipids, polynucleotides or pore monomers. A construct is substantially isolated if it is mixed with carriers or diluents which will not interfere with its intended use. For instance, a construct is substantially isolated or substantially purified if it is present in a form that comprises less than 10%, less than 5%, less than 2% or less than 1% of other components, such as lipids, polynucleotides or pore monomers.

The helicase is preferably covalently attached to the additional polynucleotide binding moiety. The helicase may be attached to the moiety at more than one, such as two or three, points.

The helicase can be covalently attached to the moiety using any method known in the art. Suitable methods are discussed above with reference to connecting the two or more parts.

The helicase and moiety may be produced separately and then attached together. The two components may be attached in any configuration. For instance, they may be attached via their terminal (i.e. amino or carboxy terminal) amino acids. Suitable configurations include, but are not limited to, the amino terminus of the moiety being attached to the carboxy terminus of the helicase and vice versa. Alternatively, the two components may be attached via amino acids within their sequences. For instance, the moiety may be attached to one or more amino acids in a loop region of the helicase. In a preferred embodiment, terminal amino acids of the moiety are attached to one or more amino acids in the loop region of a helicase.

In a preferred embodiment, the helicase is chemically attached to the moiety, for instance via one or more linker molecules as discussed above. In another preferred embodiment, the helicase is genetically fused to the moiety. A helicase is genetically fused to a moiety if the whole construct is expressed from a single polynucleotide sequence. The coding sequences of the helicase and moiety may be combined in any way to form a single polynucleotide sequence encoding the construct. Genetic fusion of a pore to a nucleic acid binding protein is discussed in International Application No. PCT/GB09/001679 (published as WO 2010/004265).

The helicase and moiety may be genetically fused in any configuration. The helicase and moiety may be fused via their terminal amino acids. For instance, the amino terminus of the moiety may be fused to the carboxy terminus of the helicase and vice versa. The amino acid sequence of the moiety is preferably added in frame into the amino acid sequence of the helicase. In other words, the moiety is preferably inserted within the sequence of the helicase. In such embodiments, the helicase and moiety are typically attached at two points, i.e. via the amino and carboxy terminal amino acids of the moiety. If the moiety is inserted within the sequence of the helicase, it is preferred that the amino and carboxy terminal amino acids of the moiety are in close proximity and are each attached to adjacent amino acids in the sequence of the helicase or variant thereof. In a preferred embodiment, the moiety is inserted into a loop region of the helicase.

The construct retains the ability of the helicase to control the movement of a polynucleotide. This ability of the helicase is typically provided by its three dimensional structure that is typically provided by its β-strands and α-helices. The α-helices and β-strands are typically connected by loop regions. In order to avoid affecting the ability of the helicase to control the movement of a polynucleotide, the moiety is preferably genetically fused to either end of the helicase or inserted into a surface-exposed loop region of the helicase. The loop regions of specific helicases can be identified using methods known in the art. In the Hel308 embodiments of the invention, the moiety is preferably not genetically fused to any of the α-helixes.

The helicase may be attached directly to the moiety. The helicase is preferably attached to the moiety using one or more, such as two or three, linkers as discussed above. The one or more linkers may be designed to constrain the mobility of the moiety. The helicase and/or the moiety may be modified to facilitate attachment of the one or more linker as discussed above.

Cleavable linkers can be used as an aid to separation of constructs from non-attached components and can be used to further control the synthesis reaction. For example, a heterobifunctional linker may react with the helicase, but not the moiety. If the free end of the linker can be used to bind the helicase protein to a surface, the unreacted helicases from the first reaction can be removed from the mixture. Subsequently, the linker can be cleaved to expose a group that reacts with the moiety. In addition, by following this sequence of linkage reactions, conditions may be optimised first for the reaction to the helicase, then for the reaction to the moiety after cleavage of the linker. The second reaction would also be much more directed towards the correct site of reaction with the moiety because the linker would be confined to the region to which it is already attached.

The helicase may be covalently attached to the bifunctional crosslinker before the helicase/crosslinker complex is covalently attached to the moiety. Alternatively, the moiety may be covalently attached to the bifunctional crosslinker before the bifunctional crosslinker/moiety complex is attached to the helicase. The helicase and moiety may be covalently attached to the chemical crosslinker at the same time.

Preferred methods of attaching the helicase to the moiety are cysteine linkage and Faz linkage as described above. In a preferred embodiment, a reactive cysteine is presented on a peptide linker that is genetically attached to the moiety. This means that additional modifications will not necessarily be needed to remove other accessible cysteine residues from the moiety.

Cross-linkage of helicases or moieties to themselves may be prevented by keeping the concentration of linker in a vast excess of the helicase and/or moiety. Alternatively, a "lock and key" arrangement may be used in which two linkers are used. Only one end of each linker may react together to form a longer linker and the other ends of the linker each react with a different part of the construct (i.e. helicase or moiety). This is discussed in more detail below.

The site of attachment is selected such that, when the construct is contacted with a polynucleotide, both the helicase and the moiety can bind to the polynucleotide and control its movement.

Attachment can be facilitated using the polynucleotide binding activities of the helicase and the moiety. For instance, complementary polynucleotides can be used to bring the helicase and moiety together as they hybridize. The helicase can be bound to one polynucleotide and the moiety can be bound to the complementary polynucleotide. The two polynucleotides can then be allowed to hybridise to each other. This will bring the helicase into close contact with the moiety, making the linking reaction more efficient. This is especially helpful for attaching two or more helicases in the correct orientation for controlling movement of a target polynucleotide. An example of complementary polynucleotides that may be used are shown below.

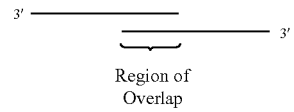
Region of Overlap

For helicase-Phi29 constructs the DNA below could be used.

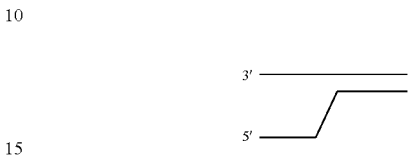

Tags can be added to the construct to make purification of the construct easier. These tags can then be chemically or enzymatically cleaved off, if their removal is necessary. Fluorophores or chromophores can also be included, and these could also be cleavable.

A simple way to purify the construct is to include a different purification tag on each protein (i.e. the helicase and the moiety), such as a hexa-His-tag and a Strep-tag®. If the two proteins are different from one another, this method is particularly useful. The use of two tags enables only the species with both tags to be purified easily.

If the two proteins do not have two different tags, other methods may be used. For instance, proteins with free surface cysteines or proteins with linkers attached that have not reacted to form a construct could be removed, for instance using an iodoacetamide resin for maleimide linkers.

Constructs of the invention can also be purified from unreacted proteins on the basis of a different DNA processivity property. In particular, a construct of the invention can be purified from unreacted proteins on the basis of an increased affinity for a polynucleotide, a reduced likelihood of disengaging from a polynucleotide once bound and/or an increased read length of a polynucleotide as it controls the translocation of the polynucleotide through a nanopore A targeted construct that binds to a specific polynucleotide sequence can also be designed.

As discussed in more detail below, the polynucleotide binding moiety may bind to a specific polynucleotide sequence and thereby target the helicase portion of the construct to the specific sequence.

Polynucleotide Binding Moiety

The constructs of the invention comprise a polynucleotide binding moiety. A polynucleotide binding moiety is a polypeptide that is capable of binding to a polynucleotide. The moiety is preferably capable of specific binding to a defined polynucleotide sequence. In other words, the moiety preferably binds to a specific polynucleotide sequence, but displays at least 10 fold less binding to different sequences or more preferably at least 100 fold less binding to different sequences or most preferably at least 1000 fold less binding to different sequences. The different sequence may be a random sequence. In some embodiments, the moiety binds to a specific polynucleotide sequence, but binding to different sequences cannot be measured. Moieties that bind to specific sequences can be used to design constructs that are targeted to such sequences.

The moiety typically interacts with and modifies at least one property of a polynucleotide. The moiety may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), cytidine monophosphate (CMP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

It is preferred that the tertiary structure of the moiety is known. Knowledge of the three dimensional structure of the moiety allows modifications to be made to the moiety to facilitate its function in the construct of the invention.

The moiety may be any size and have any structure. For instance, the moiety may be an oligomer, such as a dimer or trimer. The moiety is preferably a small, globular polypeptide formed from one monomer. Such moieties are easy to handle and are less likely to interfere with the ability of the helicase to control the movement of the polynucleotide, particularly if fused to or inserted into the sequence of the helicase.

The amino and carboxy terminii of the moiety are preferably in close proximity. The amino and carboxy terminii of the moiety are more preferably presented on same face of the moiety. Such embodiments facilitate insertion of the moiety into the sequence of the helicase. For instance, if the amino and carboxy terminii of the moiety are in close proximity, each can be attached by genetic fusion to adjacent amino acids in the sequence of the helicase.

It is also preferred that the location and function of the active site of the moiety is known. This prevents modifications being made to the active site that abolish the activity of the moiety. It also allows the moiety to be attached to the helicase so that the moiety binds to the polynucleotide and controls its movement. Knowledge of the way in which a moiety may bind to and orient polynucleotides also allows an effective construct to be designed.

The constructs of the invention are useful in Strand Sequencing. The moiety preferably binds the polynucleotide in a buffer background which is compatible with Strand Sequencing and the discrimination of the nucleotides. The moiety preferably has at least residual activity in a salt concentration well above the normal physiological level, such as from 100 mM to 2M. The moiety is more preferably modified to increase its activity at high salt concentrations. The moiety may also be modified to improve its processivity, stability and shelf life.

Suitable modifications can be determined from the characterisation of polynucleotide binding moieties from extremphiles such as halophilic, moderately halophilic bacteria, thermophilic and moderately thermophilic organisms, as well as directed evolution approaches to altering the salt tolerance, stability and temperature dependence of mesophilic or thermophilic exonucleases.

The polynucleotide binding moiety preferably comprises one or more domains independently selected from helix-hairpin-helix (HhH) domains, eukaryotic single-stranded binding proteins (SSBs), bacterial SSBs, archaeal SSBs, viral SSBs, double-stranded binding proteins, sliding clamps, processivity factors, DNA binding loops, replication initiation proteins, telomere binding proteins, repressors, zinc fingers and proliferating cell nuclear antigens (PCNAs).

The helix-hairpin-helix (HhH) domains are polypeptide motifs that bind DNA in a sequence non-specific manner. They have been shown to confer salt stability and processivity when fused to polymerases, as well as increasing their thermal stability. Suitable domains include domain H (residues 696-751) and domain HI (residues 696-802) from Topoisomerase V from *Methanopyrus kandleri* (SEQ ID NO: 129). As discussed below, the polynucleotide binding moiety may be domains H-L of SEQ ID NO: 129 as shown in SEQ ID NO: 130. Topoisomerase V from *Methanopyrus kandleri* is an example of a double-stranded binding protein as discussed below.

The HhH domain preferably comprises the sequence shown in SEQ ID NO: 94 or 107 or 108 or a variant thereof. This domain increases the processivity and the salt tolerance of a helicase when used in a construct of the invention. A variant of SEQ ID NO: 94 or 107 or 108 is a protein that has an amino acid sequence which varies from that of SEQ ID NO: 94 or 107 or 108 and which retains polynucleotide binding activity. This can be measured as described above. A variant typically has at least 50% homology to SEQ ID NO: 94 or 107 or 108 based on amino acid identity over its entire sequence (or any of the % homologies discussed above in relation to helicases) and retains polynucleotide binding activity. A variant may differ from SEQ ID NO: 94 or 107 or 108 in any of the ways discussed above in relation to helicases or below in relation to pores. A variant preferably comprises one or more substituted cysteine residues and/or one or more substituted Faz residues to facilitate attachment to the helicase as discussed above.

SSBs bind single stranded DNA with high affinity in a sequence non-specific manner. They exist in all domains of life in a variety of forms and bind DNA either as monomers or multimers. Using amino acid sequence alignment and logorithms (such as Hidden Markov models) SSBs can be classified according to their sequence homology. The Pfam family, PF00436, includes proteins that all show sequence similarity to known SSBs. This group of SSBs can then be further classified according to the Structural Classification of Proteins (SCOP). SSBs fall into the following lineage: Class; All beta proteins, Fold; OB-fold, Superfamily: Nucleic acid-binding proteins, Family; Single strand DNA-binding domain, SSB. Within this family SSBs can be classified according to subfamilies, with several type species often characterised within each subfamily.

The SSB may be from a eukaryote, such as from humans, mice, rats, fungi, protozoa or plants, from a prokaryote, such as bacteria and archaea, or from a virus.

Eukaryotic SSBs are known as replication protein A (RPAs). In most cases, they are hetero-trimers formed of different size units. Some of the larger units (e.g. RPA70 of *Saccharomyces cerevisiae*) are stable and bind ssDNA in monomeric form.

Bacterial SSBs bind DNA as stable homo-tetramers (e.g. *E. coli, Mycobacterium smegmatis* and *Helicobacter pylori*) or homo-dimers (e.g. *Deinococcus radiodurans* and *Thermotoga maritima*). The SSBs from archaeal genomes are considered to be related with eukaryotic RPAs. Few of them, such as the SSB encoded by the crenarchaeote *Sulfolobus solfataricus*, are homo-tetramers. The SSBs from most other species are closer related to the replication proteins from eukaryotes and are referred to as RPAs. In some of these species they have been shown to be monomeric (*Methanococcus jannaschii* and *Methanothermobacter thermoautotrophicum*). Still, other species of Archaea, including *Archaeoglobus fulgidus* and *Methanococcoides burtonii*, appear to each contain two open reading frames with sequence similarity to RPAs. There is no evidence at protein level and no published data regarding their DNA binding capabilities or oligomeric state. However, the presence of two oligonucleotide/oligosaccharide (OB) folds in each of these genes (three OB folds in the case of one of the *M. burtonii* ORFs) suggests that they also bind single stranded DNA.

Viral SSBs bind DNA as monomers. This, as well as their relatively small size renders them amenable to genetic fusion to other proteins, for instance via a flexible peptide linker. Alternatively, the SSBs can be expressed separately and attached to other proteins by chemical methods (e.g. cysteines, unnatural amino-acids). This is discussed in more detail below.

The SSB is preferably either (i) an SSB comprising a carboxy-terminal (C-terminal) region which does not have a net negative charge or (ii) a modified SSB comprising one or more modifications in its C-terminal region which decreases the net negative charge of the C-terminal region. Such SSBs do not block the transmembrane pore and therefore allow characterization of the target polynucleotide.

Examples of SSBs comprising a C-terminal region which does not have a net negative charge include, but are not limited to, the human mitochondrial SSB (HsmtSSB; SEQ ID NO: 118, the human replication protein A 70 kDa subunit, the human replication protein A 14 kDa subunit, the telomere end binding protein alpha subunit from Oxytricha nova, the core domain of telomere end binding protein beta subunit from Oxytricha nova, the protection of telomeres protein 1 (Pot1) from *Schizosaccharomyces pombe*, the human Pot1, the OB-fold domains of BRCA2 from mouse or rat, the p5 protein from phi29 (SEQ ID NO: 119) or a variant of any of those proteins. A variant is a protein that has an amino acid sequence which varies from that of the wild-type protein and which retains single stranded polynucleotide binding activity. Polynucleotide binding activity can be determined using methods known in the art (and as described above). For instance, the ability of a variant to bind a single stranded polynucleotide can be determined as described in the Examples.

A variant of SEQ ID NO 118 or 119 typically has at least 50% homology to SEQ ID NO: 118 or 119 based on amino acid identity over its entire sequence (or any of the % homologies discussed above in relation to helicases) and retains single stranded polynucleotide binding activity. A variant may differ from SEQ ID NO: 118 or 119 in any of the ways discussed above in relation to helicases. In particular, a variant may have one or more conservative substitutions as shown in Tables 8 and 9.

Examples of SSBs which require one or more modifications in their C-terminal region to decrease the net negative charge include, but are not limited to, the SSB of *E. coli* (EcoSSB; SEQ ID NO: 120, the SSB of *Mycobacterium tuberculosis*, the SSB of *Deinococcus radiodurans*, the SSB of *Thermus thermophiles*, the SSB from *Sulfolobus solfataricus*, the human replication protein A 32 kDa subunit (RPA32) fragment, the CDC13 SSB from *Saccharomyces cerevisiae*, the Primosomal replication protein N (PriB) from *E. coli*, the PriB from *Arabidopsis thaliana*, the hypothetical protein At4g28440, the SSB from T4 (gp32; SEQ ID NO: 121), the SSB from RB69 (gp32; SEQ ID NO: 95), the SSB from T7 (gp2.5; SEQ ID NO: 96) or a variant of any of these proteins. Hence, the SSB used in the method of the invention may be derived from any of these proteins.

In addition to the one or more modifications in the C-terminal region, the SSB used in the method may include additional modifications which are outside the C-terminal region or do not decrease the net negative charge of the C-terminal region. In other words, the SSB used in the method of the invention is derived from a variant of a wild-type protein. A variant is a protein that has an amino acid sequence which varies from that of the wild-type protein and which retains single stranded polynucleotide binding activity. Polynucleotide binding activity can be determined as discussed above.

The SSB used in the invention may be derived from a variant of SEQ ID NO: 95, 96, 120 or 121. In other words, a variant of SEQ ID NO: 95, 96, 120 or 121 may be used as the starting point for the SSB used in the invention, but the SSB actually used further includes one or more modifications in its C-terminal region which decreases the net negative charge of the C-terminal region. A variant of SEQ ID NO: 95, 96, 120 or 121 typically has at least 50% homology to SEQ ID NO: 95, 96, 120 or 121 based on amino acid identity over its entire sequence (or any of the % homologies discussed above in relation to helicases) and retains single stranded polynucleotide binding activity. A variant may differ from SEQ ID NO: 95, 96, 120 or 121 in any of the ways discussed above in relation to helicases. In particular, a variant may have one or more conservative substitutions as shown in Tables 8 and 9.

It is straightforward to identify the C-terminal region of the SSB in accordance with normal protein N to C nomenclature. The C-terminal region of the SSB is preferably about the last third of the SSB at the C-terminal end, such as the last third of the SSB at the C-terminal end. The C-terminal region of the SSB is more preferably about the last quarter, fifth or eighth of the SSB at the C-terminal end, such as the last quarter, fifth or eighth of the SSB at the C-terminal end. The last third, quarter, fifth or eighth of the SSB may be measured in terms of numbers of amino acids or in terms of actual length of the primary structure of the SSB protein. The length of the various amino acids in the N to C direction are known in the art.

The C-terminal region is preferably from about the last 10 to about the last 60 amino acids of the C-terminal end of the SSB. The C-terminal region is more preferably about the last 15, about the last 20, about the last 25, about the last 30, about the last 35, about the last 40, about the last 45, about the last 50 or about the last 55 amino acids of the C-terminal end of the SSB.

The C-terminal region typically comprises a glycine and/or proline rich region. This proline/glycine rich region gives the C-terminal region flexibility and can be used to identify the C-terminal region.

Suitable modifications for decreasing the net negative charge are disclosed in U.S. Provisional Application No. 61/673,457 (filed 19 Jul. 2012), U.S. Provisional Application No. 61/774,688 (filed 8 Mar. 2013) and the International application being filed concurrently with this application (Oxford Nanopore Ref: ONT IP 035). The SSB may be any of the SSBs disclosed in the US Provisional Applications and International application.

The modified SSB most preferably comprises a sequence selected from those shown in SEQ ID NOs: 103, 104, 122 to 125.

Double-stranded binding proteins bind double stranded DNA with high affinity. Suitable double-stranded binding proteins include, but are not limited to Mutator S (MutS; NCBI Reference Sequence: NP_417213.1; SEQ ID NO: 140), Sso7d (Sufolobus *solfataricus* P2; NCBI Reference Sequence: NP_343889.1; SEQ ID NO: 141; Nucleic Acids Research, 2004, Vol 32, No. 3, 1197-1207), Sso10b1 (NCBI Reference Sequence: NP_342446.1; SEQ ID NO: 142), Sso10b2 (NCBI Reference Sequence: NP_342448.1; SEQ ID NO: 143), Tryptophan repressor (Trp repressor; NCBI Reference Sequence: NP_291006.1; SEQ ID NO: 144), Lambda repressor (NCBI Reference Sequence: NP_040628.1; SEQ ID NO: 145), Cren7 (NCBI Reference Sequence: NP_342459.1; SEQ ID NO: 146), major histone classes H1/H5, H2A, H2B, H3 and H4 (NCBI Reference Sequence: NP_066403.2, SEQ ID NO: 147), dsbA (NCBI Reference Sequence: NP_049858.1; SEQ ID NO: 148), Rad51 (NCBI Reference Sequence: NP_002866.2; SEQ ID NO: 149), sliding clamps and Topoisomerase V Mka (SEQ ID NO: 129) or a variant of any of these proteins. A variant of SEQ ID NO: 129, 140, 141, 142, 143, 144, 145, 146, 147, 148 or 149 typically has at least 50% homology to SEQ ID NO: 129, 140, 141, 142, 143, 144, 145, 146, 147, 148 or 149 based on amino acid identity over its entire sequence (or any of the % homologies discussed above in relation to helicases) and retains single stranded polynucleotide binding activity. A variant may differ from SEQ ID NO: 129, 140, 141, 142, 143, 144, 145, 146, 147, 148 or 149 in any of the ways discussed above in relation to helicases. In particular, a variant may have one or more conservative substitutions as shown in Tables 8 and 9. Most polymerases achieve processivity by interacting with sliding clamps. In general, these are multimeric proteins (homo-dimers or homo-trimers) that encircle dsDNA. These sliding clamps require accessory proteins (clamp loaders) to assemble them around the DNA helix in an ATP-dependent process. They also do not contact DNA directly, acting as a topological tether. As sliding clamps interact with their cognate polymerases in a specific manner via a polymerase domain, this fragment could be fused to the helicase in order to incite recruitment of helicases onto the sliding clamp. This interaction could be further stabilized by the generation of a covalent bond (introduction of cysteines or unnatural amino-acids).

Related to DNA sliding clamps, processivity factors are viral proteins that anchor their cognate polymerases to DNA, leading to a dramatic increase in the length of the fragments generated. They can be monomeric (as is the case for UL42 from Herpes simplex virus 1) or multimeric (UL44 from Cytomegalovirus is a dimer), they do not form closed rings around the DNA strand and they contact DNA directly. UL42 has been shown to increase processivity without reducing the rate of its corresponding polymerase, suggesting that it interacts with DNA in a different mode to SSBs. The UL42 preferably comprises the sequence shown in SEQ ID NO: 97 or SEQ ID NO: 102 or a variant thereof. A variant of SEQ ID NO: 97 or 102 is a protein that has an amino acid sequence which varies from that of SEQ ID NO: 97 or 102 and which retains polynucleotide binding activity. This can be measured as described above. A variant typically has at least 50% homology to SEQ ID NO: 97 or 102 based on amino acid identity over its entire sequence (or any of the % homologies discussed above in relation to helicases) and retains polynucleotide binding activity. A variant may differ from SEQ ID NO: 97 or SEQ ID NO: 102 in any of the ways discussed above in relation to helicases or below in relation to pores. A variant preferably comprises one or more substituted cysteine residues and/or one or more substituted Faz residues to facilitate attachment to the helicase as discussed above.

Attaching UL42 to a helicase could be done via genetic fusion or chemical attachment (cysteines, unnatural amino-acids). As the polymerase polypeptide that binds UL42 is visible in the crystal structure, these 35 amino acids (residues 1200-1235) could be fused onto the C-terminus of the helicase and the natural affinity between this polypeptide and the processivity factor used to form a complex. The interaction could be stabilized by introducing a covalent interaction (cysteines or unnatural amino-acids). One option is to utilize a natural UL42 cysteine (C300) that is located close to the polypeptide interaction site and introduce a point mutation into the polymerase polypeptide (e.g. L1234C).

A reported method of increasing polymerase processivity is by exploiting the interaction between *E. coli* thioredoxin (Trx) and the thioredoxin binding domain (TBD) of bacteriophage T7 DNA polymerase (residues 258-333). The binding of Trx to TBD causes the polypeptide to change conformation to one that binds DNA. TBD is believed to clamp down onto a DNA strand and limit the polymerase off-rate, thus increasing processivity. Chimeric polymerases have been made by transferring TBD onto a non-processive polymerase, resulting in 1000 fold increase in polymerised fragment length. There were no attempts to attach TBD to any other class of proteins, but a covalent link between TBD and Trx was engineered and can be used to stabilise the interaction.

Some helicases use accessory proteins in-vivo to achieve processivity (e.g. cisA from phage<Dx174 and geneII protein from phage M13 for *E. coli* Rep helicase). Some of these proteins have been shown to interact with more than one helicase (e.g. MutL acts on both UvrD and Rep, though not to the same extent). These proteins have intrinsic DNA binding capabilities, some of them recognizing a specific DNA sequence. The ability of some of these accessory proteins to covalently attach themselves to a specific DNA sequence could also be used to create a set starting point for the helicase activity.

The proteins that protect the ends of chromosomes bind to telomeric ssDNA sequences in a highly specific manner. This ability could either be exploited as is or by using point mutations to abolish the sequence specificity.

Small DNA binding motifs (such as helix-turn-helix) recognize specific DNA sequences. In the case of the bacteriophage 434 repressor, a 62 residue fragment was engineered and shown to retain DNA binding abilities and specificity.

An abundant motif in eukaryotic proteins, zinc fingers consist of around 30 amino-acids that bind DNA in a specific manner. Typically each zinc finger recognizes only three DNA bases, but multiple fingers can be linked to obtain recognition of a longer sequence.

Proliferating cell nuclear antigens (PCNAs) form a very tight clamp (doughnut) which slides up and down the dsDNA or ssDNA. The PCNA from crenarchaeota is unique in being a hetero-trimer so it is possible to functionalise one subunit and retain activity. Its subunits are shown in SEQ ID NOs: 98, 99 and 100. The PCNA is preferably a trimer comprising the sequences shown in SEQ ID NOs: 98, 99 and 100 or variants thereof. PCNA sliding clamp (NCBI Reference Sequence: ZP_06863050.1; SEQ ID NO: 150) forms a dimer. The PCNA is preferably a dimer comprising SEQ ID NO: 150 or a variant thereof. A variant is a protein that has an amino acid sequence which varies from that of SEQ ID NO: 98, 99, 100 or 150 and which retains polynucleotide binding activity. This can be measured as described above. A variant is typically a trimer comprising sequences that have at least 50% homology to SEQ ID NOs: 98, 99 and 100 or a dimer comprising sequences that have at least 50% homology to SEQ ID NO: 150 based on amino acid identity over each entire sequence (or any of the % homologies discussed above in relation to helicases) and which retains polynucleotide binding activity. A variant may comprise sequences which differ from SEQ ID NO: 98, 99, 100 or 150 in any of the ways discussed above in relation to helicases or below in relation to pores. A variant preferably comprises one or more substituted cysteine residues and/or one or more substituted Faz residues to facilitate attachment to the helicase as discussed above. In a preferred embodiment, subunits 1 and 2 of the PCNA from crenarchaeota (i.e. SEQ ID NOs: 98 and 99 or variants thereof) are attached, such as genetically fused, and the resulting protein is attached to a helicase to form a construct of the invention. During use of the construct, subunit 3 (i.e. SEQ ID NO: 100 or a variant thereof) may be added to complete the PCNA clamp (or doughnut) once the construct has bound the polynucleotide. In a preferred embodiment, one monomer of the PCNA sliding clamp (i.e. SEQ ID NO: 150 or a variant thereof) is attached, such as genetically fused, to a helicase to form a construct of the invention. During use of the construct, the second monomer (i.e. SEQ ID NO: 150 or a variant thereof) may be added to complete the PCNA clamp (or doughnut) once the construct has bound the polynucleotide.

The polynucleotide binding motif may be selected from any of those shown in Table 5 below.

TABLE 5

Suitable polynucleotide binding motifs

| No. | Name | Class | Organism | Structure | Sequence | Functional form | MW (Da) | Notes |
|---|---|---|---|---|---|---|---|---|
| 1 | SSBEco | ssb | *Escherichia coli* | 1QVC, 1EYG | P0AGE0 | homo-tetramer | 18975 | |
| 2 | SSBBhe | ssb | *Bartonella henselae* | 3LGJ, 3PGZ | Q6G302 | homo-tetramer | 16737 | structure only |
| 3 | SSBCbu | ssb | *Coxiella burnetii* | 3TQY | Q83EP4 | homo-tetramer | 17437 | structure only |
| 4 | SSBTma | ssb | *Thermathoga maritima* | 1Z9F | Q9WZ73 | homo-dimer | 16298 | small, thermostable, salt independent DNA binding |
| 5 | SSBHpy | ssb | *Helicobacter pylori* | 2VW9 | O25841 | homo-tetramer | 20143 | |
| 6 | SSBDra | ssb | *Deinococcus radiodurans* | 1SE8 | Q9RY51 | homo-dimer | 32722 | |
| 7 | SSBTaq | ssb | *Thermus aquaticus* | 2FXQ | Q9KH06 | homo-dimer | 30026 | |
| 8 | SSBMsm | ssb | *Mycobacterium smegmatis* | 3A5U, 1X3E | Q9AFI5 | homo-tetramer | 17401 | tetramer more stable than *E. coli*, binding less salt dependent |
| 9 | SSBSso | ssb/RPA | *Sulfolobus solfataricus* | 1O7I | Q97W73 | homo-tetramer | 16138 | similarities with RPA |
| 10 | SSBMHsmt | ssb | *Homo sapiens* | 3ULL | Q04837 | homo-tetramer | 17260 | |
| 11 | SSBMle | ssb | *Mycobacterium leprae* | 3AFP | P46390 | homo-tetramer | 17701 | |
| 12 | gp32T4 | ssb | *Bacteriohage T4* | 1GPC | P03695 | monomer | 33506 | Homo-dimer in the absence of DNA, monomer when binding DNA. |

TABLE 5-continued

Suitable polynucleotide binding motifs

| No. | Name | Class | Organism | Structure | Sequence | Functional form | MW (Da) | Notes |
|---|---|---|---|---|---|---|---|---|
| 13 | gp32RB69 | ssb | Bacteriophage RB69 | 2A1K | Q7Y265 | monomer | 33118 | |
| 14 | gp2.5T7 | ssb | Bacteriophage T7 | 1JE5 | P03696 | monomer | 25694 | |
| 15 | UL42 | processivity factor | Herpes virus 1 | 1DML | P10226 | monomer | 51159 | binds ssDNA dsDNA, structure shows link with polymerase |
| 16 | UL44 | processivity factor | Herpes virus 5 (cytomegalovirus) | 1YYP | P16790 | homo-dimer | 46233 | forms C shaped clamp on DNA |
| 17 | pf8 | processivity factor | KSHV | 3I2M | Q77ZG5 | homo-dimer | 42378 | |
| 18 | RPAMja | RPA | Methanococcus jannaschii | 3DM3 | Q58559 | monomer | 73842 | contains 4 OB folds. Structure of fragment |
| 19 | RPAMma | RPA | Methanococcus maripaludis | 3E0E, 2K5V | Q6LYF9 | monomer | 71388 | Core domain structure |
| 20 | RPAMth | RPA | Methanothermobacter thermoautotrophicus | | | monomer | 120000 | Shown to interact directly with Hel308. Sequence from paper. |
| 21 | RPA70Sce | RPA | Saccharomyces cerevisiae | 1YNX | P22336 | hetero-trimer | 70348 | unit has two OB folds and binds DNA |
| 22 | RPAMbu1 | RPA | Methanococcoides burtonii | | Q12V72 | ? | 41227 | three OB folds identified |
| 23 | RPAMbu2 | RPA | Methanococcoides burtonii | | Q12W96 | ? | 47082 | two OB folds identified |
| 24 | RPA70Hsa | RPA | Homo sapiens | 1JMC | P27694 | hetero-trimer | 68138 | |
| 25 | RPA14Hsa | RPA | Homo sapiens | 3KDF | P35244 | hetero-trimer | 13569 | in complex with RPA32 |
| 26 | gp45T4 | sliding clamp | Bacteriophage T4 | 1CZD | P04525 | homo-trimer | 24858 | ring shape threads DNA |
| 27 | BetaEco | sliding clamp | E. coli | 3BEP | P0A988 | homo-dimer | 40587 | ring shape threads DNA, may bind ssDNA in poket |
| 28 | PCNASce | sliding clamp | Saccharomyces cerevisiae | 1PLQ, 3K4X | P15873 | homo-dimer | 28916 | ring shape threads DNA |
| 29 | PCNATko | sliding clamp | Thermococcus kodakaraensis | 3LX1 | Q5JF32 | homo-dimer | 28239 | |
| 30 | PCNAHvo | sliding clamp | Haloferax volcanii | 3IFV | D0VWY8 | homo-dimer | 26672 | |
| 31 | PCNAPfu | sliding clamp | Pyrococcus furiosus | 1GE8 | O73947 | homo-dimer | 28005 | |
| 32 | PCNAMbu | sliding clamp | Methanococcoides burtonii | | Q12U18 | homo-dimer | 27121 | Inferred from homology |
| 33 | BetaMtu | sliding clamp | Mycobacterium tuberculosis | 3P16 | Q50790 | homo-dimer | 42113 | |
| 34 | BetaTma | sliding clamp | Thermotoga maritima | 1VPK | Q9WYA0 | homo-dimer | 40948 | |
| 35 | BetaSpy | sliding clamp | Streptococcus pyogenes | 2AVT | Q9EVR1 | homo-dimer | 41867 | |
| 36 | gp45RB69 | sliding clamp | Bacteriophage RB69 | 1B77 | O80164 | homo-trimer | 25111 | Structure shows interaction with polypeptide fom polymerase |
| 37 | p55Hsa | DNA binding protein | Homo sapiens (mitochondrial) | 2G4C, 3IKL, 3IKM | Q9UHN | monomer | 54911 | interacts with specific polymerase domain |
| 38 | p55Dme | DNA binding protein | Drosophylla melanogaster | | Q9VJV8 | monomer | 41027 | associates with polymerase Gamma conferring salt tolerance, processivity and increased activity |
| 39 | p55Xla | DNA binding protein | Xenopus laevis | | Q9W6G7 | monomer | 52283 | |

TABLE 5-continued

Suitable polynucleotide binding motifs

| No. | Name | Class | Organism | Structure | Sequence | Functional form | MW (Da) | Notes |
|---|---|---|---|---|---|---|---|---|
| 40 | RepDSau | replication initiation protein | Staphylococcus aureus | | P08115 | homo-dimer | 37874 | increases processivity of PcrA, covalently and specifically links DNA |
| 41 | G2P | replication initiation protein | Enterobacteria phage 1 | | P69546 | monomer | 46168 | increases processivity of Rep, covalently and specifically links DNA |
| 42 | MutLEco | mismatch repair protein | Escherichia coli | 1BKN, 1B62, 1B63 | P23367 | homo-dimer | 67924 | increases processivity of UvrD (and Rep) |
| 43 | KuMtu | DNA repair protein | Mycobacterium tuberculosis | | O05866 | homo-dimer | 30904 | increases processivity of UvrD1. Structure available for human Ku |
| 44 | OnTEBP | telomere binding protein | Oxytricha nova-Alpha | 1OTC | P29549 | hetero-dimer | 56082 | Specific biding to 3' end T4G4T4G4. Alpha subunit may be enough |
| | | | Oxytricha nova-Beta | | P16458 | | 41446 | |
| 45 | EcrTEBP | telomere binding protein | Euplotes crassus | | Q06183 | monomer | 53360 | Homolog to OnTEBP with no Beta subunit in genome |
| 46 | TteTEBP | telomere binding protein | Tetrachymena termophila Alpha | | Q23FB9 | hetero-dimer | 53073 | Homolog to OnTEBP-Alpha |
| | | | Tetrachymena termophila Beta | | Q23FH0 | | 54757 | May be homolog to OnTEBP Beta |
| 47 | pot1Spo | telomere binding proteins | Schizosaccharomyces pombe | | O13988 | monomer | 64111 | related to TEBP |
| 48 | Cdc13pSce | telomere binding proteins | Saccharomyces cerevisiae | | C7GSV7 | monomer | 104936 | specific binding to telomeric DNA |
| 49 | C1 | repressor | Bacteriophage 434 | | P16117 | homo-dimer | 10426 | binds DNA specifically as homo-dimer |
| 50 | LexA | repressor | Escherichia coli | 1LEB | P0A7C2 | homo-dimer | 22358 | binds DNA specifically as homo-dimer |

The polynucleotide binding moiety is preferably derived from a polynucleotide binding enzyme. A polynucleotide binding enzyme is a polypeptide that is capable of binding to a polynucleotide and interacting with and modifying at least one property of the polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide binding moiety does not need to display enzymatic activity as long as it is capable of binding the polynucleotide and controlling its movement. For instance, the moiety may be derived from an enzyme that has been modified to remove its enzymatic activity or may be used under conditions which prevent it from acting as an enzyme.

The polynucleotide binding moiety is preferably derived from a nucleolytic enzyme. The enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are exonucleases, polymerases, helicases and topoisomerases, such as gyrases. Suitable exonucleases include, but are not limited to, exonuclease I from E. coli, exonuclease III enzyme from E. coli, RecJ from T. thermophilus and bacteriophage lambda exonuclease and variants thereof.

The polymerase is preferably a member of any of the Moiety Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The polynucleotide binding moiety is preferably derived from Phi29 DNA polymerase (SEQ ID NO: 101). The moiety may comprise the sequence shown in SEQ ID NO: 101 or a variant thereof. A variant of SEQ ID NO: 101 is an enzyme that has an amino acid sequence which varies from that of SEQ ID NO: 101 and which retains polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NO: 101, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 101 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described below. The variant may differ from the wild-type sequence in any of the ways discussed below with reference to SEQ ID NOs: 2 and 4.

The helicase may be any of those discussed above. Helicase dimers and multimers are discussed in detail below. The polynucleotide binding moiety may be a polynucleotide binding domain derived from a helicase. For instance, the polynucleotide binding moiety preferably comprises the sequence shown in SEQ ID NOs: 105 or 106 or a variant thereof. A variant of SEQ ID NOs: 105 or 106 is a protein that has an amino acid sequence which varies from that of SEQ ID NOs: 105 or 106 and which retains polynucleotide binding activity. This can be measured as described above. The variant may include modifications that facilitate binding of the polynucleotide and/or facilitate its activity at high salt concentrations and/or room temperature.

Over the entire length of the amino acid sequence of SEQ ID NOs: 105 or 106, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NOs: 105 or 106 over the entire sequence. There may be at least 80%, for example at least 85%, 90% or 95%, amino acid identity over a stretch of 40 or more, for example 50, 60, 70 or 80 or more, contiguous amino acids ("hard homology"). Homology is determined as described below. The variant may differ from the wild-type sequence in any of the ways discussed below with reference to SEQ ID NOs: 2 and 4.

The topoisomerase is preferably a member of any of the Moiety Classification (EC) groups 5.99.1.2 and 5.99.1.3.

The polynucleotide binding moiety may be any of the enzymes discussed above.

The moiety may be labelled with a revealing label. The label may be any of those described above.

The moiety may be isolated from any moiety-producing organism, such as *E. coli, T. thermophilus* or bacteriophage, or made synthetically or by recombinant means. For example, the moiety may be synthesized by in vitro translation and transcription as described below. The moiety may be produced in large scale following purification as described below.

Helicase Oligomers

As will be clear from the discussion above, the polynucleotide binding moiety is preferably derived from a helicase. For instance, it may be a polynucleotide domain from a helicase. The moiety more preferably comprises one or more helicases. The helicases may be any of those discussed above, including the helicases of the invention. In such embodiments, the constructs of the invention of course comprise two or more helicases attached together where at least one of the helicases is modified in accordance with the invention. The constructs may comprise two, three, four, five or more helicases. In other words, the constructs of the invention may comprise a helicase dimer, a helicase trimer, a helicase tetramer, a helicase pentamer and the like.

The two or more helicases can be attached together in any orientation. Identical or similar helicases may be attached via the same amino acid position or spatially proximate amino acid positions in each helicase. This is termed the "head-to-head" formation. Alternatively, identical or similar helicases may be attached via positions on opposite or different sides of each helicase. This is termed the "head-to-tail" formation. Helicase trimers comprising three identical or similar helicases may comprise both the head-to-head and head-to-tail formations.

The two or more helicases may be different from one another (i.e. the construct is a hetero-dimer, -trimer, -tetramer or -pentamer etc.). For instance, the constructs of the invention may comprise: (a) one or more Hel308 helicases and one or more XPD helicases; (b) one or more Hel308 helicases and one or more RecD helicases; (c) one or more Hel308 helicases and one or more TraI helicases; (d) one or more XPD helicases and one or more RecD helicases; (e) one or more XPD helicases and one or more TraI helicases; or (f) one or more RecD helicases and one or more TraI helicases. The construct may comprise two different variants of the same helicase. For instance, the construct may comprise two variants of one of the helicases discussed above with one or more cysteine residues or Faz residues introduced at different positions in each variant. In this instance, the helicases can be in a head-to-tail formation. In a preferred embodiment, a variant of SEQ ID NO: 10 comprising Q442C may be attached via cysteine linkage to a variant of SEQ ID NO: 10 comprising Q557C. Cys mutants of Hel308Mbu can also be made into hetero-dimers if necessary. In this approach, two different Cys mutant pairs such as Hel308Mbu-Q442C and Hel308Mbu-Q577C can be linked in head-to-tail fashion. Hetero-dimers can be formed in two possible ways. The first involves the use of a homo-bifunctional linker as discussed above. One of the helicase variants can be modified with a large excess of linker in such a way that one linker is attached to one molecule of the protein. This linker modified variant can then be purified away from unmodified proteins, possible homo-dimers and unreacted linkers to react with the other helicase variant. The resulting dimer can then be purified away from other species.

The second involves the use of hetero-bifunctional linkers. For example, one of the helicase variants can be modified with a first PEG linker containing maleimide or iodoacetamide functional group at one end and a cyclooctyne functional group (DIBO) at the other end. An example of this is shown below:

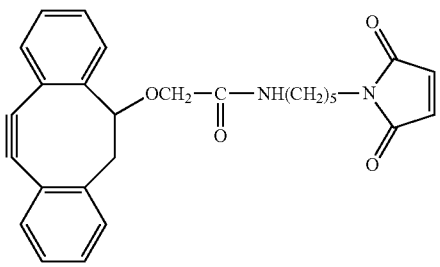

The second helicase variant can be modified with a second PEG linker containing maleimide or iodoacetamide functional group at one end and an azide functional group at the other end. An example is show below:

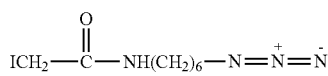

The two helicase variants with two different linkers can then be purified and clicked together (using copper free click chemistry) to make a dimer. Copper free click chemistry has been used in these applications because of its desirable properties. For example, it is fast, clean and not poisonous towards proteins. However, other suitable bio-orthogonal chemistries include, but are not limited to, Staudinger chemistry, hydrazine or hydrazide/aldehyde or ketone reagents (HyNic+4FB chemistry, including all Solulink™ reagents), Diels-Alder reagent pairs and boronic acid/salicyhydroxamate reagents.

These two ways of linking two different variants of the same helicase are also valid for any of the constructs discussed above in which the helicase and the moiety are different from one another, such as dimers of two different helicases and a helicase-polymerase dimer.

Similar methodology may also be used for linking different Faz variants. One Faz variant (such as SEQ ID NO: 10 comprising Q442Faz) can be modified with a large excess of linker in such a way that one linker is attached to one molecule of the protein. This linker modified Faz variant can then be purified away from unmodified proteins, possible homo-dimers and unreacted linkers to react with the second Faz variant (such as SEQ ID NO: 10 comprising Q577Faz). The resulting dimer can then be purified away from other species.

Hetero-dimers can also be made by linking cysteine variants and Faz variants of the same helicase or different helicases. For example, any of the above cysteine variants (such as SEQ ID NO: 10 comprising Q442C) can be used to make dimers with any of the above Faz variants (such SEQ ID NO: 10 comprising Q577Faz). Hetero-bifunctional PEG linkers with maleimide or iodoacetamide functionalities at one end and DBCO functionality at the other end can be used in this combination of mutants. An example of such a linker is shown below (DBCO-PEG4-maleimide):

The length of the linker can be varied by changing the number of PEG units between the two functional groups.

Helicase hetero-trimers can comprise three different types of helicases selected from Hel308 helicases, XPD helicases, RecD helicases, TraI helicases and variants thereof. The same is true for oligomers comprising more than three helicases. The two or more helicases within a construct may be different variants of the same helicase, such as different variants of SEQ ID NO: 10, 22, 33 or 52. The different variants may be modified at different positions to facilitate attachment via the different positions. The hetero-trimers may therefore be in a head-to-tail and head-to-head formation.

The two or more helicases in the constructs of the invention may be the same as one another (i.e. the construct is a homo-dimer, -trimer, -tetramer or -pentamer etc.) Homo-oligomers can comprise two or more Hel308 helicases, two or more XPD helicases, two or more RecD helicases, two or more TraI helicases or two or more of any of the variants discussed above. In such embodiments, the helicases are preferably attached using the same position in each helicase. The helicases are therefore attached head-to-head. The helicases may be linked using a cysteine residue or a Faz residue that has been substituted into the helicases at the same position. Cysteine residues in identical helicase variants can be linked using a homo-bifunctional linker containing thiol reactive groups such as maleimide or iodoacetamide. These functional groups can be at the end of a polyethyleneglycol (PEG) chain as in the following example:

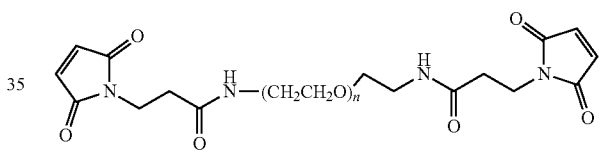

The length of the linker can be varied to suit the required applications. For example, n can be 2, 3, 4, 8, 11, 12, 16 or more. PEG linkers are suitable because they have favourable properties such as water solubility. Other non PEG linkers can also be used in cysteine linkage.

By using similar approaches, identical Faz variants can also be made into homo-dimers. Homo-bifunctional linkers with DIBO functional groups can be used to link two molecules of the same Faz variant to make homo-dimers using $Cu^{2+}$ free click chemistry. An example of a linker is given below:

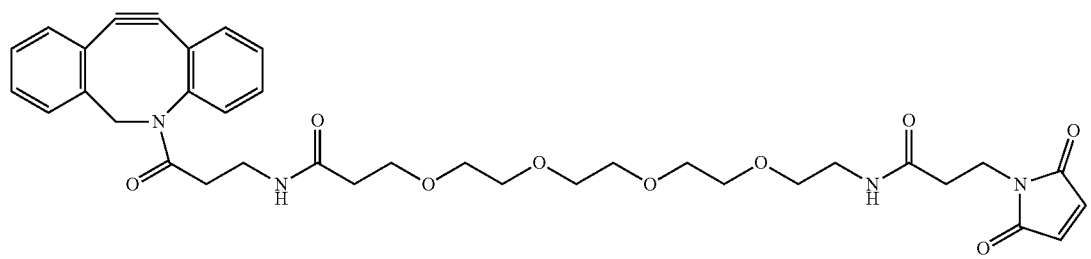 [SMILES: O=C(CCOCCOCCOCCOCCNC(=O)CCN1C(=O)C=CC1=O)NCCC(=O)N1Cc2ccccc2C#Cc2ccccc21]

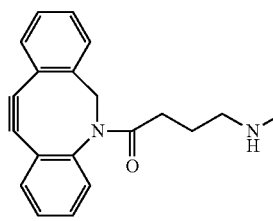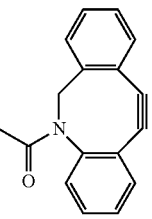

The length of the PEG linker can vary to include 2, 4, 8, 12, 16 or more PEG units. Such linkers can also be made to incorporate a florescent tag to ease quantifications. Such fluorescence tags can also be incorporated into Maleimide linkers.

The invention also provides a construct comprising a helicase of the invention and an amino acid sequence comprising SEQ ID NO: 130 (H-L domains from Topoisomerase V from *Methanopyrus kandleri*; SEQ ID NO: 129) or a variant thereof having at least 80% homology to SEQ ID NO: 130 based on amino acid identity over the entire sequence of SEQ ID NO: 130, wherein the helicase is attached to the amino acid sequence and the construct has the ability to control the movement of a polynucleotide. The helicase may be attached to the amino acid sequence in any of the ways discussed above.

Preferred constructs of the invention are shown in the Table 6 below. Each row shows a preferred construct in which the helicase in the left-hand column is attached to additional polynucleotide binding moiety in the right-hand column in accordance with the invention. If the polynucleotide binding moiety in the right-hand column is a helicase, it may also be a helicase of the invention.

| Helicase of the invention | Additional polynucleotide binding moiety |
| --- | --- |
| Hel308 helicase of the invention as defined above (preferably SEQ ID NO: 10, 22, 33 or 52 or a variant thereof as defined above) | Polymerase (preferably SEQ ID NO: 101 or a variant thereof as defined above) |
| TraI helicase of the invention as defined above (preferably SEQ ID NO: 85, 126, 134 and 138 or a variant thereof as defined above) | Polymerase (preferably SEQ ID NO: 101 or a variant thereof as defined above) |
| Hel308 helicase of the invention as defined above (preferably SEQ ID NO: 10, 22, 33 or 52 or a variant thereof as defined above) | Hel308 helicase as defined above (preferably SEQ ID NO: 10, 22, 33 or 52 or a variant thereof as defined above) |
| TraI helicase of the invention as defined above (preferably SEQ ID NO: 85, 126, 134 and 138 or a variant thereof as defined above) | TraI helicase as defined above (preferably SEQ ID NO: 85, 126, 134 and 138 or a variant thereof as defined above) |
| Hel308 helicase of the invention as defined above (preferably SEQ ID NO: 10, 22, 33 or 52 or a variant thereof as defined above) | TraI helicase as defined above (preferably SEQ ID NO: 85, 126, 134 and 138 or a variant thereof as defined above) |
| TraI helicase of the invention as defined above (preferably SEQ ID NO: 85, 126, 134 and 138 or a variant thereof as defined above) | Hel308 helicase as defined above (preferably SEQ ID NO: 10, 22, 33 or 52 or a variant thereof as defined above) |

Polynucleotide Sequences

Any of the proteins described herein may be expressed using methods known in the art. Polynucleotide sequences may be isolated and replicated using standard methods in the art. Chromosomal DNA may be extracted from a helicase producing organism, such as *Methanococcoides burtonii*, and/or a SSB producing organism, such as *E. coli*. The gene encoding the sequence of interest may be amplified using PCR involving specific primers. The amplified sequences may then be incorporated into a recombinant replicable vector such as a cloning vector. The vector may be used to replicate the polynucleotide in a compatible host cell. Thus polynucleotide sequences may be made by introducing a polynucleotide encoding the sequence of interest into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynucleotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used.

The host cell typically expresses the construct at a high level. Host cells transformed with a polynucleotide sequence will be chosen to be compatible with the expression vector used to transform the cell. The host cell is typically bacterial and preferably *E. coli*. Any cell with a λ DE3 lysogen, for example C41 (DE3), BL21 (DE3), JM109 (DE3), B834 (DE3), TUNER, Origami and Origami B, can express a vector comprising the T7 promoter.

Methods of the Invention

The invention provides a method of controlling the movement of a target polynucleotide. The method comprises contacting the target polynucleotide with a helicase of the invention or a construct of the invention and thereby controlling the movement of the polynucleotide. The method is preferably carried out with a potential applied across the pore. As discussed in more detail below, the applied potential typically results in the formation of a complex between the pore and the helicase or construct. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The invention also provides a method of characterising a target polynucleotide. The method comprises (a) contacting the target polynucleotide with a transmembrane pore and a helicase of the invention or a construct of the invention such that the helicase or construct controls the movement of the target polynucleotide through the pore. The method also comprises (b) taking one or more measurements as the polynucleotide moves with respect to the pore wherein the measurements are indicative of one or more characteristics of the target polynucleotide and thereby characterising the target polynucleotide.

Steps (a) and (b) are preferably carried out with a potential applied across the pore as discussed above. In some instances, the current passing through the pore as the polynucleotide moves with respect to the pore is used to determine the sequence of the target polynucleotide. This is Strand Sequencing.

The method of the invention is for characterising a target polynucleotide. A polynucleotide is defined above.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, 7s (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the helicase. If a linker is used, then the polynucleotide can be processed to completion. If a linker is used, the linker may be attached to the polynucleotide at any position. The linker is typically attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the helicase's active site. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 7 below.

TABLE 7

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." J Am Chem Soc 125(13): 3696-7. |
| Biotin | Stable | Nikolov, V., R. Lipowsky, et al. (2007). "Behavior of giant vesicles with anchored DNA molecules." Biophys J 92(12): 4356-68 |
| Cholesterol | Transient | Pfeiffer, I. and F. Hook (2004). "Bivalent cholesterol-based coupling of oligonucleotides to lipid membrane assemblies." J Am Chem Soc 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." Langmuir 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer with a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the amplified target DNA will contain a reactive group for coupling.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane R barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-(B1)8 and is called MS-(B2)8. The pore used in the invention is preferably MS-(B2)8. The further preferred variant comprises the mutations G75S/G77S/L88N/Q126R. The variant of SEQ ID NO: 2 has the mutations G75S/G77S/L88N/Q126R in addition to all the mutations of MS-(B1)8 and is called MS-(B2C)8. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 8 below. Where amino acids have similar polarity, this can also be determined by reference to the hydropathy scale for amino acid side chains in Table 9.

TABLE 8

Chemical properties of amino acids

| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |

TABLE 8-continued

Chemical properties of amino acids

| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 9

Hydropathy scale

| Side Chain | Hydropathy |
| --- | --- |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO:

2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described above.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the helicase or construct. The variant preferably comprises one or more reactive cysteine residues that facilitate attachment to the helicase or construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135, 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length.

Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the 1-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

The helicase or construct may be covalently attached to the pore. The helicase or construct is preferably not covalently attached to the pore. The application of a voltage to the pore and helicase or construct typically results in the formation of a sensor that is capable of sequencing target polynucleotides. This is discussed in more detail below.

Any of the proteins described herein, i.e. the helicases, the transmembrane protein pores or constructs, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the helicase, pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The helicase, pore or construct may be labelled with a revealing label. The revealing label may be any suitable label which allows the pore to be detected. Suitable labels include, but are not limited to, fluorescent molecules, radio-isotopes, e.g. $^{125}$I, $^{35}$s, enzymes, antibodies, antigens, polynucleotides and ligands such as biotin.

Proteins may be made synthetically or by recombinant means. For example, the helicase, pore or construct may be synthesized by in vitro translation and transcription (IVTT). The amino acid sequence of the helicase, pore or construct may be modified to include non-naturally occurring amino acids or to increase the stability of the protein. When a protein is produced by synthetic means, such amino acids may be introduced during production. The helicase, pore or construct may also be altered following either synthetic or recombinant production.

The helicase, pore or construct may also be produced using D-amino acids. For instance, the pore or construct may comprise a mixture of L-amino acids and D-amino acids. This is conventional in the art for producing such proteins or peptides.

The helicase, pore or construct may also contain other non-specific modifications as long as they do not interfere with pore formation or helicase or construct function. A number of non-specific side chain modifications are known in the art and may be made to the side chains of the protein(s). Such modifications include, for example, reductive alkylation of amino acids by reaction with an aldehyde followed by reduction with NaBH$_4$, amidination with methylacetimidate or acylation with acetic anhydride.

The helicase, pore and construct can be produced using standard methods known in the art. Polynucleotide sequences encoding a helicase, pore or construct may be derived and replicated using standard methods in the art. Polynucleotide sequences encoding a helicase, pore or construct may be expressed in a bacterial host cell using standard techniques in the art. The helicase, pore and/or construct may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The helicase, pore and/or construct may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured for example by determining the number of interactions between the target polynucleotide and the pore or the duration of interaction between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:
(a) contacting the target polynucleotide with a transmembrane pore and a helicase of the invention or a construct of the invention such that the target polynucleotide moves through the pore and the helicase or construct controls the movement of the target polynucleotide through the pore; and
(b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. Hel308, XPD, RecD and TraI helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method may be carried out in the presence of free nucleotides or free nucleotide analogues and/or an enzyme cofactor that facilitates the action of the helicase or construct. The method may also be carried out in the absence of free nucleotides or free nucleotide analogues and in the absence of an enzyme cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase or construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polynucleotide may be contacted with the helicase or construct and the pore in any order. In is preferred that, when the target polynucleotide is contacted with the helicase or construct and the pore, the target polynucleotide firstly forms a complex with the helicase or construct. When the voltage is applied across the pore, the target polynucleotide/helicase or construct complex then forms a complex with the pore and controls the movement of the polynucleotide through the pore.

As discussed above, helicases may work in two modes with respect to the pore. The helicases of the invention or the constructs of the invention can also work in two modes. First, the method is preferably carried out using the helicase or construct such that it moves the target sequence through the pore with the field resulting from the applied voltage. In this mode the 3' end of the DNA is first captured in the pore (for a 3'-5' helicase), and the helicase or construct moves the DNA into the pore such that the target sequence is passed through the pore with the field until it finally translocates through to the trans side of the bilayer (See FIG. 8). Alternatively, the method is preferably carried out such that the helicase or construct moves the target sequence through the pore against the field resulting from the applied voltage. In this mode the 5' end of the DNA is first captured in the pore (for a 3'-5' helicase), and the helicase or construct moves the DNA through the pore such that the target sequence is pulled out of the pore against the applied field until finally ejected back to the cis side of the bilayer (see FIG. 7).

Other Methods

The invention also provides a method of forming a sensor for characterising a target polynucleotide. The method comprises forming a complex between a pore and a helicase of the invention or a construct of the invention. The complex may be formed by contacting the pore and the helicase or construct in the presence of the target polynucleotide and then applying a potential across the pore. The applied potential may be a chemical potential or a voltage potential as described above. Alternatively, the complex may be formed by covalently attaching the pore to the helicase or construct. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a pore derived from Msp and a helicase of the invention or a construct of the invention. Any of the embodiments discussed above with reference to the methods of the invention equally apply to this method. The invention also provides a sensor produced using the method of the invention.

Kits

The present invention also provides a kit for characterising a target polynucleotide. The kit comprises (a) a pore and (b) a helicase of the invention or a construct of the invention. Any of the embodiments discussed above with reference to the method of the invention equally apply to the kits.

The kit may further comprise the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising a target polynucleotide. The apparatus comprises a plurality of pores and a plurality of helicases of the invention or a plurality of constructs of the invention. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:
a sensor device that is capable of supporting the plurality of pores and being operable to perform polynucleotide characterisation using the pores and constructs; and
at least one reservoir for holding material for performing the characterisation.

The apparatus preferably comprises:
a sensor device that is capable of supporting the plurality of pores and being operable to perform polynucleotide characterisation using the pores and helicases or constructs; and
at least one reservoir for holding material for performing the characterisation.

The apparatus preferably comprises:
a sensor device that is capable of supporting the membrane and plurality of pores and being operable to perform polynucleotide characterising using the pores and helicases or constructs;
at least one reservoir for holding material for performing the characterising;
a fluidics system configured to controllably supply material from the at least one reservoir to the sensor device; and
one or more containers for receiving respective samples, the fluidics system being configured to supply the samples selectively from one or more containers to the sensor device. The apparatus may be any of those described in International Application No. PCT/GB08/004127 (published as WO 2009/077734), PCT/GB10/000789 (published as WO 2010/122293), International Application No. PCT/GB10/002206 (not yet published) or International Application No. PCT/US99/25679 (published as WO 00/28312).

Methods of Producing Helicases of the Invention

The invention also provides methods of producing a helicase of the invention. In one embodiment, the method comprises providing a helicase formed from one or more monomers and comprising a polynucleotide binding domain which comprises an opening through which a polynucleotide can unbind from the helicase. Any of the helicases discussed above can be used in the methods.

The method also comprises modifying the helicase such that two or more parts on the same monomer of the helicase are connected to reduce the size of the opening. The site of and method of connection are selected as discussed above.

In another embodiment, the method comprises providing a Hel308 helicase. Any of the Hel308 helicases described above may be used.

The method further comprises introducing one or more cysteine residues and/or one or more non-natural amino acids at one or more of the positions which correspond to D272, N273, D274, G281, E284, E285, E287, S288, T289, G290, E291, D293, T294, N300, R303, K304, N314, S315, N316, H317, R318, K319, L320, E322, R326, N328 and S615 in Hel308 Mbu (SEQ ID NO: 10).

The method preferably further comprises (c) heating the modified helicase, for instance by heating at 50° C. for 10 minutes, (d) exposing the modified helicase to UV light, for instance by exposing the modified helicase to high intensity UV light at 254 nm for about 10 to about 15 minutes or (e) exposing the modified helicase to ferrocyanide and ferricyanide, such as potassium ferrocyanide and potassium ferricyanide. Any combination of steps (c), (d) and (e) may be performed, such as (c), (d), (e), (c) and (d), (d) and (e), (c) and (e) or (c), (d) and (e).

The method preferably further comprises determining whether or not the helicase is capable of controlling the movement of a polynucleotide. Assays for doing this are described above. If the movement of a polynucleotide can be controlled, the helicase has been modified correctly and a helicase of the invention has been produced. If the movement of a polynucleotide cannot be controlled, a helicase of the invention has not been produced.

Methods of Producing Constructs of the Invention

The invention also provides a method of producing a construct of the invention. The method comprises attaching, preferably covalently attaching a helicase of the invention to an additional polynucleotide binding moiety. Any of the helicases and moieties discussed above can be used in the methods. The site of and method of covalent attachment are selected as discussed above.

The method preferably further comprises determining whether or not the construct is capable of controlling the movement of a polynucleotide. Assays for doing this are described above. If the movement of a polynucleotide can be controlled, the helicase and moiety have been attached correctly and a construct of the invention has been produced. If the movement of a polynucleotide cannot be controlled, a construct of the invention has not been produced.

The following Example illustrates the invention.

Example 1

This Example describes the method of synthesising the Hel308 Mbu (E284C/S615C)-bismaleimidePEG3 (SEQ ID NO: 10 with the mutations E284C/S615C connected by a bismaleimidePEG3 linker). In this case a covalent link between cysteines at positions 284 and 615 in the primary sequence of Hel308 Mbu (SEQ ID NO: 10) was made by reacting these positions with a bismaleimidePEG3 linker (approximately 3.7 nm in length).

Figure 1:
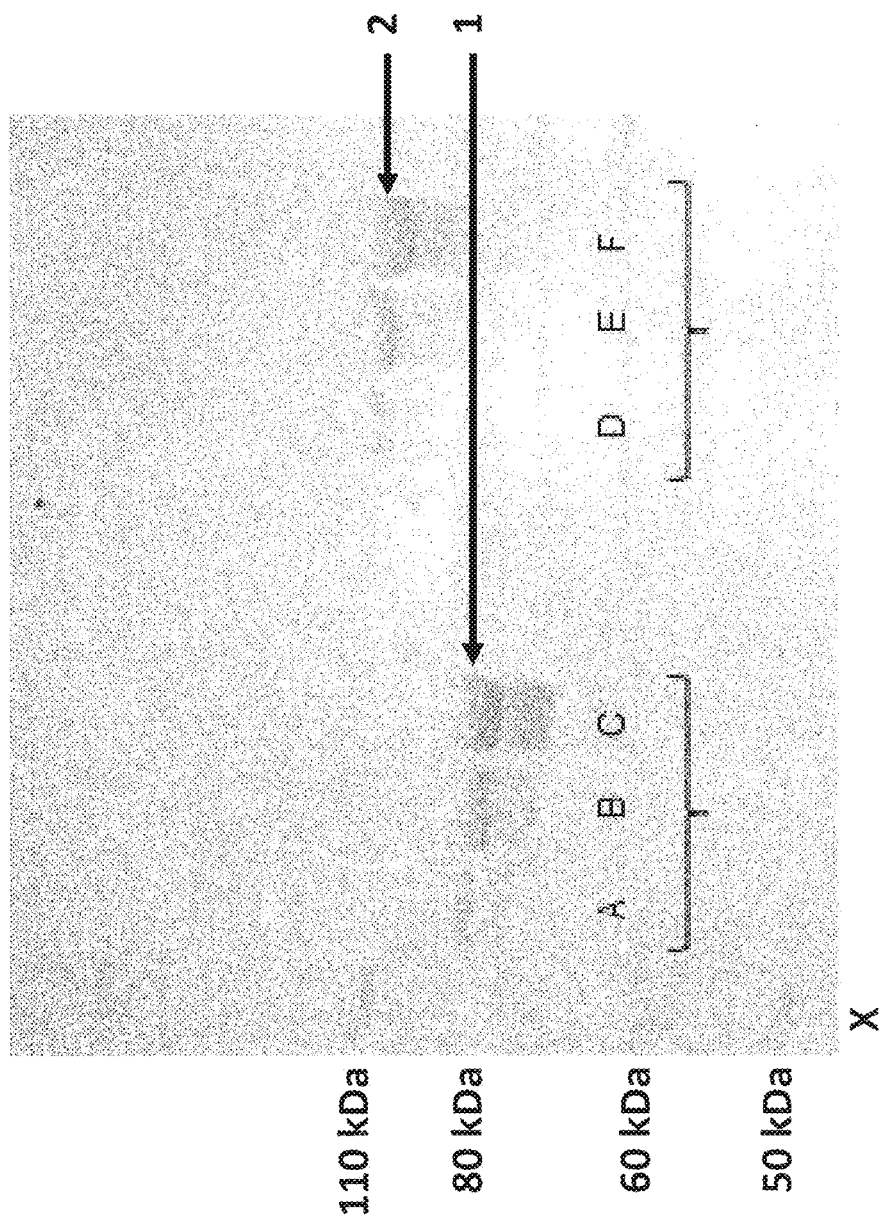
FIG. 1 shows a coomassie stained, 7.5% Tris-HCl gel (loaded with Laemmli loading buffer) of the Hel308 Mbu (E284C/S615C)-bismaleimidePEG3 reaction mixture (SEQ ID NO: 10 with mutations E284C/S615C connected by a bismaleimidePEG3 linker). Lane X shows an appropriate protein ladder (the mass unit markers are shown on the left of the gel). Lanes a-c contain 2 µL, 5 µL or 10 µL of approximately 2.5 µM Hel308 Mbu(E284C/S615C) monomer (SEQ ID NO: 10 with mutations E284C/S615C). Lanes d-f contain 2 µL, 5 µL or 10 µL of approximately 2.5 µM Hel308 Mbu(E284C/S615C)-bismaleimidePEG3 (SEQ ID NO: 10 with mutations E284C/S615C connected by a bismaleimidePEG3 linker, i.e. a helicase in which the opening has been closed), it was clear from the gel that the reaction to attach the bismaleimidePEG3 linker went to nearly 100% yield. Arrow 1 corresponds to Hel308 Mbu (E284C/S615C) monomer (SEQ ID NO: 10 with mutations E284C/S615C) and arrow 2 corresponds to Hel308 Mbu(E284C/S615C)-bismaleimidePEG3 (SEQ ID NO: 10 with mutations E284C/S615C connected by a bismaleimidePEG3 linker, i.e. a helicase in which the opening has been closed).

In detail, 6 µl of 1 M DTT was added to 600 µL of Hel308 Mbu(E284C/S615C) (SEQ ID NO: 10 with the mutations E284C/S615C, stored in 50 mM Tris-HCl pH 8.0, 421 mM NaCl, 10% Glycerol, 10 mM DTT) and the mixture was incubated at room temperature on a 10" wheel rotating at 20 rpm for 30 minutes. This mixture was buffer exchanged through Pierce 2 mL Zeba desalting columns, 7k MWCO into 100 mM potassium phosphate, 500 mM NaCl, 5 mM EDTA, 0.1% Tween-20 pH 8.0 to give 550 µL of sample. To this was added, 5.5 µL of bismaleimidePEG3 (QuantaBiodesign, Product Ref=10215) and the mixture incubated at room temperature on a 10" wheel rotating at 20 rpm for 120 minutes. To stop the reaction, 5.5 µL of 1 M DTT was added to quench any remaining maleimides. Analysis of the reaction was by 7.5% polyacrylamide gel or by reverse phase HPLC (chromatographed on a Jupiter C5 300A 5 μm 150× 4.6 mm column, using a gradient of acetonitrile in 0.1% TFA). FIG. 1 shows a coomassie stained 7.5% Tris-HCl gel (loaded with Laemmli loading buffer) of the Hel308 Mbu (E284C/S615C)-bismaleimidePEG3 (SEQ ID NO: 10 with the mutations E284C/S615C connected by a bismaleimide-PEG3 linker) reaction mixture. Lane X shows an appropriate protein ladder (the mass unit markers are shown on the left of the gel). Lanes a-c contain 2 μL, 5 μL or 10 μL of approximately 2.5 μM Hel308 Mbu(E284C/S615C) monomer (SEQ ID NO: 10 with mutations E284C/S615C). Lanes d-f contain 2 μL, 5 μL or 10 μL of approximately 2.5 μM Hel308 Mbu(E284C/S615C)-bismaleimidePEG3 (SEQ ID NO: 10 with the mutations E284C/S615C connected by a bismaleimidePEG3 linker), it was clear from the gel that the reaction to attach the bismaleimidePEG3 linker went to nearly 100% yield. The Hel308 Mbu(E284C/S615C)-bismaleimidePEG3 (SEQ ID NO: 10 with the mutations E284C/S615C connected by a bismaleimidePEG3 linker) was then buffer exchanged to 50 mM Tris, 500 mM NaCl, 2 mM DTT, 10% glycerol pH 8.0.

Example 2

This example describes the method of synthesising the Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide, SEQ ID NO: 109 corresponds to the peptide sequence SRDFWRS)). In this case a covalent link between cysteines at positions 284 and 615 in the primary sequence of Hel308 Mbu (SEQ ID NO: 10) was made by reacting these positions with a bismaleimide peptide linker (maleimide-propyl-SRDFWRS-(1,2-diaminoethane)-propyl-maleimide, SEQ ID NO: 109 corresponds to the peptide sequence SRDFWRS).

Figure 2:
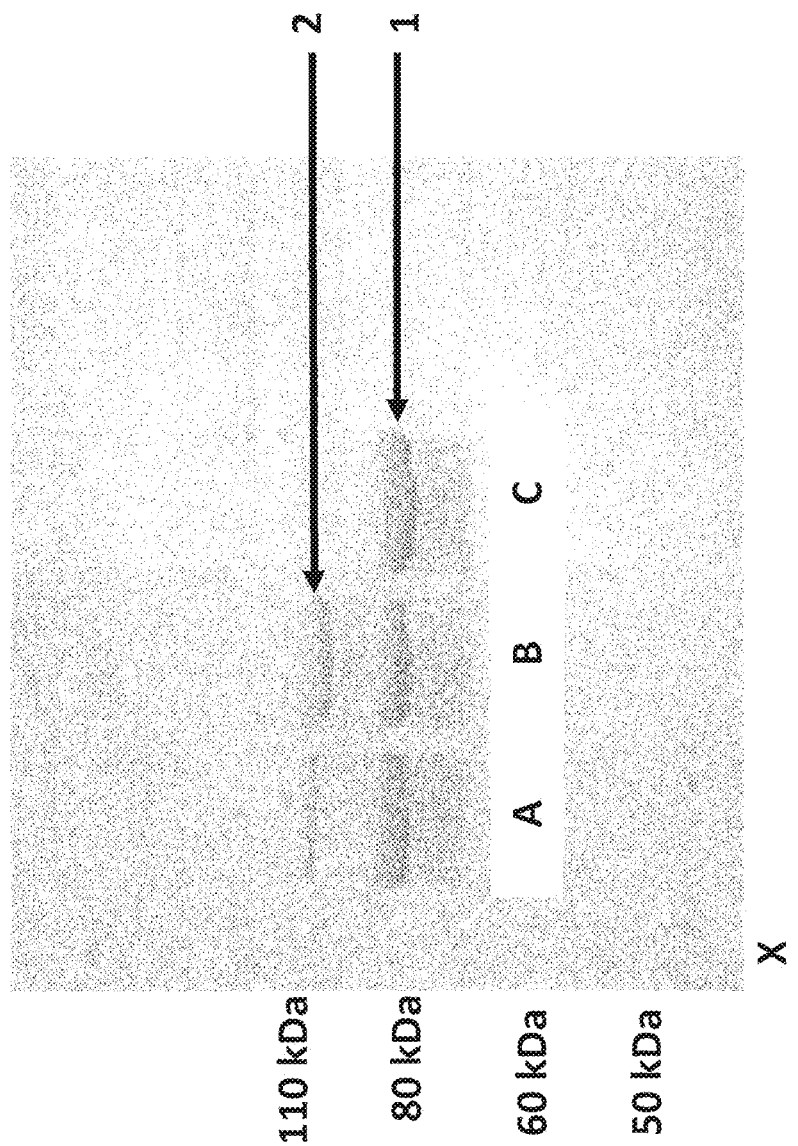
FIG. 2 shows a coomassie stained 7.5% Tris-HCl gel of the Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)) reaction mixture. Lane X shows an appropriate protein ladder (the mass unit markers are shown on the left of the gel). Lane A contains 5 of approximately 10 µM Hel308 Mbu(E284C/S615C)-bismaleimidePEG3 (SEQ ID NO: 10 with the mutations E284C/S615C connected by a bismaleimidePEG3 linker) as a reference. The upper band (labelled 2) corresponds to Hel308 Mbu(E284C/S615C)-bismaleimidePEG3 and the lower band (labelled 1) to Hel308 Mbu (E284C/S615C) (SEQ ID NO: 10 with the mutations E284C/S615C). Lane B contains 5 µL of approximately 10 µM Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide), it was clear from the gel that the reaction to attach the mal-pep-mal linker did not go to completion as a band for the Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide) (upper band) and the Hel308 Mbu (E284C/S615C) (SEQ ID NO: 10 with the mutations E284C/S615C) (lower band) are observed. Lane C contains Hel308 Mbu (E284C/S615C) (SEQ ID NO: 10 with the mutations E284C/S615C).

In detail, 2 μl of 1 M DTT was added to 200 μL of Hel308 Mbu(E284C/S615C) (SEQ ID NO: 10 with the mutations E284C/S615C, stored in 50 mM Tris-HCl pH 8.0, 421 mM NaCl, 10% Glycerol, 10 mM DTT) and the mixture was incubated at room temperature on a 10" wheel rotating at 20 rpm for 30 minutes. This mixture was buffer exchanged through Pierce 2 mL Zeba desalting columns, 7k MWCO into 100 mM potassium phosphate, 500 mM NaCl, 5 mM EDTA, 0.1% Tween-20 pH 8.0 to give 540 μL of sample. To an aliquot of 100 ul, 0.5 ul of 10 mM maleimide-propyl-SRDFWRS-(1,2-diaminoethane)-propyl-maleimide (PPRL, Product Ref=16450) was added and the mixture incubated at room temperature on a 10" wheel rotating at 20 rpm for 120 minutes. To stop the reaction, 1 ul of 1 M DTT was added to quench any remaining maleimides. Analysis of the reaction is by 7.5% polyacrylamide gel or by reverse phase HPLC (chromatographed on a Jupiter C5 300A 5 μm 150× 4.6 mm column, using a gradient of acetonitrile in 0.1% TFA). FIG. 2 shows a coomassie stained 7.5% Tris-HCl gel of the Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide) reaction mixture. Lane X shows an appropriate protein ladder (the mass unit markers are shown on the left of the gel). Lane A contains 5 μL of approximately 10 μM Hel308 Mbu (E284C/S615C)-bismaleimidePEG3 (SEQ ID NO: 10 with the mutations E284C/S615C connected by a bismaleimide-PEG3 linker) as a reference. The upper band corresponds to Hel308 Mbu(E284C/S615C)-bismaleimidePEG3 and the lower band to Hel308 Mbu (E284C/S615C) (SEQ ID NO: 10 with the mutations E284C/S615C). Lane B contains 5 μL of approximately 10 μM Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide), it was clear from the gel that the reaction to attach the mal-pep-mal linker did not go to completion as a band for the Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide) (upper band) and the Hel308 Mbu (E284C/S615C) (SEQ ID NO: 10 with the mutations E284C/S615C) (lower band) are observed. Lane C contains Hel308 Mbu (E284C/S615C) (SEQ ID NO: 10 with the mutations E284C/S615C).

The Hel308 Mbu (E284C/S615C)-mal-pep-mal (SEQ ID NO: 10 with the mutations E284C/S615C connected by a bismaleimide peptide linker (maleimide-propyl-SRDFWRS-(1,2-diaminoethane)-propyl-maleimide, SEQ ID NO: 109 corresponds to the peptide sequence SRDFWRS)) was then buffer exchanged to 50 mM Tris, 500 mM NaCl, 2 mM DTT, 10% glycerol pH 8.0.

Example 3

This example compares the enzyme processivity of two Hel308 Mbu helicases in which the opening has been closed (Hel308 Mbu(E284C/S615C)-bismaleimidePEG11 (SEQ ID NO: 10 with mutations E284C/S615C connected by a bismaleimidePEG11) and Hel308 Mbu(E284C/S615C)-bismaleimidePEG3) (SEQ ID NO: 10 with the mutations E284C/S615C connected by a bismaleimidePEG3 linker) to that of the Hel308 Mbu monomer (SEQ ID NO: 10) using a fluorescence based assay.

Materials and Methods

SEQ ID NOs: 110 to 114. SEQ ID NO: 112 has a carboxyfluorescein at the 5' end and a black-hole quencher at the 3' end.

Figure 3A:
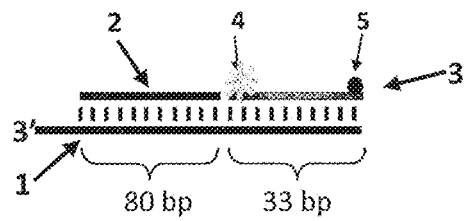
FIGS. 3A-3E show a fluorescence assay used to compare the enzyme processivity of two Hel308 Mbu helicases in which the opening has been closed (Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimide-PEG3 (SEQ ID NO: 10 with mutations E284C/S615C connected by a bismaleimidePEG3 linker)) to that of the Hel308 Mbu monomer (SEQ ID NO: 10). A custom fluorescent substrate was used to assay the ability of the helicase to displace hybridised dsDNA. The fluorescent substrate (50 nM final) has a 3' ssDNA overhang, and 80 and 33 base-pair sections of hybridised dsDNA (FIG. 3A, SEQ ID NO: 110, labelled 1). The major bottom "template" strand is hybridised to an 80 nt "blocker" strand (SEQ ID NO: 111, labelled 2), adjacent to its 3' overhang, and a 33 nt fluorescent probe (labelled 3), labelled at its 5' and 3' ends with carboxyfluorescein (FAM, labelled 4) and black-hole quencher (BHQ-1, labelled 5) bases (SEQ ID NO: 112), respectively. When hybridised, the FAM is distant from the BHQ-1 and the substrate is essentially fluorescent. In the presence of ATP (1 mM) and $MgCl_2$ (10 mM), the helicase (labelled 6, 10 nM) binds to the substrate's 3' overhang (SEQ ID NO: 110), moves along the lower strand, and begins to displace the 80 nt blocker strand (SEQ ID NO: 111), as shown in FIG. 3B. If processive, the helicase displaces the fluorescent probe too (FIG. 3C, SEQ ID NO: 112, labelled with a carboxyfluorescein (FAM) at its 5' end a black-hole quencher (BHQ-1) at its 3' end). The fluorescent probe is designed in such a way that its 5' and 3' ends are self-complementary and thus form a kinetically-stable hairpin once displaced, preventing the probe from re-annealing to the template strand (FIG. 3D). Upon formation of the hairpin product, the FAM is brought into the vicinity of the BHQ-1 and its fluorescence is quenched. A processive enzyme, capable of displacing the 80 mer "blocker" (SEQ ID NO: 111) and fluorescent (SEQ ID NO: 112, labelled with a carboxyfluorescein (FAM) at its 5' end a black-hole quencher (BHQ-1) at its 3' end) strands will therefore lead to a decrease in fluorescence over time. However, if the enzyme has a processivity of less than 80 nt it would be unable to displace the fluorescent strand (SEQ ID NO: 112, labelled with a carboxyfluorescein (FAM) at its 5' end a black-hole quencher (BHQ-1) at its 3' end) and, therefore, the "blocker" strand (SEQ ID NO: 111) would reanneal to the major bottom strand (FIG. 3E).
Figure 3B:
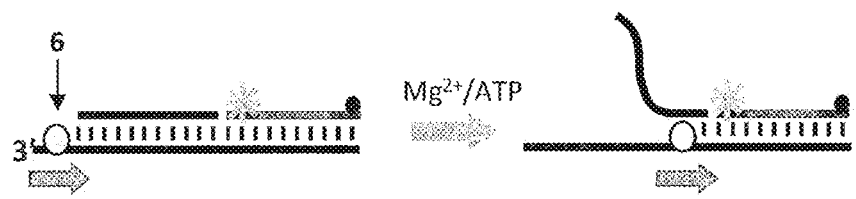
Figure 3C:
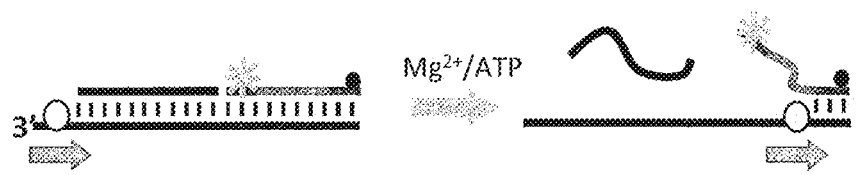
Figure 3D:
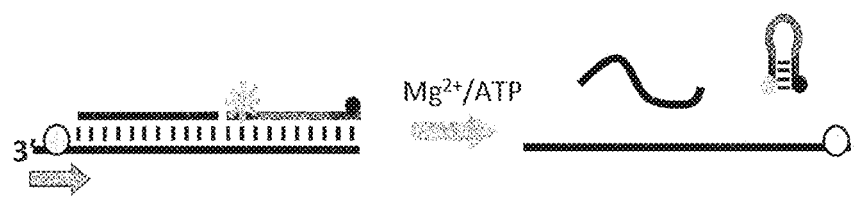
Figure 3E:
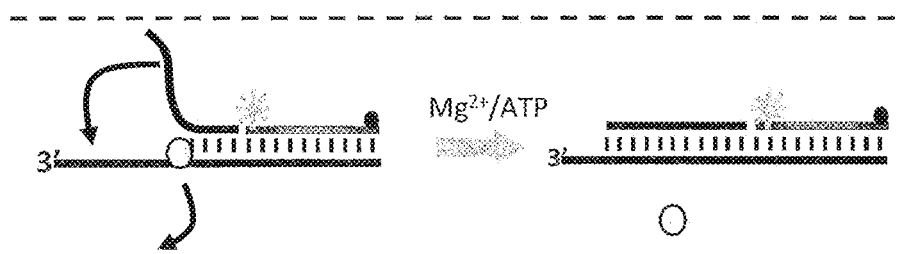

A custom fluorescent substrate was used to assay the ability of the helicase to displace hybridised dsDNA (FIGS. 3A-3E). The fluorescent substrate (50 nM final) has a 3' ssDNA overhang, and 80 and 33 base-pair sections of hybridised dsDNA (FIG. 3A, SEQ ID NO: 110). The major lower "template" strand is hybridised to an 80 nt "blocker" strand (SEQ ID NO: 111), adjacent to its 3' overhang, and a 33 nt fluorescent probe, labelled at its 5' and 3' ends with carboxyfluorescein (FAM) and black-hole quencher (BHQ-1) bases, respectively (SEQ ID NO: 112). When hybridised, the FAM is distant from the BHQ-1 and the substrate is essentially fluorescent. In the presence of ATP (1 mM) and MgCl$_2$ (10 mM), the helicase (10 nM) binds to the substrate's 3' overhang (SEQ ID NO: 110), moves along the lower strand, and begins to displace the 80 nt blocker strand (SEQ ID NO: 111), as shown in FIG. 3B. If processive, the helicase displaces the fluorescent probe (SEQ ID NO: 112, labelled with a carboxyfluorescein (FAM) at its 5' end a black-hole quencher (BHQ-1) at its 3' end) too (FIG. 3C). The fluorescent probe is designed in such a way that its 5' and 3' ends are self-complementary and thus form a kinetically-stable hairpin once displaced, preventing the probe from re-annealing to the template strand (FIG. 3D). Upon formation of the hairpin product, the FAM is brought into the vicinity of the BHQ-1 and its fluorescence is quenched. A processive enzyme, capable of displacing the 80 mer "blocker" (SEQ ID NO: 111) and fluorescent (SEQ ID NO: 112, labelled with a carboxyfluorescein (FAM) at its 5' end a black-hole quencher (BHQ-1) at its 3' end) strands will therefore lead to a decrease in fluorescence over time. However, if the enzyme has a processivity of less than 80 nt it would be unable to displace the fluorescent strand (SEQ ID NO: 112, labelled with a carboxyfluorescein (FAM) at its 5' end a black-hole quencher (BHQ-1) at its 3' end) and, therefore, the "blocker" strand (SEQ ID NO: 111) would reanneal to the major bottom strand (FIG. 3E, SEQ ID NO: 110).

Figure 4A:
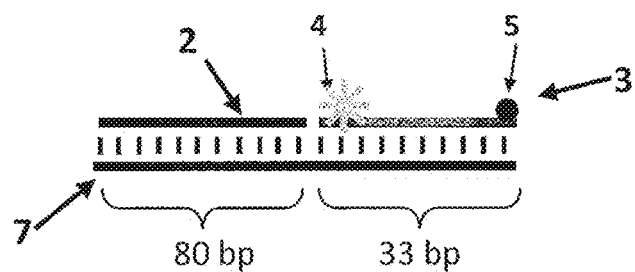
FIGS. 4A-4B show additional custom fluorescent substrates which were also used for control purposes. The substrate used as a negative control was identical to that of the one described in FIGS. 3A-3E but lacking the 3'overhang (FIG. 4A, (SEQ ID NO's: 111 (labelled 2 in figure), 112 (Strand labelled 3 in figure, labelled with a carboxyfluorescein (FAM, labelled 4 in figure) at its 5' end a black-hole quencher (BHQ-1, labelled 5 in figure) at its 3' end) and 113 labelled 7 in figure)). A similar substrate to that described in FIGS. 3A-3E but lacking the 80 base pair section (SEQ ID NO's: 112 (strand labelled 3 in figure, labelled with a carboxyfluorescein (FAM labelled 4 in figure) at its 5' end a black-hole quencher (BHQ-1, labelled 5 in figure) at its 3' end) and 114 labelled 8 in figure), was used as a positive control for active, but not necessarily processive, helicases (FIG. 4B).
Figure 4B:
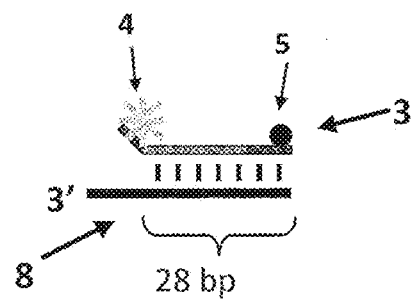

Additional custom fluorescent substrates were also used for control purposes. The substrate used as a negative control was identical to that of the one described in FIGS. 3A-3E but lacking the 3'overhang (FIG. 4A, (SEQ ID NOs: 111, 112 (labelled with a carboxyfluorescein (FAM) at its 5' end a black-hole quencher (BHQ-1) at its 3' end) and 113)). A similar substrate to that described in FIGS. 3A-3E but lacking the 80 base pair section, used as a positive control for active, but not necessarily processive, helicases (FIG. 4B, (SEQ ID NO's: 112 (labelled with a carboxyfluorescein (FAM) at its 5' end a black-hole quencher (BHQ-1) at its 3' end) and 114)).

Figure 5:
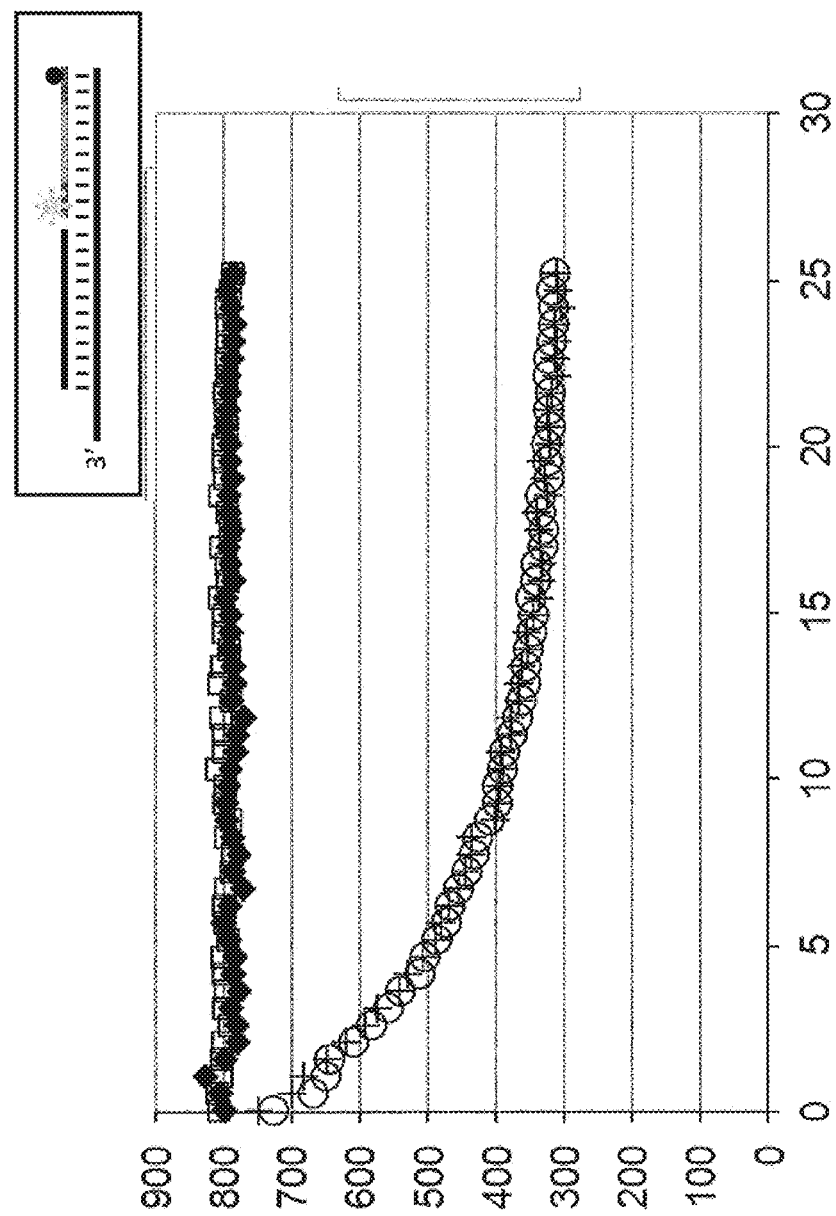
FIG. 5 shows a graph (y-axis label=Normalised fluorescence (arbitrary values), x-axis label=time (min)) of the time-dependent fluorescence changes upon testing Hel308 Mbu, Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker) against the processivity substrate shown in FIGS. 3A-3E in buffered solution (400 mM NaCl, 10 mM Hepes pH 8.0, 1 mM ATP, 10 mM MgCl$_2$, 50 nM fluorescent substrate DNA (SEQ ID NOs: 110, 111 and 112 (labelled with a carboxyfluorescein (FAM) at its 5' end a black-hole quencher (BHQ-1) at its 3' end). The data points marked with a black diamond correspond to a buffer blank, the white square data points correspond to Hel308 Mbu monomer (SEQ ID NO: 10), the black cross data points correspond to Hel308 Mbu(E284C/S615C)-bismaleimidePEG11 (SEQ ID NO: 10 with mutations E284C/S615C connected by a bismaleimidePEG11 linker) and the white circle data points correspond to Hel308 Mbu(E284C/S615C)-bismaleimidePEG3 (SEQ ID NO: 10 with mutations E284C/S615C connected by a bismaleimidePEG3 linker). The decrease in fluorescence exhibited by Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker), denote the increased processivity of these complexes as compared to Hel308 Mbu monomer (SEQ ID NO: 10).
Figure 6:
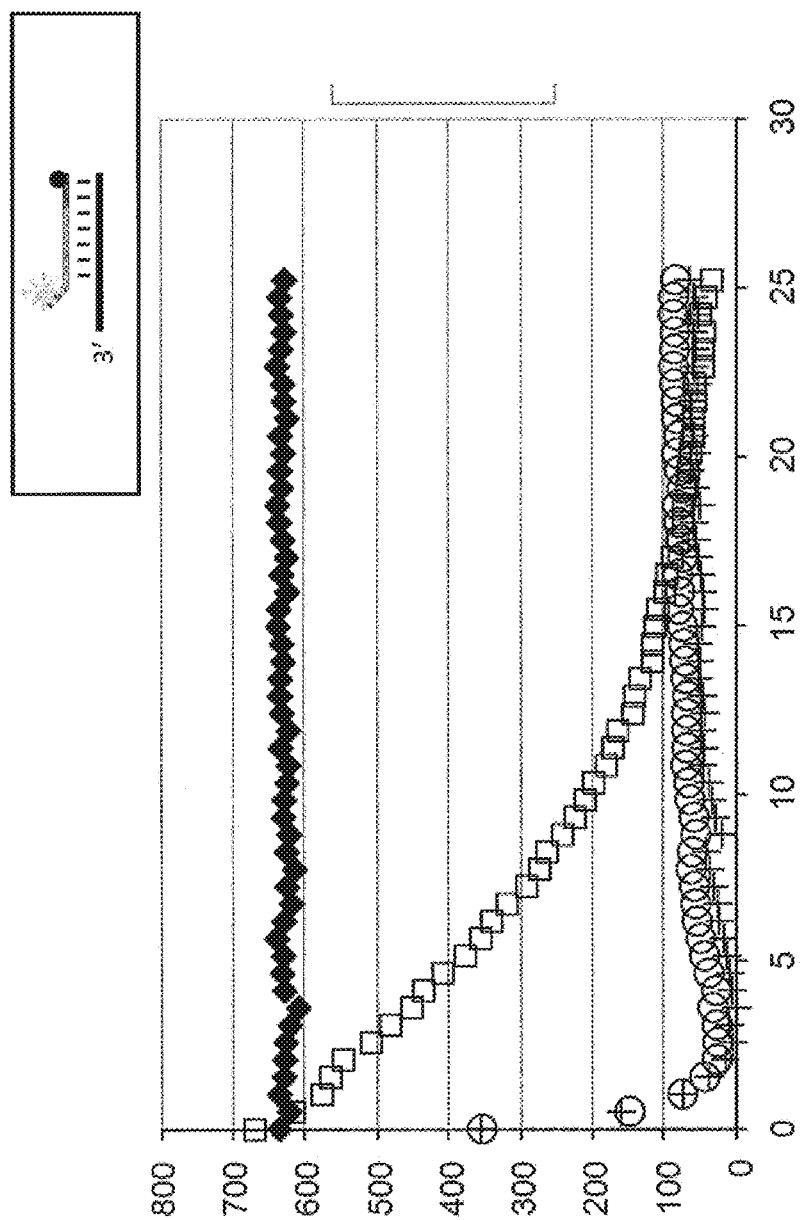
FIG. 6 shows a graph (y-axis label=Normalised fluorescence (arbitrary values), x-axis label=time (min)) of the time-dependent fluorescence changes upon testing Hel308 Mbu (SEQ ID NO: 10), Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker) against the positive control processivity substrate (shown in FIG. 4B, SEQ ID NOs: 112 (labelled with a carboxyfluorescein (FAM) at its 5' end a black-hole quencher (BHQ-1) at its 3' end) and 60) in buffered solution (400 mM NaCl, 10 mM Hepes pH 8.0, 1 mM ATP, 10 mM MgCl$_2$, 50 nM fluorescent substrate DNA (SEQ ID NOs: 112 (labelled with a carboxyfluorescein (FAM) at its 5' end a black-hole quencher (BHQ-1) at its 3' end) and 114)). The data points marked with a black diamond correspond to a buffer blank, the white square data points correspond to Hel308 Mbu monomer (SEQ ID NO: 10), the black cross data points correspond to Hel308 Mbu(E284C/S615C)-bismaleimidePEG11 (SEQ ID NO: 10 with mutations E284C/S615C connected by a bismaleimidePEG11 linker) and the white circle data points correspond to Hel308 Mbu(E284C/S615C)-bismaleimidePEG3 (SEQ ID NO: 10 with mutations E284C/S615C connected by a bismaleimidePEG3 linker). This positive control demonstrated that all complexes were indeed active, as denoted by a fluorescence decrease for all samples.

FIG. 5 shows a graph of the time-dependent fluorescence changes upon testing Hel308 Mbu monomer (SEQ ID NO: 10), Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker) against the processivity substrate shown in FIGS. 3A-3E in buffered solution (400 mM NaCl, 10 mM Hepes pH 8.0, 1 mM ATP, 10 mM MgCl$_2$, 50 nM fluorescent substrate DNA (SEQ ID NOs: 110, 111 and 112 (labelled with a carboxyfluorescein (FAM) at its 5' end a black-hole quencher (BHQ-1) at its 3' end))). The decrease in fluorescence exhibited by Hel308 Mbu(E284C/S615C)-bismaleimidePEG11 (SEQ ID NO: 10 with mutations E284C/S615C connected by a bismaleimidePEG11 linker) and Hel308 Mbu(E284C/S615C)-bismaleimidePEG3 (SEQ ID NO: 10 with mutations E284C/S615C connected by a bismaleimidePEG3 linker), denote the increased processivity of these complexes as compared to Hel308 Mbu monomer (SEQ ID NO: 10). FIG. 6 shows positive controls demonstrating that all helicases were indeed active, as denoted by a fluorescence decrease for all samples.

Example 4

Figure 7:
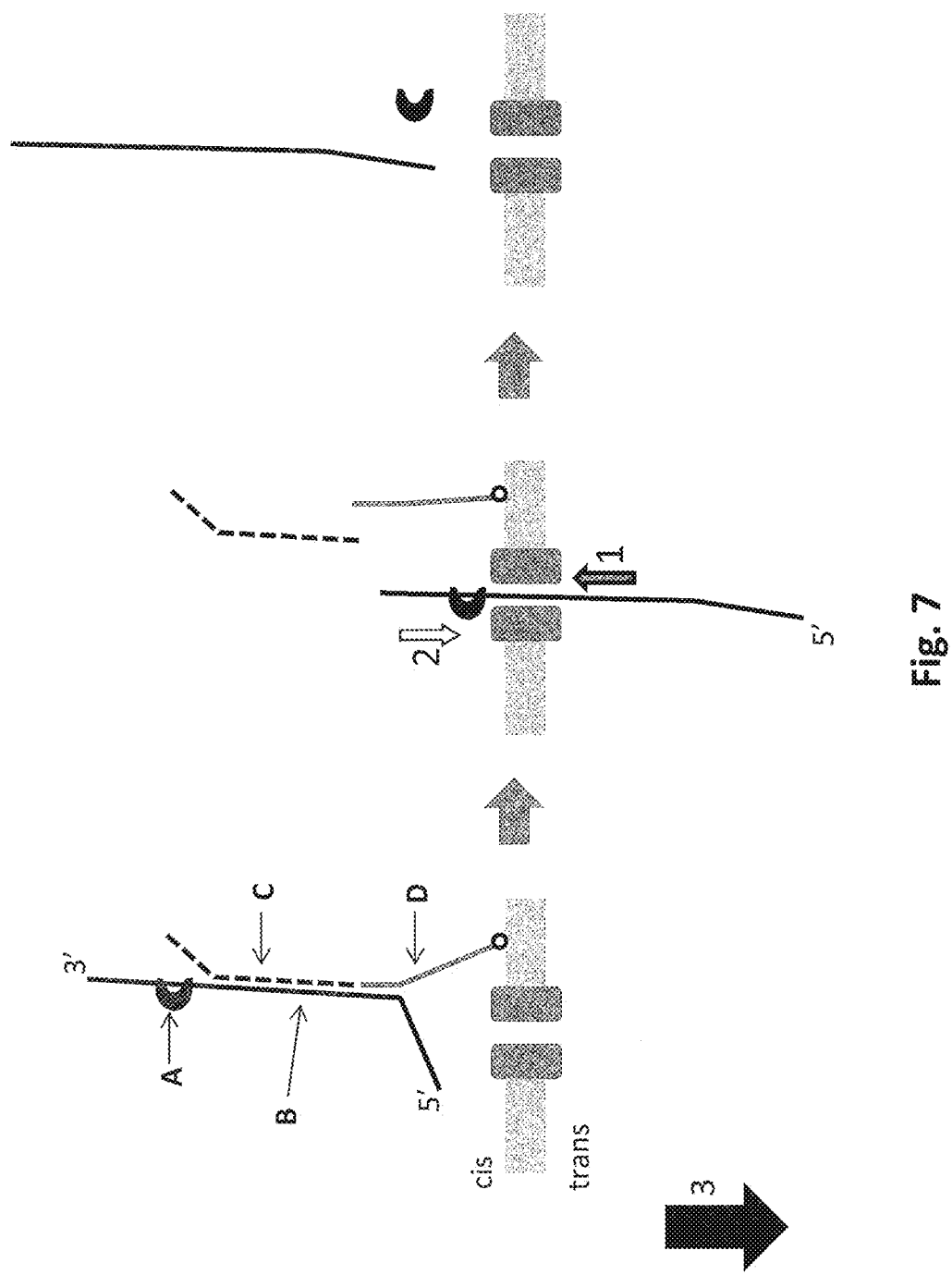
FIG. 7 shows a schematic of enzyme controlled translocation of a polynucleotide through a nanopore in a membrane, where the enzyme controls the movement of the polynucleotide against the force of the applied field. The schematic shows the example of a 3' to 5' enzyme (labelled A), where the capture of a polynucleotide in the pore by the 5' end leads to the enzyme controlling the movement of the polynucleotide (the polynucleotide sequences used in example 4 are SEQ ID NO: 115 (labelled B in FIG. 7), SEQ ID NO:116 (labelled C in FIG. 7) and SEQ ID NO: 117 (labelled D in FIG. 7)) against the force of the applied field. During DNA capture the hybridised strands are unzipped. Arrow 1 denotes the direction of DNA movement through the nanopore, the white arrow 2 denotes the direction of enzyme movement along the DNA and arrow 3 denotes the direction of the applied field. As long as the enzyme does not dissociate from the DNA the enzyme will pull the DNA out of the pore until it is finally ejected on the cis side of the membrane.
Figure 8:
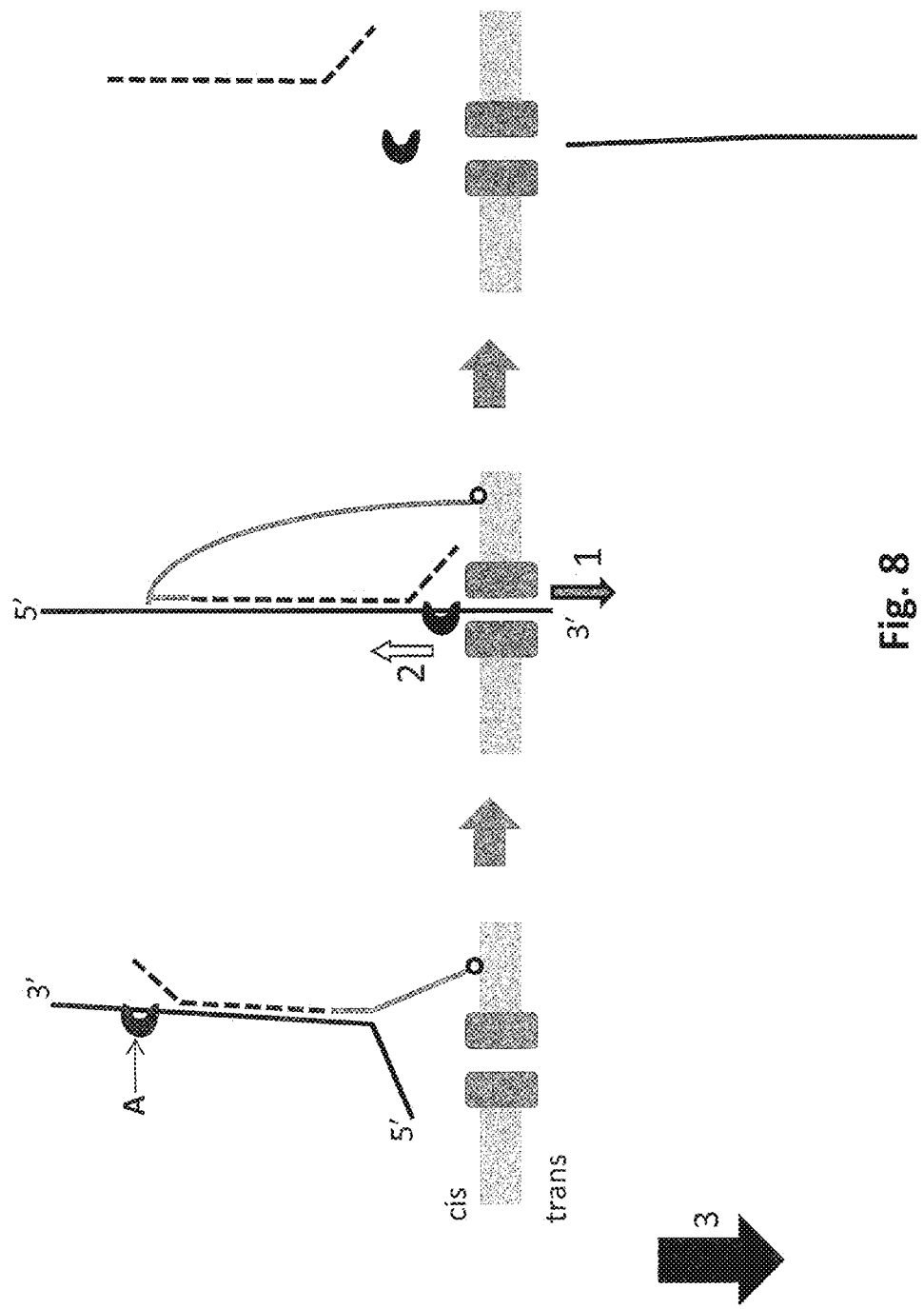
FIG. 8 shows a schematic of enzyme controlled translocation of a polynucleotide through a nanopore in a membrane, where the enzyme controls the movement of the polynucleotide in the same direction as the force of the applied field. The schematic shows the example of a 3' to 5' enzyme (labelled A), where the capture of a polynucleotide in the pore by the 3' end leads to the enzyme controlling the movement of the polynucleotide with the force of the applied field. Arrow 1 denotes the direction of the DNA movement through the nanopore, the white arrow 2 denotes the direction of enzyme movement along DNA and arrow 3 denotes the direction of the applied field. As long as the enzyme does not dissociate from the DNA the enzyme will feed the DNA through the pore until it is finally ejected on the trans side of the membrane.

This example compares the ability of a Hel308 Mbu monomer (SEQ ID NO: 10), to control the movement of intact DNA strands (900 mer) through a nanopore, to that of the Hel308 Mbu(E284C/S615C)-bismaleimidePEG3 (SEQ ID NO. 10 with the following mutations E284C/S615C connected by a bismaleimidePEG3 linker). The general method for controlled DNA translocation against the field is shown in FIG. 7 and with the field in FIG. 8.

Materials and Methods

Figure 9:
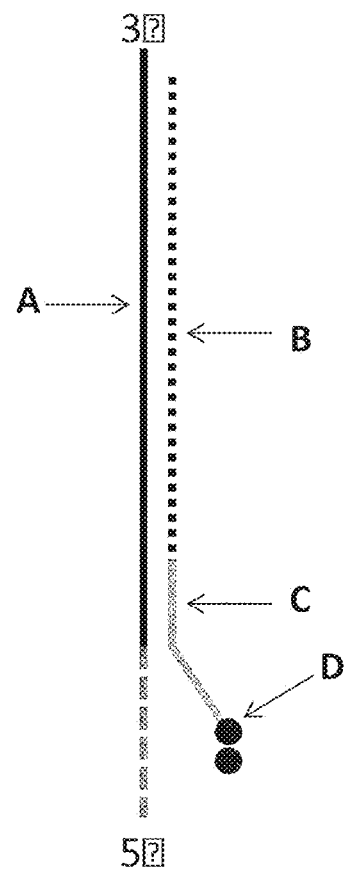
FIG. 9 shows the DNA substrate design used in Example 4. The 900mer sense strand (SEQ ID NO: 115) is labelled A, the anti-sense strand which is minus the 4 base-pair leader (SEQ ID NO: 116) is labelled B and the primer (SEQ ID NO: 117) is labelled C. The primer has a 3' cholesterol tag which is labelled D.

The DNA was formed by ligating a 50-polyT 5' leader to a ~900 base fragment of PhiX dsDNA. The leader also contains a complementary section to which SEQ ID NO: 117 (which at the 3' end of the sequence has six iSp18 spacers attached to two thymine residues and a 3' cholesterol TEG) was hybridized to allow the DNA to be tethered to the bilayer. Finally the 3' end of the PhiX dsDNA was digested with AatII digestion enzyme to yield a 4 nt 3'-overhang of ACGT (see FIG. 9 for diagram of the DNA substrate design).

Buffered solution used for Hel308 Mbu: 400 mM NaCl, 100 mM Hepes, 10 mM potassium ferrocyanide, 10 mM potassium ferricyanide pH8.0, 1 mM ATP, 1 mM MgCl$_2$, Buffered solution used for Hel308 Mbu(E284C/S615C)-bismaleimidePEG3: 400 mM NaCl, 100 mM Hepes, 10 mM potassium ferrocyanide, 10 mM potassium ferricyanide pH8.0, 2 mM ATP, 2 mM MgCl$_2$, Nanopore: E. coli MS(B1-G75S/G77S/L88N/Q126R)8 MspA (SEQ ID NO: 2 with the mutations G75S/G77S/L88N/Q126R) Enzymes: Hel308 Mbu (SEQ ID NO: 10) added at 200 nM final and Hel308 Mbu(E284C/S615C)-bismaleimidePEG3 (SEQ ID NO: 10 with the following mutations E284C/S615C connected by a bismaleimide3PEG linker) added at 10 nM final.

Electrical measurements were acquired from single MspA nanopores inserted in 1,2-diphytanoyl-glycero-3-phosphocholine lipid (Avanti Polar Lipids) bilayers. Bilayers were formed across ~100 um diameter apertures in 20 um thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers. Platinum electrodes are connected to the buffered solutions so that the cis compartment (to which both nanopore and enzyme/DNA are added) is connected to the ground of the Axopatch headstage, and the trans compartment is connected to the active electrode of the headstage.

After achieving a single pore in the bilayer, DNA complex (SEQ ID NOs: 115, 116 and 117 (which at the 3' end of the sequence has six iSp18 spacers attached to two thymine residues and a 3' cholesterol TEG)), DNA=0.1 nM for the Hel308 Mbu monomer (SEQ ID NO: 10) and 0.05 nM for the Hel308 Mbu(E284C/S615C)-bismaleimidePEG3 (SEQ ID NO: 10 with mutations E284C/S615C connected by a bismaleimidePEG3 linker), MgCl$_2$ (2 mM) and ATP (2 mM) were added to the cis compartment of the electrophysiology chamber. A control experiment was run at +140 mV. The helicase Hel308 Mbu monomer (SEQ ID NO: 10, 200 nM) or the Hel308 Mbu(E284C/S615C)-bismaleimidePEG3 (SEQ ID NO: 10 with mutations E284C/S615C connected by a bismaleimidePEG3 linker, 10 nM) was then added to the cis compartment. Experiments were carried out at a constant potential of +140 mV.

Results and Discussion

Figure 10:
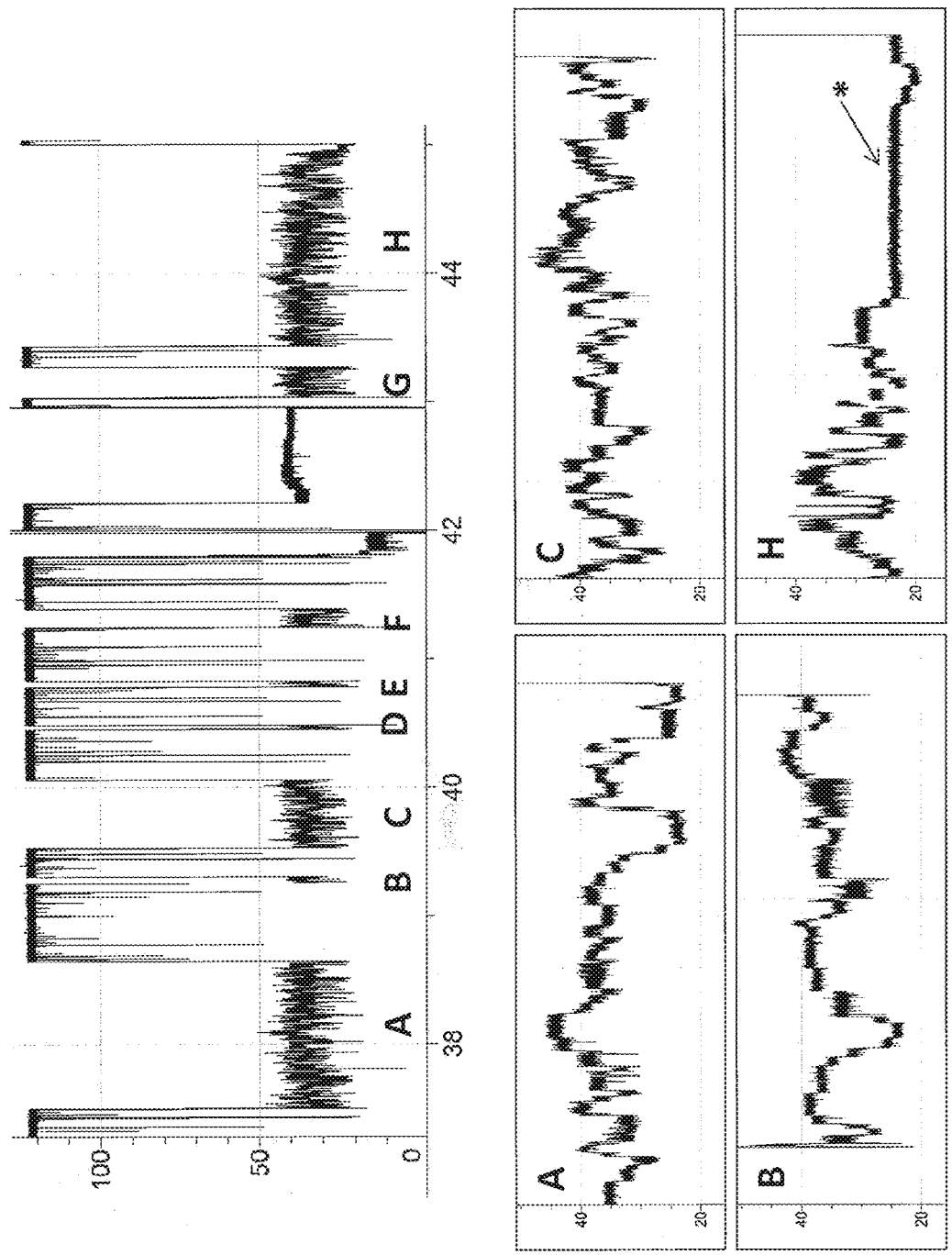
FIG. 10 shows example current traces observed when a helicase controls the translocation of DNA (+140 mV, 400 mM NaCl, 100 mM Hepes pH 8.0, 10 mM potassium ferrocyanide, 10 mM potassium ferricyanide, 0.1 nM 900mer DNA (SEQ ID NO: 115, 116 and 117 (which at the 3' end of the sequence has six iSp18 spacers attached to two thymine residues and a 3' cholesterol TEG)), 1 mM ATP, 1 mM MgCl$_2$) through an MspA nanopore (MS(B1-G75S/G77S/L88N/Q126R)8 MspA (SEQ ID NO: 2 with mutations G75S/G77S/L88N/Q126R) using Hel308 Mbu monomer (200 nM, SEQ ID NO: 10). The top electrical trace (y-axis label=current (pA), x-axis label=time (min)) shows the open pore current (~120 pA) dropping to a DNA level (20-50 pA) when DNA is captured under the force of the applied potential (+140 mV). DNA with enzyme attached results in a long block that shows stepwise changes in current as the enzyme moves the DNA through the pore. The upper trace shows a sequence of 8 separate helicase-controlled DNA movements marked A-H. All of the helicase-controlled DNA movements in this section of trace are being moved through the nanopore against the field by the enzyme (DNA captured 5'down) (see FIG. 7 for details). Below are enlargements of the last section of 4 of the helicase-controlled DNA movements as the DNA exits the nanopore. Of the 8 helicase-controlled DNA movements in this section, only 1 (H) ends in the characteristic long polyT level that indicates that the enzyme has reached the end of the DNA and moved the 50T 5'-leader of the DNA substrate through the pore (labelled with a *). In the full run with Hel308Mbu (SEQ ID NO: 10) it was found that ~30% of the helicase-controlled DNA movements end at the polyT (n=19 helicase-controlled DNA movements in this experiment).

The addition of helicase monomer-DNA substrate to MspA nanopores (as shown in FIG. 7) produces characteristic current blocks as shown in FIG. 10. The helicase Hel308 Mbu monomer (SEQ ID NO: 10) is able to move DNA through a nanopore in a controlled fashion, producing stepwise changes in current as the DNA moves through the nanopore. Example current traces observed when a helicase controls the translocation of DNA (+140 mV, 400 mM NaCl, 100 mM Hepes pH 8.0, 10 mM potassium ferrocyanide, 10 mM potassium ferricyanide, 0.1 nM 900mer DNA (SEQ ID NOs: 115, 116 and 117 (which at the 3' end of the sequence has six iSp18 spacers attached to two thymine residues and a 3' cholesterol TEG)), 1 mM ATP, 1 mM MgCl$_2$) through an MspA nanopore (MS(B1-G75S/G77S/L88N/Q126R)8 MspA (SEQ ID NO: 2 with mutations G75S/G77S/L88N/Q126R) using Hel308 Mbu (200 nM, SEQ ID NO: 10) are shown in FIG. 10. The top electrical trace shows the open pore current (~120 pA) dropping to a DNA level (20-50 pA)

when DNA is captured under the force of the applied potential (+140 mV). DNA with an enzyme attached results in a long block that shows stepwise changes in current as the enzyme moves the DNA through the pore. The upper trace shows a sequence of 8 separate helicase-controlled DNA movements marked A-H (see FIG. 10). All the helicase-controlled DNA movements in this section of trace are being moved through the nanopore against the field by the enzyme (DNA captured 5'down) (see FIG. 7 for details). Below are enlargements of the last section of 4 of the helicase-controlled DNA movements as the DNA exits the nanopore. Of the 8 helicase-controlled DNA movements in this section, only 1 (H) ends in the characteristic long polyT level that indicates that the enzyme has reached the end of the DNA and moved the 50T 5'-leader of the DNA substrate through the pore. In the full run with Hel308 Mbu monomer (SEQ ID NO: 10) it was found that ~30% of the helicase-controlled DNA movements end at the polyT (n=19 helicase-controlled DNA movements in this experiment).

Figure 11:
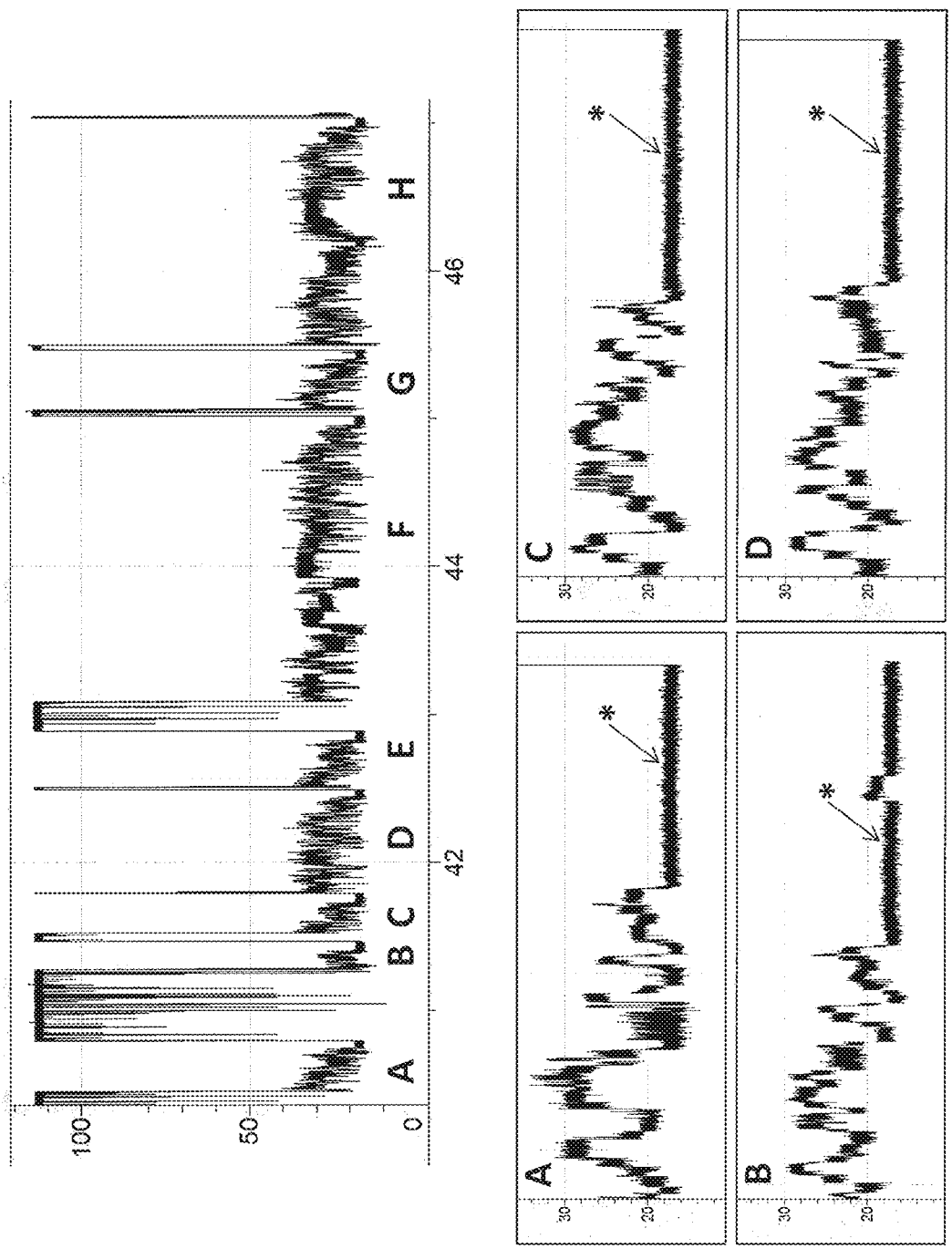
FIG. 11 shows example current traces observed when a helicase controls the translocation of DNA (+140 mV, 400 mM NaCl, 100 mM Hepes pH 8.0, 10 mM potassium ferrocyanide, 10 mM potassium ferricyanide, 0.05 nM 900mer DNA (SEQ ID NO: 115, 116 and 117 (which at the 3' end of the sequence has six iSp18 spacers attached to two thymine residues and a 3' cholesterol TEG)), 2 mM ATP, 2 mM $MgCl_2$) through an MspA nanopore (MS(B1-G75S/G77S/L88N/Q126R)8 MspA (SEQ ID NO: 2 with mutations G75S/G77S/L88N/Q126R) using the Hel308 Mbu(E284C/S615C)-bismaleimidePEG3 (10 nM, SEQ ID NO: 10 with mutations E284C/S615C connected by a bismaleimidePEG3 linker). The top electrical trace (y-axis label=current (pA), x-axis label=time (min)) shows the open pore current (~115 pA) dropping to a DNA level (15-40 pA) when DNA is captured under the force of the applied potential (+140 mV). DNA with enzyme attached results in a long block that shows stepwise changes in current as the enzyme moves the DNA through the pore. The upper trace shows a sequence of 8 separate helicase-controlled DNA movements marked A-H. All the helicase-controlled DNA movements in this section of trace are being moved through the nanopore against the field by the enzyme (DNA captured 5'down) (see FIG. 7 for details). Below are enlargements of the last section of 4 of the helicase-controlled DNA movements as the DNA exits the nanopore. Of the 8 helicase-controlled DNA movements in this section, every one ends in the characteristic long polyT level that indicates that the enzyme has reached the end of the DNA and moved the 50T 5'-leader of the DNA substrate through the pore (labelled with a *). In the full run with Hel308 Mbu (E284C/S615C)-bismaleimidePEG3 (SEQ ID NO: 10 with mutations E284C/S615C connected by a bismaleimidePEG3 linker) it was found that ~85% of the helicase-controlled DNA movements against the field (5' down) end at the polyT (n=27 helicase-controlled DNA movements in this experiment).

The Hel308 Mbu(E284C/S615C)-bismaleimidePEG3 (10 nM, SEQ ID NO: 10 with mutations E284C/S615C connected by a bismaleimidePEG3 linker) is able to move DNA through a nanopore in a controlled fashion against the field, producing stepwise changes in current as the DNA moves through the nanopore. Example current traces observed when a helicase controls the translocation of DNA (+140 mV, 400 mM NaCl, 100 mM Hepes pH 8.0, 10 mM potassium ferrocyanide, 10 mM potassium ferricyanide, 0.05 nM 900mer DNA (SEQ ID NO: 115, 116 and 117 (which at the 3' end of the sequence has six iSp18 spacers attached to two thymine residues and a 3' cholesterol TEG)), 2 mM ATP, 2 mM MgCl$_2$) through an MspA nanopore (MS(B1-G75S/G77S/L88N/Q126R)8 MspA (SEQ ID NO: 2 with mutations G75S/G77S/L88N/Q126R) using the Hel308 Mbu(E284C/S615C)-bismaleimidePEG3 (10 nM, SEQ ID NO: 10 with mutations E284C/S615C connected by a bismaleimidePEG3 linker) are shown in FIG. 11. The top electrical trace shows the open pore current (~115 pA) dropping to a DNA level (15-40 pA) when DNA is captured under the force of the applied potential (+140 mV). DNA with enzyme attached results in a long block that shows stepwise changes in current as the enzyme moves the DNA through the pore. The upper trace shows a sequence of 8 separate helicase-controlled DNA movements marked A-H (see FIG. 11). All the helicase-controlled DNA movements in this section of trace are being moved through the nanopore against the field by the enzyme (DNA captured 5'down) (see FIG. 7 for details). Below are enlargements of the last section of 4 of the helicase-controlled DNA movements as the DNA exits the nanopore. Of the 8 helicase-controlled DNA movements in this section, every one ends in the characteristic long polyT level that indicates that the enzyme has reached the end of the DNA and moved the 50T 5'-leader of the DNA substrate through the pore. In the full run with Hel308 Mbu(E284C/S615C)-bismaleimidePEG3 (SEQ ID NO: 10 with mutations E284C/S615C connected by a bismaleimidePEG3 linker) it was found that ~85% of the helicase-controlled DNA movements against the field (5' down) end at the polyT (n=27 helicase-controlled DNA movements in this experiment), thus demonstrating substantially improved processivity relative to the unmodified Hel308 Mbu This experiment required only 10 nM enzyme in order to observe helicase-controlled DNA movement, however, Hel308 Mbu monomer (SEQ ID NO: 10) experiments used 200 nM enzyme. Therefore, much lower enzyme concentrations of the helicases in which the opening has been closed can be used while still achieving long read lengths.

Figure 12:
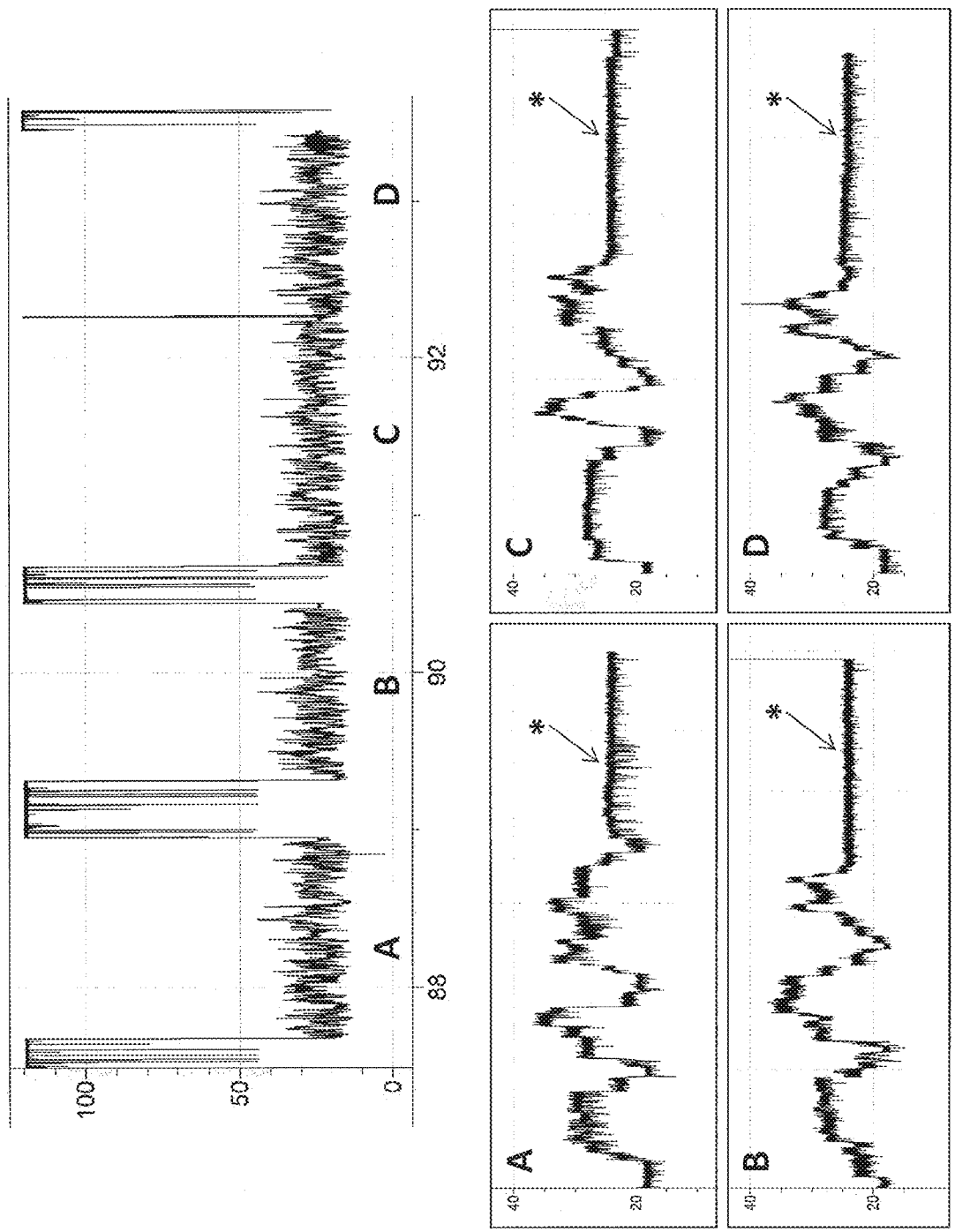
FIG. 12 shows example current traces observed when a helicase controls the translocation of DNA (+140 mV, 400 mM NaCl, 100 mM Hepes pH 8.0, 10 mM potassium ferrocyanide, 10 mM potassium ferricyanide, 0.05 nM 900mer DNA (SEQ ID NO: 115, 116 and 117 (which at the 3' end of the sequence has six iSp18 spacers attached to two thymine residues and a 3' cholesterol TEG)), 2 mM ATP, 2 mM $MgCl_2$) through an MspA nanopore (MS(B1-G75S/G77S/L88N/Q126R)8 MspA (SEQ ID NO: 2 with mutations G75S/G77S/L88N/Q126R) using the Hel308 Mbu(E284C/S615C)-bismaleimidePEG3 (10 nM, SEQ ID NO: 10 with mutations E284C/S615C connected by a bismaleimidePEG3 linker). The top electrical trace (y-axis label=current (pA), x-axis label=time (min)) shows the open pore current (~120 pA) dropping to a DNA level (15-40 pA) when DNA is captured under the force of the applied potential (+140 mV). DNA with enzyme attached results in a long block that shows stepwise changes in current as the enzyme moves the DNA through the pore. The upper trace shows a sequence of 4 separate helicase-controlled DNA movements marked A-D. All the helicase-controlled DNA movements in this section of trace are being moved through the nanopore with the field by the enzyme (DNA captured 3'down) (see FIG. 8 for details). Below are enlargements of the last section of the helicase-controlled DNA movements as the DNA exits the nanopore. 3' down DNA shows a characteristically different signature to 5' down DNA, with a different current to sequence relationship, and different variance. Of the 4 helicase-controlled DNA movements in this section, every one ends in the characteristic long polyT level that indicates that the enzyme has reached the end of the DNA and moved the 50T 5'-leader of the DNA substrate through the pore (labelled with a *). In the full run with Hel308 Mbu(E284C/S615C)-bismaleimidePEG3 (SEQ ID NO: 10 with mutations E284C/S615C connected by a bismaleimidePEG3 linker) it was found that ~87% of the helicase-controlled DNA movements with the field (3' down) end at the polyT (n=15 helicase-controlled DNA movements in this experiment).

Hel308 Mbu(E284C/S615C)-bismaleimidePEG3 (SEQ ID NO: 10 with mutations E284C/S615C connected by a bismaleimidePEG3 linker) shows enhanced ability to move DNA through a nanopore with the force of the applied field (see FIG. 8 for details), producing stepwise changes in current as the DNA moves through the nanopore. Example current traces observed when a helicase controls the translocation of DNA (+140 mV, 400 mM NaCl, 100 mM Hepes pH 8.0, 10 mM potassium ferrocyanide, 10 mM potassium ferricyanide, 0.05 nM 900mer DNA (SEQ ID NO: 115, 116 and 117 (which at the 3' end of the sequence has six iSp18 spacers attached to two thymine residues and a 3' cholesterol TEG)), 2 mM ATP, 2 mM MgCl$_2$) through an MspA nanopore (MS(B1-G75S/G77S/L88N/Q126R)8 MspA(SEQ ID NO: 2 with mutations G75S/G77S/L88N/Q126R) using the Hel308 Mbu(E284C/S615C)-bismaleimidePEG3 (10 nM, SEQ ID NO: 10 with mutations E284C/S615C connected by a bismaleimidePEG3 linker) are shown in FIG. 12. The top electrical trace shows the open pore current (~120 pA) dropping to a DNA level (15-40 pA) when DNA is captured under the force of the applied potential (+140 mV). DNA with enzyme attached results in a long block that shows stepwise changes in current as the enzyme moves the DNA through the pore. The upper trace shows a sequence of 4 separate helicase-controlled DNA movements marked A-D (see FIG. 12). All the helicase-controlled DNA movements in this section of trace are being moved through the nanopore with the field by the enzyme (DNA captured 3'down) (see FIG. 8 for details). Below are enlargements of the last section of the helicase-controlled DNA movements as the DNA exits the nanopore. 3' down DNA shows a characteristically different signature to 5' down DNA, with a different current to sequence relationship, and different variance. Of the 4 helicase-controlled DNA movements in this section, every one ends in the characteristic long polyT level that indicates that the enzyme has reached the end of the DNA and moved the 50T 5'-leader of the DNA substrate through the pore. In the full run with Hel308 Mbu(E284C/S615C)-bismaleimidePEG3 (SEQ ID NO: 10 with mutations E284C/S615C connected by a bismaleimidePEG3 linker) it was found that ~87% of helicase-controlled DNA movements with the field (3' down) end at the polyT (n=15 helicase-controlled DNA movements in this experiment). In comparison, 3' down helicase-controlled DNA movements are rarely observed when using Hel308 Mbu monomer (SEQ ID NO: 10), and when they are the movements are short with typically less than 50 states observed, indicating a high level of enzyme dissociation in this orientation. The long 3'down helicase-controlled DNA movements, with Hel308 Mbu (E284C/S615C)-bismaleimidePEG3 (SEQ ID NO: 10 with mutations E284C/S615C connected by a bismaleimidePEG3 linker), show a surprising improvement in processivity in the 3' down mode.

Example 5

This example shows that the Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)) has the ability to control the movement of intact DNA strands (SEQ ID NO: 127 attached at its 3' end to four iSpC3 spacers, the last of which is attached to the 5' end of SEQ ID NO: 128) through a nanopore. The general method for controlled DNA translocation against the field is shown in FIG. 7 and with the field in FIG. 8.

Materials and Methods

Prior to setting up the experiment, the DNA (0.5 nM, (SEQ ID NO: 127 attached at its 3' end to four iSpC3 spacers, the last of which is attached to the 5' end of SEQ ID NO: 128) and Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)) were pre-incubated together for 1 hour.

Electrical measurements were acquired from single MspA nanopores (MS(B1-G75S/G77S/L88N/Q126R)8 MspA (SEQ ID NO: 2 with mutations G75S/G77S/L88N/Q126R) inserted in block co-polymer in buffer (625 mM KCl, 100 mM Hepes, 75 mM Potassium Ferrocyanide (II), 25 mM Potassium ferricyanide (III), pH 8). $MgCl_2$ (10 mM) and ATP (1 mM) were mixed together with buffer (625 mM KCl, 100 mM Hepes, 75 mM Potassium Ferrocyanide (II), 25 mM Potassium ferricyanide (III), pH 8) and then added to the DNA (SEQ ID NO: 127 attached at its 3' end to four iSpC3 spacers, the last of which is attached to the 5' end of SEQ ID NO: 128), Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)) pre-mix. After achieving a single pore in the bilayer, the pre-mix was added to the single nanopore experimental system. Experiments were carried out at a constant potential of +120 mV and helicase-controlled DNA movement was monitored.

Results and Discussion

Figure 13:
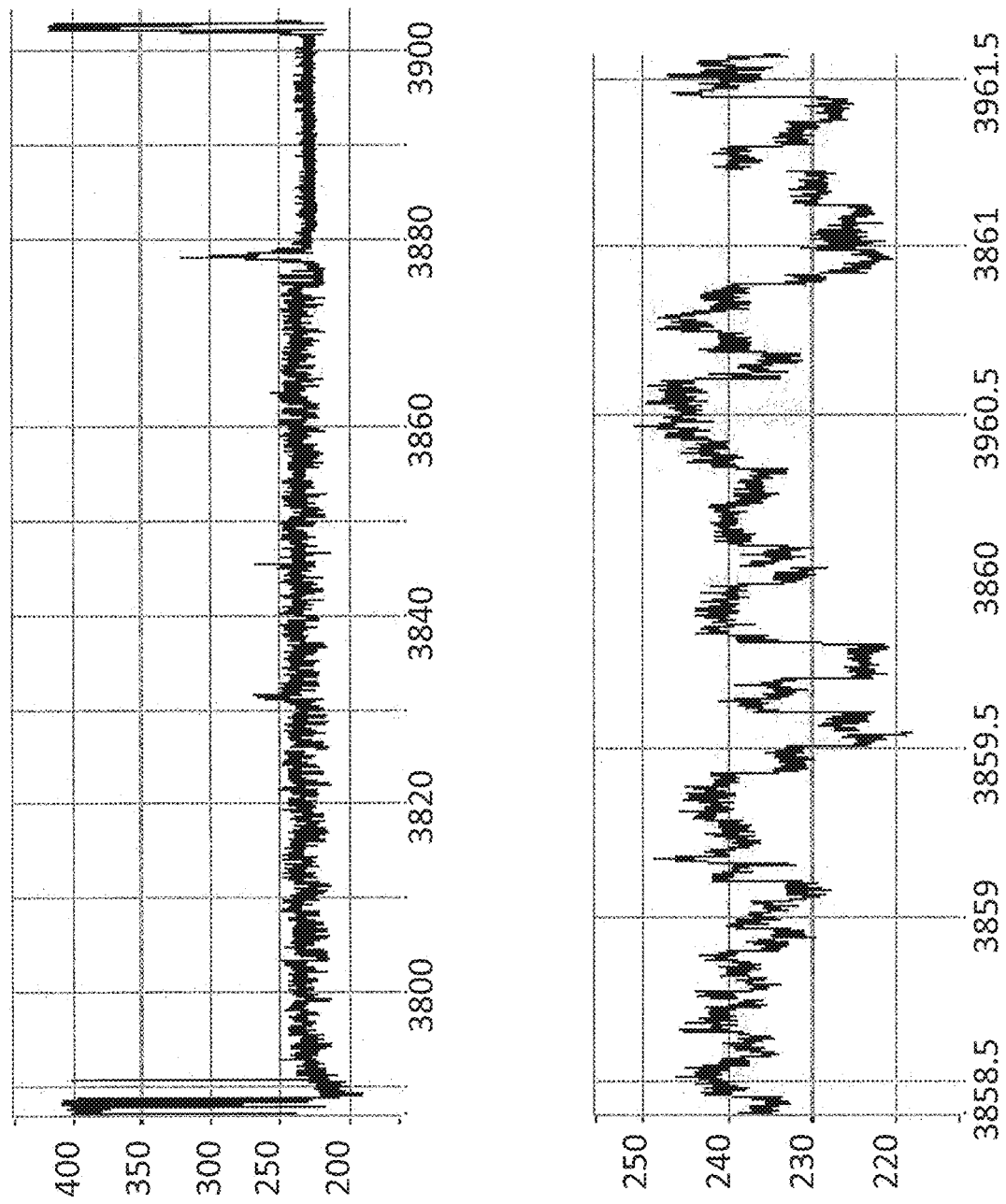
FIG. 13 shows example current traces (y-axis=current (pA), x-axis=time (s) for upper and lower traces) observed when a helicase controls the translocation of DNA (+120 mV, (625 mM KCl, 100 mM Hepes, 75 mM Potassium Ferrocyanide (II), 25 mM Potassium ferricyanide (III), pH 8, 0.5 nM DNA (SEQ ID NO: 127 attached at its 3' end to four iSpC3 spacers, the last of which is attached to the 5' end of SEQ ID NO: 128), 1 mM ATP, 10 mM $MgCl_2$) through an MspA nanopore (MS(B1-G75S/G77S/L88N/Q126R)8 MspA (SEQ ID NO: 2 with mutations G75S/G77S/L88N/Q126R) using the Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)). The top electrical trace shows the open pore current (~400 pA) dropping to a DNA level (250-220 pA) when DNA is captured under the force of the applied potential (+120 mV). DNA with enzyme attached results in a long block that shows stepwise changes in current as the enzyme moves the DNA through the pore. The lower trace is a zoomed in region of the upper trace.

Helicase controlled DNA movement was observed for the closed complex Hel308 Mbu (E284C/S615C)-mal-pep-mal (SEQ ID NO: 10 with the mutations E284C/S615C connected by a bismaleimide peptide linker (maleimide-propyl-SRDFWRS (SEQ ID NO: 109)-(1,2-diaminoethane)-propyl-maleimide)). An example of a helicase-controlled DNA movement is shown in FIG. 13.

Example 6

This example describes the method of synthesising the TrwC Cba-N691C/Q346C-PEG11 (SEQ ID NO: 126 with the mutations N691C/Q346C connected by a PEG11 linker). In this case a covalent link between cysteines at positions 346 and 691 in the primary sequence of TrwC Cba (SEQ ID NO: 126) was made by reacting these positions with a PEG11 linker.

Materials and Methods

Figure 14:
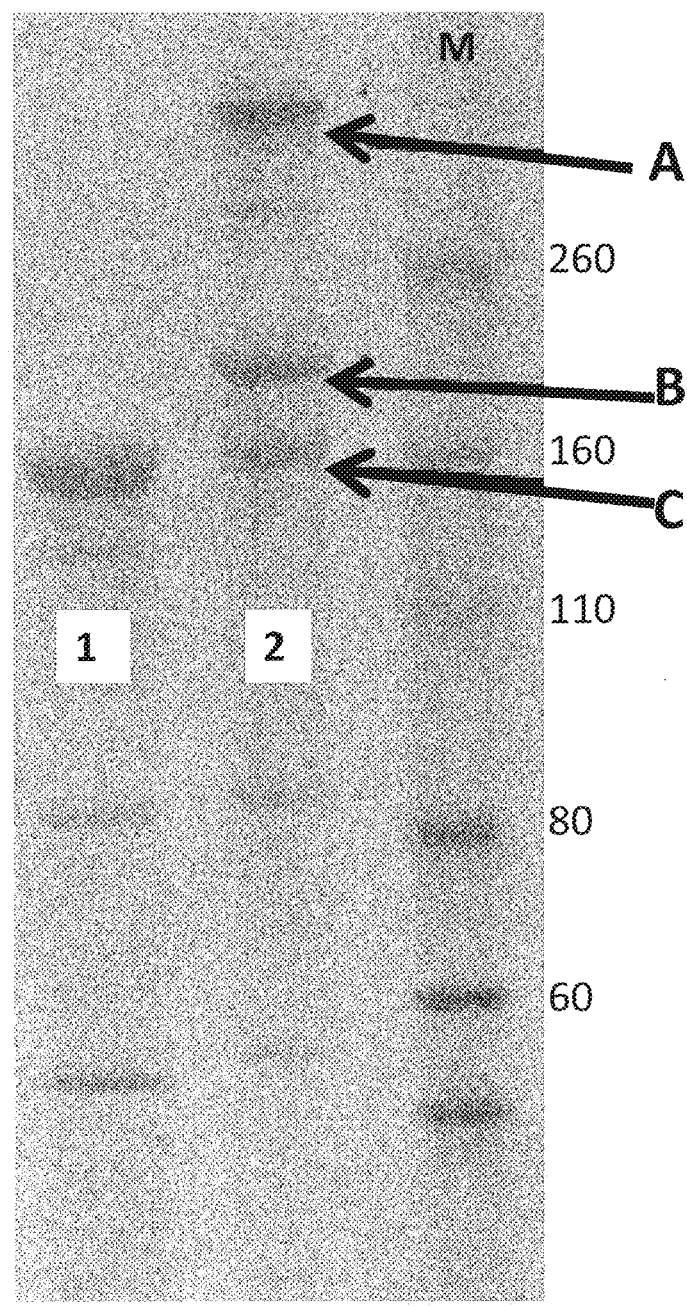
FIG. 14 shows a coomassie stained 7.5% Tris-HCl gel of the TrwC Cba-N691C/Q346C-mal-PEG11-mal (SEQ ID NO: 126 with the mutations N691C/Q346C connected by a bismaleimide polyethylene glycol linker) reaction mixture. The lane on the right of the gel (labelled M) shows an appropriate protein ladder (the mass unit markers are shown on the right of the gel). Lane 1 contains 5 μL of approximately 10 μM TrwC Cba-D657C/R339C alone (SEQ ID NO: 126 with mutation D657C/R339C) as a reference. Lane 2 contains 5 μL of approximately 10 μM TrwC Cba-N691C/Q346C-bismaleimidePEG11 (SEQ ID NO: 126 with the mutations N691C/Q346C connected by a bismaleimide PEG11 linker). As indicated in lane 2, the upper band corresponds to the dimeric enzyme species (labelled A), the middle band corresponds to the closed complex (labelled B)

In detail, DTT (2 µl, 1 M) was added to TrwC Cba-N691C/Q346C (200 µl, SEQ ID NO: 126 with the mutations N691C/Q346C, stored in 50 mM Hepes, 10% glycerol, 10 mM DTT, 692 mM NaCl pH7.5) and the mixture was incubated at room temperature on a 10" wheel rotating at 20 rpm for 30 minutes. This mixture was buffer exchanged through Pierce 2 mL Zeba desalting columns, 7k MWCO into 100 mM potassium phosphate, 500 mM NaCl, 5 mM EDTA, 0.1% Tween-20 pH 8.0 and diluted in the same buffer to give 10 µL aliquots of sample. Maleimide-PEG11-maleimide (50 uM final concentration, Quanta Biodesign, product #10397) was added to one of the aliquots and the mixture incubated at room temperature on a 10" wheel rotating at 20 rpm for 120 minutes. To stop the reaction, DTT (1 ul of 1 M) was added to quench any remaining maleimides. Analysis of the reaction is by 7.5% polyacrylamide gel. FIG. 14 shows a coomassie stained 7.5% Tris-HCl gel of the TrwC Cba-N691C/Q346C-mal-PEG11-mal (SEQ ID NO: 126 with the mutations N691C/Q346C connected by a bismaleimide polyethylene glycol linker) reaction mixture. The lane on the right of the gel (labelled M) shows an appropriate protein ladder (the mass unit markers are shown on the right of the gel). Lane 1 contains 5 µL of approximately 10 µM TrwC Cba-D657C/R339C alone (SEQ ID NO: 126 with mutation D657C/R339C) as a reference. Lane 2 contains 5 µL of approximately 10 µM TrwC Cba-N691C/Q346C-bismaleimdiePEG11 (SEQ ID NO: 126 with the mutations N691C/Q346C connected by a bismaleimide PEG11 linker). As indicated in lane 2, the upper band corresponds to the dimeric enzyme species (labelled A), the middle band corresponds to the closed complex (labelled B) TraI-Cba-N691C/Q346C-bismaleimidePEG11 (SEQ ID NO: 126 with the mutations N691C/Q346C connected by a bismaleimide PEG11 linker). It was clear from the gel that the reaction to attach the mal-PEGn1-mal linker did not go to completion as a band for unmodified starting material (labelled C) TrwC Cba-N691C/Q346C (SEQ ID NO: 126 with the mutations N691C/Q346C) was observed.

The TrwC Cba-N691C/Q346C-PEG11 (SEQ ID NO: 126 with the mutations N691C/Q346C connected by a PEG31 linker) was then buffer exchanged to 50 mM Tris, 500 mM NaCl, 2 mM DTT, pH 8.0.

Using an analogous procedure to that described in this example, it was possible to make the following closed complexes listed in Table 10 below.

TABLE 10

| Entry No. | Closed complex | Sequence |
|---|---|---|
| 1 | TrwC Cba-N691C/Q346C-mal-pep-mal | SEQ ID NO: 126 with the mutations N691C/Q346C connected by a bismaleimide peptide linker (maleimide-propyl-SRDFWRS (SEQ ID NO: 109)-(1,2-diaminoethane)-propyl-maleimide) |
| 2 | TrwC Cba-N691C/Q346C-bismaleimidePEG3 | SEQ ID NO: 126 with the mutations N691C/Q346C connected by a bismaleimide PEG3 linker |
| 3 | TrwC Cba-D657C/R339C-mal-pep-mal | SEQ ID NO: 126 with the mutations D657C/R339C connected by a bismaleimide peptide linker (maleimide-propyl-SRDFWRS (SEQ ID NO: 109)-(1,2-diaminoethane)-propyl-maleimide) |
| 4 | TrwC Cba-D657C/R339C-bismaleimidePEG3 | SEQ ID NO: 126 with the mutations D657C/R339C connected by a bismaleimide PEG3 linker |
| 5 | TrwC Cba-D657C/R339C-bismaleimidePEG11 | SEQ ID NO: 126 with the mutations D657C/R339C connected by a bismaleimide PEG11 linker |
| 6 | TrwC Cba-N691C/S350C-mal-pep-mal | SEQ ID NO: 126 with the mutations N691C/S350C connected by a bismaleimide peptide linker (maleimide-propyl-SRDFWRS (SEQ ID NO: 109)-(1,2-diaminoethane)-propyl-maleimide) |
| 7 | TrwC Cba-N691C/S350C-bismaleimidePEG3 | SEQ ID NO: 126 with the mutations N691C/S350C connected by a bismaleimide PEG3 linker |
| 8 | TrwC Cba-N691C/S350C-bismaleimidePEG11 | SEQ ID NO: 126 with the mutations N691C/S350C connected by a bismaleimide PEG11 linker |
| 9 | TrwC Cba-V690C/S350C-mal-pep-mal | SEQ ID NO: 126 with the mutations V690C/S350C connected by a bismaleimide peptide linker (maleimide-propyl-SRDFWRS (SEQ ID NO: 109)-(1,2-diaminoethane)-propyl-maleimide) |

TABLE 10-continued

| Entry No. | Closed complex | Sequence |
|---|---|---|
| 10 | TrwC Cba-V690C/S350C-bismaleimidePEG3 | SEQ ID NO: 126 with the mutations V690C/S350C connected by a bismaleimide PEG3 linker |
| 11 | TrwC Cba-V690C/S350C-bismaleimidePEG11 | SEQ ID NO: 126 with the mutations V690C/S350C connected by a bismaleimide PEG11 linker |

Example 7

This Example illustrates that when a number of helicases were investigated (Hel308 Mbu (SEQ ID NO: 10), Hel308 Mbu-E284C (SEQ ID NO: 10 with the mutation E284C), Hel308 Mbu-E284C/C301A (SEQ ID NO: 10 with the mutations E284C/C301A), Hel308 Mbu-E285C (SEQ ID NO: 10 with the mutation E285C), Hel308 Mbu-S288C (SEQ ID NO: 10 with the mutation S288C), and Hel308 Mbu-D274C (SEQ ID NO: 10 with the mutation D274C) for their rate of turnover of dsDNA molecules ($min^{-1}enzyme^{-1}$) using a fluorescent assay, the mutant helicases (Hel308 Mbu-E284C (SEQ ID NO: 10 with the mutation E284C), Hel308 Mbu-E284C/C301A (SEQ ID NO: 10 with the mutations E284C/C301A), Hel308 Mbu-E285C (SEQ ID NO: 10 with the mutation E285C), Hel308 Mbu-S288C (SEQ ID NO: 10 with the mutation S288C), and Hel308 Mbu-D274C (SEQ ID NO: 10 with the mutation D274C)) tested had increased rate of turnover of dsDNA molecules ($min^{-1}enzyme^{-1}$) in comparison to Hel308 Mbu (SEQ ID NO: 10).

Materials and Methods

A custom fluorescent substrate was used to assay the ability of a number of Hel308 Mbu helicases (Hel308 Mbu-E284C (SEQ ID NO: 10 with the mutation E284C), Hel308 Mbu-E284C/C301A (SEQ ID NO: 10 with the mutations E284C/C301A), Hel308 Mbu-E285C (SEQ ID NO: 10 with the mutation E285C), Hel308 Mbu-S288C (SEQ ID NO: 10 with the mutation S288C), and Hel308 Mbu-D274C (SEQ ID NO: 10 with the mutation D274C)) to displace hybridised dsDNA. As shown in 1) of FIG. 15, the fluorescent substrate strand (50 nM final) has both a 3' and 5' ssDNA overhang, and a 44 base section of hybridised dsDNA. The upper strand, containing the 3' ssDNA overhang, has a carboxyfluorescein base (the carboxyfluorescein (labelled c in FIG. 15) is attached to a thymine at position 6 in SEQ ID NO: 151) at the 5' end, and the hybrised complement has a black-hole quencher (BHQ-1, labelled e in FIG. 15) base (the black-hole quencher is attached to a thymine at position 81 in SEQ ID NO: 152) at the 3' end. When the two strands are hybridised the fluorescence from the fluorescein is quenched by the local BHQ-1, and the substrate is essentially non-fluorescent. 1 µM of a capture strand (SEQ ID NO: 153) that is part-complementary to the lower strand of the fluorescent substrate is included in the assay. As shown in 2), in the presence of ATP (1 mM) and $MgCl_2$ (10 mM), appropriate helicase (10 nM) added to the substrate binds to the 3' tail of the fluorescent substrate, moves along the upper strand, and displaces the complementary strand. As shown in 3), once the complementary strand with BHQ-1 is fully displaced the fluorescein on the major strand fluoresces. As shown in 4) the displaced strand preferentially anneals to an excess of capture strand to prevent re-annealing of initial substrate and loss of fluorescence.

Results and Discussion

The graphs in FIGS. 16 and 17 show the dsDNA turnover ($enzyme^{-1}min^{-1}$) in buffer (400 mM KCl, 100 mM Hepes pH 8.0, 1 mM ATP, 10 mM $MgCl_2$, 50 nM fluorescent substrate DNA (SEQ ID NOs: 151 and 152), 1 µM capture DNA (SEQ ID NO: 153)) for a number of helicases (Hel308 Mbu (labelled 1 in FIGS. 16 and 17, SEQ ID NO: 10), Hel308 Mbu-E284C (labelled 2 in FIGS. 16 and 17, SEQ ID NO: 10 with the mutation E284C), Hel308 Mbu-E284C/C301A (labelled 3 in FIG. 16, SEQ ID NO: 10 with the mutations E284C/C301A), Hel308 Mbu-E285C (labelled 4 in FIG. 16, SEQ ID NO: 10 with the mutation E285C), Hel308 Mbu-S288C (labelled 5 in FIG. 16, SEQ ID NO: 10 with the mutation S288C) and Hel308 Mbu-D274C (labelled 6 in FIG. 17, SEQ ID NO: 10 with the mutation D274C)). At the salt concentration investigated (400 mM KCl) the following helicases Hel308 Mbu-E284C (FIGS. 16 and 17 labelled 2, SEQ ID NO: 10 with the mutation E284C), Hel308 Mbu-E284C/C301A (FIG. 16 labelled 3, SEQ ID NO: 10 with the mutations E284C/C301A), Hel308 Mbu-E285C (FIG. 16 labelled 4, SEQ ID NO: 10 with the mutation E285C), Hel308 Mbu-S288C (FIG. 16 labelled 5, SEQ ID NO: 10 with the mutation S288C) and Hel308 Mbu-D274C (FIG. 17 labelled 6, SEQ ID NO: 10 with the mutation D274C) exhibited a higher rate of dsDNA turnover than the control Hel308 Mbu (FIGS. 16 and 17 labelled 1, SEQ ID NO: 10) (see FIGS. 16 and 17). This indicates that these enzymes show increased rate of turnover of dsDNA molecules ($min^{-1}enzyme^{-1}$) when compared to the Hel 308 Mbu control (SEQ ID NO: 10) under the conditions investigated.

Example 8

This example describes two procedures for the light treatment of Hel308 Mbu-E284Faz (SEQ ID NO: 10 with the mutation E284Faz) and Hel308 Mbu-S288Faz (SEQ ID NO: 10 with the mutation S288Faz).

Procedure 1—Exposure to UV light

Hel308 Mbu-E284Faz (SEQ ID NO: 10 with the mutation E284Faz) or Hel308 Mbu-S288Faz (SEQ ID NO: 10 with the mutation E288Faz) in storage buffer (50 mM Tris pH8.0 at 4° C., NaCl (360-390 mM) and 5% Glycerol) was pipetted into PCR tubes (Fisher 0.2 mL thin wall tubes). The sample was placed on ice and exposed to high intensity UV light at 254 nm (Spectroline Longlife Filter lamp (254 nm and 365 nm) from above, at a distance of 4.5 cm. The Hel308 Mbu-E284Faz (SEQ ID NO: 10 with the mutation E284Faz) sample was exposed for 15 mins and the Hel308 Mbu-S288Faz (SEQ ID NO: 10 with the mutation E288Faz) sample was exposed for 10 mins. The samples were then both centrifuged for 5 mins at 16 000 g to remove any precipitated protein. The soluble fraction was carefully removed from the insoluble pellet by pipette.

Procedure 2—Exposure to White Light (LED Source)

Hel308 Mbu-S288Faz (SEQ ID NO: 10 with the mutation E288Faz) in storage buffer (50 mM Tris pH8.0 at 4° C., NaCl (370 mM) and 5% Glycerol) was pipetted into Microcentrifuge tube (Eppendorf, 1.5 mL, Protein Lo Bind). The sample was placed on ice (with the cap open) and exposed to LED light source (Schott A20960.1) on full power from above, at a distance of 3 cm. The Hel308 Mbu-S288Faz (SEQ ID NO: 10 with the mutation E288Faz) sample was exposed for 3 hours.

Procedure 3—Exposure to White Light (LED Source) and Heating

Hel308 Mbu-S288Faz (SEQ ID NO: 10 with the mutation E288Faz) in storage buffer (50 mM Tris pH8.0 at 4° C., NaCl (370 mM) and 5% Glycerol) was pipetted into Microcentrifuge tube (Eppendorf, 1.5 mL, Protein Lo Bind). The sample was placed on ice (with the cap open) and exposed to LED light source (Schott A20960.1) on full power from above, at a distance of 1 cm. The Hel308 Mbu-S288Faz (SEQ ID NO: 10 with the mutation E288Faz) sample was exposed for 1 hour. The sample was transferred in a PCR tube (Fisher 0.2 mL thin wall tube) and heated at 50° C. for 10 min before ramping to 4° C., then centrifuged for 5 mins at 16 000 g to remove any precipitated protein. The soluble fraction was carefully removed from the insoluble pellet by pipette.

Example 9

This example compares the ability of Hel308 Mbu (SEQ ID NO: 10), to control the movement of intact DNA strands (3.6 kb) through a nanopore, to that of a number of Hel308 Mbu mutants (Hel308 Mbu-E284C (SEQ ID NO: 10 with the mutation E284C), Hel308 Mbu-S288C (SEQ ID NO: 10 with the mutation S288C), Hel308 Mbu-E284Faz (SEQ ID NO: 10 with the mutation E284Faz) and heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block)). The general method for controlled DNA translocation against the field is shown in FIG. 18.

Materials and Methods

Prior to setting up the experiment, the DNA (0.2 nM, (SEQ ID NO: 154 attached at its 5' end to four nitroindoles (labelled as x's in FIG. 18), the last of which is attached to the 3' end of SEQ ID NO: 155), SEQ ID NO: 156 and SEQ ID NO: 117) and appropriate helicase (Hel 308 Mbu (100 nM, SEQ ID NO: 10), Hel308 Mbu-E284C (100 nM, SEQ ID NO: 10 with the mutation E284C), Hel308 Mbu-S288C (100 nM, SEQ ID NO: 10 with the mutation S288C), Hel308 Mbu-E284Faz (100 nM, SEQ ID NO: 10 with the mutation E284Faz) and heat treated Hel308 Mbu-E284Faz (500 nM, SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block)) were dissolved in buffer (960 mM KCl, 25 mM potassium phosphate, 3 mM potassium ferrocyanide, 1 mM potassium ferricyanide pH 8.0, 10 mM $MgCl_2$ and 1 mM ATP).

Electrical measurements were acquired from single MspA nanopores (MS(B1-G75S/G77S/L88N/Q126R)8 MspA (SEQ ID NO: 2 with mutations G75S/G77S/L88N/Q126R) inserted in block co-polymer in buffer (960 mM KCl, 25 mM potassium phosphate, 3 mM potassium ferrocyanide, 1 mM potassium ferricyanide pH 8.0). After achieving a single pore in the block co-polymer, buffer (3 mL of 960 mM KCl, 25 mM potassium phosphate, 3 mM potassium ferrocyanide, 1 mM potassium ferricyanide pH 8.0) was then flowed through the system. Finally, the pre-mix (described above) was added to the single nanopore experimental system. Experiments were carried out at a constant potential of +120 mV and helicase-controlled DNA movement was monitored.

Results and Discussion

Helicase controlled DNA movement was observed for all of the enzymes tested—Hel 308 Mbu (SEQ ID NO: 10), Hel308 Mbu-E284C (SEQ ID NO: 10 with the mutation E284C), Hel308 Mbu-S288C (SEQ ID NO: 10 with the mutation S288C), Hel308 Mbu-E284Faz (SEQ ID NO: 10 with the mutation E284Faz) and heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block). Example current traces showing helicase controlled DNA movement are shown in FIGS. 19-23. However, the mutant Hel308 Mbu helicases (Hel308 Mbu-E284C (SEQ ID NO: 10 with the mutation E284C), Hel308 Mbu-S288C (SEQ ID NO: 10 with the mutation S288C), Hel308 Mbu-E284Faz (SEQ ID NO: 10 with the mutation E284Faz) and heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block)) showed increased processivity in comparison to Hel308 Mbu (SEQ ID NO: 10) see Table 11. Of the helicase controlled DNA movements observed in the experiments, the % of movements which processed the DNA all the way to the end of the strand (to the polyT region) were significantly higher for the mutant helicases (Hel308 Mbu-E284C (SEQ ID NO: 10 with the mutation E284C), Hel308 Mbu-S288C (SEQ ID NO: 10 with the mutation S288C), Hel308 Mbu-E284Faz (SEQ ID NO: 10 with the mutation E284Faz) and heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block)) when compared to Hel308 Mbu (SEQ ID NO: 10).

TABLE 11

| Helicase | % of Helicase Controlled DNA movement that reached the polyT region of the DNA strand (SEQ ID NO: 154 attached at its 5' end to four nitroindoles the last of which is attached to the 3' end of SEQ ID NO: 155) |
|---|---|
| Hel308 Mbu (SEQ ID NO: 10) | 2 |
| Hel308 Mbu-E284C (SEQ ID NO: 10 with the mutation E284C) | 32 |
| Hel308 Mbu-E288C (SEQ ID NO: 10 with the mutation E288C) | 49 |
| Hel308 Mbu-E284Faz (SEQ ID NO: 10 with the mutation E284Faz) | 28 |
| Heat treated Hel308 Mbu-E284Faz (SEQ ID NO: 10 with the mutation E284Faz, the enzyme was heated in 50 mM Tris pH 8.0, 375 mM NaCl, 5% Glycerol buffer from 4° C. to 50° C. for 10 mins and then cooled to 4° C. in a BioRad PCR block) | 71 |

The invention claimed is:

1. A kit for characterising a target polynucleotide comprising (a) a pore and (b) a helicase comprising a polynucleotide binding domain, wherein two amino acid residues that are located on a surface of the helicase are covalently connected via a linkage between the two amino acid residues to form a covalently-closed structure, wherein the pore is a transmembrane pore, wherein the transmembrane pore is:
   [i] derived from a hemolysin, leukocidin, *Mycobacterium smegmatis* porin A (MspA), MspB, MspC, MspD, outer membrane porin F (OmpF), outer membrane porin G (OmpG), outer membrane phospholipase A, *Neisseria* autotransporter lipoprotein (NalP) and WZA, or
   [ii] a β-barrel pore or an α-helix bundle pore, wherein at least one amino acid of the two amino acid residues is substituted with cysteine, a non-natural amino acid or 4-azido-L-phenylalanine (Faz), and wherein the two amino acid residues that are located on the surface of the helicase are on one or more loop regions connecting α-helices and β-strands of the helicase and/or are spatially located proximal to the polynucleotide binding domain.

2. The kit of claim 1, wherein the kit further comprises an array or a chip.

3. The kit of claim 1, wherein the helicase is (a) a Hel308 helicase, a RecD helicase, a TraI helicase, a TraI subgroup helicase, an XPD helicase; or (b) one of the helicases as set forth in SEQ ID NO: 10, 13, 16, 19, 22, 25, 28, 29, 32-34, 37-55, 58, 85, 126, 134, 138.

4. The kit of claim 1, wherein the helicase further comprises a second set of two amino acid residues in different structural domains of the helicase surrounding the polynucleotide binding domain that are covalently connected via a linkage between the two amino acid residues of the second set.

5. The kit of claim 1, wherein the linkage between the two amino acid residues comprises a peptide linker.

6. The kit of claim 5, wherein the peptide linker comprises a polynucleotide binding moiety.

7. The kit of claim 1, wherein the linkage between the two amino acid residues comprises a polyethyleneglycol (PEG), polysaccharide, or polyamide.

8. The kit of claim 1, wherein the linkage between the two amino acid residues comprises a deoxyribonucleic acid (DNA) sequence, peptide nucleic acid (PNA), threose nucleic acid (TNA), or glycerol nucleic acid (GNA).

9. The kit of claim 1, wherein the helicase is a member of a helicase family selected from the group consisting of: Pif1-like helicases, Upf1-like helicases, UvrD/Rep helicases, Ski-like helicases, Rad3/XPD helicases, NS3/NPH-II helicases, DEAD helicases, DEAHi RHA helicases, RecG-like helicases, REcQ-like helicases, T1R-like helicases, Swi/Snf-like helicases, and Rig-I-like helicases.

10. The kit of claim 1, wherein the helicase is a member of a helicase subfamily selected from the group consisting of: RecD helicases, Upf1 helicases, PcrA helicases, Rep helicases, UvrD helicases, Hel308 helicases, Mtr4 helicases, XPD helicases, NS3 helicases, Mss1 16 helicases, Prp43 helicases, RecG helicases, RecQ helicases, TIR helicases, RapA helicases and Hef helicases.

11. The kit of claim 1, wherein at least one amino acid of the two amino acid residues is a cysteine that has been introduced into the helicase.

12. The kit of claim 2, wherein the array or the chip comprises a membrane.

13. The kit of claim 12, wherein the membrane is an amphiphilic layer.

* * * * *

UNITED STATES PATENT AND TRADEMARK OFFICE
CERTIFICATE OF CORRECTION

| | |
|---|---|
| PATENT NO. | : 12,252,717 B2 |
| APPLICATION NO. | : 18/047589 |
| DATED | : March 18, 2025 |
| INVENTOR(S) | : Andrew John Heron et al. |

Page 1 of 1

It is certified that error appears in the above-identified patent and that said Letters Patent is hereby corrected as shown below:

In the Claims

At Column 155, Line 33, Claim 3, the text:
"helicase, a RecD helicase, a TraI helicase, a TraI subgroup"
Should read:
--helicase, a RecD helicase, a TraI helicase, a TraI subgroup--

At Column 156, Line 33, Claim 10, the text:
"helicases, RecG helicases, RecQ helicases, TIR helicases"
Should read:
--helicases, RecG helicases, RecQ helicases, T1R helicases--

Signed and Sealed this
Sixth Day of May, 2025

Coke Morgan Stewart
*Acting Director of the United States Patent and Trademark Office*

SEQUENCE LISTING

```
Sequence total quantity: 156
SEQ ID NO: 1                 moltype = DNA   length = 558
FEATURE                      Location/Qualifiers
misc_feature                 1..558
                             note = Mycobacterium smegmatis porin A mutant
                             (D90N/D91N/D93N/D118R/D134R/E139K)
source                       1..558
                             mol_type = other DNA
                             organism = synthetic construct
SEQUENCE: 1
atgggtctgg ataatgaact gagcctggtg gacggtcaag atcgtaccct gacggtgcaa    60
caatgggata cctttctgaa tggcgttttt ccgctggatc gtaatcgcct gacccgtgaa   120
tggtttcatt ccggtcgcgc aaaatatatc gtcgcaggcc cgggtgctga cgaattcgaa   180
ggcacgctgg aactgggtta tcagattggc tttccgtggt cactgggcgt tggtatcaac   240
ttctcgtaca ccacgccgaa tattctgatc aacaatggta acattaccgc accgccgttt   300
ggcctgaaca gcgtgattac gccgaacctg tttccgggtg ttagcatctc tgcccgtctg   360
ggcaatggtc cgggcattca agaagtggca acctttagtg tgcgcgtttc cggcgctaaa   420
ggcggtgtcg cggtgtctaa cgcccacggt accgttacgg gcgcggccgg cggtgtcctg   480
ctgcgtccgt tcgcgcgcct gattgcctct accggcgaca cgttacgac ctatggcgaa    540
ccgtggaata tgaactaa                                                 558

SEQ ID NO: 2                 moltype = AA    length = 184
FEATURE                      Location/Qualifiers
REGION                       1..184
                             note = Mycobacterium smegmatis porin A mutant
                             (D90N/D91N/D93N/D118R/D134R/E139K)
source                       1..184
                             mol_type = protein
                             organism = synthetic construct
SEQUENCE: 2
GLDNELSLVD GQDRTLTVQQ WDTFLNGVFP LDRNRLTREW FHSGRAKYIV AGPGADEFEG    60
TLELGYQIGF PWSLGVGINF SYTTPNILIN NGNITAPPFG LNSVITPNLF PGVSISARLG   120
NGPGIQEVAT FSVRVSGAKG GVAVSNAHGT VTGAAGGVLL RPFARLIAST GDSVTTYGEP   180
WNMN                                                                184

SEQ ID NO: 3                 moltype = DNA   length = 885
FEATURE                      Location/Qualifiers
misc_feature                 1..885
                             note = alpha-hemolysin mutant E111N/K147N
source                       1..885
                             mol_type = other DNA
                             organism = synthetic construct
SEQUENCE: 3
atggcagatt ctgatattaa tattaaaacc ggtactacag atattggaag caatactaca    60
gtaaaaacag gtgatttagt cacttatgat aagaaaatg gcatgcacaa aaaagtattt    120
tatagtttta tcgatgataa aaatcacaat aaaaaaactgc tagttattag aacaaaaggt   180
accattgctg tcaatatag agtttatagc gaagaaggtg ctaacaaaag tggtttagcc   240
tggcctctca cctttaaggt acagttgcaa ctacctgata tgaagtagc tcaaatatct   300
gattactatc caagaaattc gattgataca aaaaactata tgagtacttt aacttatgga   360
ttcaacggta atgttactgg tgatgataca ggaaaaattg gcggcctta tggtgcaaat   420
gtttcgattg tcatacact gaactatgtt caacctgatt tcaaaacaat tttagagagc   480
ccaactgata aaaagtagg ctggaaagtg atatttaaca tcggtgaa tcaaaattgg   540
ggaccatacg atcgagattc ttggaacccg gtatatggca atcaactttt catgaaaact   600
agaaatggtt ctatgaaagc agcagataac ttccttgatc ctaacaaagc aagttctcta   660
ttatcttcag ggttttcacc agacttcgct acagttatta ctatggatag aaaagcatcc   720
aaacaacaaa caaatataga tgtaatatac gaacgagttc gtgatgatta ccaattgcat   780
tggacttcaa caaattggaa aggtaccaat actaaagata aatggacaga tcgttcttca   840
gaaagatata aaatcgattg ggaaaaagaa gaaatgacaa attaa                 885

SEQ ID NO: 4                 moltype = AA    length = 293
FEATURE                      Location/Qualifiers
REGION                       1..293
                             note = alpha-hemolysin mutant E111N/K147N
source                       1..293
                             mol_type = protein
                             organism = synthetic construct
SEQUENCE: 4
ADSDINIKTG TTDIGSNTTV KTGDLVTYDK ENGMHKKVFY SFIDDKNHNK KLLVIRTKGT    60
IAGQYRVYSE EGANKSGLAW PSAPKVQLQL PDNEVAQISD YYPRNSIDTK NYMSTLTYGF   120
NGNVTGDDTG KIGGLIGANV SIGHTLNYVQ PDFKTILESP TDKKVGWKVI FNNMVNQNWG   180
PYDRDSWNPV YGNQLFMKTR NGSMKAADNF LDPNKASSLL SSGFSPDFAT VITMDRKASK   240
QQTNIDVIYE RVRDDYQLHW TSTNWKGTNT KDKWTDRSSE RYKIDWEKEE MTN          293

SEQ ID NO: 5                 moltype = AA    length = 184
FEATURE                      Location/Qualifiers
source                       1..184
                             mol_type = protein
                             note = Mycobacterium smegmatis
```

```
                              organism = unidentified
SEQUENCE: 5
GLDNELSLVD GQDRTLTVQQ WDTFLNGVFP LDRNRLTREW FHSGRAKYIV AGPGADEFEG    60
TLELGYQIGF PWSLGVGINF SYTTPNILID DGDITAPPFG LNSVITPNLF PGVSISADLG   120
NGPGIQEVAT FSVDVSGPAG GVAVSNAHGT VTGAAGGVLL RPFARLIAST GDSVTTYGEP   180
WNMN                                                                184

SEQ ID NO: 6              moltype = AA  length = 184
FEATURE                   Location/Qualifiers
source                    1..184
                          mol_type = protein
                          organism = Mycobacterium smegmatis
SEQUENCE: 6
GLDNELSLVD GQDRTLTVQQ WDTFLNGVFP LDRNRLTREW FHSGRAKYIV AGPGADEFEG    60
TLELGYQIGF PWSLGVGINF SYTTPNILID DGDITGPPFG LESVITPNLF PGVSISADLG   120
NGPGIQEVAT FSVDVSGPAG GVAVSNAHGT VTGAAGGVLL RPFARLIAST GDSVTTYGEP   180
WNMN                                                                184

SEQ ID NO: 7              moltype = AA  length = 183
FEATURE                   Location/Qualifiers
source                    1..183
                          mol_type = protein
                          organism = Mycobacterium smegmatis
SEQUENCE: 7
VDNQLSVVDG QGRTLTVQQA ETFLNGVFPL DRNRLTREWF HSGRATYHVA GPGADEFEGT    60
LELGYQVGFP WSLGVGINFS YTTPNILIDG GDITQPPFGL DTIITPNLFP GVSISADLGN   120
GPGIQEVATF SVDVKGAKGA VAVSNAHGTV TGAAGGVLLR PFARLIASTG DSVTTYGEPW   180
NMN                                                                 183

SEQ ID NO: 8              moltype = AA  length = 8
FEATURE                   Location/Qualifiers
REGION                    1..8
                          note = Amino acid sequence of the Hel308 motif
SITE                      2
                          note = MISC_FEATURE - Xaa = C, M or L
SITE                      3
                          note = MISC_FEATURE - Xaa = any amino acid
source                    1..8
                          mol_type = protein
                          organism = synthetic construct
SEQUENCE: 8
QXXGRAGR                                                              8

SEQ ID NO: 9              moltype = AA  length = 9
FEATURE                   Location/Qualifiers
REGION                    1..9
                          note = Amino acid sequence of the extended Hel308 motif
SITE                      2
                          note = MISC_FEATURE - Xaa = C, M or L
SITE                      3
                          note = MISC_FEATURE - Xaa = any amino acid
source                    1..9
                          mol_type = protein
                          organism = synthetic construct
SEQUENCE: 9
QXXGRAGRP                                                             9

SEQ ID NO: 10             moltype = AA  length = 760
FEATURE                   Location/Qualifiers
source                    1..760
                          mol_type = protein
                          organism = Methanococcoides burtonii
SEQUENCE: 10
MMIRELDIPR DIIGFYEDSG IKELYPPQAE AIEMGLLEKK NLLAAIPTAS GKTLLAELAM    60
IKAIREGGKA LYIVPLRALA SEKFERFKEL APFGIKVGIS TGDLDSRADW LGVNDIIVAT   120
SEKTDSLLRN GTSWMDEITT VVVDEIHLLD SKNRGPTLEV TITKLMRLNP DVQVVALSAT   180
VGNAREMADW LGAALVLSEW RPTDLHEGVL FGDAINFPGS QKKIDRLEKD DAVNLVLDTI   240
KAEGQCLVFE SSRRNCAGFA KTASSKVAKI LDNDIMIKLA GIAEEVESTG ETDTAIVLAN   300
CIRKGVAFHH AGLNSNHRKL VENGFRQNLI KVISSTPTLA AGLNLPARRV IIRSYRRFDS   360
NFGMQPIPVL EYKQMAGRAG RPHLDPYGES VLLAKTYDEF AQLMENYVEA DAEDIWSKLG   420
TENALRTHVL STIVNGFAST RQELFDFFGA TFFAYQQDKW MLEEVINDCL EFLIDKAMVS   480
ETEDIEDASK LFLRGTRLGS LVSMLYIDPL SGSKIVDGFK DIGKSTGGNM GSLEDDKGDD   540
ITVTDMTLLH LVCSTPDMRQ LYLRNTDYTI VNEYIVAHSD EPHEIPDKLK ETDYEWFMGE   600
VKTAMLLEEW VTEVSAEDIT RHFNVGEGDI HALADTSEWL MHAAAKLAEL LGVEYSSHAY   660
SLEKRIRYGS GLDLMELVGI RGVGRVRARK LYNAGFVSVA KLKGADISVL SKLVGPKVAY   720
NILSGIGVRV NDKHFNSAPI SSNTLDTLLD KNQKTFNDFQ                         760

SEQ ID NO: 11             moltype = AA  length = 8
FEATURE                   Location/Qualifiers
```

-continued

```
REGION                  1..8
                        note = Exemplary Hel308 motif
source                  1..8
                        mol_type = protein
                        organism = synthetic construct
SEQUENCE: 11
QMAGRAGR                                                                  8

SEQ ID NO: 12           moltype = AA   length = 9
FEATURE                 Location/Qualifiers
REGION                  1..9
                        note = Exemplary extended Hel308 motif
source                  1..9
                        mol_type = protein
                        organism = synthetic construct
SEQUENCE: 12
QMAGRAGRP                                                                 9

SEQ ID NO: 13           moltype = AA   length = 720
FEATURE                 Location/Qualifiers
source                  1..720
                        mol_type = protein
                        organism = Pyrococcus furiosus
SEQUENCE: 13
MRVDELRVDE RIKSTLKERG IESFYPPQAE ALKSGILEGK NALISIPTAS GKTLIAEIAM    60
VHRILTQGGK AVYIVPLKAL AEEKFQEFQD WEKIGLRVAM ATGDYDSKDE WLGKYDIIIA   120
TAEKFDSLLR HGSSWIKDVK ILVADEIHLI GSRDRGATLE VILAHMLGKA QIIGLSATIG   180
NPEELAEWLN AELIVSDWRP VKLRRGVFYQ GFVTWEDGSI DRFSSWEELV YDAIRKKKGA   240
LIFVNMRRKA ERVALELSKK VKSLLTKPEI RALNELADSL EENPTNEKLA KAIRGGVAFH   300
HAGLGRDERV LVEENPRKGI IKAVVATPTL SAGINTPAFR VIIRDIWRYS DPGMERIPII   360
EVHQMLGRAG RPKYDEVGEG IIVSTSDDPR EVMNHYIFGK PEKLFSQLSN ESNLRSQVLA   420
LIATFGYSTV EEILKFISNT FYAYQRKDTY SLEEKIRNIL YPLLENEFIE ISLEDKIRPL   480
SLGIRTAKLY IDPYTAKMFK DKMEEVVKDP NPIGIFHLIS LTPDITPFNY SKREFERLEE   540
EYYEFKDRLY FDDPYISGYD PYLERKFFRA FKTALVLLAW INEVPEGEIV EKYSVEPGDI   600
YRIVETAEWL VYSLKEIAKV LGAYEIVDYL ETLRVRVKYG IREELIPLMQ LPLVGRRRAR   660
ALYNSGFRSI EDISQARPEE LLKIEGIGVK TVEAIFKFLG KNVKISEKPR KSTLDYFLKS   720

SEQ ID NO: 14           moltype = AA   length = 8
FEATURE                 Location/Qualifiers
REGION                  1..8
                        note = Exemplary Hel308 motif
source                  1..8
                        mol_type = protein
                        organism = synthetic construct
SEQUENCE: 14
QMLGRAGR                                                                  8

SEQ ID NO: 15           moltype = AA   length = 9
FEATURE                 Location/Qualifiers
REGION                  1..9
                        note = Exemplary extended Hel308 motif
source                  1..9
                        mol_type = protein
                        organism = synthetic construct
SEQUENCE: 15
QMLGRAGRP                                                                 9

SEQ ID NO: 16           moltype = AA   length = 829
FEATURE                 Location/Qualifiers
source                  1..829
                        mol_type = protein
                        organism = Haloferax volcanii
SEQUENCE: 16
MRTADLTGLP TGIPEALRDE GIEELYPPQA EAVEAGLTDG ESLVAAVPTA SGKTLIAELA    60
MLSSVARGGK ALYIVPLRAL ASEKKAEFER WEEYGIDVGV STGNYESDGE WLSSRDIIVA   120
TSEKVDSLVR NNAAWMDQLT CVVADEVHLV DDRHRGPTLE VTLAKLRRLN TNLQVVALSA   180
TVGNAGVVSD WLDAELVKSD WRPIDLKMGV HYGNAVSFAD GSQREVPVGR GERQTPALVA   240
DALEGDGEGD QGSSLVFVNS RRNAESAARR MADVTERYVT GDERSDLAEL AAEIRDVSDT   300
ETSDDLANAV AKGAAFHHAG LAAEHRTLVE DAFRDRLIKC ICATPTLAAG VNTPSRRVVV   360
RDWQRYDGDY GGMKPLDVLE VHQMMGRAGR PGLDPYGEAV LLAKDADARD ELFERYIWAD   420
AEDVRSKLAA EPALRTHLLA TVASGFAHTR EGLLEFLDQT LYATQTDDPE RLGQVTDRVL   480
DYLEVNGFVE FEGETIQATP VGHTVSRLYL DPMSAAEIID GLEWAADHRT EKLRALAGET   540
PEKPTRDRSE SDESGGFQRA SEMVADDGDG GGGEDVGAN GDGSDDADG VETDRTYPTP   600
LGLYHLVCRT PDMYQLYLKS GDRETYTELC YEREPEFLGR VPSEYEDVAF EDWLSALKTA   660
KLLEDWVGEV DEDRITERYG VGPGDIRGKV ETSEWLLGAA ERLATELDLD SVYAVREAKK   720
RVEYGVREEL LDLAGVRGVG RKRARRLFEA GVETRADLRE ADKPRVLAAL RGRRKTAENI   780
LEAAGRKDPS MDAVDEDDAP DDAVPDDAGF ETAKERADQQ ASLGDFEGS              829

SEQ ID NO: 17           moltype = AA   length = 8
```

```
FEATURE                  Location/Qualifiers
REGION                   1..8
                         note = Exemplary Hel308 motif
source                   1..8
                         mol_type = protein
                         organism = synthetic construct
SEQUENCE: 17
QMMGRAGR                                                                    8

SEQ ID NO: 18            moltype = AA   length = 9
FEATURE                  Location/Qualifiers
REGION                   1..9
                         note = Exemplary extended Hel308 motif
source                   1..9
                         mol_type = protein
                         organism = synthetic construct
SEQUENCE: 18
QMMGRAGRP                                                                   9

SEQ ID NO: 19            moltype = AA   length = 824
FEATURE                  Location/Qualifiers
source                   1..824
                         mol_type = protein
                         organism = Halorubrum lacusprofundi
SEQUENCE: 19
MQPSSLSGLP AGVGEALEAE GVAELYPPQE AAVEAGVADG ESLVAAVPTA SGKTLIAELA    60
MLSSIERGGK ALYIVPLRAL ASEKKTEFER WEEFGVTVGV STGNYESDGE WLATRDIIVA   120
TSEKVDSLIR NGAPWIDDLT CVVSDEVHLV DDPNRGPTLE VTLAKLRKVN PGLQTVALSA   180
TVGNADVIAE WLDAELVESD WRPIDLRMGV HFGNAIDFAD GSKREVPVER GEDQTARLVA   240
DALDTEEDGQ GGSSLVFVNS RRNAESSARK LTDVTGPRLT DDERDQLREL ADEIRSGSDT   300
DTASDLADAV EQGSAFHHAG LRSEDRARVE DAFRDRLIKC ISATPTLAAG VNTPARRVIV   360
RDWRRYDGEF GGMKPLDVLE VHQMCGRAGR PGLDPYGEAV LLANDADTKE ELFERYLWAD   420
PEPVRSKLAA EPALRTHVLA TVASGFASTR DGLLSFLDNT LYATQTDDEG RLAAVTDTVL   480
DYLAVNDFIE RDRDGGSESL TATGIGHTVS RLYLDPMSAA EMIDGLRSVA RDAADTGASA   540
EADNGEFVRT GDADDASGGD EPGFGTYTRA GDDESGERET ENEETDEEET EASEVTPLGL   600
YHLISRTPDM YELYLKSGDR ETYTELCYER ETEFLGDVPS EYEDVRFEDW LASLKTARLL   660
EDWVNEVDED RITERYGVGP GDIRGKVDTA EWLLRAAETL ARDVEGVDGD VVVAVREARK   720
RIEYGVREEL LDLAGVRNVG RKRARRLFEA GIETRADLRE ADKAVVLGAL RGRERTAERI   780
LEHAGREDPS MDDVRPDKSA SAAATAGSAS DEDGEGQASL GDFR                    824

SEQ ID NO: 20            moltype = AA   length = 8
FEATURE                  Location/Qualifiers
REGION                   1..8
                         note = Exemplary Hel308 motif
source                   1..8
                         mol_type = protein
                         organism = synthetic construct
SEQUENCE: 20
QMCGRAGR                                                                    8

SEQ ID NO: 21            moltype = AA   length = 9
FEATURE                  Location/Qualifiers
REGION                   1..9
                         note = Exemplary extended Hel308 motif
source                   1..9
                         mol_type = protein
                         organism = synthetic construct
SEQUENCE: 21
QMCGRAGRP                                                                   9

SEQ ID NO: 22            moltype = AA   length = 707
FEATURE                  Location/Qualifiers
source                   1..707
                         mol_type = protein
                         note = Cenarchaeum symbiosum
                         organism = unidentified
SEQUENCE: 22
MRISELDIPR PAIEFLEGEG YKKLYPPQAA AAKAGLTDGK SVLVSAPTAS GKTLIAAIAM    60
ISHLSRNRGK AVYLSPLRAL AAEKFAEFGK IGGIPLGRPV RVGVSTGDFE KAGRSLGNND   120
ILVLTNERMD SLIRRRPDWM DEVGLVIADE IHLIGDRSRG PTLEMVLTKL RGLRSSPQVV   180
ALSATISNAD EIAGWLDCTL VHSTWRPVPL SEGVYQDGEV AMGDGSRHEV AATGGGPAVD   240
LAAESVAEGG QSLIFADTRA RSASLAAKAS AVIPEAKGAD AAKLAAAAKK IISSGGETKL   300
AKTLAELVEK GAAFHHAGLN QDCRSVVEEE FRSGRIRLLA STPTLAAGVN LPARRVVISS   360
VMRYNSSSGM SEPISILEYK QLCGRAGRPT YDKSGEAIVV GGVNADEIFD RYIGGEPEPI   420
RSAMVDDRAL RIHVLSLVTT SPGIKEDDVT EFFLGTLGGQ QSGESTVKFS VAVALRFLQE   480
EGMLGRRGGR LAATKMGRLV SRLYMDPMTA VTLRDAVGEA SPGRMHTLGF LHLVSECSEF   540
MPRFALRQKD HEVAEMMLEA GRGELLRPVY SYECGRGLLA LHRWIGESPE AKLAEDLKFE   600
SGDVHRMVES SGWLLRCIWE ISKHQERPDL LGELDVLRSR VAYGIKAELV PLVSIKGIGR   660
VRSRRLFRGG IKGPGDLAAV PVERLSRVEG IGATLANNIK SQLRKGG                 707
```

```
SEQ ID NO: 23            moltype = AA   length = 8
FEATURE                  Location/Qualifiers
REGION                   1..8
                         note = Exemplary Hel308 motif
source                   1..8
                         mol_type = protein
                         organism = synthetic construct
SEQUENCE: 23
QLCGRAGR                                                                   8

SEQ ID NO: 24            moltype = AA   length = 9
FEATURE                  Location/Qualifiers
REGION                   1..9
                         note = Exemplary extended Hel308 motif
source                   1..9
                         mol_type = protein
                         organism = synthetic construct
SEQUENCE: 24
QLCGRAGRP                                                                  9

SEQ ID NO: 25            moltype = AA   length = 715
FEATURE                  Location/Qualifiers
source                   1..715
                         mol_type = protein
                         organism = Sulfolobus solfataricus
SEQUENCE: 25
MSLELEWMPI EDLKLPSNVI EIIKKRGIKK LNPPQTEAVK KGLLEGNRLL LTSPTGSGKT     60
LIAEMGIISF LLKNGGKAIY VTPLRALTNE KYLTFKDWEL IGFKVAMTSG DYDTDDAWLK    120
NYDIIITTYE KLDSLWRHRP EWLNEVNYFV LDELHYLNDP ERGPVVESVT IRAKRRNLLA    180
LSATISNYKQ IAKWLGAEPV ATNWRPVPLI EGVIYPERKK KEYNVIFKDN TTKKVHGDDA    240
IIAYTLDSLS KNGQVLVFRN SRKMAESTAL KIANYMNFVS LDENALSEIL KQLDDIEEGG    300
SDEKELLKSL ISKGVAYHHA GLSKALRDLI EEGFRQRKIK VIVATPTLAA GVNLPARTVI    360
IGDIYRFNKK IAGYYDEIPI MEYKQMSGRA GRPGFDQIGE SIVVVRDKED VDRVFKKYVL    420
SDVEPIESKL GSERAFYTPL LGILSAEGNL SEKQLENFAY ESLLAKQLVD VYFDRAIRWL    480
LEHSFIKEEG NTFALTNFGK RVADLYINPF TADIIRKGLE GHKASCELAY LHLLAFTPDG    540
PLVSVGRNEE EELIELLEDL DCELLIEEPY EEDEYSLYIN ALKVALIMKD WMDEVDEDTI    600
LSKYNIGSGD LRNMVETMDW LTYSAYHLSR ELKLNEHADK LRILNLRVRD GIKEELLELV    660
QISGVGRKRA RLLYNNGIKE LGDVVMNPDK VKNLLGQKLG EKVVQEAARL LNRFH          715

SEQ ID NO: 26            moltype = AA   length = 8
FEATURE                  Location/Qualifiers
REGION                   1..8
                         note = Exemplary Hel308 motif
source                   1..8
                         mol_type = protein
                         organism = synthetic construct
SEQUENCE: 26
QMSGRAGR                                                                   8

SEQ ID NO: 27            moltype = AA   length = 9
FEATURE                  Location/Qualifiers
REGION                   1..9
                         note = Exemplary extended Hel308 motif
source                   1..9
                         mol_type = protein
                         organism = synthetic construct
SEQUENCE: 27
QMSGRAGRP                                                                  9

SEQ ID NO: 28            moltype = AA   length = 685
FEATURE                  Location/Qualifiers
source                   1..685
                         mol_type = protein
                         organism = Methanogenium frigidum
SEQUENCE: 28
MDLSLPKAFI QYYKDKGIES LYPPQSECIE NGLLDGADLL VAIPTASGKT LIAEMAMHAA     60
IARGGMCLYI VPLKALATEK AQEFKGKGAE IGVATGDYDQ KEKRLGSNDI VIATSEKVDS    120
LLRNGVPWLS QVTCLVVDEV HLIDDESRGP TLEMVITKLR HASPDMQVIG LSATIGNPKE    180
LAGWLGADLI TSDWRPVDLR EGICYHNTIY FDNEDKEIPA PAKTEDINLL LDCVADGGQC    240
LVFVSSRRNA EGYAKRAATA LKCSHAALDS IAEKLEAAAE TDMGRVLATC VKKGAAFHHA    300
GMNRMQRTLV EGGFRDGFIK SISSTPTLAA GNLPARRVI IRDYLRYSGG EGMRPIPVRE    360
YRQMAGRAGR PHLDPYGEAI LIAKTEYAVN DLHEEYVEAP DEDVTSRCGE KGVLTAHILS    420
LIATGYARSY DELMAFLEKT LYAYQHTGKK ALTRTLDDAL GFLTEAEMVT DLSGMLHATE    480
YGDLTSRLYI DPHSAEIITT ALREEGELTD LALLQLLCMT PDMFTLYVKK NDLGTLEKFF    540
FEHEEEFRTE FSYDEMEDFF RSLKTAMLLS DWTDEIGDDT ICTRFGVGPG DIFNAVQGIS    600
WLLHASGRLA RLVAPEHRDA VEETTLRVRH GIRRELIPLV RVKGIGRVRA RRLFNNGITG    660
PELLAAADPS VVGHIVGGKT AESII                                           685
```

```
SEQ ID NO: 29            moltype = AA  length = 775
FEATURE                  Location/Qualifiers
source                   1..775
                         mol_type = protein
                         organism = Methanothermococcus okinawensis
SEQUENCE: 29
MLMLMEVLKE NGIAELRPPQ KKVVEGGLLN KNKNFLICIP TASGKTLIGE MAFINHLLDN   60
NKTPTNKKGL FIVPLKALAN EKYEEFKGKY EKYGLKIALS IGDFDEKEDL KGYDLIITTA  120
EKLDSLIRHK VEWIKDISVV VIDEIHLIGD ESRGGTLEVL LTKLKTKKTI QIIGLSATIG  180
NPEELAKWLN AELIVDEWRP VKLKKGIGYG NKIMFIDDNG NTINEVIVDE ISKNNMFNLV  240
VDSILKDGSC IIFCNSKRGA VGEAKKLNLK KYLSPDEISE LRHLKEEVLS VLDNPTKTCK  300
DLAECIEKGV AFHHAGLTYE QRKIVEEGFR KKLIKAICCT PTLSAGINMP CRRAIIRDLK  360
RFSSRGYIPI PKMEIHQCIG RAGRPNLDPY GEGIIYINNT ENPELIENAK NYLIGNVEEI  420
YSKLSNQKVL RTHMLGLITT GDIKNKNDLE EFIKNTFYAY QYQNTKKILE NIYEITNFLE  480
KNGFIELNYR RDENKDKSNN SHNNKKNISN TNNSIKMLVL DNNNSLTIKS RHEEDVYYNI  540
TPLGKKVSEL YIDPLSAEYI IDGLKNLHKK TLSNPKNMEC YILHILYIIS KTTEMQPVLR  600
VRRKEENDLI NDMIKLDIDV DDVIYGISSE NLEYFKNAKL FYDWINEIPE EELLLGYNIE  660
PGILRYNVEQ AKWMIHSAKE IFNLLNIDNK VIKDCLNDLE IRMEYGAKQD IIELLKIKHI  720
GRARARILYN AGIKNANDII NNQKNIINLL GEKIARKILS ELGVDTKFGQ MRLSI       775

SEQ ID NO: 30            moltype = AA  length = 8
FEATURE                  Location/Qualifiers
REGION                   1..8
                         note = Exemplary Hel308 motif
source                   1..8
                         mol_type = protein
                         organism = synthetic construct
SEQUENCE: 30
QCIGRAGR                                                            8

SEQ ID NO: 31            moltype = AA  length = 9
FEATURE                  Location/Qualifiers
REGION                   1..9
                         note = Exemplary extended Hel308 motif
source                   1..9
                         mol_type = protein
                         organism = synthetic construct
SEQUENCE: 31
QCIGRAGRP                                                           9

SEQ ID NO: 32            moltype = AA  length = 699
FEATURE                  Location/Qualifiers
source                   1..699
                         mol_type = protein
                         organism = Methanotorris igneus
SEQUENCE: 32
MQKYSHVFEV LKENGIKELR PPQKKVIEKG LLNKEKNFLI CIPTASGKTL IGEMALINHL   60
LDENKTPTNK KGLFIVPLKA LASEKYEEFK RKYEKYGLKV ALSIGDYDEK EDLSSYNIII  120
TTAEKLDSLM RHEIDWLNYV SVAIVDEIHI INDEKRGGTL EVLLTKLKNL DVQIIGLSAT  180
IGNPEELAEW LNAELIIDNW RPVKLRKGIF FQNKIMYLNG ACKELPNFSN NPMLNLVLDC  240
VKEGGCCLVF CNSKNGAVSE AKKLNLKKYL SNSEKYELGK LKEEILSILD PPTETCKTLA  300
ECLEKGVAFH HAGLTYEHRK IVEEGFRNKL IKVICCTPTL SAGINIPCRR AIVRDLMRFS  360
NGRMKPIPIM EIHQCIGRAG RPGLDPYGEG IIFVKNERDL ERAEQYLEGK PEYIYSKLSN  420
QAVLRTQLLG MIATREIENE FDLISFIKNT FYAHQYGNLG GVLRNIKEVI NFLEENDFIA  480
DYFPTKLGKR VSELYIDPLS AKIIIDGLKE MGNVDNEELY YLYLISKTLE MMPPLLRVNSF  540
EELDLILEME EAGIYDRTYD DLAAFKNAKM LYDWINEVPE DEILKKYKIE PGILRYKVEQ  600
AKWMIYSTKE IAKLLNRNID TLSKLEIRLE YGAKEDIIEL LKIKYVGRAR ARKLYDAGIR  660
SVEDIINNPK KVASLLGEKI AKKILGELGM KFGQQTLQI                         699

SEQ ID NO: 33            moltype = AA  length = 720
FEATURE                  Location/Qualifiers
source                   1..720
                         mol_type = protein
                         organism = Thermococcus gammatolerans
SEQUENCE: 33
MKVDELPVDE RLKAVLKERG IEELYPPQAE ALKSGALEGR NLVLAIPTAS GKTLVSEIVM   60
VNKLIQEGGK AVYLVPLKAL AEEKYREFKE WEKLGLKVAA TTGDYDSTDD WLGRYDIIVA  120
TAEKFDSLLR HGARWINDVK LVVADEVHLI GSYDRGATLE MILTHMLGRA QILALSATVG  180
NAEELAEWLD ASLVVSDWRP VQLRRGVFHL GTLIWEDGKV ESYPENWYSL VVDAVKRGKG  240
ALVFVNTRRS AEKEALASLK LVSSHLTKPE KRALESLASQ LEDNPTSEKL KRALRGGVAF  300
HHAGLSRVER TLIEDAFREG LIKVITATPT LSAGVNLPSF RVIIRDTKRY AGFGWTDIPV  360
LEIQQMMGRA GRPRYDKYGE AIIVARTDEP GKLMERYIRG KPEKLFSMLA NEQAFRSQVL  420
ALITNFGIRS FPELVRFLER TFYAHQRKDL SSLEYKAKEV VYFLIENEFI DLDLEDRFIP  480
LPFGKRTSQL YIDPLTAKKF KDAFPAIERN PNPFGIFQLI ASTPDMATLT ARRREMEDYL  540
DLAYELEDKL YASIPYYEDS RFQGFLGQVK TAKVLLDWIN EVPEARIYET YSIDPGDLYR  600
LLELADWLMY SLIELYKLFE PKEEILNYLR DLHLRLRHGV REELLELVRL PNIGRKARA   660
LYNAGFRSVE AIANAKPAEL LAVEGIGAKI LDGIYRHLGI EKRVTEEKPK RKGTLEDFLR  720

SEQ ID NO: 34            moltype = AA  length = 755
```

```
FEATURE                 Location/Qualifiers
source                  1..755
                        mol_type = protein
                        organism = Thermococcus barophilus
SEQUENCE: 34
MLSTKPKAYK RFSPIGYAMQ VDELSKFGVD ERIIRKIKER GISEFYPPQA EALRSGVLNG    60
ENLLLAIPTA SGKTLVAEIV MLHKLFTGGG KAVYLVPLKA LAEEKYREFK TWEDLGVRVA   120
VTTGDYDSSE EWLGKYDIII ATSEKFDSLL RHKSRWIRDV TLIVADEIHL LGSYDRGATL   180
EMILSHMLGK AQILGLSATV GNAEELAEWL NAKLVVSDWR PVKLRKGVFA HGQLIWEDGK   240
VDKFPPQWDS LVIDAVKKGK QALVFVNTRR SAEKEAGMLG KKVRRLLTKP EARRLKELAE   300
SLESNPTNDK LKEVLVNGAA FHHAGLGRAE RTLIEDAFRE GLIKVLTATP TLAMGVNLPS   360
FRVIIRDTKR YSTFGWSDIP VLEIQQMIGR AGRPKYDKEG EAIIVAKTEK PEELMEKYIF   420
GKPEKLFSML SNDAAFRSQV LALITNFGVE SFRELIGFLE KTFYYHQRKD LEILEGKAKS   480
IVYFLLENEF IDIDLNDSFI ALPFGIRTSQ LYLDPLTAKK FKDALPQIEE NPNPLGIFQL   540
LASTPDMGTL SIKRKEQESY LDYAYEMEDY LYRSIPYWED YEFQKFLSEV KTAKLLLDWI   600
NEVSEAKLIE AYGIDTGDLY RIIELADWLM YSLIELAKVL NAGGETIKYL RRLHLRLKHG   660
VREELLELVE LPMIGRRRAR ALYNAGFKNV NDIVKAKPSE LLAVEGIGVK VLERIYRHFG   720
VELPLLKNIK DPDKPEDKPK EKPKPKKGTL DYFLK                              755

SEQ ID NO: 35           moltype = AA   length = 8
FEATURE                 Location/Qualifiers
REGION                  1..8
                        note = Exemplary Hel308 motif
source                  1..8
                        mol_type = protein
                        organism = synthetic construct
SEQUENCE: 35
QMIGRAGR                                                              8

SEQ ID NO: 36           moltype = AA   length = 9
FEATURE                 Location/Qualifiers
REGION                  1..9
                        note = Exemplary extended Hel308 motif
source                  1..9
                        mol_type = protein
                        organism = synthetic construct
SEQUENCE: 36
QMIGRAGRP                                                             9

SEQ ID NO: 37           moltype = AA   length = 744
FEATURE                 Location/Qualifiers
source                  1..744
                        mol_type = protein
                        organism = Thermococcus sibiricus
SEQUENCE: 37
MKLNKLKSYI NAFLLGMVMS MKVDELKSLG VDERILRLLR ERGIEELYPP QADALKTEVL    60
KGKNLVLAIP TASGKTLVAE IVMINKILRE GGKTVYLVPL KALAEEKYKE FKFWEKLGIR   120
IAMTTGDYDS TEEWLGKYDI IIATSEKFDS LLRHKSPWIK DINLVIADEI HLLGSYDRGA   180
TLEMILAHLD DKAQILGLSA TVGNAEEVAE WLNADLVMSE WRPVALRKGV FYHGELFWED   240
GSIERFPTQW DSLVIDALKK GKQALVFVNT RRSAEKEALL LAGKIQRFLT KPEERKLKQL   300
ADGLDTTPTN QKLKEALTKG VAFHHAGLGR TERSIIEDAF REGLIKVITA TPTLSAGVNL   360
PAYRVIIRDT KRYSNFGWVD IPVLEIQQMM GRAGRPKYDI EGQAIIIAKT EKPEDLMKRY   420
VLGKPEKLFS MLSNEASFRS QVLALITNFG VGNFKELVNF LERTFYYHQR KNLEALEGKA   480
KSIVYFLFEN EFIDIDLNDQ FMPLPLGIRT SQLYLDPVTA KKFKDAFEKL EKNPNPLGIF   540
QLLASTPDMS SLRVKRKEQE DLLDYAYEME EYLYQNIPYW EDYKFEKFLG ETKTAKLLLD   600
WINEVNDVKI LETYEIDTGD LYRILELVDW LMYSLIELYK LFDPKPEVLD FLKKLHIRVK   660
HGVREELLEL ITLPMIGRKR ARALYNAGFK GIDDIVRAKA SELLKVEGIG IGVIEKIYQH   720
FGVELPTNEK KKKVKKGTLD EFFK                                          744

SEQ ID NO: 38           moltype = AA   length = 729
FEATURE                 Location/Qualifiers
source                  1..729
                        mol_type = protein
                        note = Methanosarcina barkeri fusaro
                        organism = unidentified
SEQUENCE: 38
MKIESLDLPD EVKQFYLNSG IMELYPPQAE AVEKGLLEGR NLLAAIPTAS GKTLLAELAM    60
LKSILAGGKA LYIVPLRALA SEKFRRFREF SELGIRVGIS TGDYDLRDEG LGVNDIIVAT   120
SEKTDSLLRN ETVWMQEISV VVADEVHLID SPDRGPTLEV TLAKLRKMNP SCQILALSAT   180
VGNADELAVW LEAELVVSEW RPTELLEGVF FNGTFYCKDR EKTVEQSTKD EAVNLALDTL   240
KKDGQCLVFE SSRKNCMAFA KKAASTVKKT LSAEDRNALA GIADEILENS ETDTSTNLAV   300
CIRSGTAFHH AGLTTPLREL VEDGFRAGRI KLISSTPTLA AGLNLPARRV IIRNYRRYSS   360
EDGMQPIPVL EYKQMAGRAG RPRLDPYGEA VLVAKSYKEF VPFLFENYIEA NAEDIWSKLG   420
TENALRTHVL STISNGFART YDELMDFLEA TFFAFQYSNF GLSTVVNECL NFLRQEGMLE   480
KDDALIPTSF GKLVSRLYID PLSAARIAKG LKGAKSLSEL TLLHLVCSTP DMRLLYMRSH   540
DYQDINDYVM AHASEFVKVP SPFDTTEYEW FLGEVKTSLL LLDWIHEKSE NEICLKFGTG   600
EGDIHSIADI AEWIMHVTSQ LAGLLDLKGA REAAELEKRI HYGAAPELID LLNIRGIGRV   660
RARKLYEAGF KSSAELAEVD PEKVAALLGP KIADRIFKQI RGRGTSSGII ASEPPEKSPY   720
SGQKTISDY                                                           729
```

```
SEQ ID NO: 39          moltype = AA  length = 730
FEATURE                Location/Qualifiers
source                 1..730
                       mol_type = protein
                       organism = Methanosarcina acetivorans
SEQUENCE: 39
MKIESLDLPD EVKRFYENSG IPELYPPQAE AVEKGLLEGK NLLAAIPTAS GKTLLAELAM   60
LKSVLAGGKA LYIVPLRALA SEKFRRFQDF SELGIRVGIS TGDYDRRDEG LGINDIIVAT  120
SEKTDSLLRN ETAWMQEISV VVVDEVHLID SADRGPTLEV TLAKLRKMNP FCQILALSAT  180
VGNADELAAW LDAELVLSEW RPTDLMEGVF FDGTFFCKDK EKLIEQPTKD EAINLVLDTL  240
REGGQCLVFE SSRKNCMGFA KKATSAVKKT LSAEDKEKLA GIADEILENS ETDTASVLAS  300
CVRAGTAFHH AGLTSPLREL VETGFREGYV KLISSTPTLA AGLNLPARRV IIRSYRRYSS  360
DSGMQPIPVL EYKQMAGRAG RPRLDPYGEA VLLAKSYEEL LFLFEKYIEA GAEDIWSKLG  420
TENALRTHVL STISNGFART KEELMDFLEA TFFAYQYSNF GLSVVVDECL NFLRQEGMLE  480
QDSDALISTM FGKLVSRLYI DPLSAALIAK GLREAGTLTE LTLLHLVCST PDMRLMYMRS  540
QDYQDINDFV MAHAEEFSKV PSPFNIVEYE WFLSEVKTSL LLMDWIHEKP ENEICLKFGT  600
GEGDIHTTAD IAEWIMHVAT QLARLLDLKG AKEAAELEKR IHYGAPELM  DLLDIRGIGR  660
VRARKLYGAG FKSTADLAGA TPEKVAALVG PKIAERIFRQ IGRREAVSEI SDSERLEKSS  720
QDGQSTISDF                                                         730

SEQ ID NO: 40          moltype = AA  length = 729
FEATURE                Location/Qualifiers
source                 1..729
                       mol_type = protein
                       organism = Methanohalophilus mahii
SEQUENCE: 40
MKIEELDLPS EAIEVYLQAG IEELYPPQAD AVEKGLLQGE NLLAAIPTAS GKTLLAEMAM   60
LKAIKKGGKA LYIVPLRALA SEKFRDFKRF ESLGIKTAIS TGDFDSRDEW LGSNDIIVAT  120
SEKTDSLLRN STPWMKDITA VIVDEVHLLD SANRGPTLEV TLAKLKRLNP GAQVVALSAT  180
VGNAMEIAQW LEAKLVLSEW RPTYLHEGIF YGDAINFDED QTFIERRHKE DSVNLVIDTV  240
IQGGQCLVFD SSRRNCVGFA KKCAPAVGEL LDRQNRNELE EVAKEVLENG ETKLTETLAY  300
CIKKGVAFHH AGLNSAHRRI VEDAFRNNLI KMICSTPTLA AGLNLPARRV IIRSYKRYDP  360
NAGMQPIPVL DYKQMAGRAG RPHLDPYGEA VVIVKTYEEF TDVLERYISA SAEDIWSKLG  420
TENALRTHIL STIASGFANC HREILTFLGS TFFAHQQQSW NFEELLEDCL IFLKNEGMLE  480
QDNETIRATE LGKMISSLYI DPLSASKIIR GLEKTTHVTD MTLLQLICST PDMRLLYLRN  540
RDYEIINDYV MNHTEEFIEV PSPFKQIEYE WFLSEVKTAL LLLEWINEKS LEKIVENYQV  600
GEGDIYASSD IAEWLMHATQ RIASRINPQL ETECAKLEKR IHYGAGSELI ELVEIPNVGR  660
ARARKLFKKG YRSRQKLATA DEKQLAGIVG PKIAQKILSY LGRETDSNGY VEPETLENKK  720
QQKTFQDFI                                                          729

SEQ ID NO: 41          moltype = AA  length = 730
FEATURE                Location/Qualifiers
source                 1..730
                       mol_type = protein
                       organism = Methanosarcina mazei
SEQUENCE: 41
MKIESLDLPD EIKRFYENSG ILELYPPQAE AVEKGLLEGK NLLAAIPTAS GKTLLAELAM   60
LKSVLNGGKA LYIVPLRALA SEKFRRFQEF SVLGMRVGIS TGDYDRRDEG LGINDIIVAT  120
SEKTDSLLRN ETAWMQEISV VVADEVHLID SPDRGPTLEI TLSKLRRMNP SCQVLALSAT  180
VGNADELAAW LDAELVLSEW RPTDLMEGVF YNGIFYCKDK EKPVGQPTKD EAVNLVLDTI  240
KEGGQCLVFE SSRKNCMGFA KKAVSAVKKT LSNEDRETLA GIADEIIENS ETDVSSVLAT  300
CVRSGTAFHH AGLTTPLREL VENGFREGRI KIISSTPTLA AGLNLPARRV IIRSYRRYSS  360
DSGMQPIPVL EYKQMAGRAG RPRLDPYGEA VLLAKSYEEF VFLFEKYIEA GAEDIWSKLG  420
TENALRTHIL STISNGFART REELMDFLEA TFFAFQYSNF GLSAVVDECL DFLRREGMLE  480
KDPDALVSTV FGKLVSRLYI DPLSAALIAK GLREAGTLTE LTLLHLICST PDMRLMYMRS  540
QDYQEVNDYV MAHAGEFSKV PNPFNIAEYE WFLGEVKTSL LLMDWIHEKP ENEICLKFGI  600
GEGDIHATAD IAEWIMHVTA QLAGLLDLKG AKEASELEKR IRYGAPELM  DLLDIRSVGR  660
VRARKLYEAG FKSTAELAAA SPEHIAVLVG PKITERIFKQ IGRREAVSEF SDIEPLEKGS  720
SDGQRTISDY                                                         730

SEQ ID NO: 42          moltype = AA  length = 693
FEATURE                Location/Qualifiers
source                 1..693
                       mol_type = protein
                       note = Methanosaeta thermophila
                       organism = unidentified
SEQUENCE: 42
MLTIRDLIRW LPESVIELYE ALGIDELYPP QAEAIERGLL DGRNMIISVP TAAGKTLLAE   60
LAMLRGALSG KRSLYIVPLR ALASEKFESF SRFSKLGLRV GISTGDFEKR DERLGRNDII  120
IATSEKADSL IRNGASWVRR IGVLVVDEIH LLDSANRGPT LEMTMTKLMH LNPEMQVIGL  180
SATIANGREI ADWIKGEIVS SDWRPVRLRE GVLLEDRLVF PDGEIQLENR NRDPVLNLVL  240
DTVDQGGQML IFESTRRNAE SMAKKVSGAL QESGETIELA ERLSGEGKTA KKLAMCLRHG  300
AAFHHAGLLP EQRRLIELGF RQNVVKVIAC TPTLAAGLNL PARRVLIRSY KRYEAGLGTR  360
PIPVMEYRQM AGRAGRPGLD PYGESLIMAR SESELQKLMD HYVMGEPEDI WSKLASERAL  420
RTHVLATIAS RFADSVDSLS RLMASTFYAR QQDPSYLGET IASVLEFLVR SDMIDKDLTP  480
TPLGALVSRL YIDPLSAMVM IQEIRGIRRP TVLTLLHVIT MTPDMELLFV QQSDNWLEDF  540
ISEHSSELGN EKNFDWLLRE VKTASMLMDW INEVDHERIE DRYSISPGDL VRIAETAEWL  600
MSALHRISKH MDLGVTYLAE RLALRIHYGA GDELLQLLEL KGIGRVRARK LYQAGYRSLE  660
```

-continued

```
DLKAADKSTL SEILGPKIAE GVISQLKEPG VSA                                693

SEQ ID NO: 43            moltype = AA  length = 739
FEATURE                  Location/Qualifiers
source                   1..739
                         mol_type = protein
                         organism = Methanosalsum zhilinae
SEQUENCE: 43
MNINNLNLPE KVKKYYTDTG IVDLYPPQRE AVDKGLLDGE NIVAAIPTAS GKTLLAELCM    60
LKSIGMGGKC LYIVPLKALA SEKYSRFREF ESLGIKVGIA TGDLDSREEW LGKNDIIIAT   120
SEKVDSLLRN ESSWMKEINT VVADEVHLLN SVNRGPTLEI TLAKLIHLNP GSQIIALSAT   180
IGNPEDIAGW LGARLVVSEW RPTDLYEGIL LDGLLHIGNI KKDIQDESRD DAVNLVIDTV   240
KDKGQCLVFE SSRRNCMGFA KKAGKWVSKI LDEHDTIQLK SLSQEIGEAG ETEIADVLSR   300
CVRQGVAFHH AGLNSEHRRM VEEGFRKNLI KMISSTPTLA AGLNLPARRV IIRSYKRYDP   360
NFGMKPIPVL EYKQMAGRAG RPHLDPYGES VLIARSYDEF MDIMENYVNA DPEDIWSKLG   420
TENALRTHVL STIVNGFAYT YRGLMDFVKM TFFAYQKEAS DLHDVIEECV RFLIDNEMII   480
SDSNDILPES AFRSTATGKL ISMLYIDPLS GSLIMDGIRK ADYFEDITMM HLICSTPDMK   540
NLYMRSSDYE NVNMYVLQNK DKFISMPSPF KMIEYEWFLG EVKTALLLLD WINEVPADDI   600
CKKYGIGEGD IRMFSETAVW LMHATSRLSG LLKVSEASEK SKELEKRLSY GINSELVNIV   660
ALKGIGRVRA RKIYENGYRS IDDLKKADPL KLSKIVGSKI SQKILKQLDI DVDISEIKEK   720
DSDTVPEPES SQKTISDFT                                                739

SEQ ID NO: 44            moltype = AA  length = 733
FEATURE                  Location/Qualifiers
source                   1..733
                         mol_type = protein
                         organism = Methanohalobium evestigatum
SEQUENCE: 44
METGKLELPE YVIQFYLDTG IEKLYPPQAE AVEKGLLDNK NLLAAIPTAS GKTLISELAM    60
LKSISNGGKC LYIVPLRALA SEKFERFKQF SSIGVNIGIS TGDFDSTDEW LGSNDIIVAT   120
SEKADSLLRN ETSWMKDITT IVVDEIHLLD SADRGPTLEI TIAKLLRLNP NSQIIGLSAT   180
IGNAEEIAGW LDAELVQSQW RPIELYEGVF LEDNINFKQS QKPIKNIVKD TAVNLVLDTI   240
DENGQCLVFE SSRRNCAGFA KKAKSKVGKS LDKGLLAELN NIAEEVLETS DTETTKELAS   300
CIKRGTAFHH AGLNSAQRKI VEDNFRNNKI KVISSTPTLA AGLNLPARRV IVRNYKRYDP   360
NFGMQPIPVL DYKQMAGRAG RPSLDPYGES VLISHTYNEF TDLLDRYIDA EPEDILSKLG   420
TENALRTHVL STIVNGFATT RQGMVDFMGS SFFAYQQQKW SLIDVDDCI EFLQDNEMIK   480
DDGERLYATR LGQVISTLYI DPLSGAIIID KLKKADKVTD MTMLHIICST PDMRQLYLRS   540
KEYEKINEYV MTHSDEFVEV PNPFKSIEYE WFLGEVKTAL LINEWIDEKT LDDITAEFGV   600
GEGDINALSD ISEWLMHSAV NLANLTDLDA DKAQELEKRI HHGVNKDLIQ LVSISNIGRV   660
RARKLYEAGI QSVSDIKNTK LHILSNYLGR KTAYKVLEQL GVEPEDNQQI DEEPESIKSY   720
SGNDQGQKTF NDF                                                      733

SEQ ID NO: 45            moltype = AA  length = 747
FEATURE                  Location/Qualifiers
source                   1..747
                         mol_type = protein
                         organism = Methanococcus maripaludis
SEQUENCE: 45
MHVLDLLKEN KITELRPPQK KVIDEGLFDK TKNFLICIPT ASGKTLIGEM ALLNHILDEN    60
KNLTGKKGLF IVPLKALANE KFDEFREKYE KYGIKVGLSI GDFDTKENLS KFHIIITTSE   120
KLDSLMRHNV EWINDVSLAV IDEIHLIGDN ERGGTLEVIL TKLKNLNAQI VGLSATIGNP   180
EELSNWLNAK LIVDGWRPVE LKKGIYFENE LEFLKNPAKK IKQVSRNNLT DLIVDSVEEK   240
GSCLIFCNSK RNAVGEAKKH NLAKYLTRTE QHELNKLSEE ILSILDRPVE TCKALSKCIQ   300
NGVAFHHAGL TYKHRKIVED GFRNRLIKVI CCTPTLSAGL NLPCRRAIVR DIKRYSQNGL   360
VDIPRMEIQQ CIGRAGRPGL DPYGEGIIYI KNERDAEKAY EILTGSVENI YSKLANQKVL   420
RIHILGLIST GEIKDGQNLV NFMKNTFYAH QFGNIGAVLL NVSEVVEFLE KNKFLETTIH   480
KKTENKVREL SFDSSNNLVL DSKETSFDLT NPNSNIEFRS TKLGKRISEL YIDPMSSEII   540
IEELHELKKK CDQLDRSKID QYLFYLISKT NEMRPLLRIR PNEELDLILE MDKMGLKDYS   600
IENIEAFKNS KMFCDWVSEI PEEIILEKYG VEPGILRYKV EQAKWMIYST KEIAKLIHLD   660
NSEIYKSLLK MEVRIEYGAK EELIELLNVK NVGRIRSRKL YDAGIRSKIE INKNPEKILE   720
LFGEKIGKKI LGEHGMKYGQ QTLLNFN                                       747

SEQ ID NO: 46            moltype = AA  length = 799
FEATURE                  Location/Qualifiers
source                   1..799
                         mol_type = protein
                         organism = Natrialba magadii
SEQUENCE: 46
MNVEELSGLP PGARSHFQEQ GIEELYPPQA EAVEAGATEG ENLVAAVPTA SGKTMIAALS    60
MLSAVQRGGK ALYIVPLRAL ASEKKAEFDA YEEFGVTTGV ATGNYESTSE WLATKDIIVA   120
TSEKVDSLVR NGADWLSDLT CVVSDEVHLI DDRNRGPTLE VTLAKLRRLN PQLQVVALSA   180
TVGNADELAD WLDAELVDTD WRPIDLQMGV HYGNALNFDD GETREVPVEA GEKQEAALVR   240
DILQEGGSSL VFVNSRRNAE AAARRLGQVS SRELTAGEQN DLAALATEIR EDSDTETSQD   300
LADCVERGAA FHHAGLSSTQ RSLVEDAFRD RLLKVISATP TLAAGVNTPA RRVIVRDWRR   360
FDPSAGGMAP LDVLEVHQMM GRAGRPGLDP YGEAVLLAKS HDESQELFDR YVWADPEPVR   420
SKLAAEPALR THVLATIASG FARTREGLLE FLEATLYASQ SSEGGRLERV TDDVLSYLER   480
NDFIERSGGP EDTLNSEADA ASAFTSAADL ADSDGGDSGG TTGQEEDLEA TSLGHTVSRL   540
YLDPMSAAEI VHGLEDADER PTALGLYQLV SRTPDMYELY LRSGEDEKFG ELYYEREREL   600
LGDAPSEFEE ERFEDWLAAL KTGKLLEDWA TEDDEEQITE RYKIGPGDLR GKVDTAEWLL   660
```

```
GAAESLASEI DSEWAVAVRE ARARVEHGVG EELLELVSVS GIGRKRARRL YAAGIEEPAA    720
LRSADKGVIL HVLKGEKTAE NILENAGREE PSMDGVEPIP VEGGSGSGSS NSSGSSEPNA    780
DANATEDDAD DNQSSLGDF                                                 799

SEQ ID NO: 47            moltype = AA  length = 723
FEATURE                  Location/Qualifiers
source                   1..723
                         mol_type = protein
                         organism = Methanoregula boonei
SEQUENCE: 47
MQIQDLAIPE PLRQQYLGLG IRELYPPQAA CVERGLLDGK NLLVAIPTAS GKTLIAEMAM    60
HRHIANGGKC LYIVPLKALA SEKYEEFGNK GVKVGLSTGD LDRRDDALGK NDIIVATSEK    120
VDSLLRNGAR WIPDITLVVI DEIHLIDSPD RGPTLEMVIA KMRSKNPGMQ LIGLSATIGN    180
PKVLAGWLDA ELVTSSWRPV DLRQGVFYDN RIQFAERMRP VKQVSKNYDD LNLCLDTIAE    240
GGQCLVFVSS RRNAEAFAKR AAGAIKSEDA ALAACAERLL EGTPTEMVKT LAACVAKGAA    300
FHHAGLSRKE RSIVEEAFRK NLLKCISSTP TLAAGLNLPA RRVIIRDYLR FSAGEGMQPI    360
PVSEYRQMAG RAGRPRLDPY GEAVLIAKEA EQVPELFEVY IEAEAEDVHS RIAEPTALYT    420
HVLSLVASGF AGTRGELTEF MNRSFYVHEH KQGRLIHRAI DEALQFLITA EMVVEVGEHI    480
GATELGTLVS RMYIDPRSAF AIVTTLREQE KYADLGLIQL ICTTPDMPTL YAKNADLPAL    540
SRMLEVRGAD IWLPPPLDDD AAETYYRAVK TAMLLSDWTD ELSEEKICER YGVGPGDVFG    600
MVENINWLLH ATSQLARMFV PKFYGQIADC EICMKNGIRR ELLPLVRLRG IGRVARRLF     660
NNGITSPEEL SRHKKEDLVK ILGSGIAEQV LEQLHPSKDT GKKEPPSGDK NTNPGQSTLF    720
HFG                                                                  723

SEQ ID NO: 48            moltype = AA  length = 681
FEATURE                  Location/Qualifiers
source                   1..681
                         mol_type = protein
                         note = Ferroplasma acidarmanus
                         organism = unidentified
SEQUENCE: 48
MKLSEITPSE FLKVTDNNDF TLYEHQEEAV AKLRENKNVI VSVPTASGKT LIGYISIYDT    60
YLKGKKSMYI VPLRSLAMEK FSELLSLRNL GVKVTMSIGD YDVPPSFVKN YDVIIATSER    120
ADSMLHRDPD ILNYFGLVII DEIHMISDPS RGPRLETVIS SLLYLNPEIL LLGLSATVSN    180
IQEIAEWMNA ETVVSNFRAV PLETGIIFKG NLITDGEKKH LGRDDEVSLI KESIESGGQA    240
LVFRNSRRNA EKYAQSMVNF FDFQNDFEKL EIPPDLFNEA QANMVAHGVM PHHAGLSNDQ    300
RTMIEKLFKQ GYIKILTATP TLAAGVNLPA RTVIIRDITR FSDGYSKPIS GIEIQQMIGR    360
AGRPKDKKG YGYIYAASPG MLRVAEGYLT GELEPVISRN DSNSLIRFNV LALISSGIAT    420
DLKGIQDFYG KTLLAAQNDI DGYELAFESA LYFLKDNDFI TEENDIYSAT KFGRLTSDLY    480
IDPVSSLILK KCLDLEFSEE LYLYYISKTP DMLTFNYRAS DYEYLEEFLD RHNISDFSEE    540
SMGAAKTAII LNEWINEVPI NTIAETFGIG PGDIQAKASS ADWISYSLYR LGSMFDKENE    600
NNLLHLNIRI KEGVKEEIIR IIEIPQVGRV RGRRLYNNGF KSIDDIANAR VEDISRIFGF    660
STKLAKDIIE NAGKLNNRYY R                                              681

SEQ ID NO: 49            moltype = AA  length = 696
FEATURE                  Location/Qualifiers
source                   1..696
                         mol_type = protein
                         organism = Methanocaldococcus fervens
SEQUENCE: 49
MPTNKILEIL KDFGIEELRP PQKKALEKGL LDKNKNFLIS IPTASGKTLI GEMALINHLL    60
DENKNPTNKK GIFIVPLKAL ASEKYEEFKN KYERYGLRVA LSIGDYDEDE DLSRYHLIIT    120
TAEKLDSLWR HKIDWIDDVS VVVVDEIHLI NDESRGGTLE ILLTKLKKFN IQIIGLSATI    180
GNPEELANWL NAELIVDDWR PVELKKGIYK NGIIEFINGE NREIKAINNN DIYNLVVDCV    240
KDGGCCIVFC NTKRGAVNEA KKLNLKKFLT NEEKRKLKEV AEEILSILEP PTEMCKTLAE    300
CILNGSAFHH AGLTYQHRKI VEDAFRNKLI KVICCTPTLS VGLNLPCRRA IVKDLTRYTN    360
RGMRYIPIME IQQCIGRAGR LGLDPYGEGI IVAKNDRDYL RSYQVLTQKP EPIYSKLSNQ    420
AVLRTQLLGL IATIEIRDEY DLEWFIRNTF YAYQYGNLRE VAKNINEVIR FLEEKEFMID    480
FIPTELGKRV AELYIDPLSA KYMIDGLNEM ENEDDIYYLT NLRVYKSEEL                540
NLIDEMENLG IKSFEIEDLE AFKTAKMLYD WISEVPEDEI LKKYKIEPGI LRYKVENAVW    600
LMHALKEMAK IIGKNSEIPE KLEIRLEYGA KEDIIELLNV KYIGRVRARK LYNAGIRNVE    660
DIINNPSKVA SIIGEKITKK ILEDLGIKFG QQKLIF                              696

SEQ ID NO: 50            moltype = AA  length = 729
FEATURE                  Location/Qualifiers
source                   1..729
                         mol_type = protein
                         organism = Methanocaldococcus jannaschii
SEQUENCE: 50
MDKILEILKD FGIVELRPPQ KKALERGLLD KNKNFLISIP TASGKTLIGE MALINHLLDG    60
NKNPTNKKGI FIVPLKALAS EKYEEFKSKY ERYGLRIALS IGDYDEDEDL SKYHLIITTA    120
EKLDSLWRHK IDWINDVSVV VVDEIHLIND ETRGGTLEIL LTKLKEFNVQ IIGLSATIGN    180
PDELAEWLNA ELIVDDWRPV ELKKGIYKNE AIEFINGEIR NIKAVDNNDI YNLVVDCVKE    240
GGCCLVFCNT KRNAVNEAKK LNLKKFLTEE EKIRLKEIAE EILSILEPPT EMCKTLAECI    300
LNGSAFHHAG LTYQHRKIVE DAFRKRLIKV ICCTPTLSAG LNLPCRRAIV KDLTRFTNKG    360
MRYIPIMEIQ QCIGRAGRPG LDPYGEGIIV AKNDRDYLRA YQALTQKPEP IYSKLSNQAV    420
LRTQLLGLIA TGEIRDEYDL EWFIRNTFYA HQYGNLREVA KNINEVIRFL EENEFIIDFM    480
PTELGKRVSE LYIDPLSAKF IIDGLEEMEN EEIYYLYLI SKTLEMMPNL RVYNSEELNL    540
IDEMDSLGIK SFEIEDLEAF KTAKMLYDWI NEVPEDEILK RYKIEPGILR YKVENAVWIM    600
```

```
HALKEIAKLI GKSSDIPEKL EIRLEYGAKE DIIELLSIKY IGRVRARKLY NAGIRSIEDI   660
INNPSKVASI IGEKIAKKIL DELGVKFGQQ KLSFSGGSAW SHPQFEKGGG SGGGSGGSAW   720
SHPQFEKKL                                                          729

SEQ ID NO: 51            moltype = AA   length = 670
FEATURE                  Location/Qualifiers
source                   1..670
                         mol_type = protein
                         organism = Methanocaldococcus infernus
SEQUENCE: 51
MDEILKFLGI KELRPPQKKA LELGILDKKK NFLISIPTGA GKTVIAEMAL INHLLLDKGK    60
KGVYIVPLKA LASEKYEEFK KKYEKFGVRV ALSIGDYDED EDLENYDLII TTAEKFDSLW   120
RHGIKLSDIS VVVVDEIHVI GDSERGGTLE VLLTKLKELD VQIIGLSATI GNPEELSEWL   180
NAELLLDNWR PVELRKGIYR EGVIEYLDGE VKECQDIVKE VVKDNGSVII FCPTKKKAEN   240
RALSLDLSDL LKKSEKRKLE EISEELLSLF DPPTELCKKL ASCVRKGIAF HHSGLTYEHR   300
KIIEKAFRER ILKVICSTTT LAFGLNLPCR RVIISELKRY TRRGLTYIPI MEVQQCIGRA   360
GRPGLDEYGE GILVAKDERD YLRALQCLTQ KPEPIYSKLS NDSVLRTQIL GLIATRYVLD   420
EYDLEEFIKN TFYAYQYKNL DEIKKKIKEI IEFLEDCNFI KNFEVTPLGK KVSNLYLDPL   480
SAKIMIDNIE VKDDLHLLYI LCKCIEMKPL LRVYRKEEEE LAEELLNYEI FISYENLEEF   540
KTAKMLYDWI NEVPEDEILK TYKVEPGILR YKVEVAKWLS YSLKEIAKIL NKEVPNLELR   600
LEYGAKEELL ELLKIKYIGR VRARKLYSAG IRNREDIIKN PKKVANILGE KISKKIFEEL   660
GVRYGQQRLI                                                         670

SEQ ID NO: 52            moltype = AA   length = 799
FEATURE                  Location/Qualifiers
source                   1..799
                         mol_type = protein
                         organism = Methanospirillum hungatei
SEQUENCE: 52
MEIASLPLPD SFIRACHAKG IRSLYPPQAE CIEKGLLEGK NLLISIPTAS GKTLLAEMAM    60
WSRIAAGGKC LYIVPLRALA SEKYDEFSKK GVIRVGIATG DLDRTDAYLG ENDIIVATSE   120
KTDSLLRNRT PWLSQITCIV LDEVHLIGSE NRGATLEMVI TKLRYTNPVM QIIGLSATIG   180
NPAQLAEWLD ATLITSTWRP VDLRQGVYYN GKIRFSDSER PIQGKTKHDD LNLCLDTIEE   240
GGQCLLVFVSS RRNAEGFAKK AAGALKAGSP DSKALAQELR RLRDRDEGNV LADCVERGAA   300
FHHAGLIRQE RTIIEEGFRN GYIEVIAATP TLAAGLNLPA RRVIIRDYNR FASGLGMVPI   360
PVGEYHQMAG RAGRPHLDPY GEAVLLAKDA PSVERLFETF IDAEAERVDS QCVDDASLCA   420
HILSLIATGF AHDQEALSSF MERTFYFFQH PKTRSLPRLV ADAIRFLTTA GMVEERENTL   480
SATRLGSLVS RLYLNPCTAR LILDSLKSCK TPTLIGLLHV ICVSPDMQRL YLKAADTQLL   540
RTFLFKHKDD LILPLPFEQE EEELWLSGLK TALVLTDWAD EFSEGMIEER YGIGAGDLYN   600
IVDSGKWLLH GTERLVSVEM PEMSQVVKTL SVRVHHGVKS ELLPLVALRN IGRVRARTLY   660
NAGYPDPEAV ARAGLSTIAR IIGEGIARQV IDEITGVKRS GIHSSDDDYQ QKTPELLTDI   720
PGIGKKMAEK LQNAGIITVS DLLTADEVLL SDVLGAARAR KVLAFLSNSE KENSSSDKTE   780
EIPDTQKIRG QSSWEDFGC                                               799

SEQ ID NO: 53            moltype = AA   length = 702
FEATURE                  Location/Qualifiers
source                   1..702
                         mol_type = protein
                         organism = Archaeoglobus fulgidus
SEQUENCE: 53
MKVEELAESI SSYAVGILKE EGIEELFPPQ AEAVEKVFSG KNLLLAMPTA AGKTLLAEMA    60
MVREAIKGGK SLYVVPLRAL AGEKYESFKK WEKIGLRIGI STGDYESRDE HLGDCDIIVT   120
TSEKADSLIR NRASWIKAVS CLVVDEIHLL DSEKRGATLE ILVTKMRRMN KALRVIGLSA   180
TAPNVTEIAE WLDADYYVSD WRPVPLVEGV LCEGTLELFD GAFSTSRRVK FEELVEECVA   240
ENGGVLVFES TRRGAEKTAV KLSAITAKYV ENEGLEKAIL EENEGEMSRK LAECVRKGAA   300
FHHAGLLNGQ RRVVEDAFRR GNIKVVVATP TLAAGVNLPA RRVIVRSLYR FDGYSKRIKV   360
SEYKQMAGRA GRPGMDERGE AIIIVGKKDR EIAVKRYIFG EPERITSKLG VETHLRFHSL   420
SIICDGYAKT LEELEDFFAD TFFFKQNEIS LSYELERVVR QLENWGMVVE DHHLAPTKLG   480
SLVSRLYIDP LTGFIFHDVL SRMELSDIGA LHLICRTPDM ERTLVRKTDS WVEEEAFRLR   540
KELSYYPSDF SVEYDWFLSE VKTALCLKDW IEEKDEDEIC AKYGIAPGDL RRIVETAEWL   600
SNAMNRIAEE VGNTSVSGLT ERIKHGVKEE LLELVRIRHI GRVRARKLYN AGIRNAEDIV   660
RHREKVASLI GRGIAERVVE GISVKSLNPE SAAALEHHHH HH                     702

SEQ ID NO: 54            moltype = AA   length = 791
FEATURE                  Location/Qualifiers
source                   1..791
                         mol_type = protein
                         organism = Haloterrigena turkmenica
SEQUENCE: 54
MNLEELTGLP PGATDHFRGE GIEELYPPQA DAVEAGATDG ENLVAAVPTA SGKTMIAALS    60
MLSAVQRGGK ALYIVPLRAL ASEKKEEFEA YEEFGVTTGV TTGNYESTDD WLATKDIIVA   120
TSEKVDSLVR NGADWLSELT CVVSDEVHLI DDRNRGPTLE VTLAKLRRLN PGMQVVALSA   180
TVGNADEIAD WLDASLVDTD WRPIDLQMGV HYGNALNFDD GSTREVPVEG SEKQEAALVR   240
DILREGGSSL VFVNSRRNAE GAAKRLGQVS SREITEDERA ELAELADDIR DDSDTETSAD   300
LADCVERGAA FHHAGLSSTQ RSLVEDAFRD RLLKVISATP TLAAGVNTPA RRVIVRDWRR   360
FDPSAGGMAP LDVLEVHQMM GRAGRPGLDP YGEAVLLAKS HDESEELFDR YIWADPEPVR   420
SKLAAEPALR THVLATIASG FARTRGGLLE FLEATLYASQ SSEAGRLESV TDDVLDYLER   480
NDFIERSRDD EAEDSGEDDG PFTSAADLAE QQAAKREETL EATSLGHTVS RLYLDPMSAA   540
EIVHGLERAD ERPTALGLYQ LVSRTPDMYE LYLRSGEDEK FGELFYERET ELLGDAPSEY   600
```

```
EEDRFEDWLA ALKTGKLLED WADETDEETI TDRYKIGPGD LRGKVDTAEW LLGAAESLAA    660
EIDSEWTVAV REARARVEHG VGEELLELVS VGGVGRKRAR RLYDAGIEEP ADLRSADKGI    720
VLSVLKGEKT AENILENAGR EDPSMDGVEP ADGGPAVGAA TNGSSGGSET DETGRADAAE    780
SDDSQSSLGD F                                                        791

SEQ ID NO: 55           moltype = AA  length = 752
FEATURE                 Location/Qualifiers
source                  1..752
                        mol_type = protein
                        organism = Haladaptatus paucihalophilus
SEQUENCE: 55
MNVADLTGLP DGVPEHFHAQ GIEELYPPQA EAVEAGITEG ESVVASIPTA SGKTFIAELA     60
MLSSVARGGK ALYIVPLRAL ASEKKEEFEE FEQYGVSIGV STGNYESDGD WLASRDIIVA    120
TSEKVDSLVR NGAKWIDDLS CVVADEVHLV NDAHRGPTLE VTLAKLRRVN PDLQTVALSA    180
TVGNAGEMAD WLDATLVDST WRPIDLRKGV LYGQALHFDD GTQQELARGN EKETAALVRD    240
TLEDGGSSLV FVNSRRNAEA AAKRLADVTK THLTDDERRD LLDIADQIRD VSDTETSDDL    300
ATAIEKGAAF HHAGLASDHR SLVEDAFRDK LIKVISATPT LAAGVNTPSR RVIVRDWRRY    360
DGDIGGMQPL DVLEVHQMFG RAGRPGLDPH GEAVLIAKSH DELQELFDQY VWADPEPVHS    420
KLAAEPALRT HILATVASGF AGTEEELLDF LERTLYATQT DETGRLETVT QHVLDYLDRN    480
GFLERDDRLR ATGLGHRVSQ LYLDPMSAAE IIDGLRDADG KPTALGLYHL VSRTPDMYQL    540
YLRSGDRERY TEIAYEREPE FLGHMPSEFE DNAFEDWLSA LKTARLLEDW ASELDEDRIT    600
ERYAIGPGDI RGKVETAQWL LNAAERLAAE LQRDDAEGIP SATTTAVREA RKRVEYGVEE    660
ELLDLAGVRN VGRKRARRLY EAGIESRADL READKSVVLG ALRGRKKTAE NILENVGRQD    720
PSLDDVEADA ETAATSARAT NDGGQQSLGD FE                                 752

SEQ ID NO: 56           moltype = AA  length = 8
FEATURE                 Location/Qualifiers
REGION                  1..8
                        note = Exemplary Hel308 motif
source                  1..8
                        mol_type = protein
                        organism = synthetic construct
SEQUENCE: 56
QMFGRAGR                                                              8

SEQ ID NO: 57           moltype = AA  length = 9
FEATURE                 Location/Qualifiers
REGION                  1..9
                        note = Exemplary extended Hel308 motif
source                  1..9
                        mol_type = protein
                        organism = synthetic construct
SEQUENCE: 57
QMFGRAGRP                                                             9

SEQ ID NO: 58           moltype = AA  length = 783
FEATURE                 Location/Qualifiers
source                  1..783
                        mol_type = protein
                        note = Halobacterium sp. NRC-1
                        organism = unidentified
SEQUENCE: 58
MRVADVPGLP GGVADHFEGE GVEELYPPQA EAVERGVTEG ANLVASVPTA SGKTLIAQLA     60
MLSAIAEGGD SPTFSGDGTA LYIVPLRALA GEKAQEFEAF ERFGLSVGVS TGNYERDGAR    120
LADNDIVVAT SEKVDSLVRN GAGWIDDLSC VVADEVHLVD DDHRGPTLEV TLAKLRQQVA    180
DLQVVALSAT VGNAGELAAW LDAELVDSDW RPIELRTGVH YGQSLHYDDG TQAELSVGSG    240
SQTAAVVADT LADDGSTLVF VNSRRNAEAS ARRLADVTGN ALSSAERERL ADIAAEIRGV    300
SDTETSDELA DAVASGAAFH HAGLAREHRE LVEEAFRDRL VKAVSATPTL AAGVNTPARR    360
VVVRDWQRYD GTAGGMQPLD VLEVHQMFGR AGRPGLDPYG EAVLLANSHD ELEEELFDRYV    420
YADPEPVRSK LAAEPALRTH VLAAIATGFT TTEDGLHEFL GGTLYATQTD DTGRLRSVTG    480
DVLRYLDRNG FVERDGAALR ATATGQLVSR LYVDPMSAAT IIDGLRDAAR DATETDDEGA    540
FRPASELGDD AALPADASVE PTPLGLYHLV SRTPDMYELY LRSGDREQYT EVAYEHEDEL    600
LGATPREEQA EFEDWLSALK TARLMADWAS ELDEERIAER YDVGPGDIRG KVETAEWLLN    660
AAERLAGELD VECGPAVREA RKRVQYGVRE ELLGLAGVRN VGRKRARRLY NAGVESRADL    720
RNADKGVVLG AVRGRAATAE RILETVGHPD PGMDGVAADT DAAPESGGEA GGDEGQASLG    780
DFS                                                                 783

SEQ ID NO: 59           moltype =     length =
SEQUENCE: 59
000

SEQ ID NO: 60           moltype =     length =
SEQUENCE: 60
000

SEQ ID NO: 61           moltype =     length =
SEQUENCE: 61
000
```

```
SEQ ID NO: 62            moltype =    length =
SEQUENCE: 62
000

SEQ ID NO: 63            moltype = AA   length = 8
FEATURE                  Location/Qualifiers
REGION                   1..8
                         note = RecD motif I
SITE                     5
                         note = MISC_FEATURE - Xaa = T, V or C
SITE                     8
                         note = MISC_FEATURE - Xaa = T or S
source                   1..8
                         mol_type = protein
                         organism = synthetic construct
SEQUENCE: 63
GGPGXGKX                                                                   8

SEQ ID NO: 64            moltype = AA   length = 8
FEATURE                  Location/Qualifiers
REGION                   1..8
                         note = Preferred RecD motif I
source                   1..8
                         mol_type = protein
                         organism = synthetic construct
SEQUENCE: 64
GGPGTGKT                                                                   8

SEQ ID NO: 65            moltype = AA   length = 25
FEATURE                  Location/Qualifiers
REGION                   1..25
                         note = Extended RecD motif I
REGION                   2..17
                         note = MISC_FEATURE - Xaa = any amino acid
SITE                     22
                         note = MISC_FEATURE - Xaa = T, V or C
SITE                     25
                         note = MISC_FEATURE - Xaa = T or S
source                   1..25
                         mol_type = protein
                         organism = synthetic construct
SEQUENCE: 65
QXXXXXXXX XXXXXXXGGP GXGKX                                                25

SEQ ID NO: 66            moltype = AA   length = 26
FEATURE                  Location/Qualifiers
REGION                   1..26
                         note = Extended RecD motif I
REGION                   2..18
                         note = MISC_FEATURE - Xaa = any amino acid
SITE                     23
                         note = MISC_FEATURE - Xaa = T, V or C
SITE                     26
                         note = MISC_FEATURE - Xaa = T or S
source                   1..26
                         mol_type = protein
                         organism = synthetic construct
SEQUENCE: 66
QXXXXXXXX XXXXXXXGG PGXGKX                                                26

SEQ ID NO: 67            moltype = AA   length = 27
FEATURE                  Location/Qualifiers
REGION                   1..27
                         note = Extended RecD motif I
REGION                   2..19
                         note = MISC_FEATURE - Xaa = any amino acid
SITE                     24
                         note = MISC_FEATURE - Xaa = T, V or C
SITE                     27
                         note = MISC_FEATURE - Xaa = T or S
source                   1..27
                         mol_type = protein
                         organism = synthetic construct
SEQUENCE: 67
QXXXXXXXX XXXXXXXXG GPGXGKX                                               27

SEQ ID NO: 68            moltype =    length =
SEQUENCE: 68
000
```

```
SEQ ID NO: 69           moltype = AA  length = 10
FEATURE                 Location/Qualifiers
REGION                  1..10
                        note = RecD motif V
SITE                    1
                        note = MISC_FEATURE - Xaa = Y, W or F
SITE                    2
                        note = MISC_FEATURE - Xaa = A, M, C or V
SITE                    3
                        note = MISC_FEATURE - Xaa = I, M or L
SITE                    4
                        note = MISC_FEATURE - Xaa = T or S
SITE                    5
                        note = MISC_FEATURE - Xaa = V or I
source                  1..10
                        mol_type = protein
                        organism = synthetic construct
SEQUENCE: 69
XXXXXHKSQG                                                                10

SEQ ID NO: 70           moltype = AA  length = 13
FEATURE                 Location/Qualifiers
REGION                  1..13
                        note = MobF motif III
REGION                  2..3
                        note = MISC_FEATURE - Xaa = any amino acid
SITE                    4
                        note = MISC_FEATURE - Xaa = any amino acid except D, E, R
                         and K
REGION                  6..10
                        note = MISC_FEATURE - Xaa = any amino acid
SITE                    12
                        note = MISC_FEATURE - Xaa = any amino acid except D, E, R
                         and K
source                  1..13
                        mol_type = protein
                        organism = synthetic construct
SEQUENCE: 70
HXXXRXXXXX HXH                                                            13

SEQ ID NO: 71           moltype = AA  length = 14
FEATURE                 Location/Qualifiers
REGION                  1..14
                        note = MobF motif III
REGION                  2..3
                        note = MISC_FEATURE - Xaa = any amino acid
SITE                    4
                        note = MISC_FEATURE - Xaa = any amino acid except D, E, R
                         and K
REGION                  6..11
                        note = MISC_FEATURE - Xaa = any amino acid
SITE                    13
                        note = MISC_FEATURE - Xaa = any amino acid except D, E, R
                         and K
source                  1..14
                        mol_type = protein
                        organism = synthetic construct
SEQUENCE: 71
HXXXRXXXXX XHXH                                                           14

SEQ ID NO: 72           moltype = AA  length = 15
FEATURE                 Location/Qualifiers
REGION                  1..15
                        note = MobF motif III
REGION                  2..3
                        note = MISC_FEATURE - Xaa = any amino acid
SITE                    4
                        note = MISC_FEATURE - Xaa = any amino acid except D, E, R
                         and K
REGION                  6..12
                        note = MISC_FEATURE - Xaa = any amino acid
SITE                    14
                        note = MISC_FEATURE - Xaa = any amino acid except D, E, R
                         and K
source                  1..15
                        mol_type = protein
                        organism = synthetic construct
SEQUENCE: 72
```

```
HXXXRXXXXX XXHXH                                                      15

SEQ ID NO: 73           moltype = AA  length = 16
FEATURE                 Location/Qualifiers
REGION                  1..16
                        note = MobF motif III
REGION                  2..3
                        note = MISC_FEATURE - Xaa = any amino acid
SITE                    4
                        note = MISC_FEATURE - Xaa = any amino acid except D, E, R
                         and K
REGION                  6..13
                        note = MISC_FEATURE - Xaa = any amino acid
SITE                    15
                        note = MISC_FEATURE - Xaa = any amino acid except D, E, R
                         and K
source                  1..16
                        mol_type = protein
                        organism = synthetic construct
SEQUENCE: 73
HXXXRXXXXX XXXHXH                                                     16

SEQ ID NO: 74           moltype = AA  length = 17
FEATURE                 Location/Qualifiers
REGION                  1..17
                        note = MobF motif III
REGION                  2..3
                        note = MISC_FEATURE - Xaa = any amino acid
SITE                    4
                        note = MISC_FEATURE - Xaa = any amino acid except D, E, R
                         and K
REGION                  6..14
                        note = MISC_FEATURE - Xaa = any amino acid
SITE                    16
                        note = MISC_FEATURE - Xaa = any amino acid except D, E, R
                         and K
source                  1..17
                        mol_type = protein
                        organism = synthetic construct
SEQUENCE: 74
HXXXRXXXXX XXXXHXH                                                    17

SEQ ID NO: 75           moltype = AA  length = 18
FEATURE                 Location/Qualifiers
REGION                  1..18
                        note = MobF motif III
REGION                  2..3
                        note = MISC_FEATURE - Xaa = any amino acid
SITE                    4
                        note = MISC_FEATURE - Xaa = any amino acid except D, E, R
                         and K
REGION                  6..15
                        note = MISC_FEATURE - Xaa = any amino acid
SITE                    17
                        note = MISC_FEATURE - Xaa = any amino acid except D, E, R
                         and K
source                  1..18
                        mol_type = protein
                        organism = synthetic construct
SEQUENCE: 75
HXXXRXXXXX XXXXXHXH                                                   18

SEQ ID NO: 76           moltype = AA  length = 19
FEATURE                 Location/Qualifiers
REGION                  1..19
                        note = MobF motif III
REGION                  2..3
                        note = MISC_FEATURE - Xaa = any amino acid
SITE                    4
                        note = MISC_FEATURE - Xaa = any amino acid except D, E, R
                         and K
REGION                  6..16
                        note = MISC_FEATURE - Xaa = any amino acid
SITE                    18
                        note = MISC_FEATURE - Xaa = any amino acid except D, E, R
                         and K
source                  1..19
                        mol_type = protein
                        organism = synthetic construct
```

```
SEQUENCE: 76
HXXXRXXXXX XXXXXXHXH                                                    19

SEQ ID NO: 77            moltype = AA  length = 20
FEATURE                  Location/Qualifiers
REGION                   1..20
                         note = MobF motif III
REGION                   2..3
                         note = MISC_FEATURE - Xaa = any amino acid
SITE                     4
                         note = MISC_FEATURE - Xaa = any amino acid except D, E, R
                          and K
REGION                   6..17
                         note = MISC_FEATURE - Xaa = any amino acid
SITE                     19
                         note = MISC_FEATURE - Xaa = any amino acid
source                   1..20
                         mol_type = protein
                         organism = synthetic construct
SEQUENCE: 77
HXXXRXXXXX XXXXXXHXH                                                    20

SEQ ID NO: 78            moltype =    length =
SEQUENCE: 78
000

SEQ ID NO: 79            moltype =    length =
SEQUENCE: 79
000

SEQ ID NO: 80            moltype =    length =
SEQUENCE: 80
000

SEQ ID NO: 81            moltype =    length =
SEQUENCE: 81
000

SEQ ID NO: 82            moltype =    length =
SEQUENCE: 82
000

SEQ ID NO: 83            moltype =    length =
SEQUENCE: 83
000

SEQ ID NO: 84            moltype =    length =
SEQUENCE: 84
000

SEQ ID NO: 85            moltype = AA  length = 1756
FEATURE                  Location/Qualifiers
source                   1..1756
                         mol_type = protein
                         organism = Escherichia coli
SEQUENCE: 85
MMSIAQVRSA GSAGNYYTDK DNYYVLGSMG ERWAGKGAEQ LGLQGSVDKD VFTRLLEGRL    60
PDGADLSRMQ DGSNKHRPGY DLTFSAPKSV SMMAMLGGDK RLIDAHNQAV DFAVRQVEAL   120
ASTRVMTDGQ SETVLTGNLV MALFNHDTSR DQEPQLHTHA VVANVTQHNG EWKTLSSDKV   180
GKTGFIENVY ANQIAFGRLY REKLKEQVEA LGYETEVVGK HGMWEMPGVP VEAFSGRSQA   240
IREAVGEDAS LKSRDVAALD TRKSKQHVDP EIRMAEWMQT LKETGFDIRA YRDAADQRTE   300
IRTQAPGPAS QDGPDVQQAV TQAIAGLSER KVQFTYTDVL ARTVGILPPE NGVIERARAG   360
IDEAISREQL IPLDREKGLF TSGIHVLDEL SVRALSRDIM KQNRVTVHPE KSVPRTAGYS   420
DAVSVLAQDR PSLAIVSGQG GAAGQRERVA ELVMMAREQG REVQIIAADR RSQMNLKQDE   480
RLSGELITGR RQLLEGMAFT PGSTVIVDQG EKLSLKETLT LLDGAARHNV QVLITDSGQR   540
TGTGSALMAM KDAGVNTYRW QGGEQRPATI ISEPDRNVRY ARLAGDFAAS VKAGEESVAQ   600
VSGVREQAIL TQAIRSELKT QGVLGHPEVT MTALSPVWLD SRSRYLRDMY RPGMVMEQWN   660
PETRSHDRYV IDRVTAQSHS LTLRDAQGET QVVRISSLDS SWSLFRPEKM PVADGERLRV   720
TGKIPGLRVS GGDRLQVASV SEDAMTVVVP GRAEPASLPV SDSPFTALKL ENGWVETPGH   780
SVSDSATVFA SVTQMAMDNA TLNGLARSGR DVRLYSSLDE TRTAEKLARH PSFTVVSEQI   840
KARAGETLLE TAISLQKAGL HTPAQQAIHL ALPVLESKNL AFSMVDLLTE AKSFAAEGTG   900
FTELGGEINA QIKRGDLLYV DVAKGYGTGL LVSRASYEAE KSILRHILEG KEAVTPLMER   960
VPGELMETLT SGQRAATRMI LETSDRFTVV QGYAGVGKTT QFRAVMSAVN MLPASERPRV  1020
VGLGPTHRAV GEMRSAGVDA QTLASFLHDT QLQQRSGETP DFSNTLFLLD ESSMVGNTEM  1080
ARAYALIAAG GGRAVASGDT DQLQAIAPGQ SFRLQQTRSA ADVVIMKEIV RQTPELREAV  1140
YSLINRDVER ALSGLESVKP SQVPRLEGAW APEHSVTEFS HSQEAKLAEA QQKAMLKGEA  1200
FPDIPMTLYE AIVRDYTGRT PEAREQTLIV THLNEDRRVL NSMIHDAREK AGELGKEQVM  1260
VPVLNTANIR DGELRRLSTW EKNPDALALV DNVYHRIAGI SKDDGLITLQ DAEGNTRLIS  1320
PREAVAEGVT LYTPDKIRVG TGDRMRFTKS DRERGYVANS VWTVTAVSGD SVTLSDGQQT  1380
```

-continued

```
RVIRPGQERA EQHIDLAYAI TAHGAQGASE TFAIALEGTE GNRKLMAGFE SAYVALSRMK    1440
QHVQVYTDNR QGWTDAINNA VQKGTAHDVL EPKPDREVMN AQRLFSTARE LRDVAAGRAV    1500
LRQAGLAGGD SPARFIAPGR KYPQPYVALP AFDRNGKSAG IWLNPLTTDD GNGLRGFSGE    1560
GRVKGSGDAQ FVALQGSRNG ESLLADNMQD GVRIARDNPD SGVVVRIAGE GRPWNPGAIT    1620
GGRVWGDIPD NSVQPGAGNG EPVTAEVLAQ RQAEEAIRRE TERRADEIVR KMAENKPDLP    1680
DGKTELAVRD IAGQERDRSA ISERETALPE SVLRESQRER EAVREVAREN LLQERLQQME    1740
RDMVRDLQKE KTLGGD                                                    1756

SEQ ID NO: 86           moltype = AA  length = 8
FEATURE                 Location/Qualifiers
REGION                  1..8
                        note = RecD-like motif I of TraI Eco
source                  1..8
                        mol_type = protein
                        organism = synthetic construct
SEQUENCE: 86
GYAGVGKT                                                                8

SEQ ID NO: 87           moltype = AA  length = 10
FEATURE                 Location/Qualifiers
REGION                  1..10
                        note = RecD-like motif V of TraI Eco
source                  1..10
                        mol_type = protein
                        organism = synthetic construct
SEQUENCE: 87
YAITAHGAQG                                                             10

SEQ ID NO: 88           moltype = AA  length = 14
FEATURE                 Location/Qualifiers
REGION                  1..14
                        note = MobF motif III of TraI Eco
source                  1..14
                        mol_type = protein
                        organism = synthetic construct
SEQUENCE: 88
HDTSRDQEPQ LHTH                                                        14

SEQ ID NO: 89           moltype =     length =
SEQUENCE: 89
000

SEQ ID NO: 90           moltype = AA  length = 22
FEATURE                 Location/Qualifiers
REGION                  1..22
                        note = XPD motif VI
SITE                    2
                        note = MISC_FEATURE - Any amino acid
SITE                    3
                        note = MISC_FEATURE - Any amino acid except D, E, K, R.
                         Typically G, P, A, V, L, I, M, C, F, Y, W, H, Q, N, S or
                         T. Preferably not charged. Preferably not H. More
                         preferably V, A, L, I or M.
SITE                    6
                        note = MISC_FEATURE - Any amino acid except D, E, K, R.
                         Typically G, P, A, V, L, I, M, C, F, Y, W, H, Q, N, S or
                         T. Preferably not charged. Preferably not H. More
                         preferably V, A, L, I, M or C.
SITE                    7
                        note = MISC_FEATURE - Any amino acid except D, E, K, R.
                         Typically G, P, A, V, L, I, M, C, F, Y, W, H, Q, N, S or
                         T. Preferably not charged. Preferably not H. More
                         preferably I, H, L, F, M or V.
REGION                  9..11
                        note = MISC_FEATURE - Any amino acid.
SITE                    12
                        note = MISC_FEATURE - D or E
SITE                    13
                        note = MISC_FEATURE - Any amino acid.
SITE                    14
                        note = MISC_FEATURE - Any amino acid. Preferably G, A, S or
                         C
REGION                  15..16
                        note = MISC_FEATURE - Any amino acid.
SITE                    17
                        note = MISC_FEATURE - Any amino acid. Preferably F, V, L,
                         I, M, A, W or Y
SITE                    18
                        note = MISC_FEATURE - Any amino acid. Preferably L, F, Y,
```

```
                              M, I or V.
SITE                          19
                              note = MISC_FEATURE - Any amino acid. Preferably A, C, V,
                              L, I, M or S.
source                        1..22
                              mol_type = protein
                              organism = synthetic construct
SEQUENCE: 90
QXXGRXXRXX XXXXXXXXXD NR                                              22

SEQ ID NO: 91                 moltype = AA  length = 726
FEATURE                       Location/Qualifiers
source                        1..726
                              mol_type = protein
                              organism = Methanococcoides burtonii
SEQUENCE: 91
MSDKPAFMKY FTQSSCYPNQ QEAMDRIHSA LMQQQLVLFE GACGTGKTLS ALVPALHVGK      60
MLGKTVIIAT NVHQQMVQFI NEARDIKKVQ DVKVAVIKGK TAMCPQEADY EECSVKRENT     120
FELMETEREI YLKRQELNSA RDSYKKSHDP AFVTLRDELS KEIDAVEEKA RGLRDRACND     180
LYEVLRSDSE KFREWLYKEV RSPEEINDHA IKDGMCGYEL VKRELKHADL LICNYHHVLN     240
PDIFSTVLGW IEKEPQETIV IFDEAHNLES AARSHSSLSL TEHSIEKAIT ELEANLDLLA     300
DDNIHNLFNI FLEVISDTYN SRFKFGERER VRKNWYDIRI SDPYERNDIV RGKFLRQAKG     360
DFGEKDDIQI LLSEASELGA KLDETYRDQY KKGLSSVMKR SHIRYVADFM SAYIELSHNL     420
NYYPILNVRR DMNDEIYGRV ELFTCIPKNV TEPLFNSLFS VILMSATLHP FEMVKKTLGI     480
TRDTCEMSYG TSFPEEKRLS IAVSIPPLFA KNRDDRHVTE LLEQVLLDSI ENSKGNVILF     540
FQSAFEAKRY YSKIEPLVNV PVFLDEVGIS SQDVREEFFS IGEENGKAVL LSYLWGTLSE     600
GIDYRDGRGR TVIIIGVGYP ALNDRMNAVE SAYDHVFGYG AGWEFAIQVP TIRKIRQAMG     660
RVVRSPTDYG ARILLDGRFL TDSKKRFGKF SVFEVFPPAE RSEFVDVDPE KVKYSLMNFF     720
MDNDEQ                                                                726

SEQ ID NO: 92                 moltype = AA  length = 9
FEATURE                       Location/Qualifiers
REGION                        1..9
                              note = Motif V
source                        1..9
                              mol_type = protein
                              organism = synthetic construct
SEQUENCE: 92
YLWGTLSEG                                                               9

SEQ ID NO: 93                 moltype = AA  length = 22
FEATURE                       Location/Qualifiers
REGION                        1..22
                              note = Motif VI
source                        1..22
                              mol_type = protein
                              organism = synthetic construct
SEQUENCE: 93
QAMGRVVRSP TDYGARILLD GR                                               22

SEQ ID NO: 94                 moltype = AA  length = 65
FEATURE                       Location/Qualifiers
REGION                        1..65
                              note = HhH domain
source                        1..65
                              mol_type = protein
                              organism = synthetic construct
SEQUENCE: 94
GTGSGAWKEW LERKVGEGRA RRLIEYFGSA GEVGKLVENA EVSKLLEVPG IGDEAVARLV      60
PGGSS                                                                  65

SEQ ID NO: 95                 moltype = AA  length = 299
FEATURE                       Location/Qualifiers
source                        1..299
                              mol_type = protein
                              note = Bacteriophage RB69
                              organism = unidentified
SEQUENCE: 95
MFKRKSTADL AAQMAKLNGN KGFSSEDKGE WKLKLDASGN GQAVIRFLPA KTDDALPFAI      60
LVNHGFKKNG KWYIETCSST HGDYDSCPVC QYISKNDLYN TNKTEYSQLK RKTSYWANIL     120
VVKDPQAPDN EGKVFKYRFG KKIWDKINAM IAVDTEMGET PVDVTCPWEG ANFVLKVKQV     180
SGFSNYDESK FLNQSAIPNI DDESFQKELF EQMVDLSEMT SKDKFKSFEE LNTKFNQVLG     240
TAALGGAAAA AASVADKVAS DLDDFDKDME AFSSAKTEDD FMSSSSSDDG DLDDLLAGL      299

SEQ ID NO: 96                 moltype = AA  length = 232
FEATURE                       Location/Qualifiers
source                        1..232
                              mol_type = protein
                              note = Bacteriophage T7
```

```
                               organism    = unidentified
SEQUENCE: 96
MAKKIFTSAL GTAEPYAYIA KPDYGNEERG FGNPRGVYKV DLTIPNKDPR CQRMVDEIVK    60
CHEEAYAAAV EEYEANPPAV ARGKKPLKPY EGDMPFFDNG DGTTTFKFKC YASFQDKKTK   120
ETKHINLVVV DSKGKKMEDV PIIGGGSKLK VKYSLVPYKW NTAVGASVKL QLESVMLVEL   180
ATFGGGEDDW ADEVEENGYV ASGSAKASKP RDEESWDEDD EESEEADEDG DF           232

SEQ ID NO: 97              moltype = AA   length = 324
FEATURE                    Location/Qualifiers
source                     1..324
                           mol_type = protein
                           note = Herpes simplex virus 1
                           organism    = unidentified
SEQUENCE: 97
MDSPGGVAPA SPVEDASDAS LGQPEEGAPC QVVLQGAELN GILQAFAPLR TSLLDSLLVM    60
GDRGILIHNT IFGEQVFLPL EHSQFSRYRW RGPTAAFLSL VDQKRSLLSV FRANQYPDLR   120
RVELAITGQA PFRTLVQRIW TTTSDGEAVE LASETLMKRE LTSFVVLVPQ GTPDVQLRLT   180
RPQLTKVLNA TGADSATPTT FELGVNGKFS VFTTSTCVTF AAREEGVSSS TSTQVQILSN   240
ALTKAGQAAA NAKTVYGENT HRTFSVVVDD CSMRAVLRRL QVGGGTLKFF LTTPVPSLCV   300
TATGPNAVSA VFLLKPQKHH HHHH                                          324

SEQ ID NO: 98              moltype = AA   length = 251
FEATURE                    Location/Qualifiers
REGION                     1..251
                           note = PCNA subunit 1
source                     1..251
                           mol_type = protein
                           organism    = synthetic construct
SEQUENCE: 98
MPKIVYPNAK DFFSFINSIT NVTDSIILNF TEDGIFSRHL TEDKVLMAIM RIPKDVLSEY    60
SIDSPTSVKL DVSSVKKILS KASSKKATIE LTETDSGLKI IIRDEKSGAK STIYIKAEKG   120
QVEQLTEPKV NLAVNFTTDE SVLNVIAADV TLVGEEMRIS TEEDKIKIEA GEEGKRYVAF   180
LMKDKPLKEL SIDTSASSSY SAEMFKDAVK GLRGFSAPTM VSFGENLPMK IDVEAVSGGH   240
MIFWIAPRLL E                                                        251

SEQ ID NO: 99              moltype = AA   length = 245
FEATURE                    Location/Qualifiers
REGION                     1..245
                           note = PCNA subunit 2
source                     1..245
                           mol_type = protein
                           organism    = synthetic construct
SEQUENCE: 99
MKAKVIDAVS FSYILRTVGD FLSEANFIVT KEGIRVSGID PSRVVFLDIF LPSSYFEGFE    60
VSQEKEIIGF KLEDVNDILK RVLKDDTLIL SSNESKLTLT FDGEFTRSFE LPLIQVESTQ   120
PPSVNLEFPF KAQLLTITFA DIIDELSDLG EVLNIHSKEN KLYFEVIGDL STAKVELSTD   180
NGTLLEASGA DVSSSYGMEY VANTTKMRRA SDSMELYFGS QIPLKLRFKL PQEGYGDFYI   240
APRAD                                                               245

SEQ ID NO: 100             moltype = AA   length = 246
FEATURE                    Location/Qualifiers
REGION                     1..246
                           note = PCNA subunit 3
source                     1..246
                           mol_type = protein
                           organism    = synthetic construct
SEQUENCE: 100
MKVVYDDVRV LKDIIQALAR LVDEAVLKFK QDSVELVALD RAHISLISVN LPREMFKEYD    60
VNDEFKFGFN TQYLMKILKV AKRKEAIEIA SESPDSVIIN IIGSTNREFN VRNLEVSEQE   120
IPEINLQFDI SATISSDGFK SAISEVSTVT DNVVVEGHED RILIKAEGES EVEVEFSKDT   180
GGLQDLEFSK ESKNSYSAEY LDDVLSLTKL SDYVKISFGN QKPLQLFFNM EGGGKVTYLL   240
APKVLE                                                              246

SEQ ID NO: 101             moltype = AA   length = 608
FEATURE                    Location/Qualifiers
source                     1..608
                           mol_type = protein
                           note = Bacteriophage phi-29
                           organism    = unidentified
SEQUENCE: 101
MKHMPRKMYS CAFETTTKVE DCRVWAYGYM NIEDHSEYKI GNSLDEFMAW VLKVQADLYF    60
HNLKFDGAFI INWLERNGFK WSADGLPNTY NTIISRMGQW YMIDICLGYK GKRKIHTVIY   120
DSLKKLPFPV KKIAKDFKLT VLKGDIDYHK ERPVGYKITP EEYAYIKNDI QIIAEALLIQ   180
FKQGLDRMTA GSDSLKGFKD IITTKKFKKV FPTLSLGLDK EVRYAYRGGF TWLNDRFKEK   240
EIGEGMVFDV NSLYPAQMYS RLLPYGEPIV FEGKYVWDED YPLHIQHIRC EFELKEGYIP   300
TIQIKRSRFY KGNEYLKSSG GEIADLWLSN VDLELMKEHY DLYNVEYISG LKFKATTGLF   360
KDFIDKWTYI KTTSEGAIKQ LAKLMLNSLY GKFASNPDVT GKVPYLKENG ALGFRLGEEE   420
TKDPVYTPMG VFITAWARYT TITAAQACYD RIIYCDTDSI HLTGTEIPDV IKDIVDPKKL   480
GYWAHESTFK RAKYLRQKTY IQDIYMKEVD GKLVEGSPDD YTDIKFSVKC AGMTDKIKKE   540
```

```
VTFENFKVGF SRKMKPKPVQ VPGGVVLVDD TFTIKSGGSA WSHPQFEKGG GSGGGSGGSA  600
WSHPQFEK                                                          608

SEQ ID NO: 102           moltype = AA  length = 318
FEATURE                  Location/Qualifiers
source                   1..318
                         mol_type = protein
                         note = Herpes simplex virus 1
                         organism = unidentified
SEQUENCE: 102
TDSPGGVAPA SPVEDASDAS LGQPEEGAPC QVVLQGAELN GILQAFAPLR TSLLDSLLVM  60
GDRGILIHNT IFGEQVFLPL EHSQFSRYRW RGPTAAFLSL VDQKRSLLSV FRANQYPDLR  120
RVELAITGQA PFRTLVQRIW TTTSDGEAVE LASETLMKRE LTSFVVLVPQ GTPDVQLRLT  180
RPQLTKVLNA TGADSATPTT FELGVNGKFS VFTTSTCVTF AAREEGVSSS TSTQVQILSN  240
ALTKAGQAAA NAKTVYGENT HRTFSVVVDD CSMRAVLRRL QVGGGTLKFF LTTPVPSLCV  300
TATGPNAVSA VFLLKPQK                                                318

SEQ ID NO: 103           moltype = AA  length = 233
FEATURE                  Location/Qualifiers
source                   1..233
                         mol_type = protein
                         note = Bacteriophage RB69
                         organism = unidentified
SEQUENCE: 103
KGFSSEDKGE WKLKLDASGN GQAVIRFLPA KTDDALPFAI LVNHGFKKNG KWYIETCSST  60
HGDYDSCPVC QYISKNDLYN TNKTEYSQLK RKTSYWANIL VVKDPQAPDN EGKVFKYRFG  120
KKIWDKINAM IAVDTEMGET PVDVTCPWEG ANFVLKVKQV SGFSNYDESK FLNQSAIPNI  180
DDESFQKELF EQMVDLSEMT SKDKFKSFEE LNTKFNQVLG TAALGGAAAA AAS         233

SEQ ID NO: 104           moltype = AA  length = 210
FEATURE                  Location/Qualifiers
source                   1..210
                         mol_type = protein
                         note = Bacteriophage T7
                         organism = unidentified
SEQUENCE: 104
AKKIFTSALG TAEPYAYIAK PDYGNEERGF GNPRGVYKVD LTIPNKDPRC QRMVDEIVKC  60
HEEAYAAAVE EYEANPPAVA RGKKPLKPYE GDMPFFDNGD GTTTFKFKCY ASFQDKKTKE  120
TKHINLVVVD SKGKKMEDVP IIGGGSKLKV KYSLVPYKWN TAVGASVKLQ LESVMLVELA  180
TFGGGEDDWA DEVEENGYVA SGSAKASKPR                                  210

SEQ ID NO: 105           moltype = AA  length = 99
FEATURE                  Location/Qualifiers
source                   1..99
                         mol_type = protein
                         note = Halorubrum lacusprofundi
                         organism = unidentified
SEQUENCE: 105
SGEELLDLAG VRNVGRKRAR RLFEAGIETR ADLREADKAV VLGALRGRER TAERILEHAG  60
REDPSMDDVR PDKSASAAAT AGSASDEDGE GQASLGDFR                         99

SEQ ID NO: 106           moltype = AA  length = 102
FEATURE                  Location/Qualifiers
source                   1..102
                         mol_type = protein
                         organism = Haloferax volcanii
SEQUENCE: 106
SGEELLDLAG VRGVGRKRAR RLFEAGVETR ADLREADKPR VLAALRGRRK TAENILEAAG  60
RKDPSMDAVD EDDAPDDAVP DDAGFETAKE RADQQASLGD FE                    102

SEQ ID NO: 107           moltype = AA  length = 55
FEATURE                  Location/Qualifiers
REGION                   1..55
                         note = (HhH)2 domain
source                   1..55
                         mol_type = protein
                         organism = synthetic construct
SEQUENCE: 107
WKEWLERKVG EGRARRLIEY FGSAGEVGKL VENAEVSKLL EVPGIGDEAV ARLVP       55

SEQ ID NO: 108           moltype = AA  length = 107
FEATURE                  Location/Qualifiers
REGION                   1..107
                         note = (HhH)2-(HhH)2 domain
source                   1..107
                         mol_type = protein
                         organism = synthetic construct
SEQUENCE: 108
WKEWLERKVG EGRARRLIEY FGSAGEVGKL VENAEVSKLL EVPGIGDEAV ARLVPGYKTL  60
```

RDAGLTPAEA ERVLKRYGSV SKVQEGATPD ELRELGLGDA KIARILG            107

SEQ ID NO: 109             moltype = AA  length = 7
FEATURE                    Location/Qualifiers
REGION                     1..7
                           note = Peptide linker used in the Examples
source                     1..7
                           mol_type = protein
                           organism = synthetic construct
SEQUENCE: 109
SRDFWRS                                                         7

SEQ ID NO: 110             moltype = DNA  length = 117
FEATURE                    Location/Qualifiers
misc_feature               1..117
                           note = Polynucleotide used in the Examples
source                     1..117
                           mol_type = other DNA
                           organism = synthetic construct
SEQUENCE: 110
tcgctgctcc acaggtctca gcttgagcag cgaaaataag aacattatga tcagtaggag   60
cactacgacc tttgttctgg tgctcgtccg ggcgcccaaa gtggagcgag tgccccc    117

SEQ ID NO: 111             moltype = DNA  length = 80
FEATURE                    Location/Qualifiers
misc_feature               1..80
                           note = Polynucleotide used in the Examples
source                     1..80
                           mol_type = other DNA
                           organism = synthetic construct
SEQUENCE: 111
gcactcgctc cactttgggc gcccggacga gcaccagaac aaaggtcgta gtgctcctac   60
tgatcataat gttcttattt                                              80

SEQ ID NO: 112             moltype = DNA  length = 33
FEATURE                    Location/Qualifiers
misc_feature               1..33
                           note = Polynucleotide used in the Examples
source                     1..33
                           mol_type = other DNA
                           organism = synthetic construct
SEQUENCE: 112
tcgctgctca agctgagacc tgtggagcag cga                              33

SEQ ID NO: 113             moltype = DNA  length = 113
FEATURE                    Location/Qualifiers
misc_feature               1..113
                           note = Polynucleotide used in the Examples
source                     1..113
                           mol_type = other DNA
                           organism = synthetic construct
SEQUENCE: 113
tcgctgctcc acaggtctca gcttgagcag cgaaaataag aacattatga tcagtaggag   60
cactacgacc tttgttctgg tgctcgtccg ggcgcccaaa gtggagcgag tgc        113

SEQ ID NO: 114             moltype = DNA  length = 28
FEATURE                    Location/Qualifiers
misc_feature               1..28
                           note = Polynucleotide used in the Examples
source                     1..28
                           mol_type = other DNA
                           organism = synthetic construct
SEQUENCE: 114
tcgctgctcc acaggtctca gcttcccc                                    28

SEQ ID NO: 115             moltype = DNA  length = 974
FEATURE                    Location/Qualifiers
misc_feature               1..974
                           note = Polynucleotide used in the Examples
source                     1..974
                           mol_type = other DNA
                           organism = synthetic construct
SEQUENCE: 115
tttttttttt tttttttttt tttttttttt tttttttttt tttttttttt ggttgtttct   60
gttggtgctg atattgctgt gttctatgtc ttattctgtg tatgtatctt gtctgttagc  120
cccgattgtt accggataat tcgagctcgg tacccacccc ggttgataat cagaaaagcc  180
ccaaaaacag gaagattgta taagcaaata tttaaattgt aaacgttaat attttgttaa  240
aattcgcgtt aaatttttgt taaatcagct cattttttaa ccaataggcc gaaatcggca  300
aaatccctta taaatcaaaa gaatagaccg agatagggtt gagtgttgtt ccagtttgga  360

```
acaagagtcc agtattaaag aacgtggact ccaacgtcaa agggcgaaaa accgtctatc    420
agggcgatgg cccactacgt gaaccatcac cctaatcaag ttttttgggg tcgaggtgcc    480
gtaaagcact aaatcggaac cctaaaggga tgccccgatt tagagcttga cggggaaagc    540
cggcgaacgt ggcgagaaag gaagggaaga aagcgaaagg agcgggcgct agggcgctgg    600
caagtgtagc ggtcacgctg cgcgtaacca ccacacccgc cgcgcttaat gcgccgctac    660
agggcgcgtg gggatcctct agagtcgacc tgcaggcatg caagctatcc cgcaagaggc    720
ccggcagtac cggcataacc aagcctatgc ctacagcatc cagggtgacg gtgccgagga    780
tgacgatgag cgcattgtta gatttcatac acggtgcctg actgcgttag caatttaact    840
gtgataaact accgcattaa agctagctta tcgatgataa gctgtcaaac atgagaattc    900
ttgaagacga aagggcctcg tgatacgcct attttttatg gttaatgtca tgataataat    960
ggtttcttag acgt                                                     974

SEQ ID NO: 116          moltype = DNA   length = 893
FEATURE                 Location/Qualifiers
misc_feature            1..893
                        note = Polynucleotide used in the Examples
source                  1..893
                        mol_type = other DNA
                        organism = synthetic construct
SEQUENCE: 116
ctaagaaacc attattatca tgacattaac ctataaaaat aggcgtatca cgaggccctt    60
tcgtcttcaa gaattctcat gtttgacagc ttatcatcga taagctagct ttaatgcggt    120
agtttatcac agttaaattg ctaacgcagt caggcaccgt gtatgaaatc taacaatgcg    180
ctcatcgtca tcctcggcac cgtcacccctg gatgctgtag catagcgct ggttatgccg    240
gtactgccgg gcctcttgcg ggatagcttg catgcctgca ggtcgactct agaggatccc    300
cacgcgccct gtagcggcgc attaagcgcg gcgggtgtgg tggttacgcg cagcgtgacc    360
gctacacttg ccagcgccct agcgcccgct cctttcgctt tcttcccttc ctttctcgcc    420
acgttcgccg gctttccccg tcaagctcta aatcggggca tccctttagg gttccgattt    480
agtgctttac ggcacctcga ccccaaaaaa cttgattagg gtgatggttc acgtagtggg    540
ccatcgccct gatagacggt ttttcgccct ttgacgttgg agtccacgtt ctttaatact    600
ggactcttgt tccaaactgg aacaacactc aaccctatct cggtctattc ttttgattta    660
taagggattt tgccgatttc ggcctattgg ttaaaaaatg agctgattta acaaaaattt    720
aacgcgaatt ttaacaaaat attaacgttt acaatttaaa tatttgctta caatcttcc    780
ctgttttttgg ggcttttctg attatcaacc ggggtgggta ccgagctcga attatccggt    840
aacaatcggg gctaacagac aagatacata cacagaataa gacatagaac aca          893

SEQ ID NO: 117          moltype = DNA   length = 28
FEATURE                 Location/Qualifiers
misc_feature            1..28
                        note = Polynucleotide used in the Examples
source                  1..28
                        mol_type = other DNA
                        organism = synthetic construct
SEQUENCE: 117
gcaatatcag caccaacaga aacaacct                                      28

SEQ ID NO: 118          moltype = AA   length = 132
FEATURE                 Location/Qualifiers
source                  1..132
                        mol_type = protein
                        organism = Homo sapiens
SEQUENCE: 118
ESETTTSLVL ERSLNRVHLL GRVGQDPVLR QVEGKNPVTI FSLATNEMWR SGDSEVYQLG    60
DVSQKTTWHR ISVFRPGLRD VAYQYVKKGS RIYLEGKIDY GEYMDKNNVR RQATTIIADN    120
IIFLSDQTKE KE                                                       132

SEQ ID NO: 119          moltype = AA   length = 123
FEATURE                 Location/Qualifiers
source                  1..123
                        mol_type = protein
                        note = Bacteriophage phi-29
                        organism = unidentified
SEQUENCE: 119
ENTNIVKATF DTETLEGQIK IFNAQTGGGQ SFKNLPDGTI IEANAIAQYK QVSDTYGDAK    60
EETVTTIFAA DGSLYSAISK TVAEAASDLI DLVTRHKLET FKVKVVQGTS SKGNVFFSLQ    120
LSL                                                                 123

SEQ ID NO: 120          moltype = AA   length = 177
FEATURE                 Location/Qualifiers
source                  1..177
                        mol_type = protein
                        organism = Escherichia coli
SEQUENCE: 120
ASRGVNKVIL VGNLGQDPEV RYMPNGGAVA NITLATSESW RDKATGEMKE QTEWHRVVLF    60
GKLAEVASEY LRKGSQVYIE GQLRTRKWTD QSGQDRYTTE VVVNVGGTMQ MLGGRQGGGA    120
PAGGNIGGGQ PQGGWGQPQQ PQGGNQFSGG AQSRPQQSAP AAPSNEPPMD FDDDIPF      177

SEQ ID NO: 121          moltype = AA   length = 301
FEATURE                 Location/Qualifiers
```

| source | 1..301 |
| --- | --- |
| | mol_type = protein |
| | note = Bacteriophage T4 |
| | organism = unidentified |

SEQUENCE: 121
```
MFKRKSTAEL AAQMAKLNGN KGFSSEDKGE WKLKLDNAGN GQAVIRFLPS KNDEQAPFAI    60
LVNHGPKKNG KWYIETCSST HGDYDSCPVC QYISKNDLYN TDNKEYSLVK RKTSYWANIL   120
VVKDPAAPEN EGKVFKYRFG KKIWDKINAM IAVDVEMGET PVDVTCPWEG ANFVLKVKQV   180
SGFSNYDESK FLNQSAIPNI DDESFQKELF EQMVDLSEMT SKDKFKSFEE LNTKFGQVMG   240
TAVMGGAAAT AAKKADKVAD DLDAFNVDDF NTKTEDDFMS SSSGSSSSAD DTDLDDLLND   300
L                                                                  301
```

| SEQ ID NO: 122 | moltype = AA length = 177 |
| --- | --- |
| FEATURE | Location/Qualifiers |
| REGION | 1..177 |
| | note = EcoSSB-CterAla |
| source | 1..177 |
| | mol_type = protein |
| | organism = synthetic construct |

SEQUENCE: 122
```
ASRGVNKVIL VGNLGQDPEV RYMPNGGAVA NITLATSESW RDKATGEMKE QTEWHRVVLF    60
GKLAEVASEY LRKGSQVYIE GQLRTRKWTD QSGQDRYTTE VVVNVGGTMQ MLGGRQGGGA   120
PAGGNIGGGQ PQGGWGQPQQ PQGGNQFSGG AQSRPQQSAP AAPSNEPPMA FAAAIPF      177
```

| SEQ ID NO: 123 | moltype = AA length = 177 |
| --- | --- |
| FEATURE | Location/Qualifiers |
| REGION | 1..177 |
| | note = EcoSSB-CterNGGN |
| source | 1..177 |
| | mol_type = protein |
| | organism = synthetic construct |

SEQUENCE: 123
```
ASRGVNKVIL VGNLGQDPEV RYMPNGGAVA NITLATSESW RDKATGEMKE QTEWHRVVLF    60
GKLAEVASEY LRKGSQVYIE GQLRTRKWTD QSGQDRYTTE VVVNVGGTMQ MLGGRQGGGA   120
PAGGNIGGGQ PQGGWGQPQQ PQGGNQFSGG AQSRPQQSAP AAPSNEPPMN FGGNIPF      177
```

| SEQ ID NO: 124 | moltype = AA length = 152 |
| --- | --- |
| FEATURE | Location/Qualifiers |
| REGION | 1..152 |
| | note = EcoSSB-Q152del |
| source | 1..152 |
| | mol_type = protein |
| | organism = synthetic construct |

SEQUENCE: 124
```
ASRGVNKVIL VGNLGQDPEV RYMPNGGAVA NITLATSESW RDKATGEMKE QTEWHRVVLF    60
GKLAEVASEY LRKGSQVYIE GQLRTRKWTD QSGQDRYTTE VVVNVGGTMQ MLGGRQGGGA   120
PAGGNIGGGQ PQGGWGQPQQ PQGGNQFSGG AQ                                 152
```

| SEQ ID NO: 125 | moltype = AA length = 117 |
| --- | --- |
| FEATURE | Location/Qualifiers |
| REGION | 1..117 |
| | note = EcoSSB-G117del |
| source | 1..117 |
| | mol_type = protein |
| | organism = synthetic construct |

SEQUENCE: 125
```
ASRGVNKVIL VGNLGQDPEV RYMPNGGAVA NITLATSESW RDKATGEMKE QTEWHRVVLF    60
GKLAEVASEY LRKGSQVYIE GQLRTRKWTD QSGQDRYTTE VVVNVGGTMQ MLGGRQG      117
```

| SEQ ID NO: 126 | moltype = AA length = 970 |
| --- | --- |
| FEATURE | Location/Qualifiers |
| source | 1..970 |
| | mol_type = protein |
| | note = Citromicrobium bathyomarinum JL354 |
| | organism = unidentified |

SEQUENCE: 126
```
MLSVANVRSP SAAASYFASD NYYASADADR SGQWIGDGAK RLGLEGKVEA RAFDALLRGE    60
LPDGSSVGNP GQAHRPGTDL TFSVPKSWSL LALVGKDERI IAAYREAVVE ALHWAEKNAA   120
ETRVVEKGMV VTQATGNLAI GLFQHDTNRN QEPNLHFHAV IANVTQGKDG KWRTLKNDRL   180
WQLNTTLNSI AMARFRVAVE KLGYEPGPVL KHGNFEARGI SREQVMAFST RRKEVLEARR   240
GPGPGLDAGRIA ALDTRASKEG IEDRATLSKQ WSEAAQSIGL DLKPLVDRAR TKALGQGMEA   300
TRIGSLVERG RAWLSRFAAH VRGDPADPLV PPSVLKQDRQ TIAAAQAVAS AVRHLSQREA   360
AFERTALYKA ALDFGLPTTI ADVEKRTRAL VRSGDLIAGK GEHKGWLASR DAVVTEQRIL   420
SEVAAGKGDS SPAITPQKAA ASVQAAALTG QGFRLNEGQL AAARLILISK DRTIAVQGIA   480
GAGKSSVLKP VAEVLRDEGH PVIGLAIQNT LVQMLERDTG IGSQTLARFL GGWNKLLDDP   540
GNVALRAEAQ ASLKDHVLVL DEASMVSNED KEKLVRLANL AGVHRLVLIG DRKQLGAVDA   600
GKPFALLQRA GIARAEMATN LRARDPVVRE AQAAAQAGDV RKALRHLKSH TVEARGDGAQ   660
VAAETWLALD KETRARTSIY ASGRAIRSAV NAAVQQGLLA SREIGPAKMK LEVLDRVNTL   720
REELRHLPAY RAGRVLEVSR KQQALGLFIG EYRVIGQDRK GKLVEVEDKR GKRFRFDPAR   780
```

```
IRAGKGDDNL TLLEPRKLEI HEGDRIRWTR NDHRRGLFNA DQARVVEIAN GKVTFETSKG    840
DLVELKKDDP MLKRIDLAYA LNVHMAQGLT SDRGIAVMDS RERNLSNQKT FLVTVTRLRD    900
HLTLVVDSAD KLGAAVARNK GEKASAIEVT GSVKPTATKG SGVDQPKSVE ANKAEKELTR    960
SKSKTLDFGI                                                          970

SEQ ID NO: 127          moltype = DNA  length = 73
FEATURE                 Location/Qualifiers
misc_feature            1..73
                        note = Polynucleotide used in the Examples
source                  1..73
                        mol_type = other DNA
                        organism = synthetic construct
SEQUENCE: 127
tttttttttt tttttttttt tttttttttt tttttttttt tttttggtt gtttctgttg    60
gtgctgatat tgc                                                      73

SEQ ID NO: 128          moltype = DNA  length = 3523
FEATURE                 Location/Qualifiers
misc_feature            1..3523
                        note = Polynucleotide used in the Examples
source                  1..3523
                        mol_type = other DNA
                        organism = synthetic construct
SEQUENCE: 128
gccatcagat tgtgtttgtt agtcgctttt ttttttggga atttttttt tggaattttt    60
tttttgcgct aacaacctcc tgccgttttg cccgtgcata tcggtcacga acaaatctga   120
ttactaaaca cagtgagcctg gatttgttct atcagtaatc gaccttattc ctaattaaat  180
agagcaaatc cccttattgg gggtaagaca tgaagatgcc agaaaaacat gacctgttgg   240
ccgccattct cgcggcaaag gaacaaggca tcggggcaat ccttgcgttt gcaatggcgt   300
accttcgcgg cagatataat ggcggtgcgt ttacaaaaac agtaatcgac gcaacgatgt   360
gcgccattat cgcctagttc attcgtgacc ttctcgactt cgccggacta agtagcaatc   420
tcgcttatat aacgagcgtg tttatcggct acatcggtac tgactcgatt ggttcgctta   480
tcaaacgctt cgctgctaaa aaagccggag tagaagatgg tagaaatcaa taatcaacgt   540
aaggcgttcc tcgatatgct ggcgtggtcg gagggaactg ataacggacg tcagaaaacc   600
agaaatcatg gttatgacgt cattgtaggc ggagagctat ttactgatta ctccgatcac   660
cctcgcaaac ttgtcacgct aaacccaaaa ctcaaatcaa caggcgccgg acgctaccag   720
cttctttccc gttggtggga tgcctaccgc aagcagcttg gcctgaaaga cttctctccg   780
aaaagtcagg acgctgtggc attgcagcag attaaggagc gtgcgctttt acctatgatt   840
gatcgtggtg atatccgtca ggcaatcgac cgttgcgaca atatctgggc ttcactgccg   900
ggcgctggtt atggtcagtt cgagcataag gctgacagcc tgattgcaaa attcaaagaa   960
gcgggcggaa cggtcagaga gattgatgta tgagcagagt caccgcgatt atctccgctc  1020
tggttatctg catcatcgtc tgcctgtcat gggctgttaa tcattaccgt gataacgcca  1080
ttacctacaa agcccagcgc gacaaaaatg ccagagaact gaagctggcg aacgcggcaa  1140
ttactgacat gcagatgcgt cagcgtgatg ttgctgcgct cgatgcaaaa tacacgcaagg  1200
agttagctga tgctaaagct gaaaatgatg ctctgcgtga tgatgttgcc gctggtcgtc  1260
gtcggttgca catcaaagca gtctgtcagt cagtgcgtga agccaccacc gctccggcg   1320
tggataatgc agcctccccc cgactggcag acaccgctga acgggattat ttcaccctca  1380
gagagaggct gatcactatg caaaacaac tggaaggaac ccagaagtat attaatgagc   1440
agtgcagata gagttgccca tatcgatggg caactcatgc aattattgtg agcaatacac   1500
acgcgcttcc agcggagtat aaatgcctaa agtaataaaa ccgagcaatc catttacgaa   1560
tgtttgctgg gtttctgttt taacaacatt ttctgcgccg ccacaaattt tggctgcatc   1620
gacagttttc ttctgcccaa ttccagaaac gaagaaatga tgggtgatgg tttcctttgg   1680
tgctactgct gccggtttgt tttgaacagt aaacgtctgt tgagcacatc ctgtaataag   1740
cagggccagc gcagtagcga gtagcatttt tttcatggtg ttattcccga tgcttttga   1800
agttcgcaga atcgtatgtg tagaaaatta aacaaaccct aaacaatgag ttgaaatttc   1860
atattgttaa tatttattaa tgtatgtcag gtgcgatgaa tcgtcattgt attcccggat   1920
taactatgtc cacagccctg acggggaact ctctgcgggg agtgtccggg aataattaaa   1980
acgatgcaca cagggtttag cgcgtacacg tattgcatta tgccaacgcc ccggtgctga   2040
cacggaagaa accggacgtt atgatttagc gtggaaagat ttgtgtagtg ttctgaatgc   2100
tctcagtaaa tagtaatgaa ttatcaaagg tatagtaata tcttttatgt tcatgtgatat  2160
ttgtaaccca tcggaaaact cctgcttag caagatttc cctgtattgc tgaaatgtga    2220
tttctcttga tttcaaccta tcataggacg tttctataag atgcgtgttt cttgagaatt   2280
taacatttac aaccttttta agtccttta ttaacacggt gttatcgttt tctaacacga    2340
tgtgaatata tctgtggcta gatagtaaat ataatgtgac gttttagttc gttttagttc   2400
agaatgaaac aattcacagt ctaaatcttt tcgcacttga tcgaatattt ctttaaaaat   2460
ggcaacctga gccattggta aaccttcca tgtgatacga gggcgcgtag tttgcattat    2520
cgttttatc gtttcaatct ggtctgacct ccttgtgttt tgttgatgat ttatgtcaaa    2580
tattaggaat gttttcactt aatagtattg gttgcgtaac aaagtgcggt cctgctgtta   2640
ttctggaggg aaatacaacc gacagtgta tgtaaggcca acgtgctcaa atcttcatac    2700
agaaagattt gaagtaatat tttaaccgct agatgaagag caagcgcatg gagcgacaaa   2760
atgaataaag aacaatctgc tgatgatccc tccgtggatc tgattcgtgt aaaaaaatatg   2820
cttaatagca cccatttctat gagttacct gatgttgtaa ttgcatgtat agaacataag   2880
gtgtctctgg aagcattcag agcaattgag gcagcgttg tgaagcacga taataatatg    2940
aaggattatt ccctggtggt tgactgatca ccataactgc taatcattca aactatttag   3000
tctgtgacag agccaacacg cagtctgtca ctgtcaggaa agtggtaaaa ctgcaactca   3060
attactgcaa tgccctcgta attaagtgaa tttacaatat cgtcctgttc ggagggaaga   3120
acgcgggatg ttcattcttc atcactttta attgatgtat atgctctctt ttctgacgtt   3180
agtctccgac ggcaggcttc aatgacccag gctgagaaat tccgacccc tttttgctca   3240
agagcgatgt taattgtttc aatcatttgg ttaggaaagc ggatgttgcg ggttgttgtt   3300
```

```
ctgcgggttc tgttcttcgt tgacatgagg ttgccccgta ttcagtgtcg ctgatttgta   3360
ttgtctgaag ttgtttttac gttaagttga tgcagatcaa ttaatacgat acctgcgtca   3420
taattgatta tttgacgtgg tttgatggcc tccacgcacg ttgtgatatg tagatgataa   3480
tcattatcac tttacgggtc ctttccggtg aaaaaaaagg tac                    3523

SEQ ID NO: 129          moltype = AA   length = 984
FEATURE                 Location/Qualifiers
source                  1..984
                        mol_type = protein
                        organism = Methanopyrus kandleri
SEQUENCE: 129
MALVYDAEFV GSEREFEEER ETFLKGVKAY DGVLATRYLM ERSSSAKNDE ELLELHQNFI    60
LLTGSYACSI DPTEDRYQNV IVRGVNFDER VQRLSTGGSP ARYAIVYRRG WRAIAKALDI   120
DEEDVPAIEV RAVKRNPLQP ALYRILVRYG RVDLMPVTVD EVPPEMAGEF ERLIERYDVP   180
IDEKEERILE ILRENPWTPH DEIARRLGLS VSEVEGEKDP ESSGIYSLWS RVVVNIEYDE   240
RTAKRHVKRR DRLLEELYEH LEELSERYLR HPLTRRWIVE HKRDIMRRYL EQRIVECALK   300
LQDRYGIRED VALCLARAFD GSISMIATTP YRTLKDVCPD LTLEEAKSVN RTLATLIDEH   360
GLSPDAADEL IEHFESIAGI LATDLEEIER MYEEGRLSEE AYRAAVEIQL AELTKKEGVG   420
RKTAERLLRA FGNPERVKQL AREFEIEKLA SVEGVGERVL RSLVPGYASL ISIRGIDRER   480
AERLLKKYGG YSKVREAGVE ELREDGLTDA QIRELKGLKT LESIVGDLEK ADELKRKYGS   540
ASAVRRLPVE ELRRELGFSDD EIAEIKGIPK KLREAFDLET AAELYERYGS LKEIGRRLSY   600
DDLLELGATP KAAAEIKGPE FKFLLNIEGV GPKLAERILE AVDYDLERLA SLNPEELAEK   660
VEGLGEELAE RVVYAARERV ESRRKSGRQE RSEEEWKEWL ERKVGEGRAR RLIEYFGSAG   720
EVGKLVENAE VSKLLEVPGI GDEAVARLVP GYKTLRDAGL TPAEAERVLK RYGSVSKVQE   780
GATPDELREL GLGDAKIARI LGLRSLVNKR LDVDTAYELK RRYGSVSAVR KAPVKELREL   840
GLSDRKIARI KGIPETMLQV RGMSVEKAER LLERFDTWTK VKEAPVSELV RVPGVGLSLV   900
KEIKAQVDPA WKALLDVKGV SPELADRLVE ELGSPYRVLT AKKSDLMRVE RVGPKLAERI   960
RAAGKRYVEE RRSRRERIRR KLRG                                         984

SEQ ID NO: 130          moltype = AA   length = 299
FEATURE                 Location/Qualifiers
source                  1..299
                        mol_type = protein
                        organism = Methanopyrus kandleri
SEQUENCE: 130
SGRQERSEEE WKEWLERKVG EGRARRLIEY FGSAGEVGKL VENAEVSKLL EVPGIGDEAV    60
ARLVPGYKTL RDAGLTPAEA ERVLKRYGSV SKVQEGATPD ELRELGLGDA KIARILGLRS   120
LVNKRLDVDT AYELKRRYGS VSAVRKAPVK ELRELGLSDR KIARIKGIPE TMLQVRGMSV   180
EKAERLLERF DTWTKVKEAP VSELVRVPGV GLSLVKEIKA QVDPAWKALL DVKGVSPELA   240
DRLVEELGSP YRVLTAKKSD LMRVERVGPK LAERIRAAGK RYVEERRSRR ERIRRKLRG   299

SEQ ID NO: 131          moltype = AA   length = 8
FEATURE                 Location/Qualifiers
REGION                  1..8
                        note = RecD-like motif I of TrwC Cba
source                  1..8
                        mol_type = protein
                        organism = synthetic construct
SEQUENCE: 131
GIAGAGKS                                                             8

SEQ ID NO: 132          moltype = AA   length = 10
FEATURE                 Location/Qualifiers
REGION                  1..10
                        note = RecD-like motif V of TrwC Cba
source                  1..10
                        mol_type = protein
                        organism = synthetic construct
SEQUENCE: 132
YALNVHMAQG                                                          10

SEQ ID NO: 133          moltype = AA   length = 14
FEATURE                 Location/Qualifiers
REGION                  1..14
                        note = MobF motif III of TrwC Cba
source                  1..14
                        mol_type = protein
                        organism = synthetic construct
SEQUENCE: 133
HDTNRNQEPN LHFH                                                     14

SEQ ID NO: 134          moltype = AA   length = 943
FEATURE                 Location/Qualifiers
source                  1..943
                        mol_type = protein
                        note = Halothiobacillus neapolitanus c2
                        organism = unidentified
SEQUENCE: 134
MLRIKNLKGD PSAIIDYAEN KKNHPDQKSG YYDAKGAPSA WGGALAADLG LSGSVQAADL    60
```

-continued

```
KKLLSGELSD GTRFAKEDPD RRLGIDMSFS APKSVSLAAL VGGDERIIQA HDAAVRTAMS      120
MIEQEYATAR FGHAGRNVVC SGKLVYAAYR HEDARTVDDI ADPQLHTHCI VSNITIDPET      180
GKPRSIDFAW GQDGIKLAGA MYRAELARRL KEMGYELRKS EEGFELAQIS DEQVETFSRR      240
RVQVDQALEQ QGTDREHASS ELKTAVTLAT RQGKAQLSAE DQYEEWQQRA AEEAELDLSQP     300
VGPRVSVTPP EIDLDHTFEH LSERASVINK DAVRLDALIN HMSEGATLST VDKAIQGAAV      360
TGDVFEIEDG IKRKIITRET LKREQQILLL AQQGRGVNSV LIGVGDTKHL IEDAEQAQGF      420
RFSEGQRRAI NLTATTTDQV SGIVGAAGAG KTTAMKTVAD LAKSQGLTVV GIAPSSAAAD      480
ELKSAGADDT MTLATFNLKG EAAGPRLLIL DEAGMVSARD GEALLKKLGK EDRLIFVGDP      540
KQLAAVEAGS PFAQLMRSGA IQYAEITEIN RQKDQKLLDI AQHFAKGKAE EAVALATKYV      600
TEVPVTLPDK PEHKITRQAK TEARRLAIAS ATAKRYLELS QEERATTLVL SGTNAVRKQV      660
NEQVRKGLID KGEINGESFT VSTLDKADMT RAKMRKAGNY KPGQVIKTAG KQAEQSEVVA      720
VNLDQNLIQV KLSDGTLKSI DASRFDVKKT QVFNPRQIDI AAGDKIIFTN NDQATETKNN      780
QIGLIEEIKD GKAIINSNGA KVEIDIQRKL HIDHAYCITI HRSQGQTVDS VIVAGEASRT      840
TTAEAAYVAC TRERYKLEII TDNTERLSKN WVRYADRQTA AEALKSSEEK YPHLDEIREE      900
LRRELQQELE RQEPTNITPE LEIEMERSMF DQYTLHSRQP RSY                       943

SEQ ID NO: 135            moltype = AA  length = 8
FEATURE                   Location/Qualifiers
REGION                    1..8
                          note = RecD-like motif I of TrwC Hne
source                    1..8
                          mol_type = protein
                          organism = synthetic construct
SEQUENCE: 135
GAAGAGKT                                                                8

SEQ ID NO: 136            moltype = AA  length = 10
FEATURE                   Location/Qualifiers
REGION                    1..10
                          note = RecD-like motif V of TrwC Hne
source                    1..10
                          mol_type = protein
                          organism = synthetic construct
SEQUENCE: 136
YCITIHRSQG                                                             10

SEQ ID NO: 137            moltype = AA  length = 18
FEATURE                   Location/Qualifiers
REGION                    1..18
                          note = MobF motif III of TrwC Hne
source                    1..18
                          mol_type = protein
                          organism = synthetic construct
SEQUENCE: 137
HEDARTVDDI ADPQLHTH                                                    18

SEQ ID NO: 138            moltype = AA  length = 960
FEATURE                   Location/Qualifiers
source                    1..960
                          mol_type = protein
                          note = Erythrobacter litoralis HTCC2594
                          organism = unidentified
SEQUENCE: 138
MLSVANVRSP TAAASYFASD NYYASADADR SGQWIGGGAK RLGLEGKVEA KAFDALLRGE       60
LPDGSSVGNP GQAHRPGTDL SFSVPKSWSL LALVGKDERI IAAYREAVVE ALQWAEKNAA      120
ETRIVEKGKM VTQATGNLAV GLFQHDTNRN QEPNLHFHAV IANVTQGKDG KWRTLKNDRL      180
WQLNTTLNSI AMARFRVAVE KLGYEPGPVL KHGNFEARGI SREQIMAFST RRKEVLEARR      240
GPGLEAGRIA ALDTRASKEE IEDRATLGKQ WSETAQSIGL DLTPLVDRAR TNALGQSMEA      300
TRIGSLVERG RAWLSRFAAH VRGDPADPLV PPSVLKQDRQ TIAAAQAVAS AIRHLSQREA      360
AFERTALYKA ALDFGLPATI ADVEKRTRAL VRSGDLISGK GEHKGWLASR EAVVTEQRIL      420
SEVAAGKGNS SPAIEPQKAA ASVQAAAATG QGFRLNEGQL AAAELILTSK DRTIAIQGIA      480
GAGKSSVLKP VAEVLRDEGH PVIGLAIQNT LVQMLERETG IGSQTLARFL RGWTKLLGDP      540
GNVALRTEAQ ASLKDHVLVL DEASMVSNED KEKLVRLANL AGVHRLVLIG DRKQLGAVDA      600
GKPFALLQRA GIARAEMATN LRARDPVVRE AQASAQAGDV RNALRHLKSH TVEAKGDGAQ      660
VAAETWLALD KETRARTSIY ASGRAIRSAV NAAVQQGLLA NREIGPGMMK LDVLDRVNAT      720
REELRHLPAY RAGQVLEISR KQQALGLSVG EYRVLGQDRK GRLVEVEDKR GKRFRFDPAR      780
IKAGKGDENL TLLEPRKLEI HEGDRIRWTR NDHRRGLFNA DQARVVAIAG GKITFETSQG      840
DQVELKRDDP MLKRIDLAYA LNAHMAQGLT SDRGIAVMTS SERNLSNQKT PMVTVTRLRD      900
HLTLVVDNAE KLGAAVARNK GEKASALEVT GSVKSTAAKG SGVDQLKPEE ANKAEKELTR      960

SEQ ID NO: 139            moltype = AA  length = 10
FEATURE                   Location/Qualifiers
REGION                    1..10
                          note = RecD-like motif V of TrwC Eli
source                    1..10
                          mol_type = protein
                          organism = synthetic construct
SEQUENCE: 139
YALNAHMAQG                                                             10
```

-continued

```
SEQ ID NO: 140            moltype = AA  length = 853
FEATURE                   Location/Qualifiers
source                    1..853
                          mol_type = protein
                          organism = Escherichia coli
SEQUENCE: 140
MSAIENFDAH TPMMQQYLRL KAQHPEILLF YRMGDFYELF YDDAKRASQL LDISLTKRGA   60
SAGEPIPMAG IPYHAVENYL AKLVNQGESV AICEQIGDPA TSKGPVERKV VRIVTPGTIS  120
DEALLQERQD NLLAAIWQDS KGFGYATLDI SSGRFRLSEP ADRETMAAEL QRTNPAELLY  180
AEDFAEMSLI EGRRGLRRRP LWEFEIDTAR QQLNLQFGTR DLVGFGVENA PRGLCAAGCL  240
LQYAKDTQRT TLPHIRSITM EREQDSIIMD AATRRNLEIT QNLAGGAENT LASVLDCTVT  300
PMGSRMLKRW LHMPVRDTRV LLERQQTIGA LQDFTAGLQP VLRQVGDLER ILARLALRTA  360
RPRDLARMRH AFQQLPELRA QLETVDSAPV QALREKMGEF AELRDLLERA IIDTPPVLVR  420
DGGVIASGYN EELDEWRALA DGATDYLERL EVRERERTGL DTLKVGFNAV HGYYIQISRG  480
QSHLAPINYM RRQTLKNAER YIIPELKEYE DKVLTSKGKA LALEKQLYEE LFDLLLPHLE  540
ALQQSASALA ELDVLVNLAE RAYTLNYTCP TFIDKPGIRI TEGRHPVVEQ VLNEPFIANP  600
LNLSPQRRML IITGPNMGGK STYMRQTALI ALMAYIGSYV PAQKVEIGPI DRIFTRVGAA  660
DDLASGRSTF MVEMTETANI LHNATEYSLV LMDEIGRGTS TYDGLSLAWA CAENLANKIK  720
ALTLFATHYF ELTQLPEKME GVANVHLDAL EHGDTIAFMH SVQDGAASKS YGLAVAALAG  780
VPKEVIKRAR QKLRELESIS PNAAATQVDG TQMSLLSVPE ETSPAVEALE NLDPDSLTPR  840
QALEWIYRLK SLV                                                    853

SEQ ID NO: 141            moltype = AA  length = 64
FEATURE                   Location/Qualifiers
source                    1..64
                          mol_type = protein
                          organism = Sulfolobus solfataricus
SEQUENCE: 141
MATVKFKYKG EEKEVDISKI KKVWRVGKMI SFTYDEGGGK TGRGAVSEKD APKELLQMLE   60
KQKK                                                               64

SEQ ID NO: 142            moltype = AA  length = 99
FEATURE                   Location/Qualifiers
source                    1..99
                          mol_type = protein
                          organism = Sulfolobus solfataricus
SEQUENCE: 142
EKMSSGTPTP SNVVLIGKKP VMNYVLAALT LLNQGVSEIV IKARGRAISK AVDTVEIVRN   60
RFLPDKIEIK EIRVGSQVVT SQDGRQSRVS TIEIAIRKK                          99

SEQ ID NO: 143            moltype = AA  length = 88
FEATURE                   Location/Qualifiers
source                    1..88
                          mol_type = protein
                          organism = Sulfolobus solfataricus
SEQUENCE: 143
TEKLNEIVVR KTKNVEDHVL DVIVLFNQGI DEVILKGTGR EISKAVDVYN SLKDRLGDGV   60
QLVNVQTGSE VRDRRRISYI LLRLKRVY                                     88

SEQ ID NO: 144            moltype = AA  length = 107
FEATURE                   Location/Qualifiers
source                    1..107
                          mol_type = protein
                          organism = Escherichia coli
SEQUENCE: 144
AQQSPYSAAM AEQRHQEWLR FVDLLKNAYQ NDLHLPLLNL MLTPDEREAL GTRVRIVEEL   60
LRGEMSQREL KNELGAGIAT ITRGSNSLKA APVELRQWLE EVLLKSD                107

SEQ ID NO: 145            moltype = AA  length = 237
FEATURE                   Location/Qualifiers
source                    1..237
                          mol_type = protein
                          note = Bacteriophage lambda
                          organism = unidentified
SEQUENCE: 145
MSTKKKPLTQ EQLEDARRLK AIYEKKKNEL GLSQESVADK MGMGQSGVGA LFNGINALNA   60
YNAALLAKIL KVSVEEFSPS IAREIYEMYE AVSMQPSLRS EYEYPVFSHV QAGMFSPELR  120
TFTKGDAERW VSTTKKASDS AFWLEVEGNS MTAPTGSKPS FPDGMLILVD PEQAVEPGDF  180
CIARLGGDEF TFKKLIRDSG QVFLQPLNPQ YPMIPCNESC SVVGKVIASQ WPEETFG     237

SEQ ID NO: 146            moltype = AA  length = 60
FEATURE                   Location/Qualifiers
source                    1..60
                          mol_type = protein
                          note = Crenarchaea
                          organism = unidentified
SEQUENCE: 146
MSSGKKPVKV KTPAGKEAEL VPEKVWALAP KGRKGVKIGL FKDPETGKYF RHKLPDDYPI   60
```

```
SEQ ID NO: 147           moltype = AA   length = 136
FEATURE                  Location/Qualifiers
source                   1..136
                         mol_type = protein
                         organism = Homo sapiens
SEQUENCE: 147
MARTKQTARK STGGKAPRKQ LATKAARKSA PATGGVKKPH RYRPGTVALR EIRRYQKSTE   60
LLIRKLPFQR LVREIAQDFK TDLRFQSSAV MALQEASEAY LVGLFEDTNL CAIHAKRVTI  120
MPKDIQLARR IRGERA                                                  136

SEQ ID NO: 148           moltype = AA   length = 89
FEATURE                  Location/Qualifiers
source                   1..89
                         mol_type = protein
                         note = Bacteriophage T4
                         organism = unidentified
SEQUENCE: 148
MAKKEMVEFD EAIHGEDLAK FIKEASDHKL KISGYNELIK DIRIRAKDEL GVDGKMFNRL   60
LALYHKDNRD VFEAETEEVV ELYDTVFSK                                     89

SEQ ID NO: 149           moltype = AA   length = 339
FEATURE                  Location/Qualifiers
source                   1..339
                         mol_type = protein
                         organism = Homo sapiens
SEQUENCE: 149
MAMQMQLEAN ADTSVEEESF GPQPISRLEQ CGINANDVKK LEEAGFHTVE AVAYAPKKEL   60
INIKGISEAK ADKILAEAAK LVPMGFTTAT EFHQRRSEII QITTGSKELD KLLQGGIETG  120
SITEMFGEFR TGKTQICHTL AVTCQLPIDR GGGEGKAMYI DTEGTFRPER LLAVAERYGL  180
SGSDVLDNVA YARAFNTDHQ TQLLYQASAM MVESRYALLI VDSATALYRT DYSGRGELSA  240
RQMHLARFLR MLLRLADEFG VAVVITNQVV AQVDGAAMFA ADPKKPIGGN IIAHASTTRL  300
YLRKGRGETR ICKIYDSPCL PEAEAMFAIN ADGVGDAKD                         339

SEQ ID NO: 150           moltype = AA   length = 375
FEATURE                  Location/Qualifiers
source                   1..375
                         mol_type = protein
                         note = Citromicrobium bathyomarinum JL354
                         organism = unidentified
SEQUENCE: 150
MKATIERATL LRCLSHVQSV VERRNTIPIL SNVLIDADAG GGVKVMATDL DLQVVETMTA   60
ASVESAGAIT VSAHLLFDIA RKLPDGSQVS LETADNRMVV KAGRSRFQLP TLPRDDFPVI  120
VEGELPTSFE LPARELAEMI DRTRFAISTE ETRYYLNGIF LHVSDEARPV LKAAATDGHR  180
LARYTLDRPE GAEGMPDVIV PRKAVGELRK LLEEALDSNV QIDLSASKIR FALGGEGGVV  240
LTSKLIDGTF PDYSRVIPTG NDKLLRLDPK AFFQGVDRVA TIATEKTRAV KMGLDEDKVT  300
LSVTSPDNGT AAEEIAAEYK AEGFEIGFNA NYLKDILGQI DSDTVELHLA DAGAPTLIRR  360
DENSPALYVL MPMRV                                                   375

SEQ ID NO: 151           moltype = DNA   length = 88
FEATURE                  Location/Qualifiers
misc_feature             1..88
                         note = Polynucleotide used in the Examples
source                   1..88
                         mol_type = other DNA
                         organism = synthetic construct
SEQUENCE: 151
cgtggtcacg aggagctcgt cctcacctcg acgtctgcac gagcttttt tttttttttt   60
tttttttttt tttttttttt tttttttt                                      88

SEQ ID NO: 152           moltype = DNA   length = 88
FEATURE                  Location/Qualifiers
misc_feature             1..88
                         note = Polynucleotide used in the Examples
source                   1..88
                         mol_type = other DNA
                         organism = synthetic construct
SEQUENCE: 152
tttttttttt tttttttttt tttttttttt tttttttttt ttttgctcgt gcagacgtcg   60
aggtgaggac gagctcctcg tgaccacg                                      88

SEQ ID NO: 153           moltype = DNA   length = 44
FEATURE                  Location/Qualifiers
misc_feature             1..44
                         note = Polynucleotide used in the Examples
source                   1..44
                         mol_type = other DNA
                         organism = synthetic construct
SEQUENCE: 153
```
cgtggtcacg aggagctcgt cctcacctcg acgtctgcac gagc 44

SEQ ID NO: 154        moltype = DNA   length = 3560
FEATURE              Location/Qualifiers
misc_feature       1..3560
                    note = Polynucleotide used in the Examples
source              1..3560
                    mol_type = other DNA
                    organism = synthetic construct

SEQUENCE: 154

```
gccatcagat tgtgtttgtt agtcgctttt tttttttgga atttttttt tggaattttt   60
ttttgcgct aacaacctcc tgccgtttg cccgtgcata tcggtcacga acaaatctga  120
ttactaaaca cagtagcctg gatttgttct atcagtaatc gaccttattc ctaattaaat  180
agagcaaatc cccttattgg gggtaagaca tgaagatgcc agaaaaacat gacctgttgg  240
ccgccattct cgcggcaaag gaacaaggca tcggggcaat ccttgcgttt gcaatggcgt  300
accttcgcgg cagatataat ggcggtgcgt ttacaaaaac agtaatcgac gcaacgatgt  360
gcgccattat cgcctagttc attcgtgacc ttctcgactt cgccggacta agtagcaatc  420
tcgcttatat aacgagcgtg tttatcggct acatcggtac tgactcgatt ggttcgctta  480
tcaaacgctt cgctgctaaa aaagccggag tagaagatgg tagaaatcaa taatcaacgt  540
aaggcgttcc tcgatatgct ggcgtggtcg gagggaactg ataacggacg tcagaaaacc  600
agaaatcatg gttatgacgt cattgtaggc ggagagctat ttactgatta ctccgatcac  660
cctcgcaaac ttgtcacgct aaacccaaaa ctcaaatcaa caggcgccgg acgctaccag  720
cttcttccc gttggtggga tgcctaccgc aagcagcttg gcctgaaaga cttctctccg  780
aaaagtcagg acgctgtggc attgcagcag attaaggagc gtggcgcttt acctatgatt  840
gatcgtggtg atatccgtca ggcaatcgac cgttgcagca atatctgggc ttcactgccg  900
ggcgctggtt atggtcagtt cgagcataag gctgacagcc tgattgcaaa attcaaagaa  960
gcgggcggaa cggtcagaga gattgatgta tgagcagagt caccgcgatt atctccgctc 1020
tggttatctg catcatcgtc tgcctgtcat gggctgttaa tcattaccgt gataacgcca 1080
ttacctacaa agcccagcgc gacaaaaatg ccagagaact gaagctggcg aacgcggcaa 1140
ttactgacat gcagatgcgt cagcgtgatg ttgctgcgct cgatgcaaaa tacacgaagg 1200
agttagctga tgctaaagct gaaaatgatg ctctgcgtga tgatgttgcc gctggtcgtc 1260
gtcggttgca catcaaagca gtctgtcagt cagtgcgtga agccaccacc gcctccggcg 1320
tggataatgc agcctccccc cgactggcag acaccgctga acgggattat ttcaccctca 1380
gagagaggct gatcactatg caaaaacaac tggaaggaac ccagaagtat attaatgagc 1440
agtgcagata gagttgccca tatcgatggg caactcatgc aattattgtg agcaatacac 1500
acgcgcttcc agcggagtat aaatgcctaa agtaataaaa ccgagcaatc catttacgaa 1560
tgtttgctgg gtttctgttt taacaacatt tctgcgccg ccacaaattt tggctgcatc 1620
gacagttttc ttctgcccaa ttccagaaac gaagaaatga tgggtgatgg tttcctttgg 1680
tgctactgct gccggtttgt tttgaacagt aaacgtctgt tgagcacatc ctgtaataag 1740
cagggccagc gcagtagcga gtagcatttt tttcatggtg ttattcccga tgcttttga 1800
agttcgcaga atcgtatgtg tagaaaatta acaaaccct aaacaatgag ttgaaatttc 1860
atattgttaa tatttattaa tgtatgtcag gtgcgatgaa tcgtcattgt attcccggat 1920
taactatgtc cacagccctg acggggaact tctctgcggg agtgtccggg aataattaaa 1980
acgatgcaca cagggtttag cgcgtacacg tattgcatta tgccaacgcc ccggtgctga 2040
cacggaagaa accggacgtt atgatttagc gtgaaagat ttgtgtagtg ttctgaatgc 2100
tctcagtaaa tagtaatgaa ttatcaaagg tatagtaata tcttttatgt tcatggatat 2160
ttgtaaccca tcggaaaact cctgctttag caagattttc cctgtattgc tgaaatgtga 2220
tttctcttga tttcaaccta tcataggacg tttctataag atgcgtgttt cttgagaatt 2280
taacatttac aaccttttta agtccttta ttaacacggt gttatcgttt tctaacacga 2340
tgtgaatatt atctgtggct agatagtaaa taatagtga gacgttgtga cgtttttagtt 2400
cagaataaaa caattcacag tctaaatctt ttcgcacttg atcgaatatt tctttaaaaa 2460
tggcaacctg agccattggt aaaaccttcc atgtgatacg agggcgcgta gtttgcatta 2520
tcgttttat cgtttcaatc tggtctgacc tccttgtgtt ttgttgatga tttatgtcaa 2580
atattaggaa tgttttcact taatagtatt ggttgcgtaa caaagtgcgg tcctgctggc 2640
attctggagg gaaatacaac cgacagatgt atgtaaggcc aacgtgctca atcttcata 2700
cagaaagatt tgaagtaata ttttaaccgc tagatgaaga gcaagcgcat ggagcgacaa 2760
aatgaataaa gaacaatctg ctgatgatcc ctccgtggat ctgattcgtg taaaaaatat 2820
gcttaatagc accatttcta tgagttaccc tgatgttgta attgcatgta tagaacataa 2880
ggtgtctctg gaagcattca gagcaattga ggcagcgttg gtgaagcacg ataataatat 2940
gaaggattat tccctggtgg ttgactgatc accataactg ctaatcattc aaactattta 3000
gtctgtgaca gagccaacac gcagtctgtc actgtcagga aagtggtaaa actgcaactc 3060
aattactgca atgccctcgt aattaagtga atttacaata tcgtcctgtt cggagggaag 3120
aacgcgggat gttcattctt catcactttt aattgatgta tatgctctct tttctgacgt 3180
tagtctccga cggcaggctt caatgaccca ggctgagaaa ttcccggacc ttttttgctc 3240
aagagcgatg ttaatttgtt caatcatttg gttaggaaag cggatgttgc gggttgttga 3300
tctgcgggtt ctgttcttcg ttgacatgag gttgccccgt attcagtgtc gctgatttgt 3360
attgtctgaa gttgttttta cgttaagttg atgcagatca attaatacga tacctgcgtc 3420
ataattgatt atttgacgtg gtttgatggc ctccacgcac gttgtgatat gtagatgata 3480
atcattatca ctttacgggt ccttttccggt gaaaaaaag gtaccaaaaa aaacatcgtc 3540
gtgagtagtg aaccgtaagc                                             3560
```

```
SEQ ID NO: 155         moltype = DNA   length = 52
FEATURE                Location/Qualifiers
misc_feature           1..52
                       note = Polynucleotide used in the Examples
source                 1..52
                       mol_type = other DNA
                       organism = synthetic construct
SEQUENCE: 155
ttttttttttt tttttttttt ttttttggttg tttctgttgg tgctgatatt gc        52

SEQ ID NO: 156         moltype = DNA   length = 3556
FEATURE                Location/Qualifiers
misc_feature           1..3556
                       note = Polynucleotide used in the Examples
source                 1..3556
                       mol_type = other DNA
                       organism = synthetic construct
SEQUENCE: 156
acggttcact actcacgacg atgttttttt tggtaccttt tttttcaccg gaaaggaccc    60
gtaaagtgat aatgattatc atctacatat cacaacgtgc gtggaggcca tcaaaccacg   120
tcaaataatc aattatgacg caggtatcgt attaattgat ctgcatcaac ttaacgtaaa   180
aacaacttca gacaatacaa atcagcgaca ctgaatacgg ggcaacctca tgtcaacgaa   240
gaacagaacc cgcagaacaa caacccgcaa catccgcttt cctaaccaaa tgattgaaca   300
aattaacatc gctcttgagc aaaaagggtc cgggaatttc tcagcctggg tcattgaagc   360
ctgccgtcgg agactaacgt cagaaaagag agcatataca tcaattaaaa gtgatgaaga   420
atgaacatcc cgcgttcttc cctccgaaca ggacgatatt gtaaattcac ttaattacga   480
gggcattgca gtaattgagt tgcagtttta ccactttcct gacagtgaca gactgcgtgt   540
tggctctgtc acagactaaa tagtttgaat gattagcagt tatggtgatc agtcaaccac   600
cagggaataa tccttcatat tattatcgtg cttccaaac gctgcctcaa ttgctctgaa    660
tgcttccaga gacaccttat gttctataca tgcaattaca acatcagggt aactcataga   720
aatggtgcta ttaagcatat tttttacacg aatcagatcc acggagggat catcagcagg   780
ttgttcttta ttcattttgt cgctccatgc gcttgctctt catctagcgg ttaaaatatt   840
acttcaaatc tttctgtatg aagatttgag cacgttggcc ttacatacat ctgtcggttg   900
tatttccctc cagaatgcca gcaggaccgc actttgttac gcaaccaata ctattaagtg   960
aaaacattcc taatatttga cataaatcat caacaaaaca caaggaggtc agaccagatt  1020
gaaacgataa aaacgataat gcaaactacg cgccctcgta tcacatggaa ggttttacca  1080
atggctcagg ttgccatttt taaagaaata ttcgatcaag tgcgaaaaga tttagactgt  1140
gaattgtttt attctgaact aaaacgtcac aacgtctcac attatattta ctatctagcc  1200
acagataata ttcacatcgt gttagaaaac gataacaccg tgttaataaa aggacttaaa  1260
aaggttgtaa atgttaaatt ctcaagaaac acgcatctta tagaaacgtc ctatgatagg  1320
ttgaaatcaa gagaaatcac atttcagcaa tacagggaaa atcttgctaa agcaggagtt  1380
ttccgatggg ttacaaatat ccatgaacat aaaagatatt actatccttt tgataattca  1440
ttactatttta ctgagagcat tcagaacact acacaaatct ttccacgcta aatcataacg  1500
tccggttttct tccgtgtcag caccggggcg ttggcataat gcaatacgtg tacgcgctaa  1560
accctgtgtg catcgtttta attattcccg gacactccg cagagaagtt ccccgtcagg  1620
gctgtggaca tagttaatcc gggaatacaa tgacgattca tcgcacctga catacattaa  1680
taaatattaa caatatgaaa tttcaactca ttgtttaggg tttgtttaat tttctacaca  1740
tacgattctg cgaacttcaa aaagcatcgg gaataacacc atgaaaaaaa tgctactcgc  1800
tactgcgctg gccctgctta ttacaggatg tgctcaacag acgtttactg ttcaaaacaa  1860
accggcagca gtagcaccaa aggaaaccat cacccatcat ttcttcgttt ctggaattgg  1920
gcagaagaaa actgtcgatg cagccaaaat ttgtggcggc gcagaaaatg ttgttaaaac  1980
agaaacccag caaacattcg taaatggatt gctcggtttt attactttag gcatttatac  2040
tccgctggaa gcgcgtgtgt attgctcaca ataattgcat gagttgccca tcgatatggg  2100
caactctatc tgcactgctc attaatatac ttctgggttc cttccagttg tttttgcata  2160
gtgatcagcc tctctctgag ggtgaaataa tcccgttcag cggtgtctgc cagtcggggg  2220
gaggctgcat tatccacgcc ggaggcggtg gtggcttcac gcactgactg acagactgct  2280
ttgatgtgca accgacgacg accagcggca acatcatcac gcagagcatc atttcagct   2340
ttagcatcag ctaactcctt cgtgtatttt gcatcgagcg cagcaacatc acgctgacgc  2400
atctgcatgt cagtaattgc cgcgttcgcc agcttcagtt ctctggcatt tttgtcgcgc  2460
tgggcttttgt aggtaatggc gttatcacgg taatgattaa cagcccatga caggcagacg  2520
atgatgcaga taaccagagc ggagataatc gcggtgactc tgctcataca tcaatctctc  2580
tgaccgttcc gcccgcttct ttgaattttg caatcaggct gtcagcctta tgctcgaact  2640
gaccataacc agcgcccggc agtgaagccc agatattgct caaccggtcg attgcctgac  2700
ggatatcacc acgatcaatc ataggtaaag cgccacgctc cttaatctgc tgcaatgcca  2760
cagcgtcctg acttttcgga gagaagtctt tcaggccaag ctgcttgcgg taggcatccc  2820
accaacggga aagaagctgg tagcgtccgg cgcctgttga tttgagtttt gggtttagcg  2880
tgacaagttt gcgagggtga tcggagtaat cagtaaaatag ctctccgcct acaatgacgt  2940
cataaccatg atttcggtt ttctgacgtc cgttatcgat tccctccgac cacgccagca  3000
tatcgaggaa cgccttacgt tgattattga tttctaccat cttctactcc ggcttttta  3060
gcagcgaagc gtttgataag cgaaccaatc gagtcagtac cgatgtagcc gataaacacg  3120
ctcgttatat aagcgagatt gctacttagt ccggcgaagt cgagaggtc acgaatgaac  3180
taggcgataa tggcgcacat cgttgcgtcg attactgttt ttgtaaacgc accgccatta  3240
tatctgccgc gaaggtacgc cattgcaaac gcaaggattg ccccgatgcc ttgttccttt  3300
gccgcgagaa tggcggccaa caggtcatgt ttttctggca tcttcatgtc ttaccccaa   3360
```

```
taagggatt  tgctctattt  aattaggaat  aaggtcgatt  actgatagaa  caaatccagg  3420
ctactgtgtt  tagtaatcag  atttgttcgt  gaccgatatg  cacgggcaaa  acggcaggag  3480
gttgttagcg  caaaaaaaaa  attccaaaaa  aaaaattcca  aaaaaaaaaa  gcgactaaca  3540
aacacaatct  gatggc                                                     3556
```